(12) United States Patent
Zhu et al.

(10) Patent No.: US 11,203,586 B2
(45) Date of Patent: Dec. 21, 2021

(54) IRIDINESULFONAMIDE COMPOUND AND USE METHOD THEREOF

(71) Applicants: Chia Tai Tianqing Pharmaceutical Group Co., Ltd., Lianyungang (CN); Lianyungang Runzhong Pharmaceutical Co., Ltd., Lianyungang (CN); Centaurus Biopharma Co., Ltd., Beijing (CN)

(72) Inventors: Li Zhu, Beijing (CN); Yanqing Yang, Beijing (CN); Liguang Dai, Beijing (CN); Xiaowei Duan, Beijing (CN); Zhao Yang, Beijing (CN); Hui Zhang, Beijing (CN); Yuandong Hu, Beijing (CN); Yong Peng, Beijing (CN); Yongxin Han, Beijing (CN); Rui Zhao, Lianyungang (CN); Xin Tian, Lianyungang (CN); Shanchun Wang, Lianyungang (CN)

(73) Assignees: Chia Tai Tianqing Pharmaceutical Group Co., Ltd., Lianyungang (CN); Lianyungang Runzhong Pharmaceutical Co., Ltd., Lianyungang (CN); Centaurus Biopharma Co., Ltd., Beijin (CN)

( * ) Notice: Subject to any disclaimer, the term of this patent is extended or adjusted under 35 U.S.C. 154(b) by 558 days.

(21) Appl. No.: 16/087,396

(22) PCT Filed: Mar. 22, 2017

(86) PCT No.: PCT/CN2017/077611
§ 371 (c)(1),
(2) Date: Sep. 21, 2018

(87) PCT Pub. No.: WO2017/162156
PCT Pub. Date: Sep. 28, 2017

(65) Prior Publication Data
US 2021/0155610 A1 May 27, 2021

(30) Foreign Application Priority Data
Mar. 22, 2016 (CN) .......................... 201610166113.8

(51) Int. Cl.
*C07D 403/12* (2006.01)
*C07D 203/24* (2006.01)
*C07D 401/12* (2006.01)

(52) U.S. Cl.
CPC ......... *C07D 403/12* (2013.01); *C07D 203/24* (2013.01); *C07D 401/12* (2013.01)

(58) Field of Classification Search
CPC ... C07D 403/12; C07D 203/24; C07D 401/12
USPC ..................................................... 514/210.18
See application file for complete search history.

(56) References Cited

FOREIGN PATENT DOCUMENTS

| WO | WO 2011/072174 A1 | 6/2011 | |
|---|---|---|---|
| WO | WO 2012/009678 A1 | 1/2012 | |
| WO | WO 2012/171337 A1 | 1/2012 | |
| WO | WO-2012009678 A1 * | 1/2012 | .......... C07D 249/18 |
| WO | WO 2013107405 A1 | 7/2013 | |
| WO | WO 2014/062511 A1 | 4/2014 | |
| WO | WO 2015/010297 A1 | 1/2015 | |

OTHER PUBLICATIONS

International Search Report in International Application No. PCT/CN2017/077611, dated Jun. 16, 2017 (8 pages, w/English translation).
Written Opinion in International Application No. PCT/CN2017/077611, dated Jun. 16, 2017 (14 pages, w/English translation).

* cited by examiner

*Primary Examiner* — Rita J Desai
(74) *Attorney, Agent, or Firm* — Nixon Peabody LLP

(57) ABSTRACT

An iridinesulfonamide compound having isocitrate dehydrogenase 1 (IDH1) inhibitory activity, pharmaceutically acceptable salts, solvates or hydrates thereof, a pharmaceutical composition, as well as use of the compound or the pharmaceutically acceptable salts, solvates or hydrates thereof, and the pharmaceutical composition thereof in treating IDH1 mutation induced cancer.

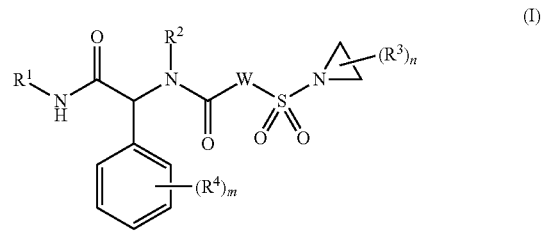

(I)

16 Claims, 2 Drawing Sheets

IRIDINESULFONAMIDE COMPOUND AND USE METHOD THEREOF

CROSS-REFERENCE TO RELATED APPLICATIONS

This application is a U.S. national stage of PCT/CN2017/077611 filed on Mar. 22, 2017, which claims the benefit of Chinese Patent Application No. 201610166113.8 filed to the State Intellectual Property Office of the People's Republic of China on Mar. 22, 2016, the contents of which are incorporated herein by reference it their entireties.

FIELD OF THE INVENTION

The present application relates to an aziridinesulfonamide compound for use in treating cancer and application methods thereof.

BACKGROUND OF THE INVENTION

As the most important key enzyme in intracellular tricarboxylic acid cycle, IDH (full name: isocitrate dehydrogenase) can catalyze oxidative decarboxylation of isocitric acid to produce 2-oxoglutarate (i.e., α-ketoglutaric acid). There are two different subtypes of IDH, one using NAD(+) as an electron acceptor and the other using NADP(+) as the electron acceptor. Five types of IDH have been reported, three of which are NAD(+)-dependent isocitrate dehydrogenases, locating in the mitochondrial matrix; and the other two of which are NADP(+)-dependent isocitrate dehydrogenases, wherein one locates in the mitochondria and the other locates in the cytoplasm.

Researches have shown that many tumors (such as neuroglioma, sarcoma, and acute myelocytic leukemia) have an IDH mutation at arginine residue in a catalytic center (IDH1/R132H, IDH/R140Q, and IDH2/R172K). In 2009, Bleeker et al. have detected IDH1 mutations in 672 tumor samples obtained from different sources and 84 cell lines from different tumor lineages, and found that these mutations specifically and centrally occurred in gliomas (Bleeker et al, 2009. IDH1 mutations at residue p.R132(IDH1(R132)) occur frequently in high-grade gliomas but not in other solid tumors. Hum Mutat. 30: 7-11). However, the later literature reports have shown that IDH1 mutations also exist in acute myeloid leukemia, prostate cancer, and paraganglioma and the like (Green et al, 2010, Somatic mutations of IDH1 and IDH2 in the leukemic transformation of myeloproliferative neoplasms. N Engl J Med. 362: 369-370). Bleeker et al. found that in IDH1 mutation cases, R132H accounts for 86.9%, and other types such as R132C, R132G, R132L, R132V and R132S account for a small proportion (Bleeker et al, 2009. IDH1 mutations at residue p.R132(IDH1(R132)) occur frequently in high-grade gliomas but not in other solid tumers. Hum Mutat. 30: 7-11.) The mutated IDH acquires a new ability to catalyze the conversion of α-ketoglutaric acid (α-KG) to 2-hydroxyglutaric acid (2-HG). Researches have shown that the structure of α-ketoglutaric acid is similar to that of 2-hydroxyglutaric acid, and 2-HG competes with α-KG, thereby reducing the activity of α-KG-dependent enzymes, and resulting in a hypermethylation of chromatin. Such supermethylation is considered to interfere with a normal cell differentiation, and leads to an excessive proliferation of immature cells, thereby causing cancers.

AG-120 (i.e., ivosidenib), an inhibitor of IDH1m developed by Agios Pharmaceuticals, has a significant efficacy for acute myeloid erythroleukemia, and researches directed to other malignant solid tumors such as bile duct cancer, chondrosarcoma, neuroglioma are also underway.

SUMMARY OF THE INVENTION

In one aspect, the present application provides a compound of Formula I, or a pharmaceutically acceptable salt, solvate or hydrate thereof:

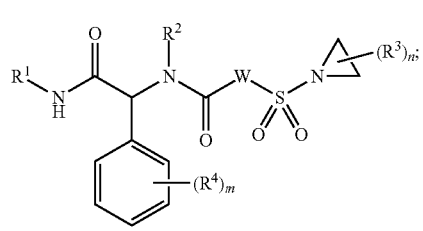

(I)

wherein,

W is $-(X^1)_p-(X^2)_q-(X^3)_r-$;

$X^1$ is selected from $C_{1-6}$ alkylene, which may be optionally substituted with one or more groups independently selected from $R^5$;

$X^2$ is selected from $C_{3-6}$ cycloalkyl or $C_{3-6}$ heterocycloalkyl, which may be optionally substituted with one or more groups independently selected from $R^6$;

$X^3$ is selected from $-NR^7-$;

p is 0 or 1;

q is 0 or 1;

r is 0 or 1;

and p, q, r are not 0 simultaneously;

$R^1$ is selected from $C_{3-6}$ cycloalkyl or $C_{3-6}$ heterocycloalkyl, which may be optionally substituted with one or more groups independently selected from $R^8$;

$R^2$ is selected from phenyl, or 5- or 6-membered heteroaryl containing 1 to 2 atoms selected from N, O or S, which may be optionally substituted with one or more groups independently selected from $R^9$;

each of $R^3$ and $R^4$ is each independently selected from halogen, amino, hydroxyl, halogenated $C_{1-3}$ alkyl or $C_{1-6}$ alkyl;

$R^5$, $R^6$ and $R^8$ are each independently selected from halogen, amino, hydroxyl, cyano, halogenated $C_{1-3}$ alkyl, $C_{1-6}$ alkyl or $C_{3-6}$ cycloalkyl;

$R^7$ is selected from hydrogen, $C_{1-3}$ alkyl or amino protecting group;

$R^9$ is selected from halogen, amino, hydroxyl, cyano, halogenated $C_{1-3}$ alkyl or aminosulfonyl;

m is 0 or 1;

n is 0 or 1.

In one embodiment of the compound of Formula I in the present application, each $R^4$ is independently selected from fluorine, chlorine, bromine or trifluoromethyl.

In another aspect, the present application provides a compound as represented by Formula I-1, or a pharmaceutically acceptable salt, solvate or hydrate thereof:

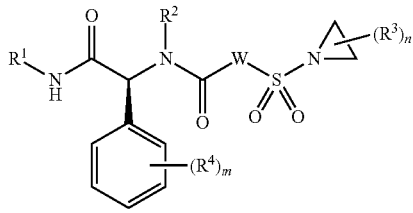

(I-1)

wherein the substituents are as defined in the compound of Formula I.

In another aspect, the present application provides a compound as represented by Formula I-2, or a pharmaceutically acceptable salt, solvate or hydrate thereof:

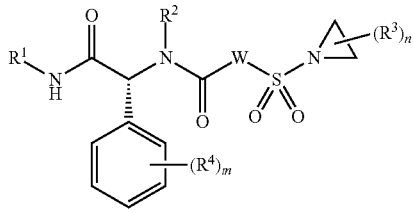

(I-2)

wherein the substituents are as defined in the compound of Formula I.

As an embodiment of the present application, a compound as represented by Formula II, or a pharmaceutically acceptable salt, solvate or hydrate thereof is provided:

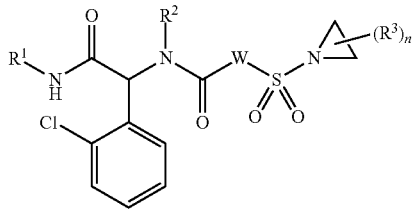

(II)

wherein,
W is —$(X^1)_p$—$(X^2)_q$—$(X^3)_r$—;
$X^1$ is selected from $C_{1-6}$ alkylene, which may be optionally substituted with one or more groups independently selected from $R^5$;
$X^2$ is selected from $C_{3-6}$ cycloalkyl or $C_{3-6}$ heterocycloalkyl, which may be optionally substituted with one or more groups independently selected from $R^6$;
$X^3$ is selected from —$NR^7$—;
p is 0 or 1;
q is 0 or 1;
r is 0 or 1;
and p, q, r are not 0 simultaneously;
$R^1$ is selected from $C_{3-6}$ cycloalkyl or $C_{3-6}$ heterocycloalkyl, which may be optionally substituted with one or more groups independently selected from $R^8$;

$R^2$ is selected from phenyl, or 5- to 6-membered heteroaryl containing 1 to 2 atoms selected from N, O or S, which may be optionally substituted with one or more groups independently selected from $R^9$;
each $R^3$ is independently selected from halogen, amino, hydroxyl, halogenated $C_{1-3}$ alkyl or $C_{1-6}$ alkyl;
$R^5$, $R^6$ and $R^8$ are each independently selected from halogen, amino, hydroxyl, cyano, halogenated $C_{1-3}$ alkyl, $C_{1-6}$ alkyl or $C_{3-6}$ cycloalkyl;
$R^7$ is selected from hydrogen, $C_{1-3}$ alkyl or amino protecting group;
$R^9$ is selected from halogen, amino, hydroxyl, cyano, halogenated $C_{1-3}$ alkyl or aminosulfonyl;
n is 0 or 1.

In one embodiment of the compound of Formula II in the present application, $X^1$ is selected from $C_{1-6}$ alkylene.

In one embodiment of the compound of Formula II in the present application, $X^1$ is selected from —$CH_2$—, —$CH_2CH_2$—, —$CH(CH_3)$—, —$CH_2CH_2CH_2$—, —$CH(CH_3)CH_2$—, —$CH_2CH_2CH_2CH_2$—, —$CH(CH_3)CH_2CH_2$—, —$CH_2CH(CH_3)CH_2$—, —$CH_2CH_2CH_2CH_2CH_2$—, —$CH(CH_3)CH_2CH_2CH_2$—, —$CH_2CH(CH_3)CH_2CH_2$—, —$CH_2CH_2CH_2CH_2CH_2CH_2$—, —$CH(CH_3)CH_2CH_2CH_2CH_2$—, —$CH_2CH(CH_3)CH_2CH_2CH_2$— or —$CH_2CH_2CH(CH_3)CH_2CH_2$—.

In one embodiment of the compound of Formula II in the present application, $X^1$ is selected from —$CH_2$—, —$CH_2CH_2$—, —$CH_2CH_2CH_2$—, —$CH_2CH_2CH_2CH_2$— or —$CH(CH_3)$—.

In one embodiment of the compound of Formula II in the present application. $X^2$ is selected from cyclopropyl, cyclobutyl, cyclopentyl, cyclohexyl,

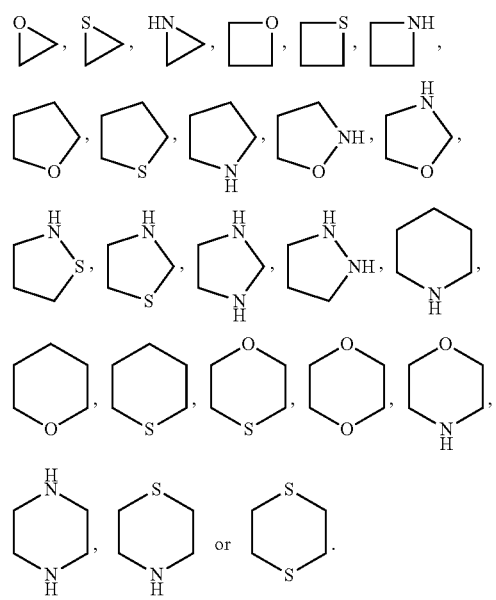

In one embodiment of the compound of Formula II in the present application, $X^2$ is selected from pyrrolidinyl, cyclobutyl, or azetidinyl.

In one embodiment of the compound of Formula II in the present application, $X^2$ is selected from

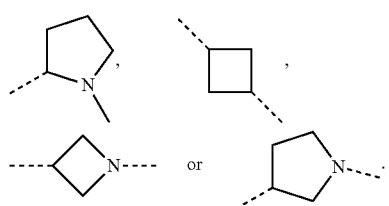

In one embodiment of the compound of Formula II in the present application, $X^3$ is selected from —NH—, —N(CH$_3$)— or —N(Boc)-.

In one embodiment of the compound of Formula II in the present application, $X^1$ is selected from $C_{1-6}$ alkylene; $X^2$ is selected from pyrrolidinyl, cyclobutyl, or azetidinyl; $X^3$ is selected from —NR$^7$—.

In one embodiment of the compound of Formula II in the present application, $X^1$ is selected from —CH$_2$—, —CH$_2$CH$_2$—, —CH$_2$CH$_2$CH$_2$—, —CH$_2$CH$_2$CH$_2$CH$_2$— or —CH(CH$_3$)—; $X^2$ is selected from

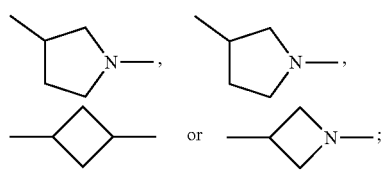

$X^3$ is selected from —NR$^7$—.

In one embodiment of the compound of Formula II in the present application, W is —CH$_2$NR$^7$—, —CH(CH$_3$)NR$^7$—, —CH$_2$CH$_2$NR$^7$—, —CH$_2$CH$_2$CH$_2$NR$^7$—, —CH$_2$—, —CH$_2$CH$_2$—, —CH$_2$CH$_2$CH$_2$—, —CH$_2$CH$_2$CH$_2$CH$_2$—,

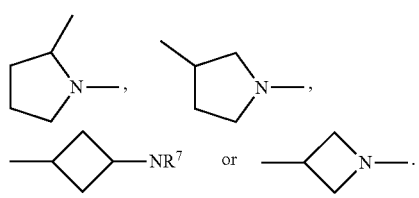

In one embodiment of the compound of Formula II in the present application, W is —CH$_2$—, —CH$_2$NH—, —CH$_2$N(CH$_3$)—, —CH$_2$N(Boc)-, —CH(CH$_3$)NH—, —CH$_2$CH$_2$—, —CH$_2$CH$_2$NH—, —CH$_2$CH$_2$CH$_2$—, —CH$_2$CH$_2$CH$_2$NH—, —CH$_2$CH$_2$CH$_2$CH$_2$—,

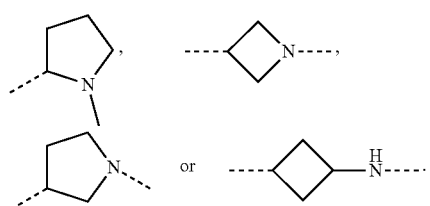

In a preferred and particular embodiment in the present application, in the compound as represented by Formula II, or the pharmaceutically acceptable salt, solvate or hydrate thereof, $R^1$ is selected from cyclopropyl, cyclobutyl, cyclopentyl, cyclohexyl, pyrrolidinyl or piperidinyl, which may be optionally substituted with one or more groups independently selected from $R^8$; $R^8$ is selected from halogen. Preferably, $R^1$ is selected from cyclobutyl or cyclohexyl, which may be optionally substituted with 1 or 2 independent fluoro groups; more preferably, $R^1$ is

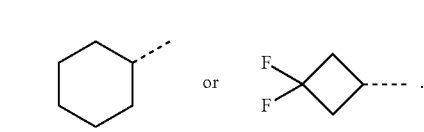

In one embodiment of the compound of Formula II in the present application, $R^1$ is selected from cyclopropyl, cyclobutyl, cyclopentyl, cyclohexyl, pyrrolidinyl or piperidinyl, which may be optionally substituted with 1 or 2 groups independently selected from $R^8$.

In one embodiment of the compound of Formula II in the present application, $R^1$ is selected from cyclobutyl or cyclohexyl, which may be optionally substituted with 1 or 2 independent fluoro groups.

In one embodiment of the compound of Formula II in the present application, $R^1$ is selected from

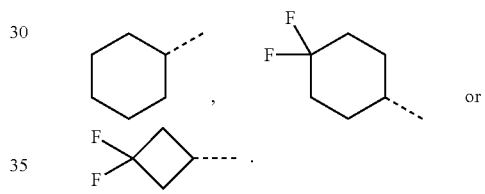

In one embodiment of the compound of Formula II in the present application, $R^1$ is selected from

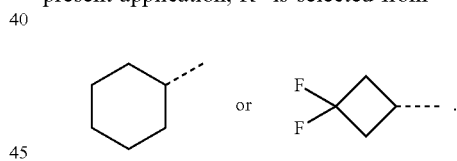

In one embodiment of the compound of Formula II in the present application, $R^8$ is selected from halogen.

In a preferred and particular embodiment in the present application, in the compound as represented by Formula II, or the pharmaceutically acceptable salt, solvate or hydrate thereof, $R^2$ is selected from phenyl, furyl, thienyl, pyrrolyl, pyrazolyl, imidazolyl, pyridyl, pyrimidinyl, pyridazinyl, pyrazinyl, thiazolyl, isothiazolyl, oxazolyl, isoxazolyl, tetrazolyl or triazinyl, which may be optionally substituted with one or more groups independently selected from $R^9$; $R^9$ is selected from halogen, cyano, monofluoromethyl, difluoromethyl, trifluoromethyl, monofluoroethyl, difluoroethyl, trifluoroethyl, tetrafluoroethyl, pentafluoroethyl, monochloromethyl, dichloromethyl, trichloromethyl or aminosulfonyl. Preferably, $R^2$ is selected from phenyl or pyridyl, which may be optionally substituted with one or more groups independently selected from $R^9$; $R^9$ is selected from halogen, cyano, trifluoromethyl or —SO$_2$NH$_2$.

In one embodiment of the compound of Formula II in the present application, $R^2$ is selected from phenyl, furanyl, thienyl, pyrrolyl, pyrazolyl, imidazolyl, pyridyl, pyrimidinyl, pyridazinyl, pyrazinyl, thiazolyl isothiazolyl, oxazolyl, isoxazolyl, tetrazolyl or triazinyl, which may be optionally substituted with one or more groups independently selected from $R^9$.

In one embodiment of the compound of Formula II in the present application, $R^2$ is selected from phenyl or pyridyl, which may be optionally substituted with one or more groups independently selected from $R^9$.

In one embodiment of the compound of Formula II in the present application, $R^9$ is selected from halogen, cyano, monofluoromethyl, difluoromethyl, trifluoromethyl, monofluoroethyl, difluoroethyl, trifluoroethyl, tetrafluoroethyl, pentafluoroethyl, monochloromethyl, dichloromethyl, trichloromethyl or aminosulfonyl.

In one embodiment of the compound of Formula II in the present application, $R^9$ is selected from halogen, cyano, trifluoromethyl or —$SO_2NH_2$.

In one embodiment of the compound of Formula II in the present application, $R^2$ is selected from

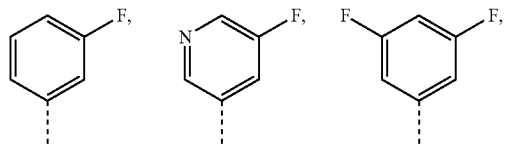

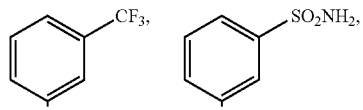

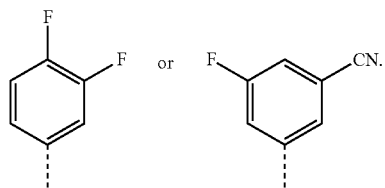

In one embodiment of the compound of Formula II in the present application, each $R^3$ is independently selected from methyl, ethyl, propyl, isopropyl or t-butyl.

In one embodiment of the compound of Formula II in the present application, each $R^3$ is independently selected from methyl or isopropyl.

In one embodiment of the compound of Formula II in the present application, $R^7$ is selected from hydrogen, methyl, ethyl, t-butoxycarbonyl, benzyloxycarbonyl, p-toluenesulfonyl, triphenylmethyl, formyl, 2-biphenyl-2-propoxycarbonyl or trifluoroacetyl.

In one embodiment of the compound of Formula II in the present application, $R^7$ is selected from hydrogen, methyl, t-butoxycarbonyl or benzyloxycarbonyl.

As an embodiment of the present application, a compound of Formula II-1, or a pharmaceutically acceptable salt, solvate or hydrate thereof is provided:

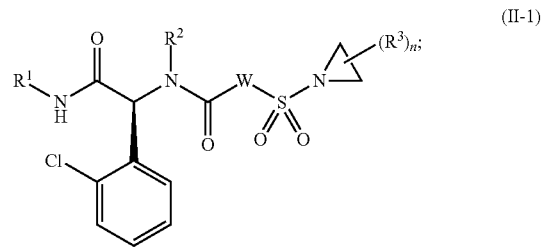

(II-1)

wherein the substituents are as defined in Formula II.

As an embodiment of the present application, a compound of Formula II-2, or a pharmaceutically acceptable salt, solvate or hydrate thereof is provided:

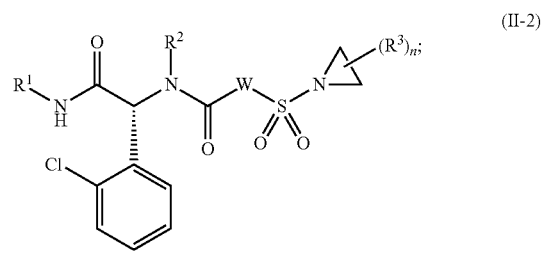

(II-2)

wherein the substituents are as defined in Formula II.

In the present application, the following compounds and the pharmaceutically acceptable salts, solvates or hydrates thereof are preferred:

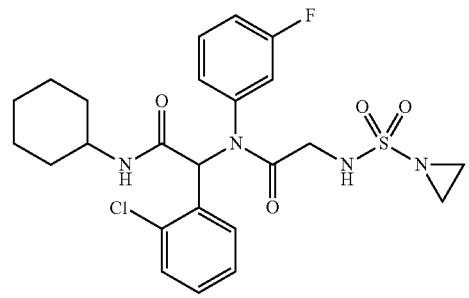 [SMILES: O=C(NC1CCCCC1)C(c1ccccc1Cl)N(C(=O)CNS(=O)(=O)N1CC1)c1cccc(F)c1]

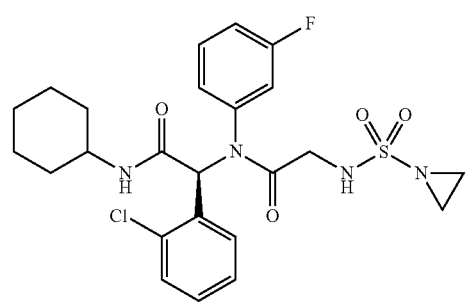

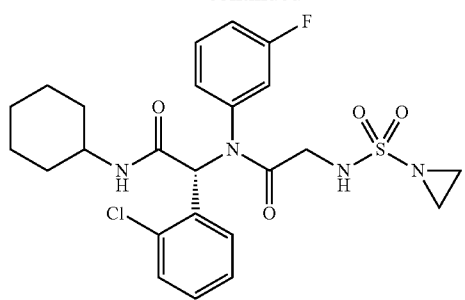
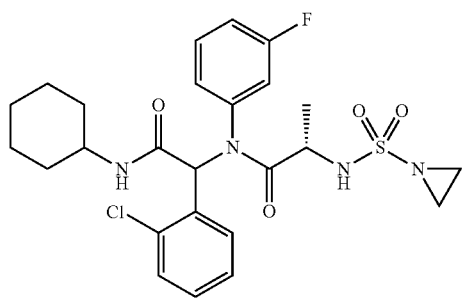 [SMILES: C[C@H](NS(=O)(=O)N1CC1)C(=O)N(c1cccc(F)c1)C(C(=O)NC1CCCCC1)c1ccccc1Cl]
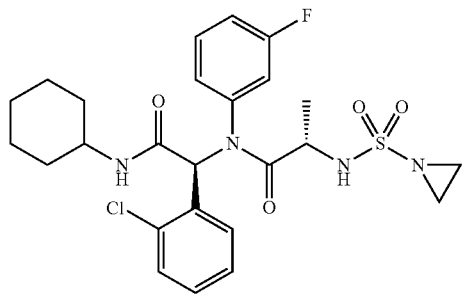
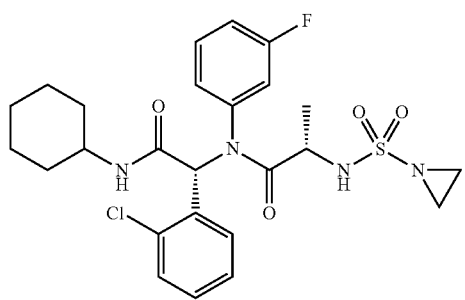
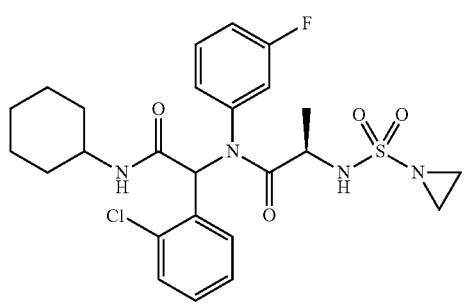 [SMILES: C[C@@H](NS(=O)(=O)N1CC1)C(=O)N(c1cccc(F)c1)[C@@H](C(=O)NC1CCCCC1)c1ccccc1Cl]
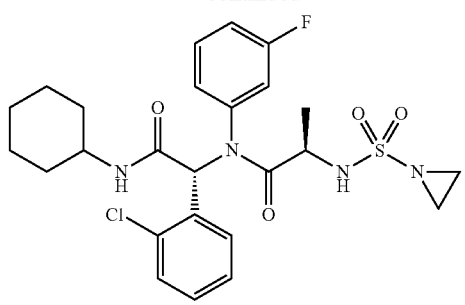
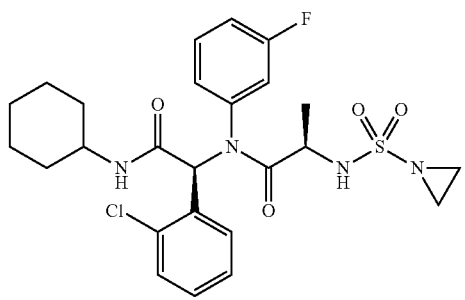 [SMILES: C[C@@H](NS(=O)(=O)N1CC1)C(=O)N(c1cccc(F)c1)[C@H](C(=O)NC1CCCCC1)c1ccccc1Cl]
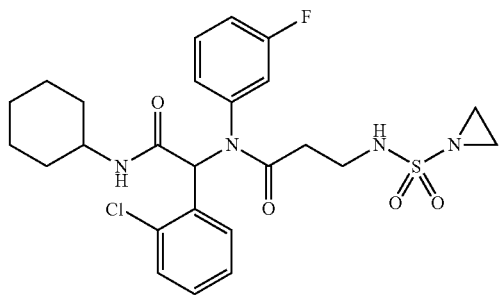 [SMILES: O=C(NC1CCCCC1)C(c1ccccc1Cl)N(C(=O)CCNS(=O)(=O)N1CC1)c1cccc(F)c1]
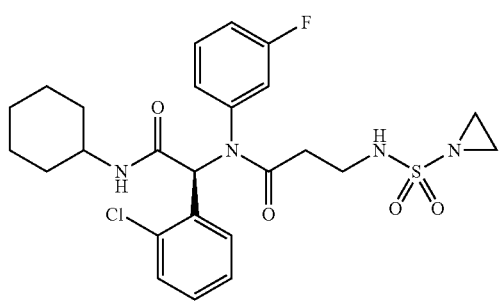
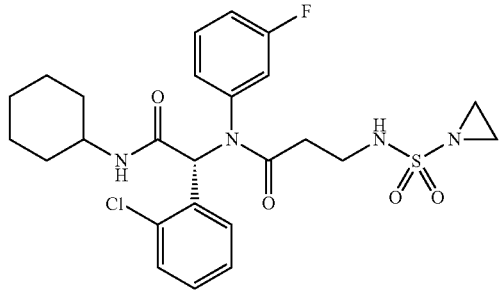

11
-continued
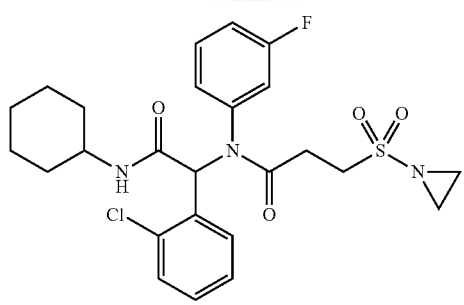 [SMILES: O=C(NC1CCCCC1)C(c1ccccc1Cl)N(C(=O)CCS(=O)(=O)N1CC1)c1cccc(F)c1]
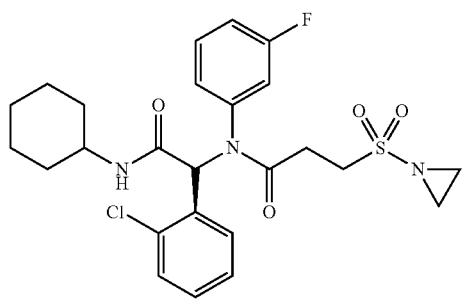
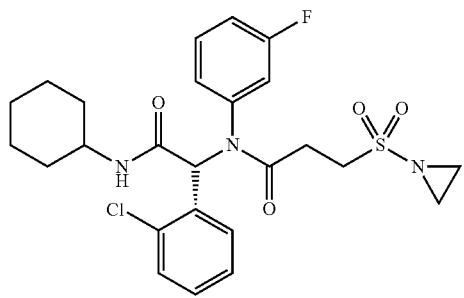
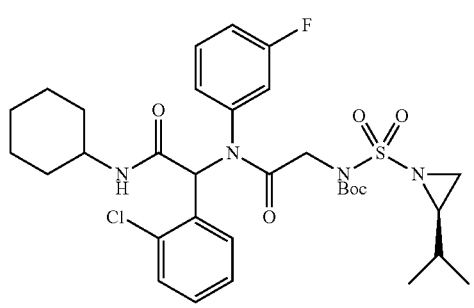
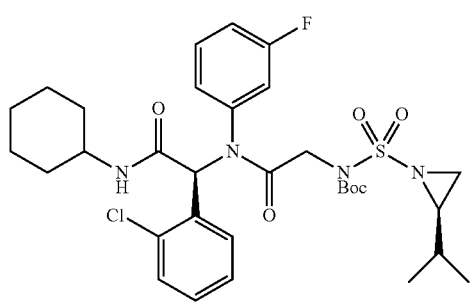
12
-continued
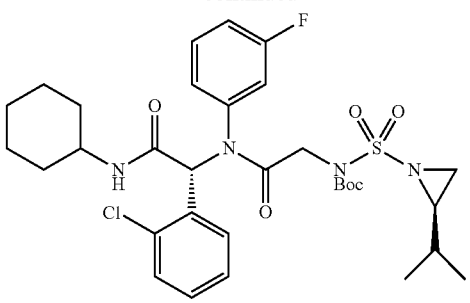
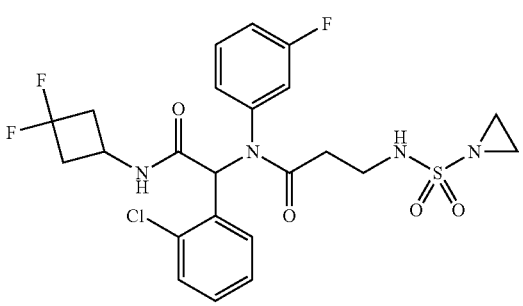
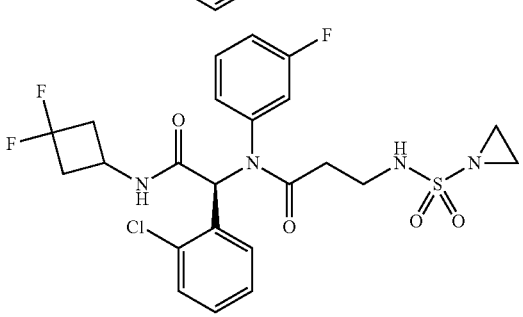
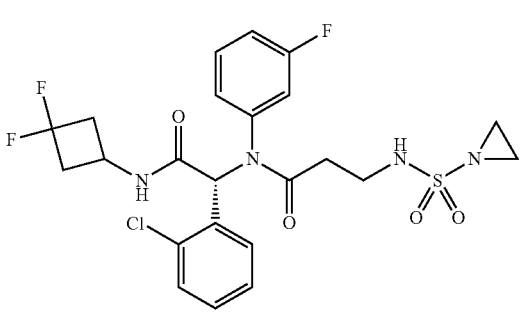
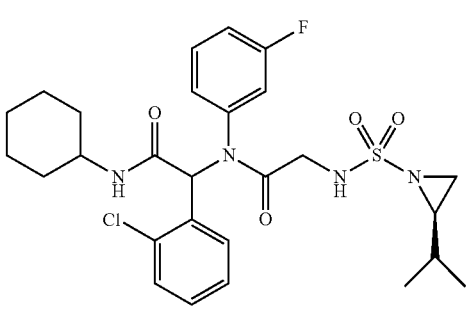

13
-continued
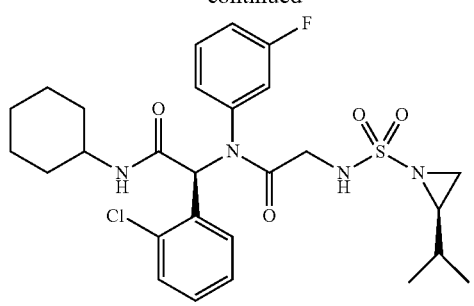
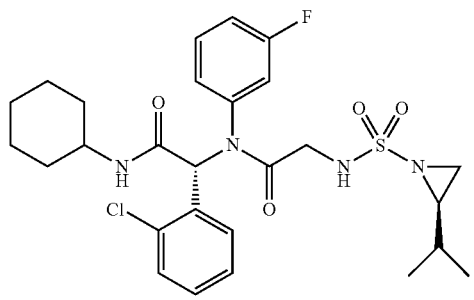
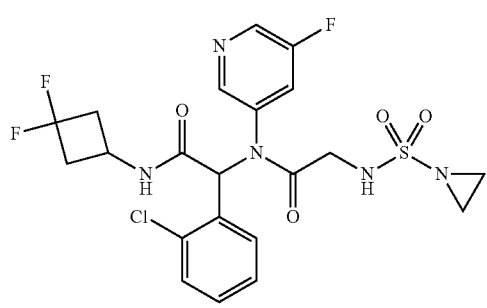
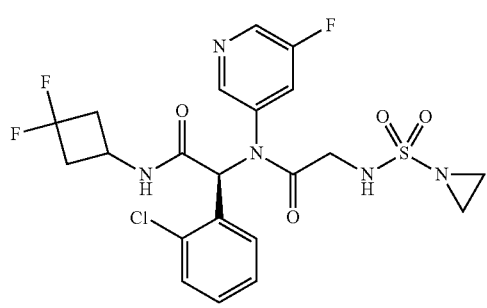
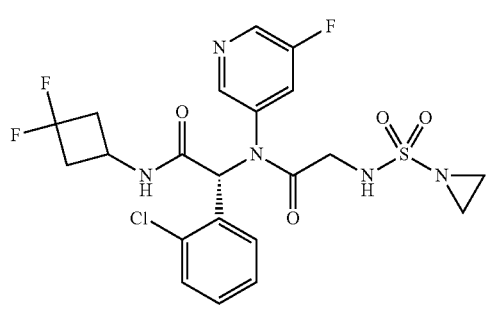
14
-continued
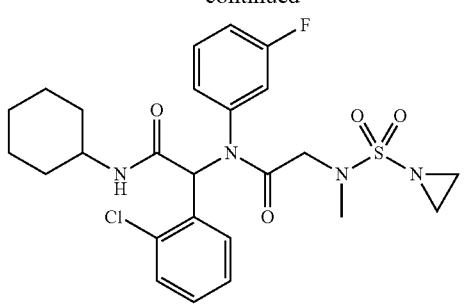
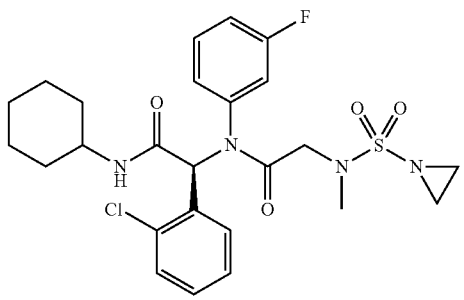
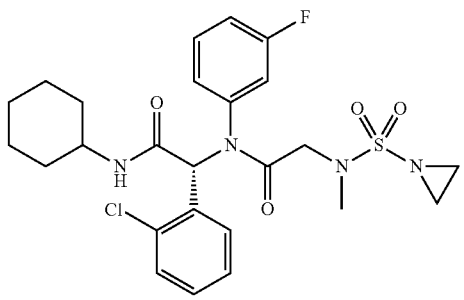
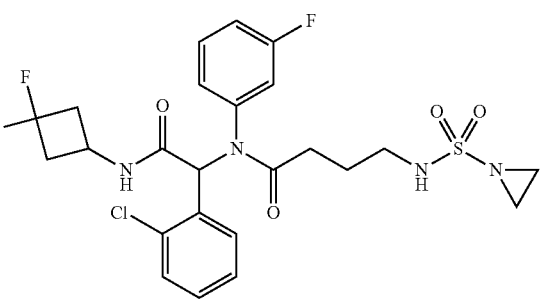
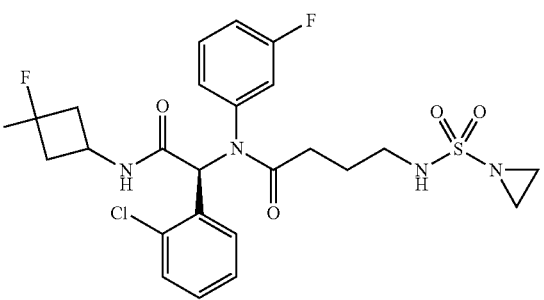

15
-continued
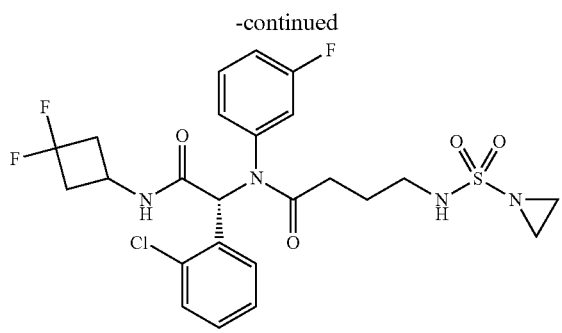
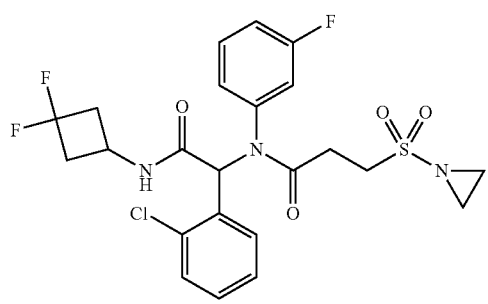
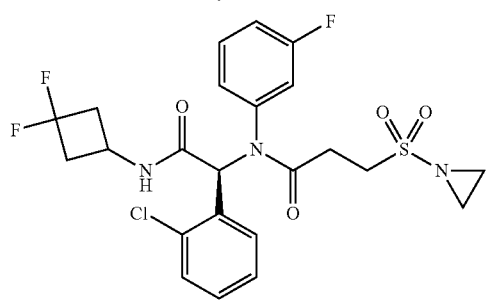
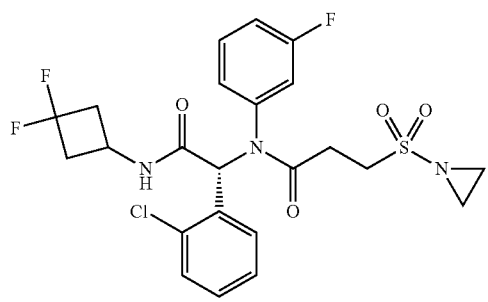
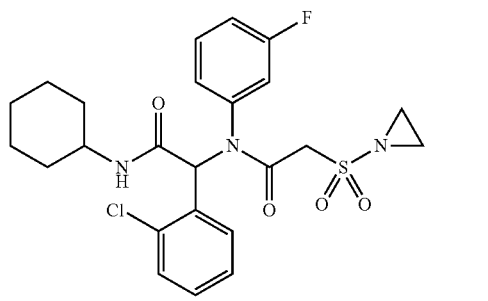
16
-continued
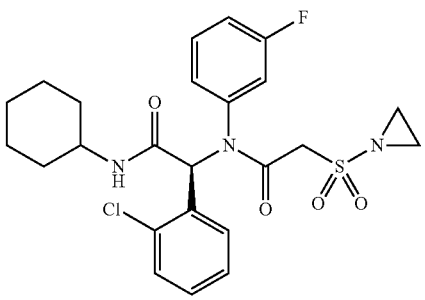
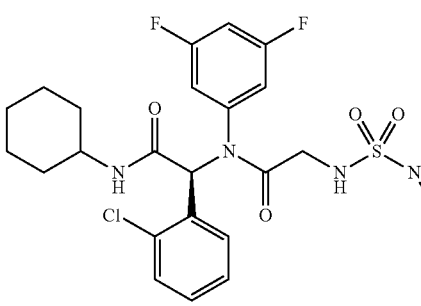
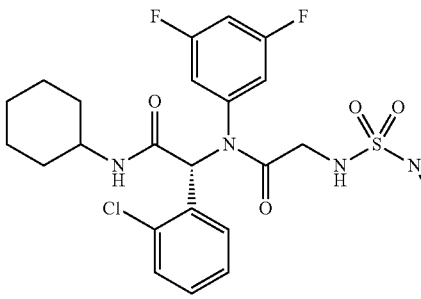

17
-continued
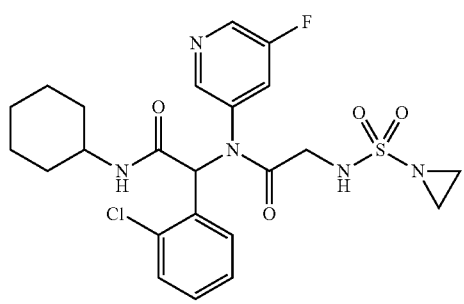
18
-continued
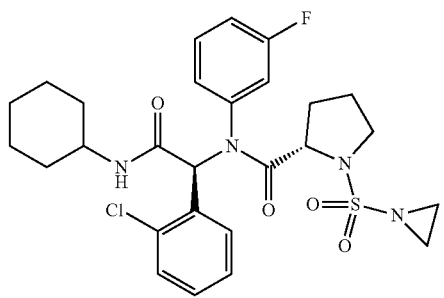

-continued
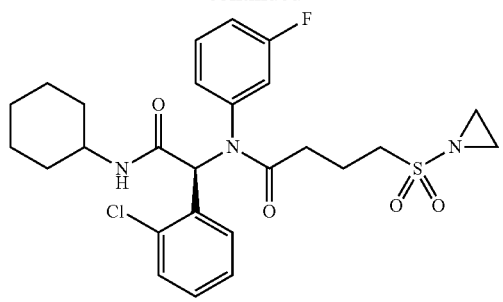
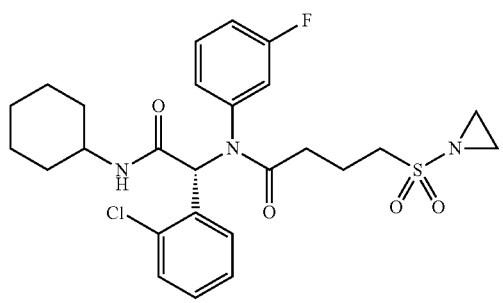
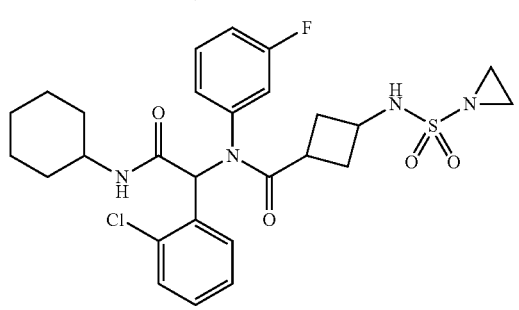
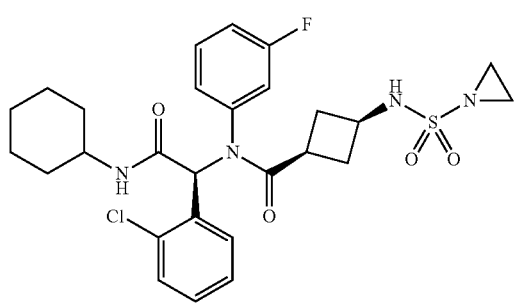
-continued
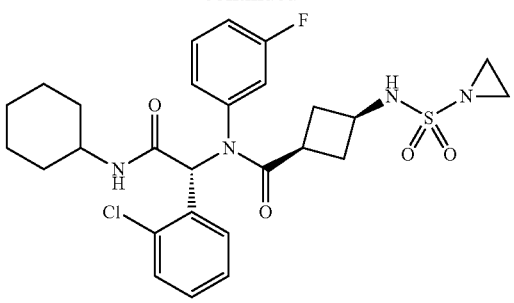
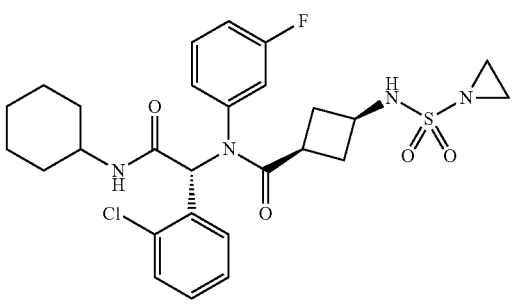
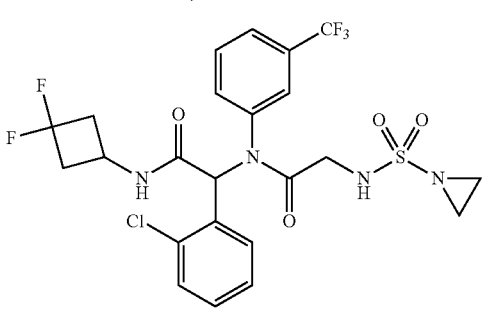
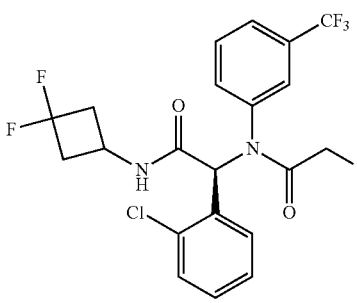
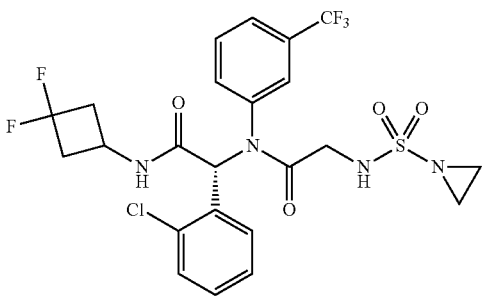

21
-continued
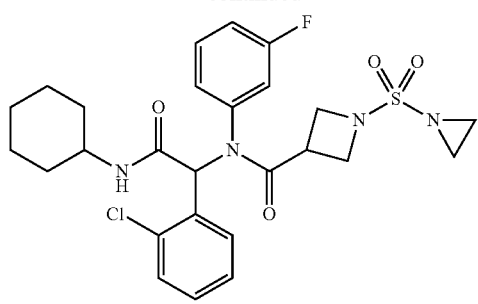
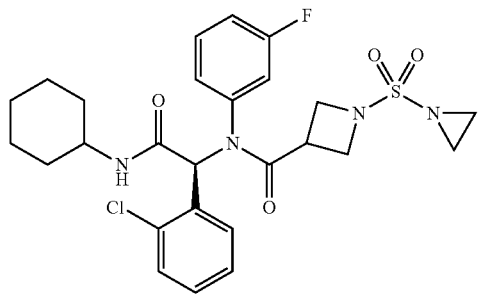
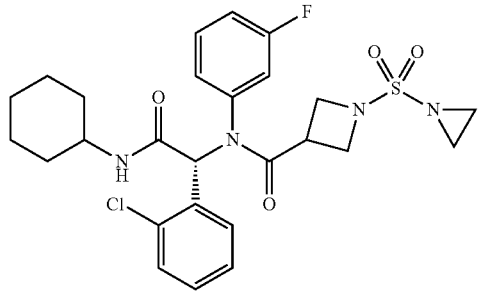
22
-continued
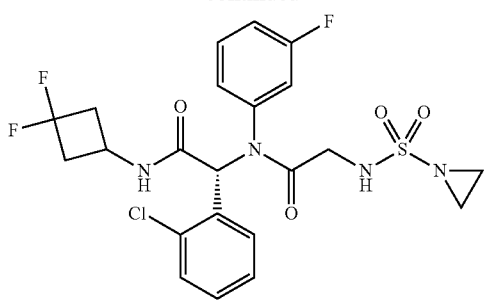
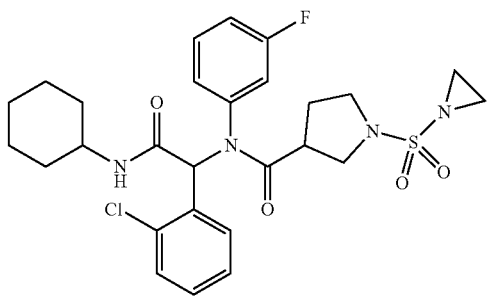
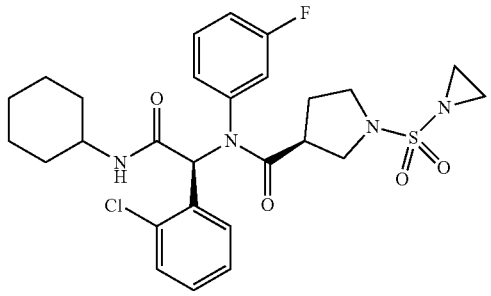
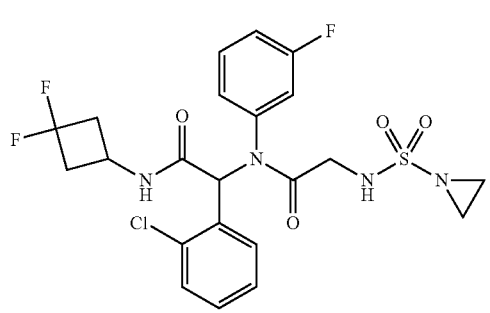
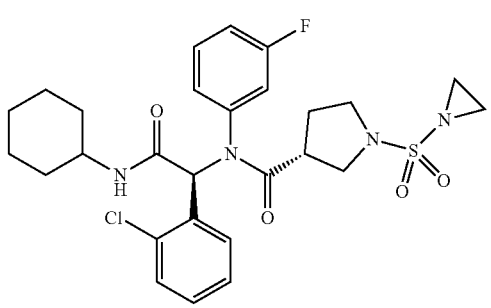
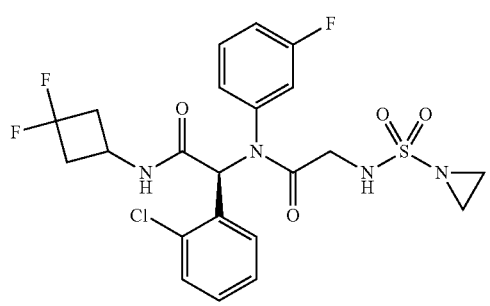
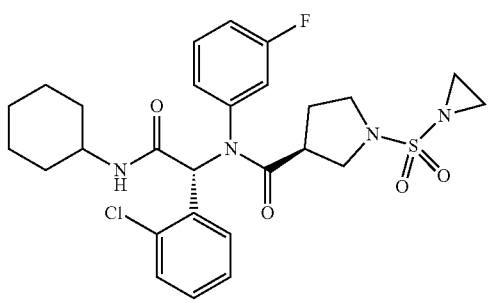

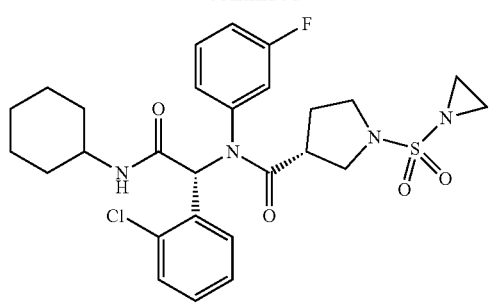
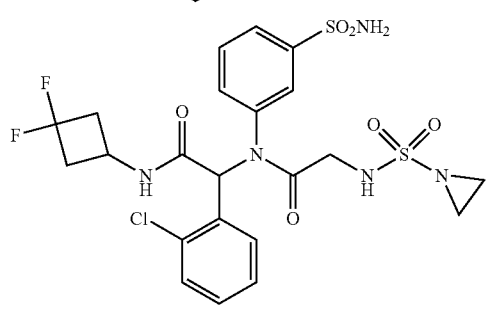
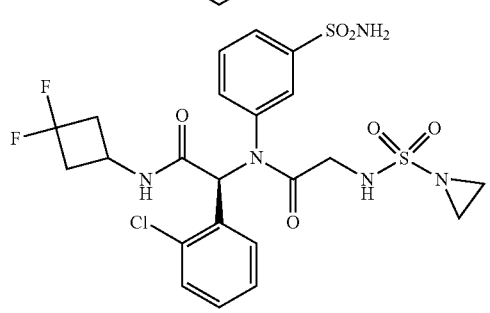
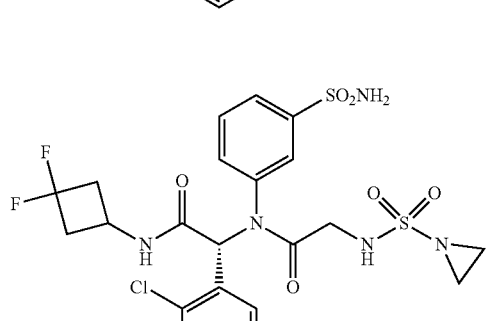
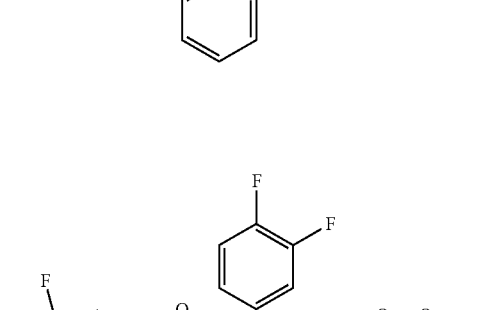
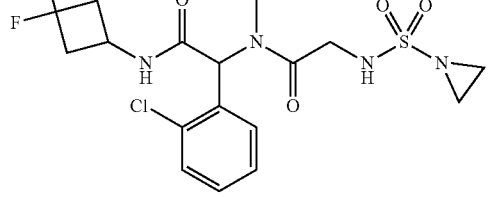
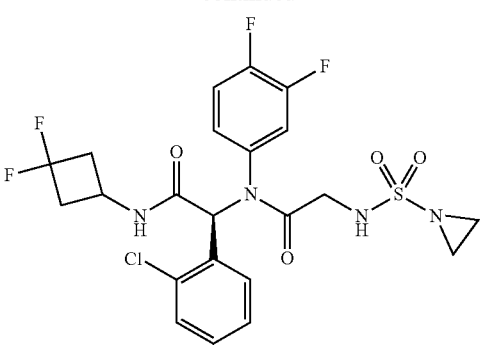
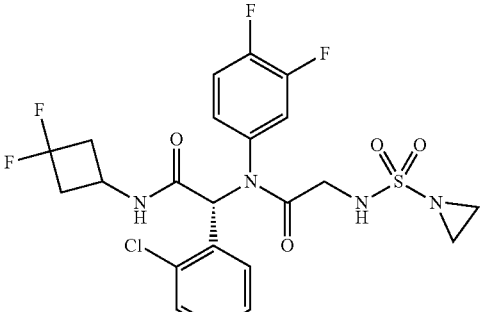
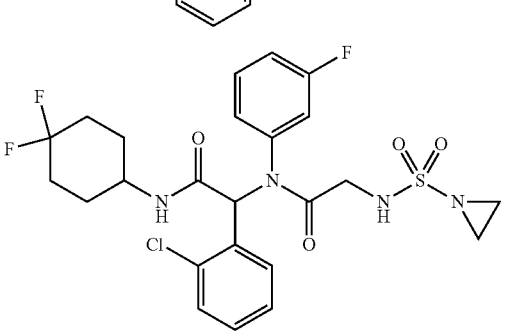
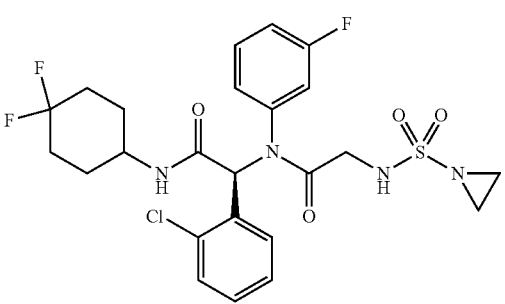
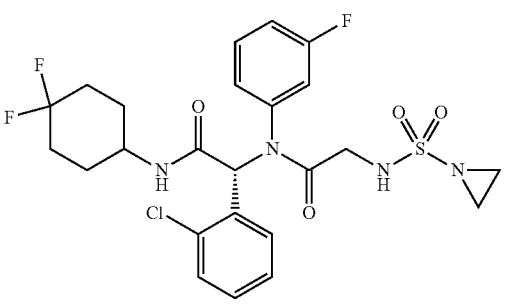

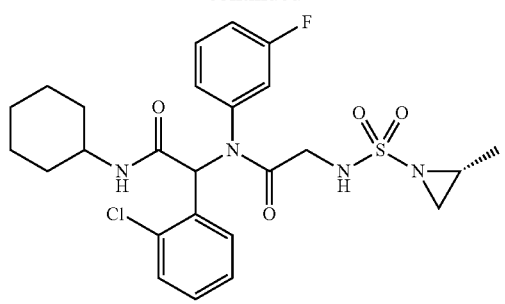
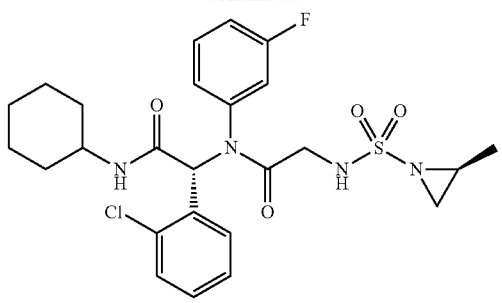
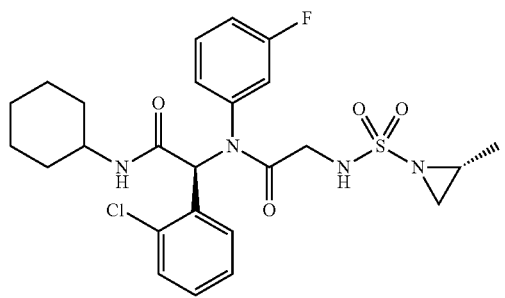
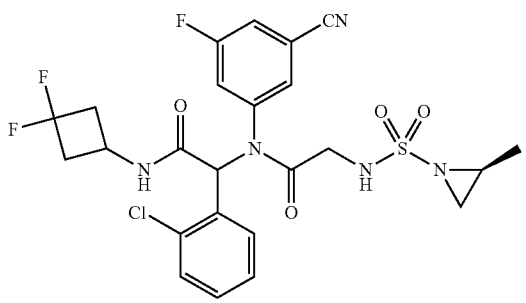
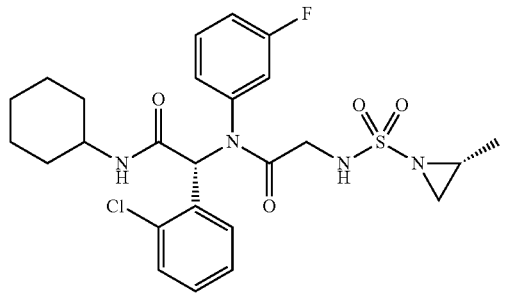
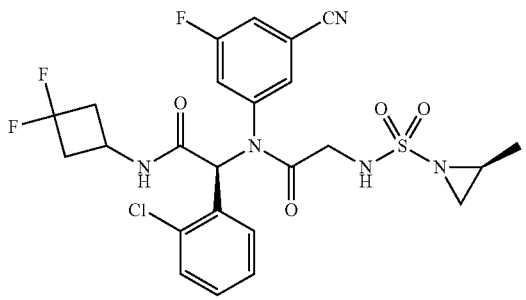
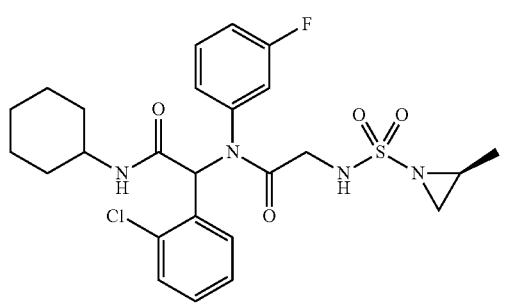
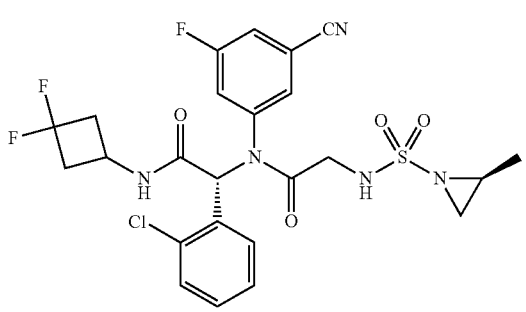
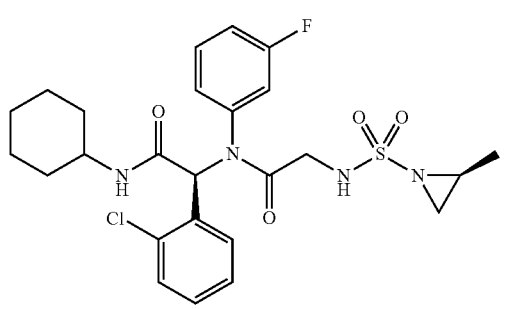
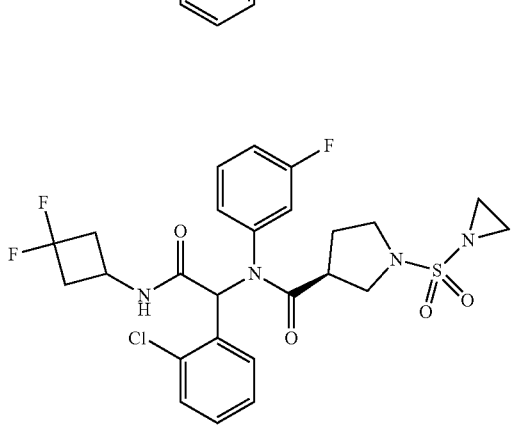

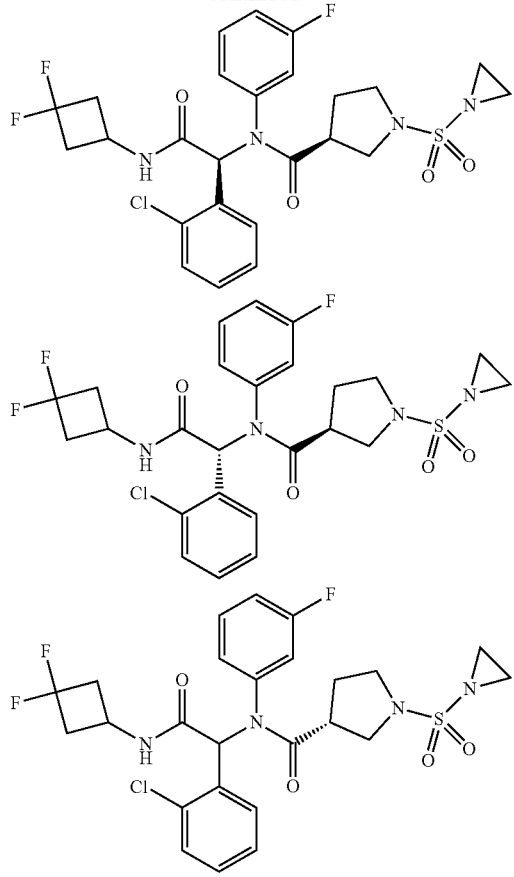
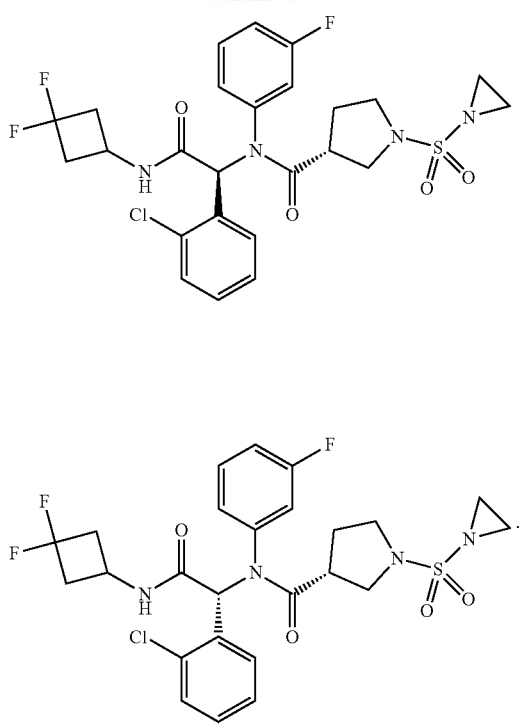
In the present application, the following compounds and the pharmaceutically acceptable salts, solvates or hydrates thereof are further preferred:
| Compound No. | structure |
|---|---|
| 1 | 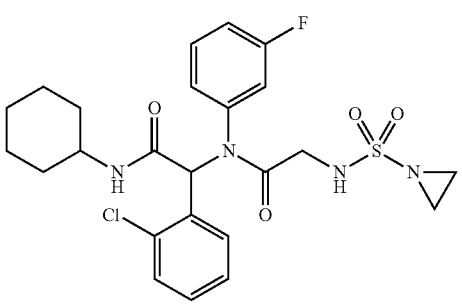 |
| 2 | 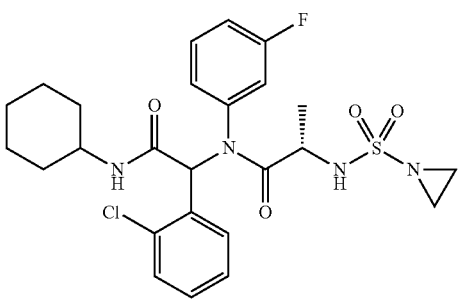 |

-continued
| Compound No. | structure |
|---|---|
| 3 | 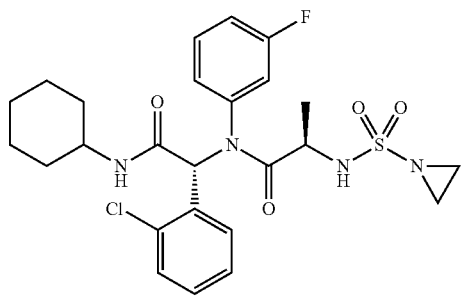 |
| 4 | 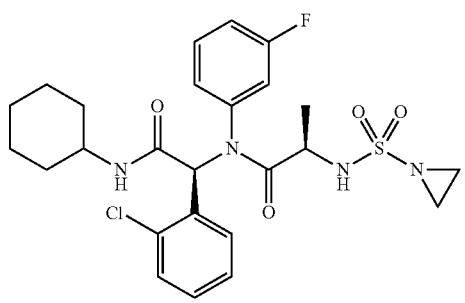 |
| 5 | 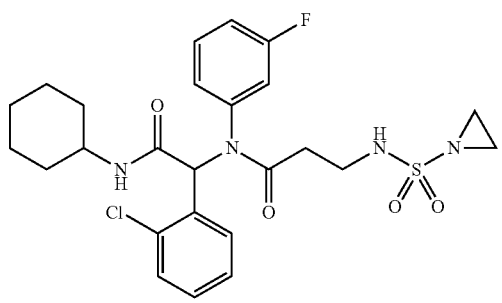 |
| 6 | 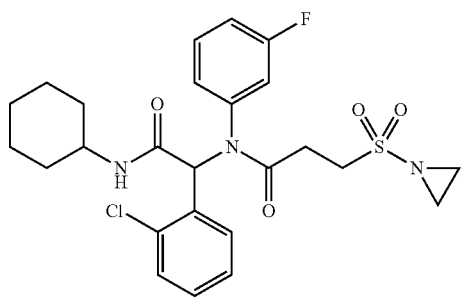 |
| 7 | 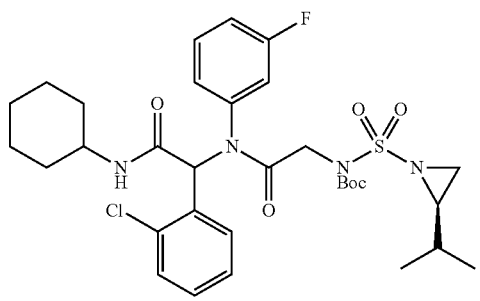 [SMILES: CC(C)[C@@H]1CN1S(=O)(=O)N(CC(=O)N(c1cccc(F)c1)C(C(=O)NC1CCCCC1)c1ccccc1Cl)C(=O)OC(C)(C)C] |

-continued
| Compound No. | structure |
|---|---|
| 8 | 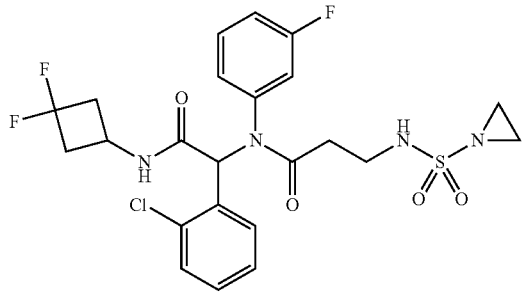 [SMILES: O=C(NC1CC(F)(F)C1)C(c1ccccc1Cl)N(C(=O)CCNS(=O)(=O)N1CC1)c1cccc(F)c1] |
| 9 | 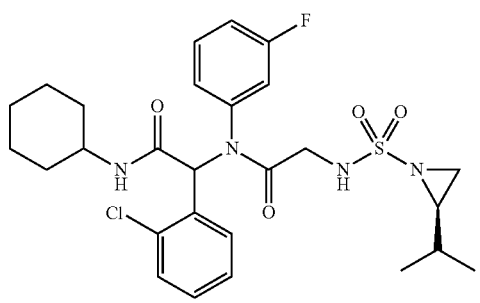 [SMILES: CC(C)[C@@H]1CN1S(=O)(=O)NCC(=O)N(c1cccc(F)c1)C(C(=O)NC1CCCCC1)c1ccccc1Cl] |
| 10 | 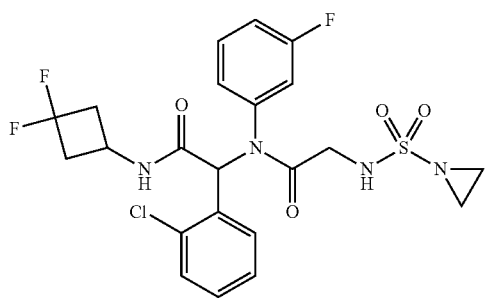 [SMILES: O=C(NC1CC(F)(F)C1)C(c1ccccc1Cl)N(C(=O)CNS(=O)(=O)N1CC1)c1cccc(F)c1] |
| 11 | 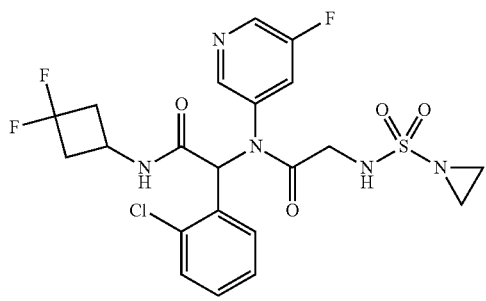 [SMILES: O=C(NC1CC(F)(F)C1)C(c1ccccc1Cl)N(C(=O)CNS(=O)(=O)N1CC1)c1cncc(F)c1] |
| 12 | 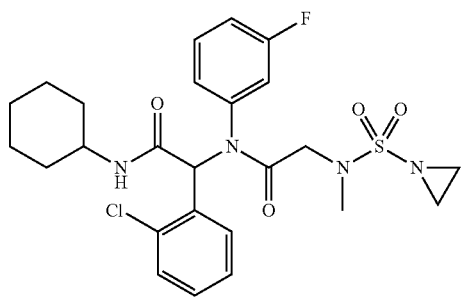 [SMILES: CN(CC(=O)N(c1cccc(F)c1)C(C(=O)NC1CCCCC1)c1ccccc1Cl)S(=O)(=O)N1CC1] |

-continued
| Compound No. | structure |
|---|---|
| 13 | 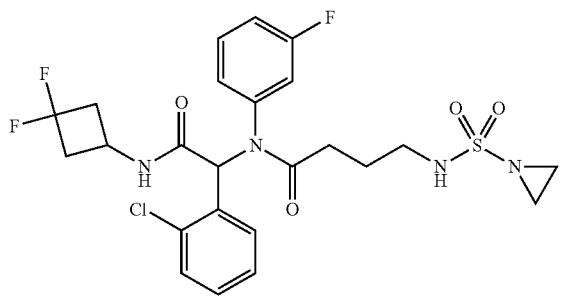 [SMILES: O=C(NC1CC(F)(F)C1)C(c1ccccc1Cl)N(C(=O)CCCNS(=O)(=O)N1CC1)c1cccc(F)c1] |
| 14 | 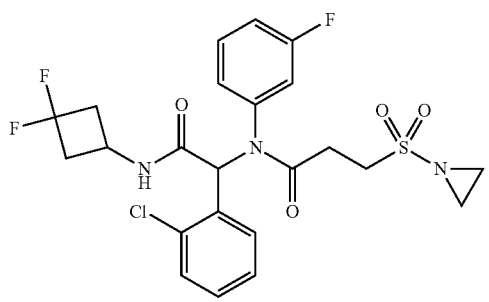 [SMILES: O=C(NC1CC(F)(F)C1)C(c1ccccc1Cl)N(C(=O)CCS(=O)(=O)N1CC1)c1cccc(F)c1] |
| 15 | 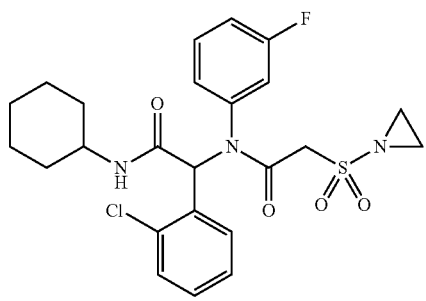 [SMILES: O=C(NC1CCCCC1)C(c1ccccc1Cl)N(C(=O)CS(=O)(=O)N1CC1)c1cccc(F)c1] |
| 16 | 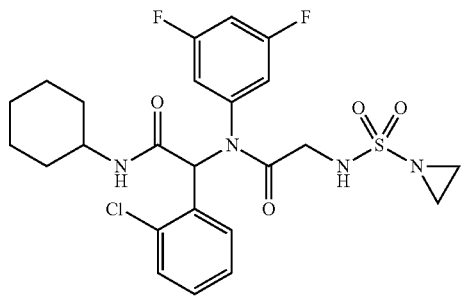 [SMILES: O=C(NC1CCCCC1)C(c1ccccc1Cl)N(C(=O)CNS(=O)(=O)N1CC1)c1cc(F)cc(F)c1] |
| 17 | 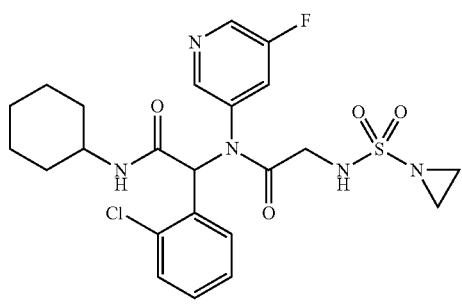 [SMILES: O=C(NC1CCCCC1)C(c1ccccc1Cl)N(C(=O)CNS(=O)(=O)N1CC1)c1cncc(F)c1] |

-continued
| Compound No. | structure |
|---|---|
| 18 | 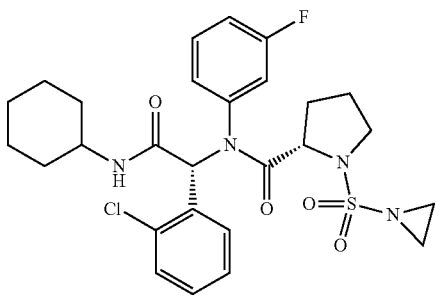 [SMILES: O=C(NC1CCCCC1)[C@@H](c1ccccc1Cl)N(C(=O)[C@@H]1CCCN1S(=O)(=O)N1CC1)c1cccc(F)c1] |
| 19 | 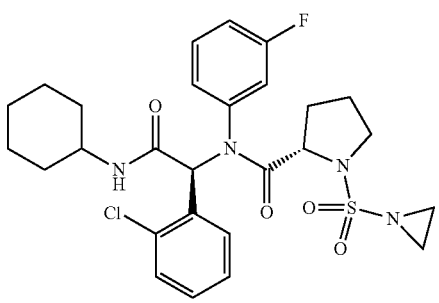 [SMILES: O=C(NC1CCCCC1)[C@H](c1ccccc1Cl)N(C(=O)[C@@H]1CCCN1S(=O)(=O)N1CC1)c1cccc(F)c1] |
| 20 | 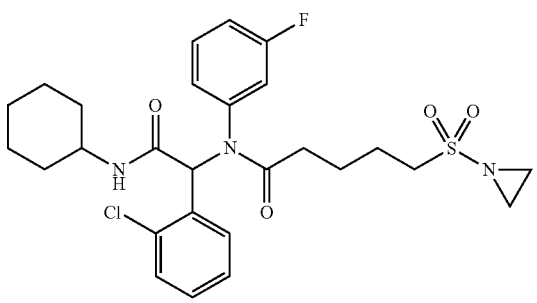 [SMILES: O=C(NC1CCCCC1)C(c1ccccc1Cl)N(C(=O)CCCCS(=O)(=O)N1CC1)c1cccc(F)c1] |
| 21 | 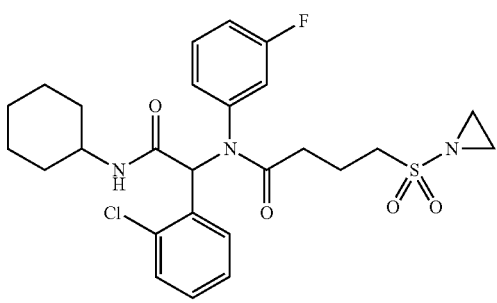 [SMILES: O=C(NC1CCCCC1)C(c1ccccc1Cl)N(C(=O)CCCS(=O)(=O)N1CC1)c1cccc(F)c1] |
| 22 | 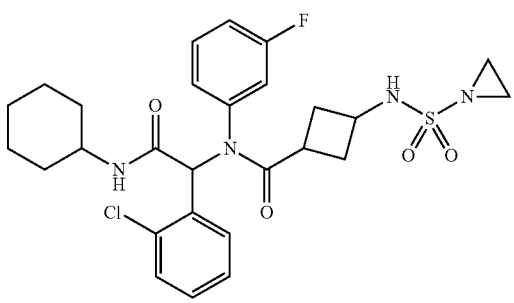 [SMILES: O=C(NC1CCCCC1)C(c1ccccc1Cl)N(C(=O)C1CC(NS(=O)(=O)N2CC2)C1)c1cccc(F)c1] |

-continued
| Compound No. | structure |
|---|---|
| 23 | 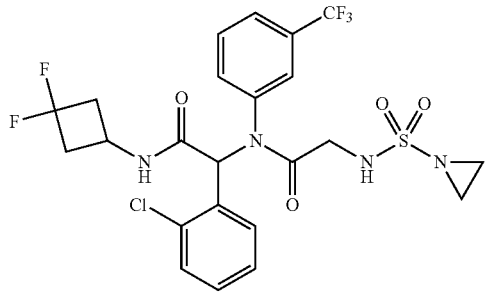 [SMILES: O=C(NC1CC(F)(F)C1)C(c1ccccc1Cl)N(C(=O)CNS(=O)(=O)N1CC1)c1cccc(C(F)(F)F)c1] |
| 24 | 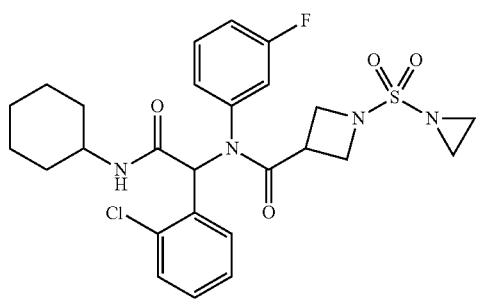 [SMILES: O=C(NC1CCCCC1)C(c1ccccc1Cl)N(C(=O)C1CN(S(=O)(=O)N2CC2)C1)c1cccc(F)c1] |
| 25 | 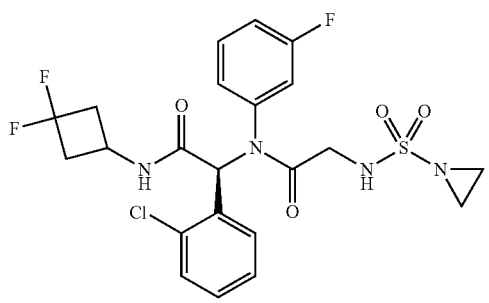 |
| 26 | 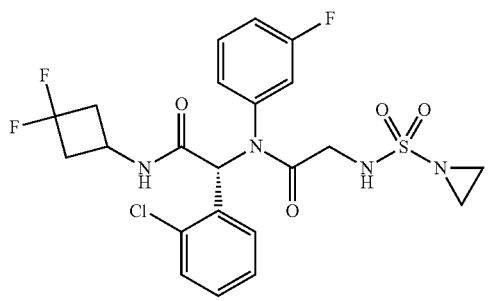 [SMILES: O=C(NC1CC(F)(F)C1)[C@@H](c1ccccc1Cl)N(C(=O)CNS(=O)(=O)N1CC1)c1cccc(F)c1] |
| 27 | 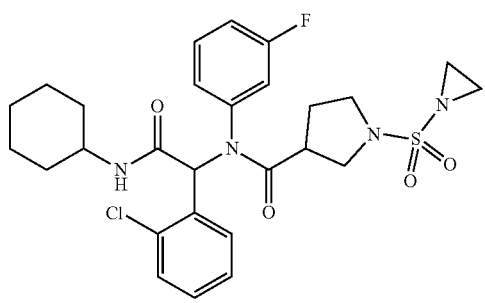 [SMILES: O=C(NC1CCCCC1)C(c1ccccc1Cl)N(C(=O)C1CCN(S(=O)(=O)N2CC2)C1)c1cccc(F)c1] |

-continued

| Compound No. | structure |
|---|---|
| 28 | (structure) |
| 29 | (structure) |
| 30 | (structure) |
| 31 | (structure) |
| 32 | (structure) |

-continued
| Compound No. | structure |
|---|---|
| 33 | 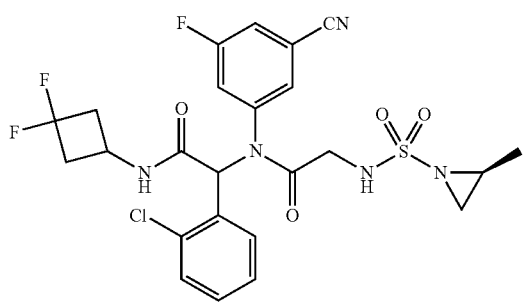 [SMILES: C[C@H]1CN1S(=O)(=O)NCC(=O)N(c1cc(F)cc(C#N)c1)C(C(=O)NC1CC(F)(F)C1)c1ccccc1Cl] |
| 34 | 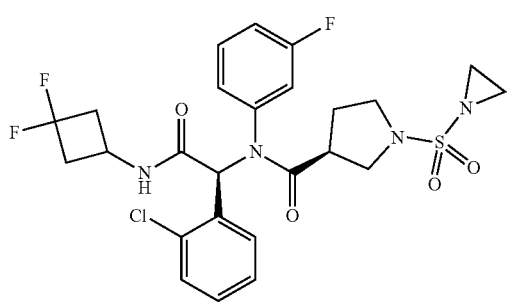 [SMILES: O=C(NC1CC(F)(F)C1)[C@H](c1ccccc1Cl)N(C(=O)[C@H]1CCN(S(=O)(=O)N2CC2)C1)c1cccc(F)c1] |
| 35 | 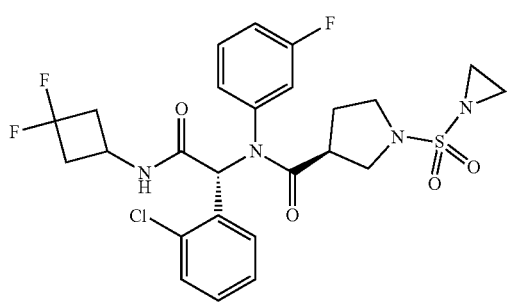 [SMILES: O=C(NC1CC(F)(F)C1)[C@@H](c1ccccc1Cl)N(C(=O)[C@H]1CCN(S(=O)(=O)N2CC2)C1)c1cccc(F)c1] |
| 36 | 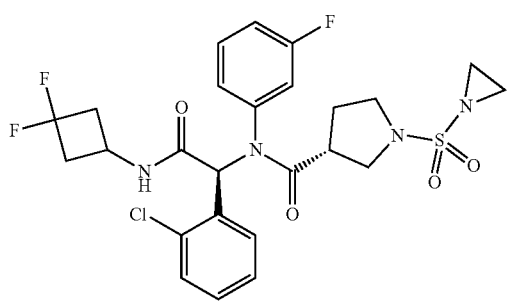 [SMILES: O=C(NC1CC(F)(F)C1)[C@H](c1ccccc1Cl)N(C(=O)[C@@H]1CCN(S(=O)(=O)N2CC2)C1)c1cccc(F)c1] |
| 37 | 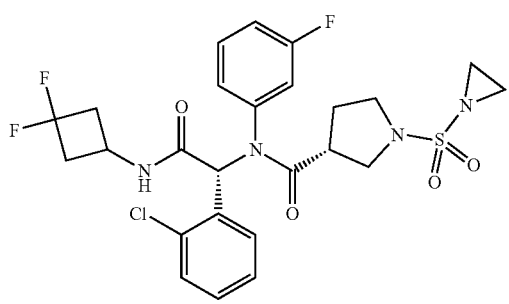 [SMILES: O=C(NC1CC(F)(F)C1)[C@@H](c1ccccc1Cl)N(C(=O)[C@@H]1CCN(S(=O)(=O)N2CC2)C1)c1cccc(F)c1] |

In another aspect, the present application provides a pharmaceutical composition comprising a therapeutically effective amount of the compound of Formula I or II, or a pharmaceutically acceptable salt, solvate or hydrate thereof, and one or more pharmaceutically acceptable carriers or excipients. The pharmaceutical composition according to the present application may further comprise one or more additional therapeutic agents.

In another aspect, the present application provides a method for treating IDH1 mutation-induced cancer, wherein the IDH1 mutation has R132X mutation. In some embodiments, the R132X mutation is selected from R132H, R132C, R132L, R132V, R132S and R132G. In some preferred embodiments, the R132X mutation is selected from R132H. The method comprises administering a therapeutically effective amount of the compound of Formula I or II, or the pharmaceutically acceptable salt, solvate or hydrate thereof, or the pharmaceutical composition.

In another aspect, the present application provides use of a compound of Formula I or II, or the pharmaceutically acceptable salt, solvate or hydrate thereof, or the pharmaceutical composition, in the manufacture of a medicament for treating IDH1 mutation-induced cancer.

In another aspect, the present application provides a compound of Formula I or II, or the pharmaceutically acceptable salt, solvate or hydrate thereof, or the pharmaceutical composition, for use in treating IDH1 mutation-induced cancer.

In some embodiments of the present application, the IDH1 mutation-induced cancer is selected from: glioblastoma (glioma), myelodysplastic syndrome (MDS), myeloproliferative neoplasm (MPN), acute myelogenous leukemia (AML), sarcoma, melanoma, non-small cell lung cancer, chondrosarcoma, bile duct cancer or angioimmunoblastic non-Hodgkin's lymphoma (NHL). In a more specific embodiment, the cancer to be treated is glioma, myelodysplastic syndrome (MDS), myeloproliferative neoplasm (MPN), acute myelogenous leukemia (AML), bile duct cancer, chondrosarcoma or angioimmunoblastic non-Hodgkin's lymphoma (NHL) and the like, preferably including acute myeloid leukemia (AML), myelodysplastic syndrome (MDS), glioma, bile duct cancer or chondrosarcoma.

The compound represented by formula I or II, or the pharmaceutically acceptable salt, solvate or hydrate thereof provided herein shows very good inhibitory activity against IDH1, which is comparable or superior to the activity of AG-120, and has a very good metabolism level in vivo and a very long half-life in vivo, and is promising to become a drug more suitable for the treatment of IDH1 mutation-induced cancers.

The pharmaceutical composition of the present application can be prepared by combining a compound of the present application or a pharmaceutically acceptable salt, solvate or hydrate thereof with suitable pharmaceutically acceptable carriers. For example, it can be formulated into solid, semi-solid, liquid or gaseous preparations, such as tablets, pills, capsules, powders, granules, ointments, emulsions, suspensions, solutions, suppositories, injections, inhalants, gels, microspheres, and aerosols, and the like.

Typical administration routes of compounds of the present application or pharmaceutically acceptable salts, solvates or hydrates thereof, or pharmaceutical compositions thereof include, but are not limited to, oral, rectal, transmucosal, intestinal administration, or topical, transdermal, inhalation, parenteral, sublingual, intravaginal, intranasal, intraocular, intraperitoneal, intramuscular, subcutaneous, intravenous administration.

The pharmaceutical composition of the present application may be manufactured by methods well-known in the art, such as conventional mixing method, dissolution method, granulation method, method for preparing sugar-coated pills, grinding method, emulsification method, freeze-drying method and the like.

For oral administration, the pharmaceutical composition can be formulated by mixing an active compound with a pharmaceutically acceptable carrier well-known in the art. These carriers can allow the compounds of the present application to be formulated into tablets, pills, troches, dragees, capsules, solutions, gels, slurries, suspensions and the like, for oral administration to patients.

A solid oral composition can be prepared by conventional mixing, filling or tableting method. For example, it can be obtained by the following method: mixing the active compound with solid excipients, optionally milling the resultant mixture, adding other suitable adjuvants if necessary, and then processing the mixture into granules, to produce tablet cores or dragee cores. Suitable adjuvants include, but are not limited to, adhesives, diluents, disintegrants, lubricants, glidants, sweeteners, flavoring agents or the like. The adjuvants can be, such as, microcrystalline cellulose, glucose solution, acacia mucilage, gelatin solution, sucrose and starch paste; talc, starch, magnesium stearate, calcium stearate or stearic acid; lactose, sucrose, starch, mannitol, sorbitol or dicalcium phosphate; silicon dioxide; croscarmellose sodium, pregelatinized starch, sodium starch glycolate, alginic acid, corn starch, potato starch, methylcellulose, agar, carboxymethyl cellulose, crosslinked polyvinylpyrrolidone and the like. The dragee core can be optionally coated, especially with an enteric coating, according to methods recognized in common drug practice.

The pharmaceutical composition can also be suitable for parenteral administration, such as sterile solutions, suspensions or freeze-dried products in a suitable unit dosage form. An appropriate excipient such as a filler, a buffering agent, or surfactant can be used.

The compound represented by formula I or II, or the pharmaceutically acceptable salt, solvate or hydrate thereof described herein can be administered by any suitable routes and methods, for example orally or parenterally (e.g., intravenously) administered. The therapeutically effective amount of the compound of formula I or II ranges from about 0.0001 mg/Kg of body weight to 20 mg/Kg of body weight per day, for example from 0.001 mg/Kg of body weight to 10 mg/Kg of body weight per day.

The dosing frequency of the compound of formula I or II depends on needs of individual patients, for example, once or twice every day or more times every day. Administration can be intermittent, for example, during a period of several days, patients receive a daily dose of the compound of formula I or II, and during a period of next several or more days, they do not receive a daily dose of the compound of formula I or II.

Related Definitions

Unless otherwise indicated, the following terms and phrases used herein are intended to have the following meanings. A particular term or phrase should not be considered to be indefinite or unclear in the absence of a specific definition, but should be interpreted as its ordinary meanings. When a trade name appears herein, it is intended to refer to the corresponding commodity or active ingredient thereof.

The term "optional" or "optionally" means that the subsequently described event or situation may occur or not, and the description includes the event or situation occurs and not. For example, an ethyl is "optionally" substituted by a halogen, meaning that the ethyl may be unsubstituted ($CH_2CH_3$), monosubstituted (e.g., $CH_2CH_2F$), polysubstituted (e.g., $CHFCH_2F$, $CH_2CHF_2$, etc.) or completely substituted ($CF_2CF_3$). It can be understood by the skilled in the art that, for any groups containing one or more substituents, any substitutions or substitution patterns that are unable to exist spatially and/or cannot be synthesized will not be introduced.

The $C_{m-n}$, used herein means that this moiety has m-n carbon atoms. For example, "$C_{3-10}$ cycloalkyl" means that said cycloalkyl has 3 to 10 carbon atoms. "$C_{0-6}$ alkylene" means that said alkylene has 0 to 6 carbon atoms, and the alkylene is a bond when this group has 0 carbon atom.

A numerical range herein refers to each integer within a given range. For example, "$C_{1-10}$" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms or 10 carbon atoms.

The group herein is not limited to the one which loses one hydrogen atom to form a monovalent group; in some cases, which can lose two hydrogen atoms to form a divalent group. For example, for —$X^1$—$X^2$—$X^3$—, $X^2$ therein is a divalent group formed by losing two hydrogen atoms, and the group of $X^2$ should also be understood as a divalent group if it is defined as a common substituent.

The term "substituted" means that any one or more of the hydrogen atoms on a specific atom are substituted by a substituent, as long as the valence state of the specific atom is normal and the substituted compound is stable. When the substituent is a ketone group (i.e., =O), it means that two hydrogen atoms are substituted, and the keto-substitution will not occur on an aromatic group.

When any variable (e.g., R) appears more than once in composition or structure of a compound, its definition in each case is independent. Thus, for example, if a group is substituted by 0-2 R, this group may be optionally substituted by at most two R, and R in each case has independent options. Furthermore, the combination of substituents and/or variants thereof is allowed only if such combination results in stable compounds.

Unless otherwise specified, the term "hetero" means a heteroatom or a heteroatom group (i.e., a group containing a heteroatom), i.e., atoms except for carbon and hydrogen atoms or an atom group containing such atoms. A heteroatom is independently selected from oxygen, nitrogen, sulfur, phosphorus, silicon, germanium, aluminum and boron. In an embodiment where two or more heteroatoms are involved, the two or more heteroatoms may be identical, or parts or all of the two or more heteroatoms may be different.

The term "halogen" or "halo/halogenated" refers to any group of fluorine, chlorine, bromine or iodine.

The term "hydroxyl" refers to —OH.

The term "cyano" refers to —CN.

The term "amino" refers to —$NH_2$, —NH(alkyl) and —N(alkyl)$_2$, and specific examples of an amino include, but are not limited to, —$NH_2$, —$NHCH_3$, —$NHCH(CH_3)_2$, —$N(CH_3)_2$, —$NHC_2H_5$, —$N(CH_3)C_2H_5$ and the like.

The term "alkyl" refers to a straight or branched saturated aliphatic hydrocarbon group consisting of carbon atoms and hydrogen atoms, such as, methyl, ethyl, propyl, butyl, pentyl, hexyl, heptyl, octyl, nonyl, decyl and the like. The specific alkyl includes all isomers thereof. For example, propyl includes —$CH_2CH_2CH_3$ and —$CH(CH_3)_2$. For example, butyl includes —$CH_2CH_2CH_2CH_3$, —$CH(CH_3)(CH_2CH_3)$, —$C(CH_3)_3$ and —$CH_2CH(CH_3)_2$. The term "$C_{1-8}$ alkyl" refers to an alkyl having 1 to 6 carbon atoms. The term "$C_{1-4}$ alkyl" refers to an alkyl having 1 to 4 carbon atoms. The term "$C_{1-3}$ alkyl" refers to an alkyl having 1 to 3 carbon atoms. The "alkyl", "$C_{1-8}$ alkyl", "$C_{1-8}$ alkyl" or "$C_{1-3}$ alkyl" may be unsubstituted or substituted with one or more substituents selected from hydroxyl, halogen or amino.

The term "haloalkyl/halogenated alkyl" intends to include monohaloalkyl and polyhaloalkyl. For example, the term "$C_{1-3}$ haloalkyl" intends to include, but is not limited to, trifluoromethyl, 2,2,2-trifluoroethyl, 3-bromopropyl and the like. Examples of the haloalkyl include, but are not limited to, trifluoromethyl, trichloromethyl, pentafluoroethyl and pentachloroethyl.

The term "alkylene" refers to a divalent alkyl group, such as —$CH_2$—, —$CH_2CH_2$— or —$CH_2CH_2CH_2$—, which may be unsubstituted, or may be substituted with one or more substituents selected from halogen, amino, hydroxyl, cyano, halogenated $C_{1-3}$ alkyl, $C_{1-6}$ alkyl or $C_{3-6}$ cycloalkyl.

The term "cycloalkyl" refers to an all-carbon monocyclic saturated hydrocarbon group consisting of carbon atoms and hydrogen atoms, such as, $C_{3-20}$ cycloalkyl, preferably $C_{3-6}$ cycloalkyl such as cyclopropyl, cyclobutyl, cyclopentyl, cyclohexyl and the like. The cycloalkyl may be unsubstituted or substituted, and the substituent includes, but is not limited to, alkyl, alkoxy, cyano, carboxyl, aryl, heteroaryl, amino, halogen, sulfonyl, sulfinyl, phosphoryl and hydroxyl.

The term "heteroaromatic ring" refers to a single or fused ring having 5 to 12 ring atoms, such as, 5, 6, 7, 8, 9, 10, 11 or 12 ring atoms, wherein 1, 2, 3 or 4 ring atoms are selected from N, O and S, and the rest of ring atom(s) is(are) carbon atom(s), and the ring has a completely conjugated π-electron system.

The term "heteroaryl" refers to a residue after one hydrogen atom is removed from a "heteroaromatic ring" molecule. The heteroaryl may be unsubstituted or substituted, and the substituent includes, but is not limited to, alkyl, alkoxy, aryl, aralkyl, amino, halogen, hydroxyl, cyano, nitro, carbonyl and heteroalcyl. Non-limiting examples of unsubstituted heteroaryl include, but are not limited to, pyrrolyl, furyl, thienyl, imidazolyl, oxazolyl, pyrazolyl, pyridyl, pyrimidyl, pyrazinyl, quinolyl, isoquinolyl, tetrazolyl, triazinyl.

The term "heteroalicyclic ring" refers to a single or fused ring having 3-12 ring atoms, for example, 3, 4, 5, 6, 7, 8, 9, 10, 11 or 12 ring atoms, in which 1 or 2 ring atoms are heteroatoms selected from N, O, S(O)$_n$ (wherein n is 0, 1 or 2), and the rest of ring atom(s) is(are) C. Such ring may be saturated or unsaturated (e.g., having one or more double bonds), but it does not have a completely conjugated π-electron system. Examples of 3-membered saturated heteroalicyclic ring include, but are not limited to,

Examples of 4-membered saturated heteroalicyclic ring include, but are not limited to,

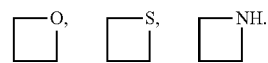

Examples of 5-membered saturated heteroalicyclic ring include, but are not limited to,

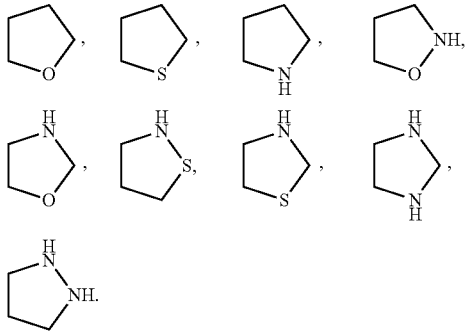

Examples of 6-membered saturated heteroalicyclic ring include, but are not limited to,

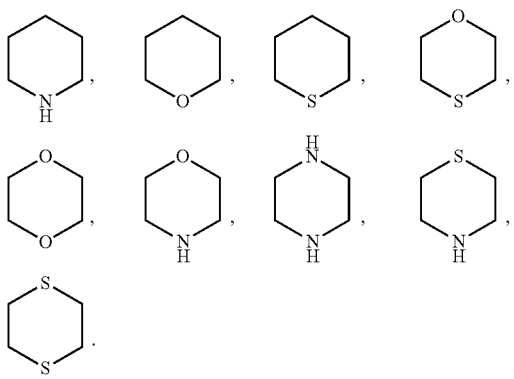

Examples of 7-membered saturated heteroalicyclic ring include, but are not limited to,

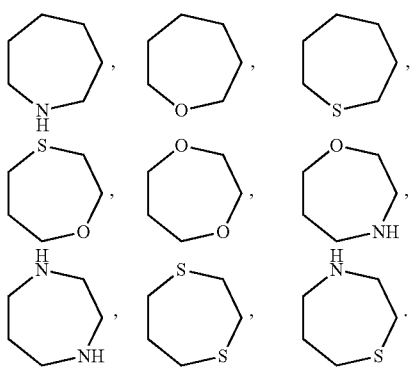

Examples of 5-membered unsaturated heteroalicyclic ring include, but are not limited to,

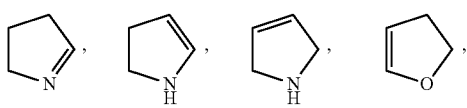

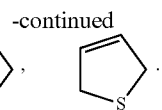

Examples of 6-membered unsaturated heteroalicyclic ring include, but are not limited to,

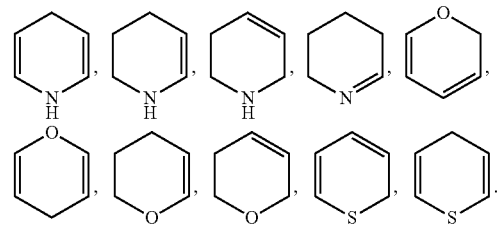

The term "heterocycloalkyl" refers to a residue after one hydrogen atom is removed from a "heteroalicyclic ring" molecule. The heterocycloalkyl may be unsubstituted or the hydrogen atom therein is optionally substituted with a substituent, and the substituent includes, but is not limited to, alkyl, alkoxy, =O, aryl, aralkyl, —COOH, —CN, amino, halogen or hydroxyl.

The term "amino protecting group" means that the hydrogen in an amino group is substituted with one or two protecting groups including, but not limited to, benzyloxycarbonyl, t-butoxycarbonyl, fluorenylmethoxycarbonyl, allyloxycarbonyl, trimethylsilylethoxycarbonyl, methoxycarbonyl, ethoxycarbonyl, phthaloyl, p-toluenesulfonyl, trifluoroacetyl, o-nitrophenylsulfonyl, p-nitrophenylsulfonyl, pivaloyl, benzoyl, triphenylmethyl, 2,4-dimethoxybenzyl, p-methoxybenzyl or benzyl.

"DMF" refers to N,N-dimethylformamide.
"THF" refers to tetra hydrofuran.
"DCM" refers to dichloromethane.
"Boc-" refers to tert-butoxycarbonyl.
"DIAD" refers to diisopropyl azodicarboxylate.
"TFA" refers to trifluoroacetic acid.
"DIEA" refers to N,N-diisopropylethylamine.
"TEA" refers to triethylamine.
"m-CPBA" refers to m-chloroperoxybenzoic acid.
"PE" refers to petroleum ether.
"EA" refers to ethyl acetate.
"Dess-Martin oxidant" refers to (1,1,1-triacetoxy)-1,1-dihydro-1,2-benziodoxol-3(1H)-one.

The term "Ugi reaction" refers to a multi-component reaction in which a molecule of a ketone or aldehyde, a molecule of an amine, a molecule of an isonitrile and a molecule of a carboxylic acid are condensed to produce an α-amidoamide.

The term "Mitsunobu reaction" refers to a reaction in which alcoholic hydroxyl is substituted with a nucleophilic agent under the action of diethyl azodicarboxylate (DEAD) and triphenylphosphine, and at the same time the carbon atom linked to the hydroxyl group occurs an inversion of configuration.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As a pharmaceutically acceptable salt, for example, a metal salt, an ammonium salt, a salt formed with organic base, a salt formed with inorganic acid, a salt formed with organic acid, a salt formed with basic or acidic amino acid, etc. can be mentioned.

The pharmaceutically acceptable salt of the present application can be synthesized from a parent compound containing an acid radical or basic group via conventional chemical methods. In general, such a salt is prepared by a method of allowing these compounds in the form of free acid or base to react with a stoichiometric amount of an appropriate base or acid in water or an organic solvent or a mixture thereof. Generally, a non-aqueous medium, such as, ether, ethyl acetate, ethanol, isopropanol or acetonitrile, and the like, is preferable.

Certain compounds of the present application may exist in a non-solvated or solvated form, including a hydrate form. In general, the solvated form is equivalent to the non-solvated form, both of which are encompassed within the scope of the present application. Certain compounds of the present application may exist in a polymorphic or amorphous form.

Certain compounds of the present application may have an asymmetric carbon atom (optical center) or a double bond. Racemates, diastereomers, geometric isomers and individual isomers are all encompassed within the scope of the present application.

The graphic representations of racemic, ambiscalemic and scalemic, or enantiomerically pure compounds herein are from Maehr, *J. Chem. Ed.* 1985, 62: 114-120. Unless otherwise stated, the absolute configuration of a stereocenter is represented by solid and broken wedges. When the compounds described herein contain olefinic double bonds or other geometric asymmetrical centers, unless otherwise specified, they include E, Z geometric isomers. Likewise, all tautomeric forms are included within the scope of the present invention.

The compound of the present application may exist in specific geometric or stereoisomeric forms. All such compounds envisaged by the present application include cis and trans isomers, (−)- and (+)-enantiomers, (R)- and (S)-enantiomers, diastereomers, (D)-isomers, (L)-isomers, and racemic mixtures and other mixtures thereof, such as enantiomers or diastereomers enriched mixtures, all of which fall within the scope of the present application. Other asymmetric carbon atoms may be present in the substituents such as alkyl. All these isomers and their mixtures are included in the scope of the present application.

The optically active (R)- and (S)-isomers as well as the D and L isomers can be prepared by chiral synthesis or chiral reagents or other conventional techniques. If an enantiomer of a certain compound of the present invention is desired, it may be prepared by asymmetric synthesis, or by derivatization with a chiral auxiliary, wherein the resulting diastereomeric mixture is separated and the ancillary group is cleaved to provide the pure desired enantiomers. Alternatively, when a molecule contains a basic functional group (such as an amino) or an acidic functional group (such as a carboxyl), it forms a salt of diastereomer with a suitable optically active acid or base, and then a diastereomer resolution is performed by a fractional crystallization or chromatography well-known in the art, followed by recovering to give pure enantiomers. In addition, the separation of the enantiomers and diastereomers is generally accomplished by the use of chromatography adopting a chiral stationary phase, and optionally in combination with chemical derivatization method (e.g., forming carbamates from amines).

The compound of the present application may contain non-natural proportions of atomic isotopes on one or more atoms which constitute the compound. For example, the compound may be labeled with a radioisotope, such as tritium ($^3H$), iodine-125 ($^{125}I$) or C-14 ($^{14}C$). Any isotopic composition transformations of the compound of the present application, whether are radioactive or not, are included in the scope of the present application.

The term "pharmaceutically acceptable carrier" refers to a carrier that does not cause significant irritation to an organism, and does not deteriorate the biological activity and properties of the active compound. The "pharmaceutically acceptable carrier" refers to an inert material that is administered together with an active ingredient and facilitates the administration of the active ingredient, including but not limited to, any glidants, sweeteners, diluents, preservatives, dyes/coloring agents, flavor enhancers, surfactants, wetting agents, dispersants, disintegrants, suspending agents, stabilizers, isotonic agents, solvent or emulsifier, which are acceptable for human or animal (e.g., livestock) and approved by the China Food and Drug Administration. Non-limited examples of the carriers include calcium carbonate, calcium phosphate, various carbohydrates and various kinds of starches, cellulose derivatives, gelatin, vegetable oils, polyethylene glycol and the like. Other information about carriers can refer to Remington: The Science and Practice of Pharmacy, 21$^{st}$ Ed., Lippincott, Williams & Wilkins (2005), the contents of which are incorporated herein by reference.

The term "excipient" generally refers to the carrier, diluent, and/or medium required to prepare an effective pharmaceutical composition.

With regard to a drug or pharmacologically active agent, the term "effective amount" or "therapeutically effective amount" refers to a sufficient amount of drug or agent that is non-toxic but can achieve the desired effect. For an oral dosage form in this application, an "effective amount" of an active substance in the composition refers to the amount needed to achieve the desired effect when used in combination with another active substance in the composition. The determination of the effective amount varies from person to person, depending on the age and general condition of the recipient, as well as the specific active substance, and the appropriate effective amount in the specific case can be determined by a person skilled in the art according to routine experimentation.

The terms "active ingredient", "therapeutic agent", "active substance" or "active agent" refer to a chemical entity that can effectively treat a target disorder, disease or condition.

The compounds of the present application can be prepared by a variety of synthetic methods well known to those skilled in the art, including the specific embodiments listed below, combinations thereof with other chemical synthesis methods, and those equivalent alternatives well known to those skilled in the art, preferred embodiments include, but not limited to, embodiments of the present application.

The chemical reactions of the specific embodiments of the present application are carried out in a suitable solvent which is suitable for the chemical changes of the present application and the reagents and materials required thereof. In order to obtain the compounds of the present application, it is sometimes necessary for those skilled in the art to modify or select the synthetic steps or reaction schemes based on the existing embodiments.

The compound of formula II in the present application may be prepared by a person skilled in the organic synthesis field by using a standard method in the art through the following route:

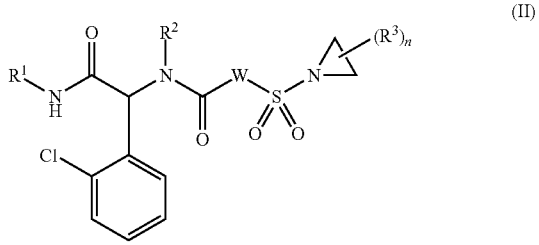

wherein,
W, R¹, R², R³ and n are as defined in the compound of Formula II. This preparation is shown in FIG. 3 using a standard method in the art.

As shown in FIG. 3, isonitrile compound 1, o-chlorobenzaldehyde 2, amino compound 3, and aziridinesulfonamide carboxylic acid compound 7 are directly subjected to Ugi reaction to give a aziridinesulfonamide compound of Formula II.

Compounds 1, 2, 3 and hydroxycarboxylic acid compound 4 are subjected to Ugi reaction to give intermediate 5; and intermediate 5 and aziridinesulfonamide intermediate 6 are subject to Mitsunobu reaction to give the compound of Formula II.

Compounds 1, 2, 3 and chloroethylaminosulfonyl carboxylic acid compound 8 are subjected to Ugi reaction to give intermediate 9; and intermediate 9 is subjected to intramolecular cyclization to give the compound of Formula II.

Compounds 1, 2, 3 and amino-protected (PG) carboxylic acid compound 10 are subjected to Ugi reaction to give intermediate 11; intermediate 11 undergoes deprotection of the amino group (PG) to give intermediate 12; and intermediate 12 and chloroethylaminosulfonyl chloride 13 are reacted to give the compound of Formula II.

DETAILED EMBODIMENTS OF THE INVENTION

Figure 1:
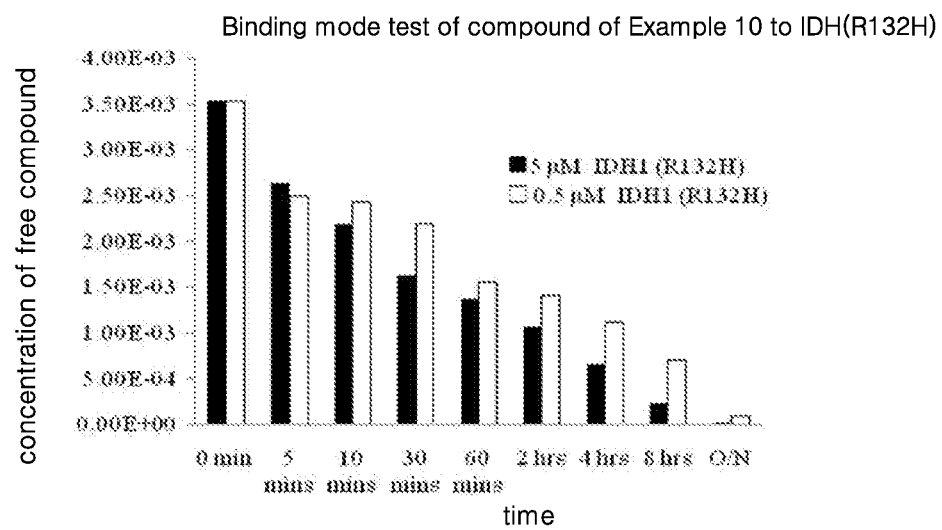
FIG. 1 is an analysis chart showing the binding mode of the compound of Example 10 to IDH1 (R132H).

The following specific examples are provided to enable those skilled in the art to more clearly understand and practice the application. They should not be deemed as limiting the scope of the application, but are merely illustrations and typical representatives of the application. Those skilled in the art should understand that there are other synthetic routes for preparing the compounds of the present application, and ones provided below are non-limiting examples.

Unless otherwise stated, the temperature is Celsius temperature. The reagents were purchased from commercial suppliers such as Sinopharm Chemical Reagent Beijing Co., Ltd., Alfa Aesar, or Beijing J&K Scientific Co., Ltd., and the like, and these reagents can be directly used without further purification, unless otherwise stated.

Unless otherwise stated, the following reactions were carried out in an anhydrous solvent, under a positive pressure of nitrogen or argon gas, or using a drying tube. The reaction flasks were equipped with a rubber diaphragm so as to add substrates and reagents by a syringe. The glassware was dried in an oven and/or dried by heating.

Unless otherwise stated, the purification by column chromatography was performed with silica gel (200-300 mesh) produced by Qingdao Haiyang Chemical Co., Ltd. The separation by preparative thin layer chromatography was performed by using thin layer chromatography silica gel prefabricated plates (HSGF254) manufactured by Yantai Chemical Industry Research Institute. MS was measured by using Thermo LCQ Fleet type (ESI) liquid chromatography-mass spectrometer. The optical rotation was measured by using SGW-3 automatic polarimeter from Shanghai Shenguang Instrument Co., Ltd.

Unless otherwise stated, NMR data ($^1$H-NMR) were taken at 400 MHz by using an equipment from Varian. The solvents used for NMR include $CDCl_3$, $CD_3OD$, $D_2O$, DMSO-$d_6$ and the like, and tetramethylsilane (0.00 ppm) was used as a baseline or residual solvent was used as a baseline ($CDCl_3$: 7.26 ppm; $CD_3OD$: 3.31 ppm; $D_2O$: 4.79 ppm; DMSO-$d_6$: 2.50 ppm). Upon indicating peak shape diversity, the following abbreviations represent different peak shapes: s (singlet), d (doublet), t (triplet), q (quartet), m (multiplet), br (broad), dd (doublet of doublets), dt (doublet of triplets). If a coupling constant is given, the unit thereof is Hertz (Hz).

Unless otherwise indicated, the absolute configuration of the chiral center or the relative positions of substituents in the rings is not indicated for the title compounds in some Examples of the present application, and a mixture of all isomers was obtained during the preparation of such compounds. Although the isomers cannot be separated by an ordinary column chromatography, it does not mean that there are no isomers for such compounds.

EXAMPLES

Example 1: 2-(aziridinyl-1-sulfonylamino)-N-(1-(2-chlorophenyl)-2-(cyclohexylamino)-2-oxoethyl)-N-(3-fluorophenyl)acetamide

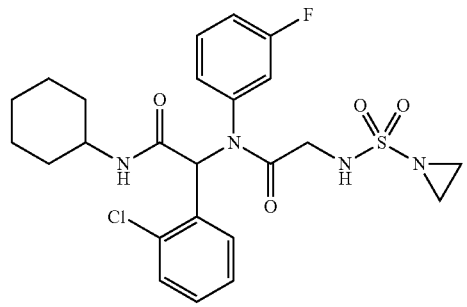 [SMILES: O=C(NC1CCCCC1)C(c1ccccc1Cl)N(C(=O)CNS(=O)(=O)N1CC1)c1cccc(F)c1]

Step A: (2-chloroethyl)sulfonyl chloride

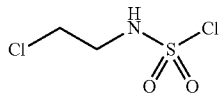

Chlorosulfonic acid (8.4 mL, 103.4 mmol) was added to a solution of 2-chloroethylamine hydrochloride (2.0 g, 17.2 mmol) in acetonitrile. The reaction solution was then heated to 80° C. and reacted for 18 h, and after cooling down to room temperature, the solvent was spin-evaporated under reduced pressure. The residue was diluted by adding with diethyl ether, and filtered to remove the undissolved substance. The filtrate was concentrated under reduced pressure, to give (2-chloroethyl)sulfonyl chloride (1.22 g, yield of 40%).

$^1$H-NMR (400 MHz, CDCl$_3$): δ=6.13 (s, 1H), 3.81 (t, J=5.2 Hz, 2H), 3.72-3.68 (m, 2H).

Step B: 2-(2-chlorophenyl)-N-cyclohexyl-2-(2-(1,3-dioxoisoindolin-2-yl)-N-(3-fluorophenyl)acetamido)acetamide

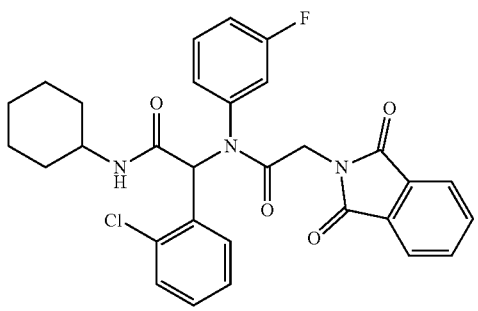 [SMILES: O=C(NC1CCCCC1)C(c1ccccc1Cl)N(C(=O)CN1C(=O)c2ccccc2C1=O)c1cccc(F)c1]

o-Chlorobenzaldehyde (187.4 μL, 1.66 mmol) was added in a solution of 3-fluoroaniline (160 μL, 1.66 mmol) in methanol at room temperature with stirring. After the reaction was performed for 15 min, N-phthaloylglycine (341.4 mg, 1.66 mmol) was added. The reaction was further performed for 30 min. Following addition of cyclohexyl isocyanate (207 μL, 1.66 mmol), the mixture was reacted at room temperature overnight, evaporated under reduced pressure and concentrated, and separated by column chromatography on silica gel to give 2-(2-chlorophenyl)-N-cyclohexyl-2-(2-(1,3-dioxoisoindolin-2-yl)-N-(3-fluorophenyl)acetamido)acetamide (708 mg, yield of 78%).

$^1$H-NMR (400 MHz, CDCl$_3$): δ=7.86-7.83 (m, 2H), 7.73-7.68 (m, 2H), 7.35 (d, J=7.9 Hz, 1H), 7.19-7.05 (m, 3H), 7.00-6.92 (m, 3H), 6.87-6.62 (m, 1H), 6.42 (s, 1H), 5.68 (d, J=7.8 Hz, 1H), 4.18 (d, J=2.0 Hz, 2H), 3.94-3.74 (m, 1H), 1.97 (d, J=12.2 Hz, 1H), 1.88 (d, J=12.6 Hz, 1H), 1.75-1.54 (m, 4H), 1.42-0.94 (m, 4H).

m/z=548 [M+H]$^+$.

Step C: 2-amino-N-(1-(2-chlorophenyl)-2-(cyclohexylamino)-2-oxoethyl)-N-(3-fluorophenyl)acetamide

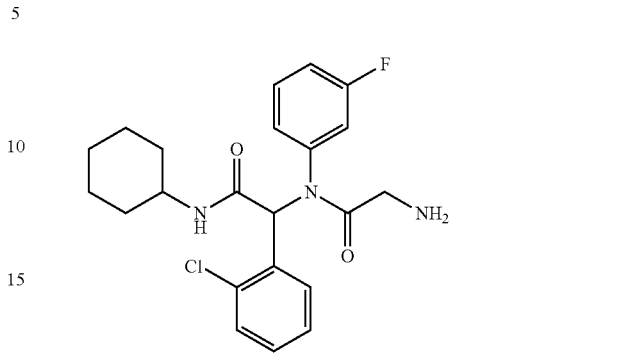

Hydrazine hydrate (222 μL, 3.656 mmol) was added in a solution of 2-(2-chlorophenyl)-N-cyclohexyl-2-(2-(1,3-dioxoisoindolin-2-yl)-N-(3-fluorophenyl)acetamido)acetamide (400 mg, 0.731 mmol) in ethanol. The reaction solution was then heated to 90° C. and reacted overnight, filtered, concentrated in vacuo, and separated by column chromatography on silica gel to give 2-amino-N-(1-(2-chlorophenyl)-2-(cyclohexylamino)-2-oxoethyl)-N-(3-fluorophenyl)acetamide (290 mg, yield of 95%).

$^1$H-NMR (400 MHz, CDCl$_3$): δ=7.33 (dd, J=8.0, 1.0 Hz, 1H), 7.18-7.04 (m, 3H), 7.05-6.92 (m, 2H), 6.89-6.84 (m, 1H), 6.79 (s, 1H), 6.42 (s, 1H), 5.55 (d, J=7.6 Hz, 1H), 3.93-3.76 (m, 1H), 3.15 (d, J=5.5 Hz, 2H), 2.07-1.93 (m, 3H), 1.87 (d, J=10.8 Hz, 1H), 1.78-1.55 (m, 4H), 1.42-1.06 (m, 4H).

m/z=418 [M+H]$^+$.

Step D: 2-((N-(2-chloroethyl)aminosulfonyl)amino)-N-(1-(2-chlorophenyl)-2-(cyclohexylamino)-2-oxoethyl)-N-(3-fluorophenyl)acetamide

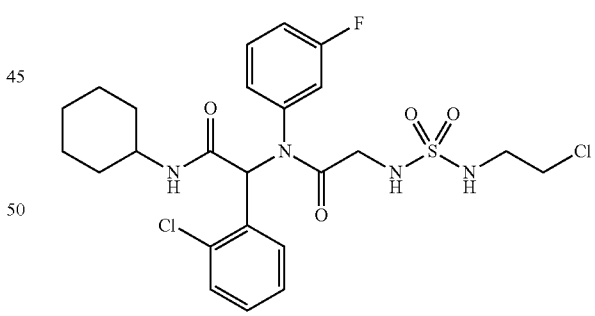

Under stirring in an ice bath, triethylamine (66 μL, 0.478 mmol) was added to a solution of 2-amino-N-(1-(2-chlorophenyl)-2-(cyclohexylamino)-2-oxoethyl)-N-(3-fluorophenyl)acetamide (100 mg, 0.239 mmol) in dichloromethane, and (2-chloroethylamino)sulfonyl chloride (59 mg, 0.33 mmol) was then added dropwise thereto. After completion of the addition, the reaction solution was warmed up to room temperature and stirred overnight. The reaction solution was added with saturated ammonium chloride solution to quench the reaction, and the reaction solution was then extracted with dichloromethane. The combined organic phase was washed with brine, dried over sodium sulfate, filtered, concentrated in vacuo, and separated by column chromatography on silica gel to give 2-((N-(2-chloroethyl)aminosulfonyl)amino)-N-(1-(2-chlorophenyl)-2-(cyclohexylamino)-2-oxoethyl)-N-(3-fluorophenyl)acetamide (109 mg, yield of 82%).

$^1$H-NMR (400 MHz, CDCl$_3$): δ=7.34 (d, J=7.9 Hz, 1H), 7.22-7.05 (m, 3H), 7.03-6.87 (m, 4H), 6.42 (s, 1H), 5.46 (d, J=8.1 Hz, 1H), 5.32 (t, J=5.2 Hz, 1H), 4.89 (t, J=6.4 Hz, 1H), 3.88-3.81 (m, 1H), 3.67 (t, J=5.9 Hz, 2H), 3.59-3.57 (m, 2H), 3.45-3.30 (m, 2H), 1.99 (d, J=10.5 Hz, 1H), 1.88 (d, J=10.5 Hz, 1H), 1.78-1.50 (m, 4H), 1.48-0.95 (m, 4H).

m/z=559 [M+H]$^+$.

Step E: 2-(aziridine-1-sulfonylamino)-N-(1-(2-chlorophenyl)-2-(cyclohexylamino)-2-oxoethyl)-N-(3-fluorophenyl)acetamide

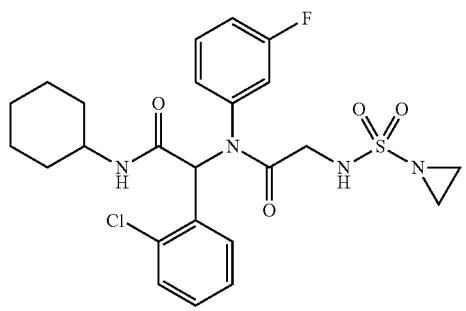

Potassium carbonate (36 mg, 0.258 mmol) was added in a solution of 2-((N-(2-chloroethyl)aminosulfonyl)amino)-N-(1-(2-chlorophenyl)-2-(cyclohexylamino)-2-oxoethyl)-N-(3-fluorophenyl)acetamide (72 mg, 0.129 mmol) in DMF. The reaction solution was stirred at room temperature overnight, added with water to quench, and then extracted with ethyl acetate. The combined organic phase was washed with brine three times, dried over sodium sulfate, filtered, concentrated in vacuo, and separated by column chromatography on silica gel to give 2-(aziridine-1-sulfonylamino)-N-(1-(2-chlorophenyl)-2-(cyclohexylamino)-2-oxoethyl)-N-(3-fluorophenyl)acetamide (30 mg, yield of 44%).

$^1$H-NMR (400 MHz, CDCl$_3$): δ=7.86-7.48 (m, 1H), 7.36 (d, J=8.0 Hz, 1H), 7.24-7.09 (m, 2H), 7.06-6.88 (m, 4H), 6.43 (s, 1H), 5.50-5.48 (m, 2H), 3.95-3.66 (m, 3H), 2.31 (s, 4H), 2.01 (d, J=12.5 Hz, 1H), 1.89 (d, J=11.8 Hz, 1H), 1.82-1.47 (m, 4H), 1.47-0.96 (m, 4H).

m/z=523 [M+H]$^+$.

Example 2: (2)-2-(aziridine-1-sulfonylamino)-N-(1-(2-chlorophenyl)-2-(cyclohexylamino)-2-oxoethyl)-N-(3-fluorophenyl)propanamide

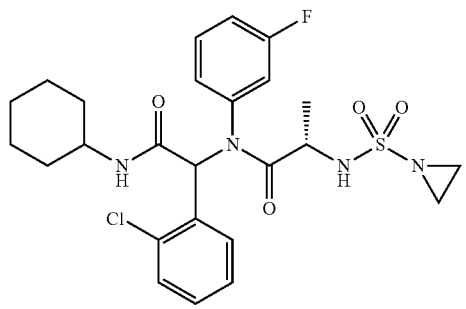 [SMILES: C[C@H](NS(=O)(=O)N1CC1)C(=O)N(c1cccc(F)c1)C(C(=O)NC1CCCCC1)c1ccccc1Cl]

Step A: tert-butyl (2S)-1-((1-(2-chlorophenyl)-2-(cyclohexylamino)-2-oxoethyl)(3-fluorophenyl)amino)-1-oxopropan-2-yl-carbamate

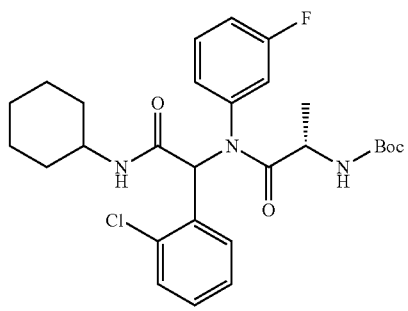 [SMILES: C[C@H](NC(=O)OC(C)(C)C)C(=O)N(c1cccc(F)c1)C(C(=O)NC1CCCCC1)c1ccccc1Cl]

2-Chloro-benzaldehyde (400 mg, 2.846 mmol) and 3-fluoroaniline (317 mg, 2.846 mmol) were added to MeOH (12 mL) with stirring at room temperature, Boc-L-alanine (540 mg, 2.846 mmol) was added after 30 min, and the reaction mixture was stirred for 10 min. Cyclohexyl isocyanate (311 mg, 2.846 mmol) was then added therein, and the reaction mixture was stirred at room temperature overnight. The solvent was removed in vacuo, and the residue was separated by column chromatography on silica gel to give tert-butyl (2S)-1-((1-(2-chlorophenyl)-2-(cyclohexylamino)-2-oxoethyl)(3-fluorophenyl)amino)-1-oxopropan-2-yl-carbamate (1.15 g, yield of 76%).

$^1$H-NMR (400 MHz, CDCl$_3$): δ=7.36 (d, J=7.9 Hz, 1H), 7.28 (d, J=8.1 Hz, 1H), 7.16-7.10 (m, 3H), 7.01-6.96 (m, 3H), 6.44 (s, 1H), 6.12 (s, 1H), 5.52 (d, J=7.9 Hz, 1H), 5.18 (d, J=34.2 Hz, 1H), 4.24 (s, 1H), 2.03-1.87 (m, 4H), 1.79-1.56 (m, 4H), 1.48-1.39 (m, 12H), 1.38-0.98 (m, 2H).

m/z=532 [M+H]$^+$.

Step B: (2S)-2-amino-N-(1-(2-chlorophenyl)-2-(cyclohexylamino)-2-oxoethyl)-N-(3-fluorophenyl)propenamide

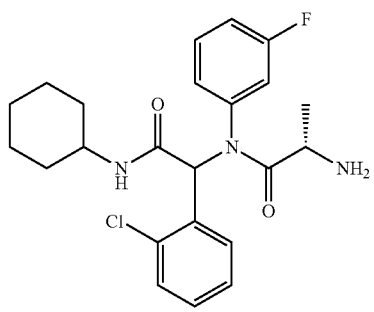 [SMILES: C[C@H](N)C(=O)N(c1cccc(F)c1)C(C(=O)NC1CCCCC1)c1ccccc1Cl]

Concentrated hydrochloric acid (2.0 mL) was slowly added dropwise with stirring in a solution of tert-butyl (2S)-1-((1-(2-chlorophenyl)-2-(cyclohexylamino)-2-oxoethyl)(3-fluorophenyl)amino)-1-oxopropan-2-yl-carbamate (1.14 g, 2.141 mmol) in THF in an ice bath, and the reaction mixture was stirred overnight at room temperature. After completion of the reaction, the reaction was quenched and neutralized with saturated aqueous sodium hydrogen carbonate solution, followed by extraction with ethyl acetate. The combined organic phase was washed with brine, dried over sodium sulfate, filtered, concentrated in vacuo, and separated by column chromatography on silica gel, to give (2S)-2-amino-N-(1-(2-chlorophenyl)-2-(cyclohexylamino)-2-oxoethyl)-N-(3-fluorophenyl)propanamide (900 mg, yield of 97.2%).

$^1$H-NMR (400 MHz, CDCl$_3$): δ=7.34 (dd, J=17.6, 8.0 Hz, 2H), 7.24-6.81 (m, 7H), 6.43 (d, J=39.0 Hz, 1H), 5.59 (d, J=7.7 Hz, 1H), 3.93-3.77 (m, 1H), 3.43-3.33 (m, 1H), 2.01 (d, J=10.7 Hz, 1H), 1.95-1.83 (m, 2H), 1.78-1.58 (m, 4H), 1.42-1.25 (m, 2H), 1.20-1.11 (m, 5H).

m/z=432 [M+H]$^+$.

Step C: (2S)-2-((N-(2-chloroethyl)sulfonylamino)amino)-N-(1-(2-chlorophenyl)-2-(cyclohexylamino)-2-oxoethyl)-N-(3-fluorophenyl)propanamide

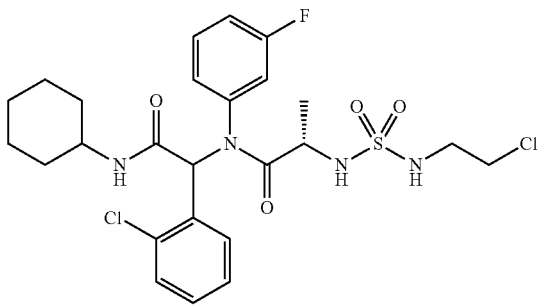 [SMILES: C[C@H](NS(=O)(=O)NCCCl)C(=O)N(c1cccc(F)c1)C(C(=O)NC1CCCCC1)c1ccccc1Cl]

2-Chloroethyl sulfamoyl chloride (452 mg, 2.775 mmol) was added with stirring to a mixture of (2S)-2-amino-N-(1-(2-chlorophenyl)-2-(cyclohexylamino)-2-oxoethyl)-N-(3-fluorophenyl)propanamide (400 mg, 0.925 mmol), pyridine (366 mg, 4.625 mmol) and DCM (20 mL) in an ice bath, and the reaction mixture was warmed up to room temperature and stirred overnight. The reaction was quenched with water, followed by extraction with DCM. The combined organic phase was washed with brine, dried over sodium sulfate, filtered, concentrated in vacuo, and separated by column chromatography on silica gel, to give (2S)-2-((N-(2-chloroethyl)sulfonylamino)amino)-N-(1-(2-chlorophenyl)-2-(cyclohexylamino)-2-oxoethyl)-N-(3-fluorophenyl)propanamide (111 mg, yield of 21%).

m/z=573 [M+H]$^+$.

Step D: (2S)-2-(aziridine-1-sulfonylamino)-N-(1-(2-chlorophenyl)-2-(cyclohexylamino)-2-oxoethyl)-N-(3-fluorophenyl)propanamide

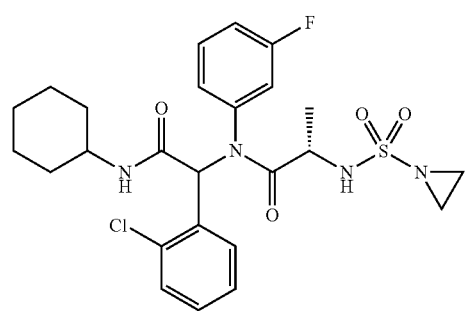 [SMILES: C[C@H](NS(=O)(=O)N1CC1)C(=O)N(c1cccc(F)c1)C(C(=O)NC1CCCCC1)c1ccccc1Cl]

Potassium carbonate (80 mg, 0.576 mmol) was added with stirring in a solution of (2S)-2-((N-(2-chloroethyl)sulfonylamino)amino)-N-(1-(2-chlorophenyl)-2-(cyclohexylamino)-2-oxoethyl)-N-(3-fluorophenyl)propanamide (110 mg, 0.192 mmol) in DMF at room temperature, and the reaction mixture was stirred overnight at room temperature. After completion of the reaction, the reaction mixture was added with water, and then extracted with ethyl acetate. The combined organic phase was washed with brine, dried over sodium sulfate, filtered, concentrated in vacuo, and separated by column chromatography on silica gel, to give (2S)-2-(aziridine-1-sulfonylamino)-N-(1-(2-chlorophenyl)-2-(cyclohexylamino)-2-oxoethyl)-N-(3-fluorophenyl)propanamide (46 mg, yield of 44.7%).

$^1$H-NMR (400 MHz, CDCl$_3$): δ=7.80-7.52 (m, 1H), 7.39 (d, J=7.9 Hz, 1H), 7.25-7.12 (m, 1H), 6.99-6.88 (m, 4H), 6.56-6.36 (m, 1H), 6.32 (s, 1H), 5.54 (d, J=7.8 Hz, 1H), 5.39 (d, J=10.0 Hz, 1H), 4.15-4.05 (m, 1H), 3.86-3.70 (m, 1H), 2.50-2.24 (m, 4H), 1.98 (d, J=10.9 Hz, 1H), 1.84 (d, J=12.4 Hz, 1H), 1.74 (d, J=13.4 Hz, 1H), 1.61 (d, J=16.0 Hz, 2H), 1.42-1.34 (m, 2H), 1.28 (d, J=7.0 Hz, 3H), 1.22-0.97 (m, 3H).

m/z=537 [M+H]$^+$.

Example 3: (R)-2-(aziridine-1-sulfonylamino)-N—((R)-(2-chlorophenyl)-2-(cyclohexylamino)-2-oxoethyl)-N-(3-fluorophenyl)propanamide Example 4: (R)-2-(aziridine-1-sulfonylamino)-N—((S)-1-(2-chlorophenyl)-2-(cyclohexylamino)-2-oxoethyl)-N-(3-fluorophenyl)propanamide (Example 3)

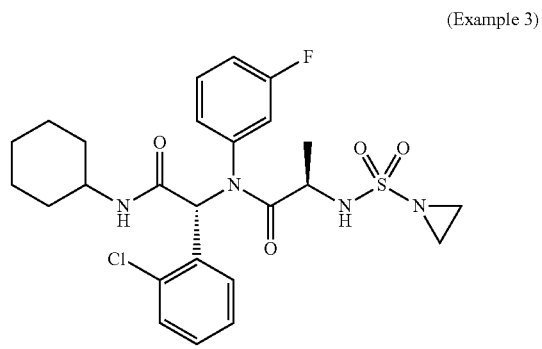

(Example 4)

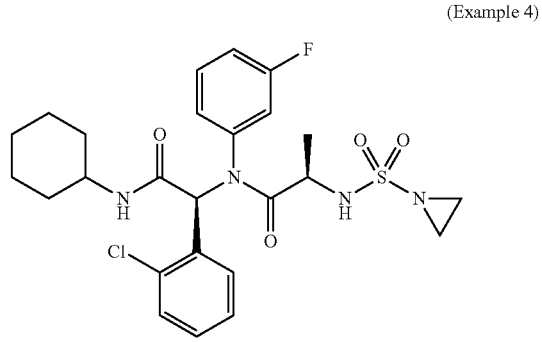

Step A: tert-butyl (2R)-1-((1-(2-chlorophenyl)-2-(cyclohexylamino)-2-oxoethyl)(3-fluorophenyl)amino)-1-oxopropan-2-yl-carbamate

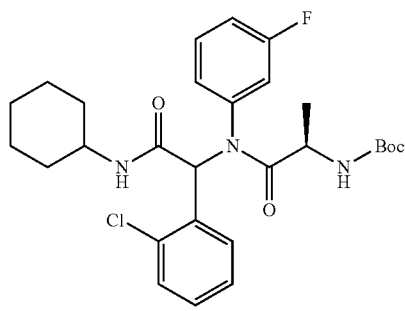 [SMILES: C[C@@H](NC(=O)OC(C)(C)C)C(=O)N(c1cccc(F)c1)C(C(=O)NC1CCCCC1)c1ccccc1Cl]

2-Chloro-benzaldehyde (400 mg, 2.846 mmol) and 3-fluoroaniline (317 mg, 2.846 mmol) were mixed and stirred in MeOH (12 mL) at room temperature for 30 min. Boc-D-alanine (540 mg, 2.846 mmol) was then added thereto, and the reaction mixture was stirred for 10 min. Following adding with cyclohexyl isocyanate (311 mg, 2.846 mmol), the reaction mixture was stirred overnight at room temperature. The solvent was removed in vacuo, and the residue was separated by column chromatography on silica gel to give tert-butyl (2R)-1-((1-(2-chlorophenyl)-2-(cyclohexylamino)-2-oxoethyl)(3-fluorophenyl)amino)-1-oxopropan-2-yl-carbamate (1.272 g, yield of 84%).

m/z=532 [M+H]$^+$.

Step B: (2R)-2-amino-N-(1-(2-chlorophenyl)-2-(cyclohexylamino)-2-oxoethyl)-N-(3-fluorophenyl)propenamide

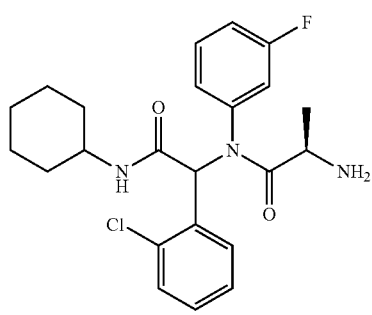 [SMILES: C[C@@H](N)C(=O)N(c1cccc(F)c1)C(C(=O)NC1CCCCC1)c1ccccc1Cl]

In an ice bath, 6N concentrated hydrochloric acid (4.0 mL, 23.87 mmol) was slowly added dropwise with stirring to a solution of tert-butyl (2R)-1-((1-(2-chlorophenyl)-2-(cyclohexylamino)-2-oxoethyl)(3-fluorophenyl)amino)-1-oxopropan-2-yl-carbamate (1.27 g, 2.387 mmol) in THF. The reaction mixture was stirred overnight at room temperature. After completion of the reaction, the reaction mixture was quenched and neutralized with saturated aqueous sodium hydrogen carbonate solution, and extracted with ethyl acetate. The combined organic phase was washed with brine, dried over sodium sulfate, filtered, concentrated in vacuo, and separated by column chromatography on silica gel, to give (2R)-2-amino-N-(1-(2-chlorophenyl)-2-(cyclohexylamino)-2-oxoethyl)-N-(3-fluorophenyl)propanamide (798 mg, yield of 77.5%).

m/z=432 [M+H]$^+$.

Step C: (2R)-2-((N-(2-chloroethyl)sulfonylamino)amino)-N-(1-(2-chlorophenyl)-2-(cyclohexylamino)-2-oxoethyl)-N-(3-fluorophenyl)propanamide

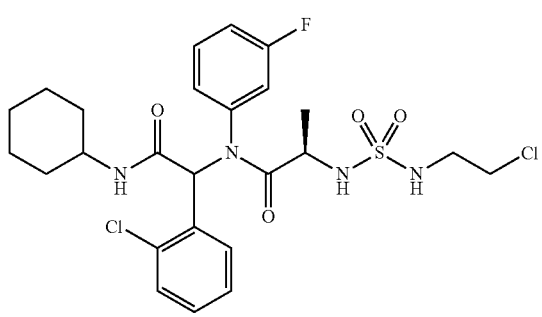 [SMILES: C[C@@H](NS(=O)(=O)NCCCl)C(=O)N(c1cccc(F)c1)C(C(=O)NC1CCCCC1)c1ccccc1Cl]

In an ice bath, 2-chloroethyl sulfamoyl chloride (136 mg, 0.832 mmol) was added with stirring to a mixture of (2R)-2-amino-N-(1-(2-chlorophenyl)-2-(cyclohexylamino)-2-oxoethyl)-N-(3-fluorophenyl)propanamide (180 mg, 0.416 mmol) and pyridine (177 mg, 2.08 mmol) in DCM (10 mL). The reaction mixture was warmed up to room temperature and stirred overnight. The reaction was then quenched with water, followed by extraction with DCM. The combined organic phase was washed with brine, dried over sodium sulfate, filtered, concentrated in vacuo, and separated by column chromatography on silica gel, to give (2R)-2-((N-(2-chloroethyl)sulfonylamino)amino)-N-(1-(2-chlorophenyl)-2-(cyclohexylamino)-2-oxoethyl)-N-(3-fluorophenyl)propanamide (102 mg, yield of 43%).

m/z=573 [M+H]$^+$.

Step D: (R)-2-(aziridine-1-sulfonylamino)-N—((R)-1-(2-chlorophenyl)-2-(cyclohexylamino)-2-oxoethyl)-N-(3-fluorophenyl)propanamide (Example 3)

(R)-2-(aziridine-1-sulfonylamino)-N—((S)-1-(2-chlorophenyl)-2-(cyclohexylamino)-2-oxoethyl)-N-(3-fluorophenyl)propanamide (Example 4)

(Example 3)

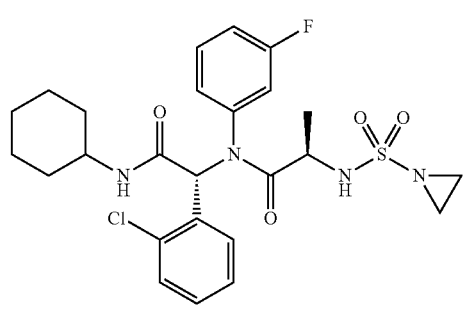

-continued (Example 4)

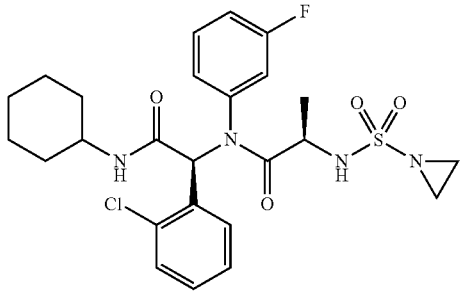

Potassium carbonate (74 mg, 0.534 mmol) was added with stirring to a solution of (2R)-2-((N-(2-chloroethyl)sulfonylamino)amino)-N-(1-(2-chlorophenyl)-2-(cyclohexylamino)-2-oxoethyl)-N-(3-fluorophenyl)propanamide (102 mg, 0.178 mmol) in DMF at room temperature. The reaction mixture was stirred overnight at room temperature. After completion of the reaction, the reaction mixture was added with water, and extracted with ethyl acetate. The combined organic phase was washed with brine, dried over sodium sulfate, filtered, concentrated in vacuo, and separated by column chromatography on silica gel, to give (R)-2-(aziridine-1-sulfonylamino)-N—((R)-1-(2-chlorophenyl)-2-(cyclohexylamino)-2-oxoethyl)-N-(3-fluorophenyl)propenamide (46 mg, yield of 48%) and (R)-2-(aziridine-1-sulfonylamino)-N—((S)-1-(2-chlorophenyl)-2-(cyclohexylamino)-2-oxoethyl)-N-(3-fluorophenyl)propanamide (46 mg, yield of 48%).

Example 3: $^1$H-NMR (400 MHz, CDCl$_3$): δ=7.80-7.53 (m, 1H), 7.39 (d, J=7.9 Hz, 1H), 7.23-7.14 (m, 2H), 7.03-6.88 (m, 3H), 6.60-6.35 (m, 1H), 6.32 (s, 1H), 5.57 (d, J=8.0 Hz, 1H), 5.43 (d, J=9.9 Hz, 1H), 4.19-4.05 (m, 1H), 3.87-3.67 (m, 1H), 2.45-2.24 (m, 4H), 2.08-1.92 (m, 1H), 1.85 (d, J=12.6 Hz, 1H), 1.79-1.67 (m, 1H), 1.63-1.45 (m, 2H), 1.40-1.00 (m, 8H).

m/z=537 [M+H]$^+$.

Example 4: $^1$H-NMR (400 MHz, CDCl$_3$): δ=7.79-7.63 (m, 1H), 7.33-7.18 (m, 1H), 7.16-6.72 (m, 6H), 6.44 (s, 1H), 5.70 (d, J=9.5 Hz, 1H), 5.56 (d, J=8.1 Hz, 1H), 4.25-4.16 (m, 1H), 3.93-3.80 (m, 1H), 2.58-2.20 (m, 4H), 2.00 (d, J=12.3 Hz, 1H), 1.91 (d, J=10.7 Hz, 1H), 1.79-1.49 (m, 3H), 1.41-0.98 (m, 8H).

m/z=537 [M+H]$^+$.

Example 5: 3-(aziridine-1-sulfonylamino)-N-(1-(2-chlorophenyl)-2-(cyclohexylamino)-2-oxoethyl)-N-(3-fluorophenyl)propanamide

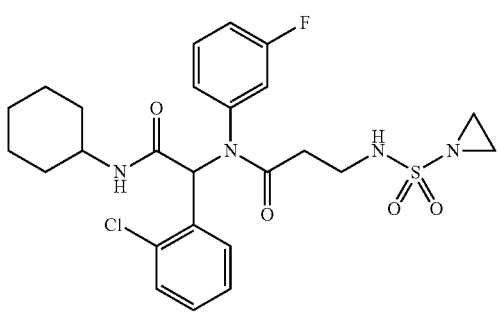 [SMILES: O=C(NC1CCCCC1)C(c1ccccc1Cl)N(C(=O)CCNS(=O)(=O)N1CC1)c1cccc(F)c1]

Step A: tert-butyl 3-((1-(2-chlorophenyl)-2-(cyclohexylamino)-2-oxoethyl)(3-fluorophenyl)amino)-3-oxopropyl)carbamate

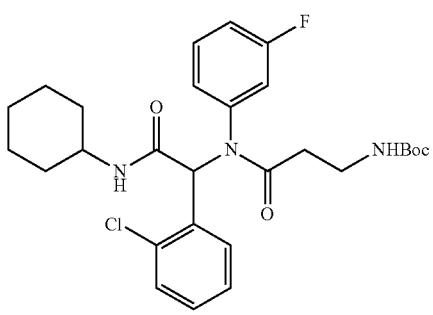 [SMILES: CC(C)(C)OC(=O)NCCC(=O)N(c1cccc(F)c1)C(C(=O)NC1CCCCC1)c1ccccc1Cl]

tert-Butyl 3-((1-(2-chlorophenyl)-2-(cyclohexylamino)-2-oxoethyl)(3-fluorophenyl)amino)-3-oxopropyl)carbamate (1.02 g, yield of 68%) was obtained with reference to Step B of Example 1.

$^1$H-NMR (400 MHz, CDCl$_3$): δ=7.35 (d, J=8.0 Hz, 1H), 7.23-6.94 (m, 6H), 6.90-6.86 (m, 1H), 6.43 (s, 1H), 5.52 (d, J=7.6 Hz, 1H), 5.32 (m, 1H), 3.95-3.82 (m, 1H), 3.45-3.35 (m, 2H), 2.43-2.18 (m, 2H), 2.04 (d, J=11.2 Hz, 1H), 1.90 (d, J=11.2 Hz, 1H), 1.85-1.55 (m, 4H), 1.53-0.96 (m, 13H).

m/z=532 [M+H]$^+$.

Step B: 3-amino-N-(1-(2-chlorophenyl)-2-(cyclohexylamino)-2-oxoethyl)-N-(3-fluorophenyl)propanamide

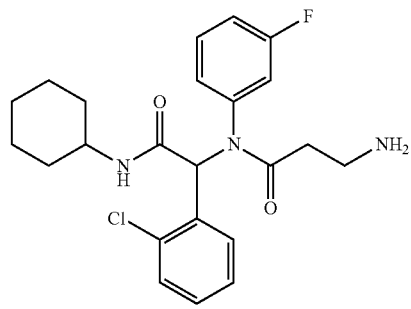 [SMILES: NCCC(=O)N(c1cccc(F)c1)C(C(=O)NC1CCCCC1)c1ccccc1Cl]

Concentrated hydrochloric acid (3 mL, 12 M, 34 mmol) was added with stirring to a solution of tert-butyl 3-((1-(2-chlorophenyl)-2-(cyclohexylamino)-2-oxoethyl)(3-fluorophenyl)amino)-3-oxopropyl)carbamate (912 mg, 1.7 mmol) in tetrahydrofuran at room temperature, and the reaction was performed overnight. The reaction mixture was added with saturated sodium hydrogen carbonate solution, and extracted with ethyl acetate. The combined organic phase was washed with brine, dried over sodium sulfate, filtered and concentrated in vacuo, and separated by column chromatography on silica gel, to give 3-amino-N-(1-(2-chlorophenyl)-2-(cyclohexylamino)-2-oxoethyl)-N-(3-fluorophenyl)propanamide (547 mg, yield of 74%).

¹H-NMR (400 MHz, CDCl₃): δ=7.31 (d, J=8.0 Hz, 1H), 7.17-6.91 (m, 5H), 6.86 (t, J=7.4 Hz, 2H), 6.46 (s, 1H)), 5.69 (d, J=7.8 Hz, 1H), 3.90-3.80 (m, 1H), 2.94 (t, J=6.2 Hz, 2H), 2.25 (t, J=6.0 Hz, 2H), 1.99 (d, J=11.6 Hz, 1H), 1.88 (d, J=11.6 Hz, 1H), 1.75-1.55 (m, 6H), 1.45-0.97 (m, 4H).
m/z=432 [M+H]⁺.

Step C: 3-((N-(2-chloroethyl)sulfonylamino)amino)-N-(1-(2-chlorophenyl)-2-(cyclohexylamino)-2-oxoethyl)-N-(3-fluorophenyl)propanamide

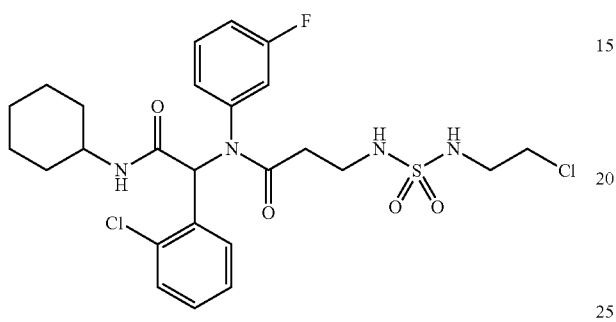

3-((N-(2-chloroethyl)sulfonylamino)amino)-N-(1-(2-chlorophenyl)-2-(cyclohexylamino)-2-oxoethyl)-N-(3-fluorophenyl)propanamide (101 mg, yield of 62%) was obtained with reference to Step D of Example 1.

¹H-NMR (400 MHz, CDCl₃): δ=7.35-7.32 (m, 1H), 7.21-7.07 (m, 3H), 7.03-6.96 (m, 4H), 6.47 (s, 1H), 5.94 (s, 1H), 5.70 (s, 1H), 5.44 (s, 1H), 3.90-3.80 (m, 1H), 3.76-3.67 (m, 2H), 3.63 (t, J=5.9 Hz, 2H), 3.45-3.41 (m, 2H), 2.64-2.27 (m, 2H), 2.05-1.85 (m, 2H), 1.79-1.51 (m, 4H), 1.42-0.97 (m, 4H).
m/z=572 [M+H]⁺.

Step D: 3-(aziridine-1-sulfonylamino)-N-(1-(2-chlorophenyl)-2-(cyclohexylamino)-2-oxoethyl)-N-(3-fluorophenyl)propanamide

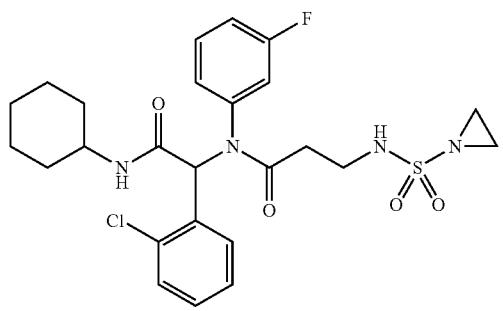 [SMILES: O=C(NC1CCCCC1)C(c1ccccc1Cl)N(C(=O)CCNS(=O)(=O)N1CC1)c1cccc(F)c1]

3-(Aziridine-1-sulfonylamino)-N-(1-(2-chlorophenyl)-2-(cyclohexylamino)-2-oxoethyl)-N-(3-fluorophenyl)propenamide (60 mg, yield of 40%) was obtained with reference to Step E of Example 1.

¹H-NMR (400 MHz, CDCl₃): δ=7.35 (d, J=7.8 Hz, 1H), 7.23-7.07 (m, 3H), 7.02-6.98 (m, 3H), 6.89-6.87 (m, 1H), 6.44 (s, 1H), 5.63 (s, 1H), 5.41-5.35 (d, J=8.0 Hz, 1H), 3.87-3.82 (s, 1H), 3.47 (m, 2H), 2.46 (t, J=5.2 Hz, 2H), 2.32 (s, 4H), 1.97 (m, 2H), 1.58 (m, 4H), 1.46-0.77 (m, 4H).
m/z=537 [M+H]⁺.

Example 6: 3-(aziridin-1-ylsulfonyl)-N-(1-(2-chlorophenyl)-2-(cyclohexylamino)-2-oxoethyl)-N-(3-fluorophenyl)propanamide

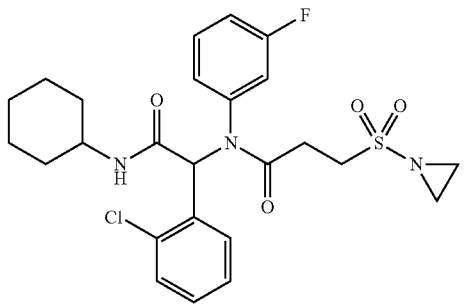 [SMILES: O=C(NC1CCCCC1)C(c1ccccc1Cl)N(C(=O)CCS(=O)(=O)N1CC1)c1cccc(F)c1]

Step A: methyl 3-(chlorosulfonyl)propanoate

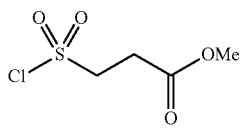

In an ice bath, chlorine gas was introduced into a solution of methyl 3-mercaptopropionate (6.5 g, 54 mmol) and ice in dichloromethane with stirring, until the reaction solution turned pale green, and the chlorine gas was further introduced for 0.5 hour. The chlorine gas in the reaction system was driven off by introducing nitrogen gas. The reaction solution was extracted with dichloromethane. The combined organic phase was washed with brine, dried over sodium sulfate, filtered and concentrated in vacuo, to give methyl 3-(chlorosulfonyl)propanoate (9.7 g, yield of 96%).

¹H-NMR (400 MHz, CDCl₃): δ=4.05 (t, J=7.2 Hz, 2H), 3.82 (s, 3H), 3.10 (t, J=7.6 Hz, 2H).

Step B: methyl 3-(N-(2-chloroethyl)aminosulfonyl)propanoate

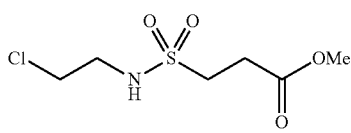 [SMILES: COC(=O)CCS(=O)(=O)NCCCl]

Triethylamine (18.7 mL, 134 mmol) was added with stirring to a solution of 2-chloroethylamine hydrochloride (5.0 g, 26.8 mmol) in dichloromethane in an ice bath, followed by dropwise addition with methyl 3-(chlorosulfonyl)propanoate (3.42 g, 29.5 mmol). After completion of dropwise addition, the reaction solution was warmed up to room temperature and stirred overnight. The reaction solution was added with saturated ammonium chloride solution to quench the reaction, and then extracted with dichloromethane. The combined organic phase was washed with brine, dried over sodium sulfate, filtered and concentrated in vacuo, and separated by column chromatography on silica gel, to give methyl 3-(N-(2-chloroethyl)aminosulfonyl)propanoate (4.7 g, yield of 76%).

¹H-NMR (400 MHz, CDCl₃): δ=4.77 (s, 1H), 3.74 (s, 3H), 3.68 (t, J=5.6 Hz, 2H), 3.47 (dt, J=11.6, 5.7 Hz, 2H), 3.40 (t, J=7.3 Hz, 2H), 2.86 (t, J=7.2 Hz, 2H).

Step C: 3-(aziridin-1-ylsulfonyl)propanoic Acid

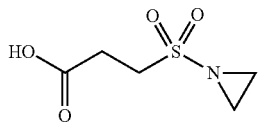 [SMILES: O=C(O)CCS(=O)(=O)N1CC1]

Lithium hydroxide (260 mg, 10.9 mmol) was added to a mixture solution of methyl 3-(N-(2-chloroethyl)aminosulfonyl)propanoate (500 mg, 2.2 mmol) in methanol and water (methanol/water=5/1). The reaction mixture was stirred overnight at room temperature, and evaporated under reduced pressure to remove methanol. The resulting solution was adjusted to pH 4 with hydrochloric acid solution of pH=1, extracted with ethyl acetate, dried over sodium sulfate, filtered and concentrated in vacuo, to give 3-(aziridin-1-ylsulfonyl)propanoic acid (190 mg, yield of 49%).

¹H-NMR (400 MHz, CDCl₃): δ=9.26 (s, 1H), 3.48 (t, J=7.4 Hz, 2H), 2.98 (t, J=7.4 Hz, 2H), 2.39 (s, 4H).

Step D: 3-(aziridin-1-ylsulfonyl)-N-(1-(2-chlorophenyl)-2-(cyclohexylamino)-2-oxoethyl)-N-(3-fluorophenyl)propanamide

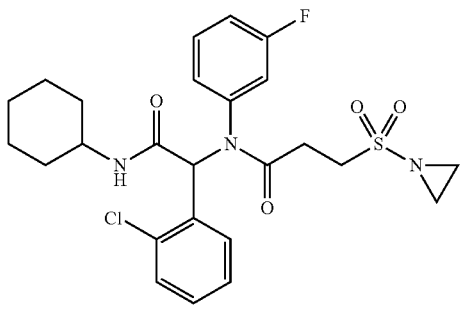 [SMILES: O=C(NC1CCCCC1)C(c1ccccc1Cl)N(C(=O)CCS(=O)(=O)N1CC1)c1cccc(F)c1]

3-(Aziridin-1-ylsulfonyl)-N-(1-(2-chlorophenyl)-2-(cyclohexylamino)-2-oxoethyl)-N-(3-fluorophenyl)propanamide (62 mg, yield of 31%) was obtained with reference to Step B of Example 1.

¹H-NMR (400 MHz, CDCl₃): δ=7.33 (d, J=7.9 Hz, 1H), 7.18-7.06 (m, 3H), 7.01-6.80 (m, 4H), 6.42 (s, 1H), 5.53 (d, J=8.3 Hz, 1H), 3.95-3.76 (m, 1H), 3.53 (t, J=7.4 Hz, 2H), 2.77-2.60 (m, 2H), 2.32 (s, 4H), 1.99 (d, J=10.6 Hz, 1H), 1.88 (d, J=12.5 Hz, 1H), 1.81-1.58 (m, 4H), 1.43-0.95 (m, 4H).

m/z=522 [M+H]⁺.

Example 7: tert-butyl 2-((1-(2-chlorophenyl)-2-(cyclohexylamino)-2-oxoethyl)(3-fluorophenyl)amino)-2-oxoethyl)(((R)-2-isopropylaziridin-1-yl)sulfonyl) carbamate

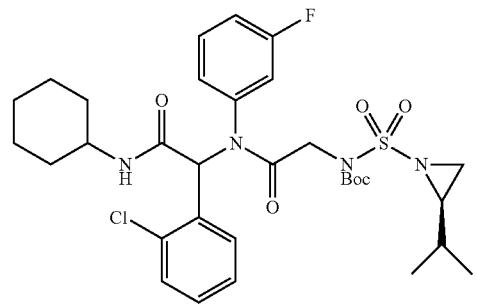 [SMILES: CC(C)[C@@H]1CN1S(=O)(=O)N(CC(=O)N(c1cccc(F)c1)C(C(=O)NC1CCCCC1)c1ccccc1Cl)C(=O)OC(C)(C)C]

Step A: tert-butyl (R)—N-(1-hydroxy-3-methylbutan-2-yl)sulfamoyl carbamate

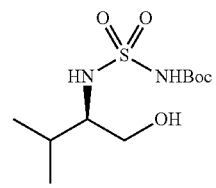 [SMILES: CC(C)[C@H](CO)NS(=O)(=O)NC(=O)OC(C)(C)C]

A solution of Boc-sulfamoyl chloride (1.15 g, 5.33 mmol) in dichloromethane was added dropwise to a solution of D-valinol (500 mg, 4.85 mmol) and triethylamine (1.35 mL, 9.69 mmol) in dichloromethane (15 mL) at 0° C., and then warmed up to room temperature and reacted for 1 hour. After completion of the reaction, the reaction was neutralized with 1N HCl. The organic layer was then separated, and allowed to stand to precipitate a solid product of tert-butyl (R)—N-(1-hydroxy-3-methylbutan-2-yl)sulfamoyl carbamate (750 mg, yield of 55%).

¹H-NMR (400 MHz, CDCl₃): δ=7.36 (br s, 1H), 5.32 (d, J=8.4 Hz, 1H), 3.76-3.72 (m, 1H), 3.69-3.66 (m, 1H), 3.27-3.23 (m, 1H), 2.20-2.19 (m, 1H), 1.49 (d, J=5.2 Hz, 9H), 0.99 (m, 6H).

Step B: tert-butyl (R)-(2-isopropylaziridin-1-yl)sulfonyl carbamate

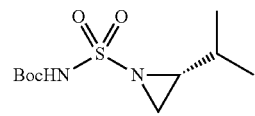 [SMILES: CC(C)[C@@H]1CN1S(=O)(=O)NC(=O)OC(C)(C)C]

DIAD (1.05 mL, 5.32 mmol) was added dropwise to a solution of tert-butyl (R)—N-(1-hydroxy-3-methylbutan-2-yl)sulfamoyl carbamate (750 mg, 2.65 mmol) and triphenylphosphine (1.39 g, 5.32 mmol) in tetrahydrofuran (30 mL) at 0° C., then warmed up to room temperature and stirred overnight. After completion of the reaction, the solvent was removed under reduced pressure, and then the obtained residue was separated by column chromatography on silica gel (PE:EA=3:1) to give the product of tert-butyl (R)-2-isopropylaziridin-1-ylsulfonyl carbamate (362 mg, yield of 52%).

$^1$H-NMR (400 MHz, CDCl$_3$): δ=7.71 (br s, 1H), 2.74 (d, J=6.8 Hz, 1H), 2.69-2.66 (m, 1H), 2.27 (d, J=4.8 Hz, 1H), 1.55 (d, J=6.8 Hz, 1H), 1.51-1.49 (m, 9H), 1.08-1.04 (m, 3H), 1.01-0.98 (m, 3H).

Step C: tert-butyl 2-((1-(2-chlorophenyl)-2-(cyclohexylamino)-2-oxoethyl)(3-fluorophenyl)amino)-2-oxoethyl)(((R)-2-isopropylaziridin-1-yl)sulfonyl) carbamate

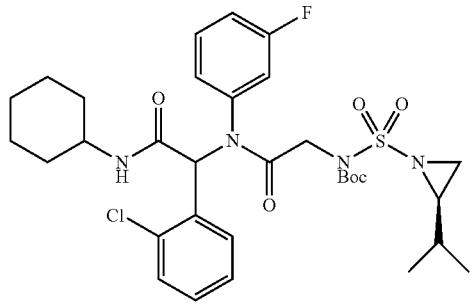 [SMILES: CC(C)[C@@H]1CN1S(=O)(=O)N(CC(=O)N(c1cccc(F)c1)C(C(=O)NC1CCCCC1)c1ccccc1Cl)C(=O)OC(C)(C)C]

Under protection of nitrogen gas, N-(1-(2-chlorophenyl)-2-cyclohexylamino-2-oxoethyl)-N-(3-fluorophenyl)-2-hydroxyacetamide (79 mg, 0.19 mmol), tert-butyl (R)—N-(1-hydroxy-3-methylbutan-2-yl)sulfamoyl carbamate (50 mg, 0.19 mmol) and triphenyl phosphine (99 mg, 0.38 mmol) were added to 15 mL of tetrahydrofuran. After cooling down to 0° C., the reaction solution was added dropwise with DIAD (75 µL, 0.38 mmol), and then warmed up to room temperature and stirred overnight. After completion of the reaction, the solvent was removed under reduced pressure, and the obtained residue was separated by column chromatography on silica gel (PE:EA=2:1) to give tert-butyl 2-((1-(2-chlorophenyl)-2-(cyclohexylamino)-2-oxoethyl)(3-fluorophenyl)amino)-2-oxoethyl)(((R)-2-isopropylaziridin-1-yl)sulfonyl)carbamate (80 mg, yield of 64%).

$^1$H-NMR (400 MHz, CDCl$_3$): δ=7.33 (d, J=8.4 Hz, 1H), 7.15-6.91 (m, 7H), 6.51 (s, 1H), 4.52-4.16 (m, 1H), 4.13-4.10 (m, 1H), 3.83-3.82 (m, 2H), 2.77-2.72 (m, 2H), 2.30-2.27 (m, 1H), 2.05-1.99 (m, 2H), 1.88-1.85 (m, 1H), 1.72-1.22 (m, 17H), 1.06-1.03 (m, 3H), 1.00-0.97 (m, 3H).

m/z=665 [M+H]$^+$.

Example 8: 3-(aziridine-1-sulfonylamino)-N-(1-(2-chlorophenyl)-2-((3,3-difluorocyclobutyl)amino)-2-oxoethyl)-N-(3-fluorophenyl)propanamide

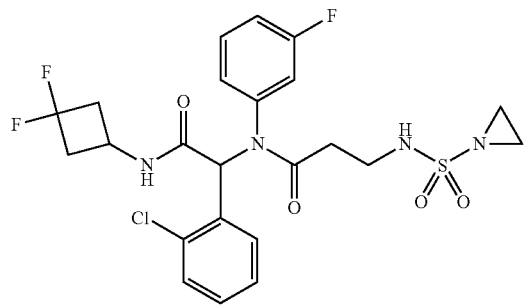 [SMILES: O=C(NC1CC(F)(F)C1)C(c1ccccc1Cl)N(C(=O)CCNS(=O)(=O)N1CC1)c1cccc(F)c1]

Step A: tert-butyl 3-((1-(2-chlorophenyl)-2-((3,3-difluorocyclobutyl)amino)-2-oxoethyl)(3-fluorophenyl)amino)-3-oxopropyl]carbamate

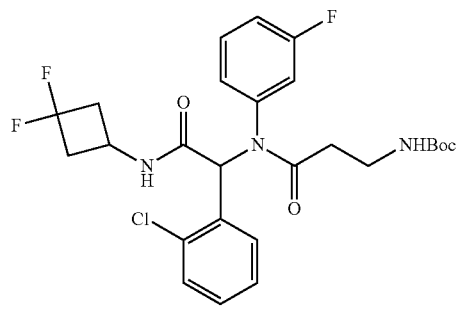 [SMILES: CC(C)(C)OC(=O)NCCC(=O)N(c1cccc(F)c1)C(C(=O)NC1CC(F)(F)C1)c1ccccc1Cl]

With reference to Step B of Example 1, tert-butyl 3-((1-(2-chlorophenyl)-2-((3,3-difluorocyclobutyl)amino)-2-oxoethyl)(3-fluorophenyl)amino)-3-oxopropyl]carbamate (2.33 g, yield of 62%) was obtained from 1,1-difluoro-3-isocyanocyclobutane (prepared by the method as described in Patent CN 201180043254.6) (1.0 g, 8.54 mmol).

m/z=540 [M+H]$^+$.

Step B: 3-amino-N-(1-(2-chlorophenyl)-2-((3,3-difluorocyclobutyl)amino)-2-oxoethyl)-N-(3-fluorophenyl)propanamide

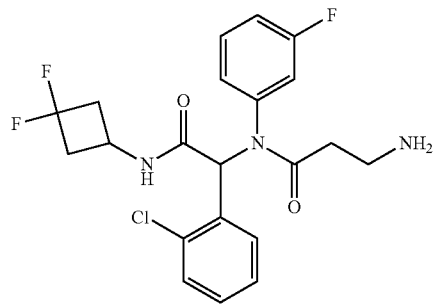 [SMILES: NCCC(=O)N(c1cccc(F)c1)C(C(=O)NC1CC(F)(F)C1)c1ccccc1Cl]

With reference to step B of Example 5, 3-amino-N-(1-(2-chlorophenyl)-2-((3,3-difluorocyclobutyl)amino)-2-oxoethyl)-N-(3-fluorophenyl)propanamide (900 mg, yield of 47%) was obtained from tert-butyl 3-((1-(2-chlorophenyl)-2-((3,3-difluorocyclobutyl)amino)-2-oxoethyl))(3-fluorophenyl)amino)-3-oxopropyl]carbamate (2.33 g, 4.32 mmol).

Step C: 3-((N-(2-chloroethyl)sulfonylamino)amino)-N-(1-(2-chlorophenyl)-2-((3,3-difluorocyclobutyl)amino)-2-oxoethyl)-N-(3-fluorophenyl)propanamide

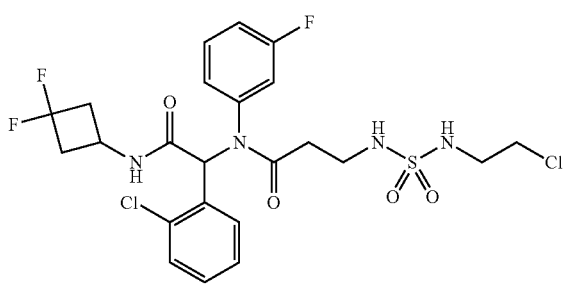 [SMILES: O=C(NC1CC(F)(F)C1)C(c1ccccc1Cl)N(C(=O)CCNS(=O)(=O)NCCCl)c1cccc(F)c1]

DIEA (74 μL, 0.445 mmol) was added with stirring to a solution of 3-amino-N-(1-(2-chlorophenyl)-2-((3,3-difluorocyclobutyl)amino)-2-oxoethyl)-N-(3-fluorophenyl)propanamide (50 mg, 0.114 mmol) in dichloromethane in an ice bath, followed by dropwise addition of (2-chloroethyl)sulfonyl chloride (37 mg, 0.227 mmol). After completion of dropwise addition, the reaction solution was warmed up to room temperature and stirred overnight. The reaction solution was added with saturated ammonium chloride solution to quench the reaction, and then extracted with dichloromethane. The combined organic phase was washed with brine, dried over sodium sulfate, filtered and concentrated in vacuo, and separated by column chromatography on silica gel, to give 3-((N-(2-chloroethyl)sulfonylamino)amino)-N-(1-(2-chlorophenyl)-2-((3,3-difluorocyclobutyl))amino)-2-oxoethyl)-N-(3-fluorophenyl)propanamide (63 mg, yield of 95%).

$^1$H-NMR (400 MHz, CDCl$_3$): δ=7.34 (d, J=7.9 Hz, 1H), 7.21-7.06 (m, 3H), 7.01-6.88 (m, 4H), 6.46 (s, 1H), 6.25 (d, J=6.5 Hz, 1H), 5.47 (t, J=6.3 Hz, 1H), 4.83 (t, J=6.3 Hz, 1H), 4.36-4.29 (m, 1H), 3.69 (t, J=5.7 Hz, 2H), 3.42-3.38 (m, 2H), 3.34-3.25 (m, 2H), 3.14-2.90 (m, 2H), 2.66-2.30 (m, 4H).
m/z=581 [M+H]$^+$.

Step D: 3-(aziridine-1-sulfonylamino)-N-(1-(2-chlorophenyl)-2-((3,3-difluorocyclobutyl)amino)-2-oxoethyl)-N-(3-fluorophenyl)propanamide

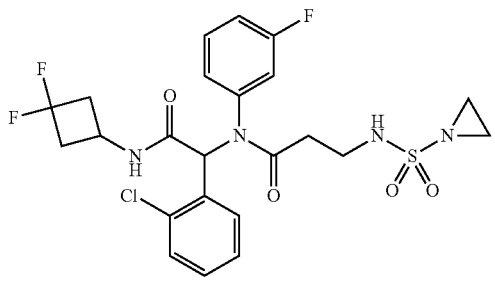 [SMILES: O=C(NC1CC(F)(F)C1)C(c1ccccc1Cl)N(C(=O)CCNS(=O)(=O)N1CC1)c1cccc(F)c1]

With reference to Step E of Example 1, 3-(aziridine-1-sulfonylamino)-N-(1-(2-chlorophenyl)-2-((3,3-difluorocyclobutyl)amino)-2-oxoethyl)-N-(3-fluorophenyl)propanamide (38 mg, yield of 74%) was obtained from 3-((N-(2-chloroethyl)sulfonylamino)amino)-N-(1-(2-chlorophenyl)-2-(3,3-difluorocyclobutyl)amino)-2-oxoethyl)-N-(3-fluorophenyl)propanamide (55 mg, 0.0946 mmol).

$^1$H-NMR (400 MHz, CDCl$_3$): δ=7.36 (d, J=7.9 Hz, 1H), 7.17 (m, 3H), 6.95 (m, 4H), 6.44 (s, 1H), 5.99 (d, J=6.6 Hz, 1H), 5.62 (t, J=6.4 Hz, 1H), 4.37-4.30 (m, 1H), 3.48-3.43 (m, 2H), 3.09-2.96 (m, 2H), 2.66-2.37 (m, 4H), 2.30 (s, 4H).
m/z=545 [M+H]$^+$.

Example 9: 2-(2-chlorophenyl)-N-cyclohexyl-2-(N-(3-fluorophenyl)-2-((R)-2-isopropylaziridine-1-sulfonylamino)acetamido)acetamide

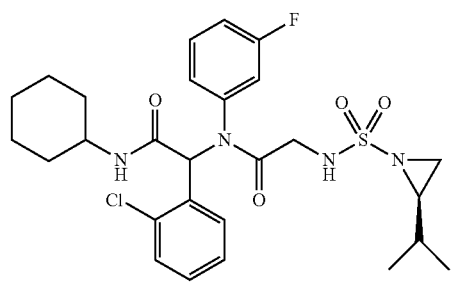 [SMILES: CC(C)[C@@H]1CN1S(=O)(=O)NCC(=O)N(c1cccc(F)c1)C(C(=O)NC1CCCCC1)c1ccccc1Cl]

1 mL of TFA was added to a solution of tert-butyl 2-((1-(2-chlorophenyl)-2-(cyclohexylamino)-2-oxoethyl)(3-fluorophenyl)amino)-2-oxoethyl)(((R)-2-isopropylaziridin-1-yl)sulfonyl)carbamate (prepared in Example 7, 80 mg, 0.12 mmol) in dichloromethane, and the mixture was stirred at room temperature for 1 h. The solvent was removed under reduced pressure, and then the obtained residue was separated by column chromatography on silica gel (PE:EA=2:1) to give the product (41 mg, yield of 60%).

$^1$H-NMR (400 MHz, CDCl$_3$): δ=7.78-7.59 (brs, 1H), 7.34 (d, J=8.4 Hz, 1H), 7.16-7.14 (m, 3H), 7.01-6.90 (m, 4H), 6.42 (d, J=8.0 Hz, 1H), 5.53 (d, J=4.0 Hz, 2H), 3.87-3.63 (m, 3H), 2.47-2.40 (m, 2H), 2.08-2.05 (m, 1H)), 2.01-1.98 (m, 1H), 1.88-1.85 (m, 1H), 1.72-1.22 (m, 8H), 1.06-1.03 (m, 3H), 1.00-0.97 (m, 3H).
m/z=565 [M+H]$^+$.

Example 10: 2-(aziridine-1-sulfonylamino)-N-(1-(2-chlorophenyl)-2-((3,3-difluorocyclobutyl)amino)-2-oxoethyl)-N-(3-fluorophenyl)acetamide

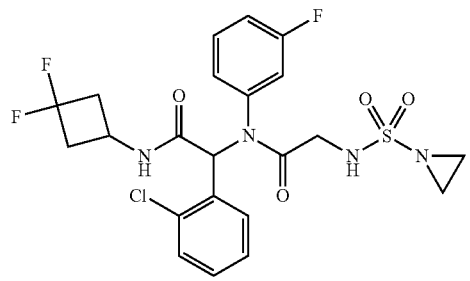 [SMILES: O=C(NC1CC(F)(F)C1)C(c1ccccc1Cl)N(C(=O)CNS(=O)(=O)N1CC1)c1cccc(F)c1]

Step A: tert-butyl 2-((N-(2-chloroethyl)sulfonylamino)amino)acetate

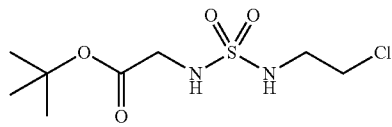 [SMILES: CC(C)(C)OC(=O)CNS(=O)(=O)NCCCl]

With reference to step D of Example 1, tert-butyl 2-((N-(2-chloroethyl)sulfonylamino)amino)acetate (4.67 g, yield of 96%) was obtained from 2-aminoacetic acid tert-butyl ester hydrochloride (3 g, 17.9 mmol).

$^1$H-NMR (400 MHz, CDCl$_3$): δ=4.86 (s, 1H), 4.76 (s, 1H), 3.75 (d, J=5.6 Hz, 2H), 3.69 (t, J=5.6 Hz, 2H), 3.48-3.38 (m, 2H), 1.49 (s, 9H).

Step B: 2-((N-(2-chloroethyl)aminosulfonyl)amino)acetic Acid

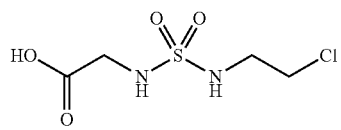 [SMILES: O=C(O)CNS(=O)(=O)NCCCl]

In an ice bath, trifluoroacetic acid (12 mL) was added dropwise with stirring to a solution of tert-butyl 2-((N-(2-chloroethyl)sulfonylamino)amino)acetate (2.2 g, 8.0 mmol, 1.0 eq.) in dichloromethane. After the reaction was performed overnight at room temperature, the reaction solution was evaporated under reduced pressure to fully remove trifluoroacetic acid and dichloromethane, then slurried with methylene chloride, and filtered with suction to give 2-((N-(2-chloroethyl)aminosulfonyl)amino)acetic acid (1.65 g, yield of 94%) as a white solid.

$^1$H-NMR (400 MHz, CDCl$_3$): δ=12.62 (s, 1H), 7.33 (t, J=6.1 Hz, 1H), 7.21 (t, J=5.8 Hz, 1H), 3.66-3.52 (m, 4H), 3.17-3.12 (m, 2H).

Step C: 2-((N-(2-chloroethyl)sulfonylamino)amino)-N-(1-(2-chlorophenyl)-2-((3,3-difluorocyclobutyl))amino)-2-oxoethyl)-N-(3-fluorophenyl)acetamide

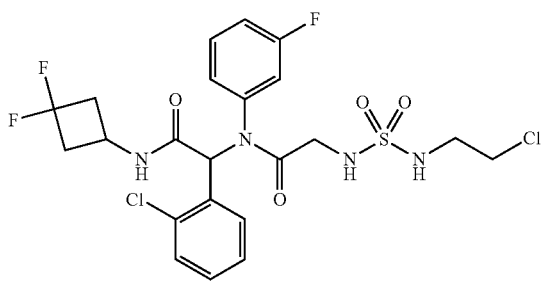 [SMILES: O=C(NC1CC(F)(F)C1)C(c1ccccc1Cl)N(C(=O)CNS(=O)(=O)NCCCl)c1cccc(F)c1]

With reference to Step C of Example 13, 2-((N-(2-chloroethyl)sulfonylamino)amino)-N-(1-(2-chlorophenyl)-2-((3,3-difluorocyclobutyl)amino)-2-oxoethyl)-N-(3-fluorophenyl)acetamide (61 mg, yield of 26%) was obtained from 2-((N-(2-chloroethyl)aminosulfonyl)amino)acetic acid (90 mg, 0.415 mmol).

Step D: 2-(aziridine-1-sulfonylamino)-N-(1-(2-chlorophenyl)-2-((3,3-difluorocyclobutyl)amino)-2-oxoethyl}-N-(3-fluorophenyl)acetamide

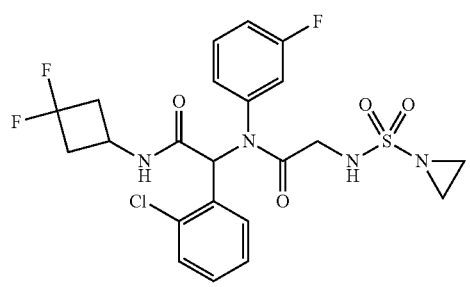

With reference to Step E of Example 1, 2-(aziridine-1-sulfonylamino)-N-(1-(2-chlorophenyl)-2-((3,3-difluorocyclobutyl)amino)-2-oxoethyl}-N-(3-fluorophenyl)acetamide (34 mg, yield of 60%) was obtained from 2-((N-(2-chloroethyl)sulfonylamino)amino)-N-(1-(2-chlorophenyl)-2-((3,3-difluorocyclobutyl))amino)-2-oxoethyl)-N-(3-fluorophenyl)acetamide (61 mg, 0.108 mmol).

$^1$H-NMR (400 MHz, CDCl$_3$): δ=7.55-7.45 (m, 1H), 7.38-7.36 (m, 2H), 7.22-7.12 (m, 2H), 7.02-6.92 (m, 3H), 6.43 (s, 1H), 5.97 (d, J=6.5 Hz, 1H), 5.51 (s, 1H), 4.32-4.13 (m, 1H), 3.80-3.69 (m, 2H), 3.07-2.95 (m, 2H), 2.59-2.33 (m, 2H), 2.30 (s, 4H).

m/z=531 [M+H]$^+$.

Example 11: 2-(aziridine-1-sulfonylamino)-N-(1-(2-chlorophenyl)-2-((3,3-difluorocyclobutyl)amino)-2-oxoethyl)-N-(5-fluoropyridin-3-yl)acetamide

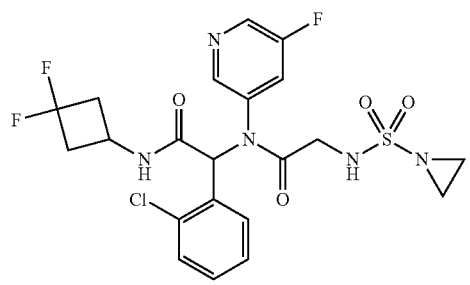

Step A: 2-((N-(2-chloroethyl)sulfonylamino)amino)-N-(1-(2-chlorophenyl)-2-((3,3-difluorocyclobutyl)amino)-2-oxoethyl)-N-(5-fluoropyridin-3-yl)acetamide

Example 12: 2-(2-chlorophenyl)-N-cyclohexyl-2-(N-(3-fluorophenyl)-2-(N-methylaziridine-1-sulfonylamino)acetamido)acetamide

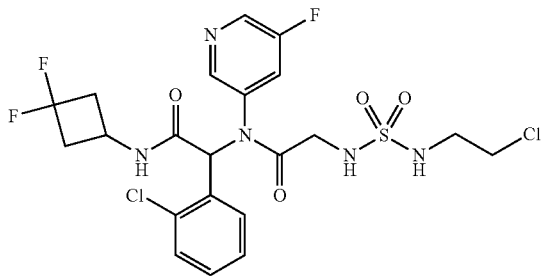 [SMILES: O=C(NC1CC(F)(F)C1)C(c1ccccc1Cl)N(C(=O)CNS(=O)(=O)NCCCl)c1cncc(F)c1]

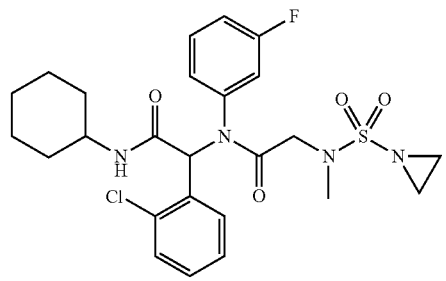 [SMILES: CN(CC(=O)N(c1cccc(F)c1)C(C(=O)NC1CCCCC1)c1ccccc1Cl)S(=O)(=O)N1CC1]

With reference to Step C of Example 13, 2-((N-(2-chloroethyl)sulfonylamino)amino)-N-(1-(2-chlorophenyl)-2-((3,3-difluorocyclobutyl)amino)-2-oxoethyl)-N-(5-fluoropyridin-3-yl)acetamide (46 mg, yield of 19%) was obtained from 3-amino-5-fluoropyridine (46.5 mg, 0.415 mmol) and 2-((N-(2-chloroethyl)sulfonylamino)amino)acetic acid (90 mg, 0.415 mmol).

m/z=568 [M+H]$^+$.

Step B: 2-(aziridine-1-sulfonylamino)-N-(1-(2-chlorophenyl)-2-((3,3-difluorocyclobutyl)amino)-2-oxoethyl)-N-(5-fluoropyridin-3-yl)acetamide

Step A: 2-oxazolidinone-3-sulfonyl chloride

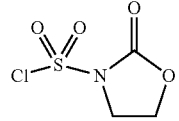

At 0° C., bromoethanol (4.41 g, 35.33 mmol) was added dropwise to a solution of chlorosulfonyl isocyanate (5 g, 35.33 mmol) in dichloromethane (200 mL), stirred for 30 min and concentrated, to give a white solid of 2-oxazolidinone-3-sulfonyl chloride (9.5 g, yield of 100%).

$^1$H-NMR (400 MHz, CDCl$_3$): δ=4.64-4.59 (m, 2H), 3.61-3.56 (m, 2H).

Step B: tert-butyl 2-(2-oxazolidinone-3-sulfonylamino)acetate

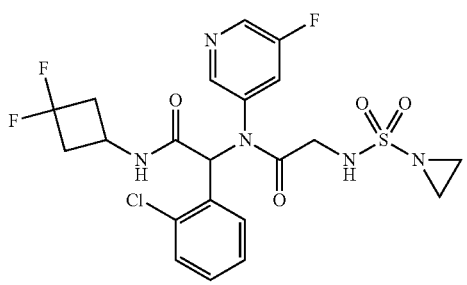

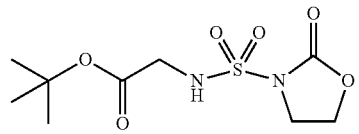 [SMILES: CC(C)(C)OC(=O)CNS(=O)(=O)N1CCOC1=O]

According to the synthesis procedure as described in step E of Example 1, 2-(aziridine-1-sulfonylamino)-N-(1-(2-chlorophenyl)-2-((3,3-difluorocyclobutyl)amino)-2-oxoethyl)-N-(5-fluoropyridin-3-yl)acetamide (4 mg, yield of 9.3%) was obtained from 2-((N-(2-chloroethyl)sulfonylamino)amino)-N-(1-(2-chlorophenyl)-2-((3,3-difluorocyclobutyl)amino)-2-oxoethyl)-N-(5-fluoropyridin-3-yl)acetamide (46 mg, 0.081 mmol).

$^1$H NMR (400 MHz, CDCl$_3$) δ 8.35 (s, 1H), 7.68-7.42 (m, 2H), 7.39 (d, J=8.0 Hz, 1H), 7.23-7.20 (m, 1H), 7.05-7.01 (m, 1H), 6.94 (d, J=7.1 Hz, 1H), 6.49 (s, 1H), 6.24 (s, 1H), 5.70 (s, 1H), 4.34-4.27 (m, 1H), 3.83-3.58 (m, 2H), 3.04-2.96 (m, 2H), 2.69-2.38 (m, 4H), 2.31 (s, 4H).

m/z=532 [M+1]$^+$.

2-Oxazolidinone-3-sulfonyl chloride (3.68 g, 19.83 mmol), tert-butyl glycinate (2.60 g, 19.82 mmol) and triethylamine (2.00 g, 39.64 mmol) were added to 200 mL of dichloromethane at 0° C., warmed up to room temperature and stirred overnight. After completion of the reaction, the reaction mixture was added with 1N HCl to neutralize the reaction, and washed successively with water and brine. The organic phase was separated, dried over anhydrous sodium sulfate, concentrated under reduced pressure, and separated by column chromatography on silica gel (PE:EA=1:1) to give a solid product of tert-butyl 2-(2-oxazolidinone-3-sulfonylamino)acetate (1.11 g, yield of 20%).

$^1$H-NMR (400 MHz, CDCl$_3$): δ=5.73 (br s, 1H), 4.44-4.36 (m, 2H), 4.07-4.04 (m, 2H), 3.95 (d, J=5.6 Hz, 2H), 1.48 (s, 9H).

Step C: tert-butyl 2-(N-methyl-2-oxazolidinone-3-sulfonylamino)acetate

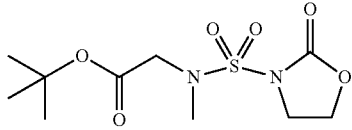 [SMILES: CN(CC(=O)OC(C)(C)C)S(=O)(=O)N1CCOC1=O]

At 0° C., sodium hydrogen (51.41 mg, 2.14 mmol) was added to a solution of tert-butyl 2-(2-oxazolidinone-3-sulfonyl)aminoacetate (500 mg, 1.78 mmol) in DMF, and methyl iodide (167 μL, 2.68 mmol) was added thereto after stirring for 30 min. The mixture was warmed up to room temperature and stirred overnight. After completion of the reaction, 50 mL of water was added to quench the reaction, followed by extraction with ethyl acetate (20 mL×3). The organic phase was dried over anhydrous sodium sulfate, concentrated under reduced pressure, and separated by column chromatography on silica gel (PE:EA=2:1) to give a solid product of tert-butyl 2-(N-methyl-2-oxazolidinone-3-sulfonylamino)acetate (339 mg, yield of 65%).

$^1$H-NMR (400 MHz, CDCl$_3$): δ=4.43-4.39 (m, 2H), 4.09-4.05 (m, 4H), 3.13 (s, 3H), 1.48 (s, 9H).

Step D: 2-(N-methyl-2-oxazolidinone-3-sulfonylamino)acetic Acid

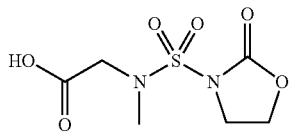

1 mL of TFA was added to a solution of tert-butyl 2-(N-methyl-2-oxazolidinone-3-sulfonylamino)acetate (180 mg, 0.61 mmol) in dichloromethane at 0° C., and stirred at room temperature for 1 hour. After completion of the reaction, TFA and the solvent were removed by spin-evaporation under reduced pressure, and a solid product of 2-(N-methyl-2-oxazolidinone-3-sulfonylamino)acetic acid (149 mg, yield of 100%) was obtained.

$^1$H-NMR (400 MHz, CDCl$_3$): δ=4.46-4.42 (m, 2H), 4.28 (s, 2H), 4.11-4.05 (m, 2H), 3.13 (s, 3H).

Step E: 2-(2-chlorophenyl)-N-cyclohexyl-2-(N-(3-fluorophenyl)-2-(N-methyl-2-oxazolidinone-3-sulfonylamino)acetamido)acetamide

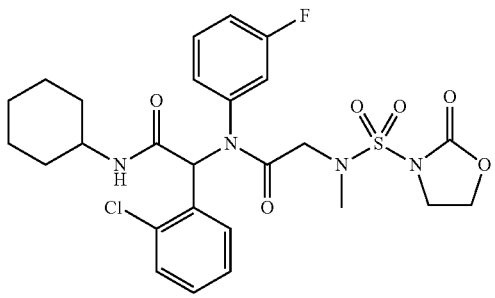 [SMILES: CN(CC(=O)N(c1cccc(F)c1)C(C(=O)NC1CCCCC1)c1ccccc1Cl)S(=O)(=O)N1CCOC1=O]

At room temperature, o-chlorobenzaldehyde (69 μL, 0.61 mmol) and m-fluoroaniline (59 μL, 0.61 mmol) were added in 10 mL of methanol, and after stirring for 10 min, 2-(N-methyl-2-oxazolidinone-3-sulfonylamino)acetic acid (145 mg, 0.61 mmol) was added thereto, followed by stirring for another 10 min. Cyclohexyl isocyanide (67 mg, 0.61 mmol) was then added, and the mixture was stirred overnight at room temperature. After completion of the reaction, the solvent was removed under reduced pressure, and a solid product of 2-(2-chlorophenyl)-N-cyclohexyl-2-(N-(3-fluorophenyl)-2-(N-methyl-2-oxazolidinone-3-sulfonylamino)acetamido)acetamide (240 mg, yield of 68%) was obtained by separation with column chromatography on silica gel (PE:EA=2:1).

$^1$H-NMR (400 MHz, CDCl$_3$): δ=7.35 (d, J=8.0 Hz, 1H), 7.15 (t, J=7.2 Hz, 3H), 6.99-6.90 (m, 4H), 6.51 (s, 1H)), 5.71 (d, J=7.6 Hz, 1H), 4.42-4.38 (m, 2H), 4.14-4.07 (m, 2H), 4.01-3.82 (m, 3H), 3.19 (s, 3H), 1.99-1.89 (m, 2H), 1.76-1.68 (m, 2H), 1.39-1.09 (m, 6H).

m/z=581 [M+H]$^+$.

Step F: 2-(2-chlorophenyl)-N-cyclohexyl-2-(N-(3-fluorophenyl)-2-((N-(2-hydroxyethyl)sulfamoyl)(methyl)amino)acetamido)acetamide

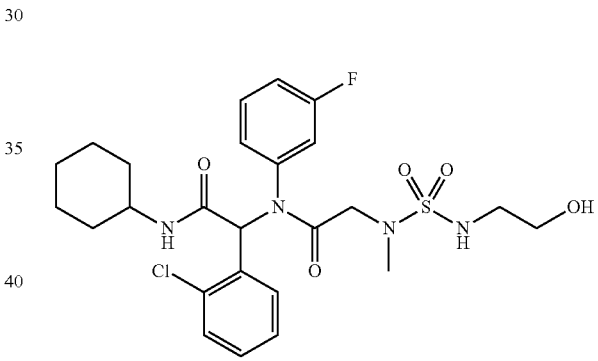

At room temperature, 3N sodium hydroxide solution was added in a solution of 2-(2-chlorophenyl)-N-cyclohexyl-2-(N-(3-fluorophenyl)-2-(N-methyl-2-oxazolidinone-3-sulfonylamino)acetamido)acetamide (120 mg, 0.206 mmol) in methanol, and stirred for 15 min. After completion of the reaction, the reaction solution was distilled under reduced pressure to remove the solvent, extracted with ethyl acetate (20 mL×3), dried over anhydrous sodium sulfate, and concentrated, to give a solid product of 2-(2-chlorophenyl)-N-cyclohexyl-2-(N-(3-fluorophenyl)-2-((N-(2-hydroxyethyl)sulfamoyl)(methyl)amino)acetamido)acetamide (113 mg, yield of 99%).

$^1$H-NMR (400 MHz, CDCl$_3$): δ=7.35 (d, J=8.0 Hz, 1H), 7.16 (t, J=7.2 Hz, 2H), 6.99-6.91 (m, 4H), 6.43 (s, 1H), 5.48 (s, 1H), 5.46 (s, 1H), 3.86-3.75 (m, 5H), 3.37-3.33 (m, 2H), 2.97 (s, 3H), 2.94 (s, 1H), 2.01-1.84 (m, 2H), 1.79-1.70 (m, 2H), 1.40-1.06 (m, 6H).

m/z=555 [M+H]$^+$.

Step G: 2-(2-chlorophenyl)-N-cyclohexyl-2-(N-(3-fluorophenyl)-2-(N-methylaziridine-1-sulfonylamino)acetamido)acetamide

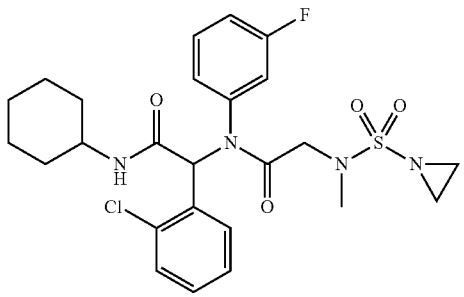 [SMILES: CN(CC(=O)N(c1cccc(F)c1)C(C(=O)NC1CCCCC1)c1ccccc1Cl)S(=O)(=O)N1CC1]

Under protection of nitrogen gas, 2-(2-chlorophenyl)-N-cyclohexyl-2-(N-(3-fluorophenyl)-2-((N-(2-hydroxyethyl)sulfamoyl)(methyl)amino)acetamido)acetamide (112 mg, 0.20 mmol) and triphenylphosphine (169 mg, 0.60 mmol) were added in 10 mL of tetrahydrofuran, and the mixture was then cooled down to 0° C. DIAD (119 µL, 0.60 mmol) was added dropwise to the reaction, followed by warming up to room temperature and stirring overnight. After completion of the reaction, the solvent was removed under reduced pressure, and a solid product of 2-(2-chlorophenyl)-N-cyclohexyl-2-(N-(3-fluorophenyl)-2-(N-methylaziridine-1-sulfonylamino)acetamido)acetamide (18 mg, yield of 17%) was obtained by separation by column chromatography on silica gel (PE:EA=2:1).

$^1$H-NMR (400 MHz, CDCl$_3$): δ=7.34 (d, J=8.0 Hz, 1H), 7.12 (t, J=7.2 Hz, 2H), 7.01-6.96 (m, 3H), 6.89-6.86 (m, 1H), 6.46 (s, 1H), 5.49 (d, J=8.0 Hz, 1H), 3.93-3.83 (m, 2H), 3.72 (d, J=17.2 Hz, 1H), 3.09 (s, 3H), 2.26 (s, 4H), 2.01-1.98 (m, 2H), 1.91-1.88 (m, 1H), 1.75-1.58 (m, 3H), 1.41-0.94 (m, 5H).

m/z=537 [M+H]$^+$.

Example 13: 4-(aziridine-1-sulfonylamino)-N-(1-(2-chlorophenyl)-2-((3,3-difluorocyclobutyl)amino)-2-oxoethyl)-N-(3-fluorophenyl)butanamide

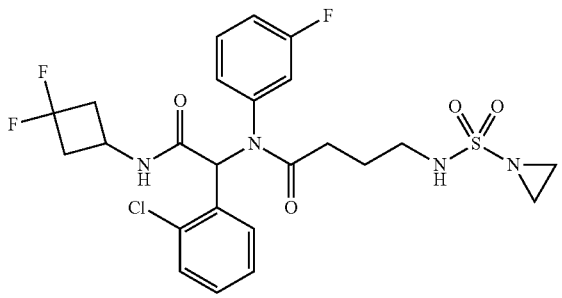 [SMILES: O=C(NC1CC(F)(F)C1)C(c1ccccc1Cl)N(C(=O)CCCNS(=O)(=O)N1CC1)c1cccc(F)c1]

Step A: methyl 4-((N-(2-chloroethyl)aminosulfonyl)amino)butanoate

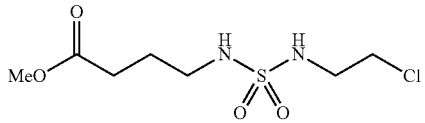 [SMILES: COC(=O)CCCNS(=O)(=O)NCCCl]

With reference to step D of Example 1, methyl 4-((N-(2-chloroethyl)aminosulfonyl)amino)butanoate (787 mg, yield of 47%) was obtained from methyl 4-aminobutyrate hydrochloride (1 g, 6.51 mmol).

$^1$H-NMR (400 MHz, CDCl$_3$): δ=4.69 (s, 1H), 4.49 (s, 1H), 3.76-3.68 (m, 5H), 3.44-3.40 (m, 2H), 3.18-3.14 (m, 2H), 2.45 (t, J=7.0 Hz, 2H), 1.96-1.89 (m, 2H).

Step B: 4-(aziridine-1-sulfonylamino)butanoic Acid

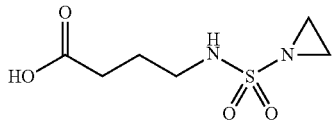 [SMILES: O=C(O)CCCNS(=O)(=O)N1CC1]

With reference to step C of Example 6, 4-(aziridine-1-sulfonylamino)butanoic acid (590 mg, yield of 93%) was obtained from methyl 4-((N-(2-chloroethyl)aminosulfonyl)amino)butanoate (787 mg, 3.04 mmol).

Step C: 4-(aziridine-1-sulfonylamino)-N-(1-(2-chlorophenyl)-2-((3,3-difluorocyclobutyl)amino)-2-oxoethyl)-N-(3-fluorophenyl)butanamide

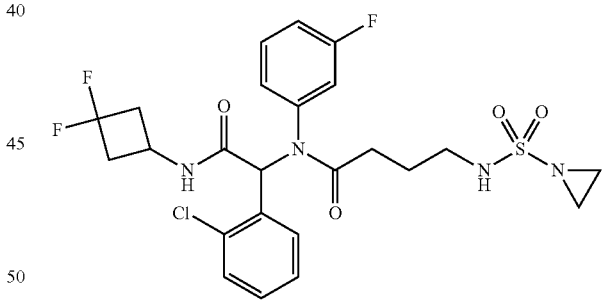

With stirring and at room temperature, o-chlorobenzaldehyde (46 µL, 0.405 mmol) was added in a solution of 3-fluoroaniline (39 µL, 0.405 mmol) in methanol; after reacting for 15 min, 4-(aziridine-1-sulfonylamino)butanoic acid (90 mg, 0.432 mmol) was added thereto; and following further reacting for 30 min, 1,1-difluoro-3-isocyanocyclobutane (47 mg, 0.405 mmol) was added. The mixture was reacted overnight at room temperature, evaporated under reduced pressure and concentrated, and separated by column chromatography on silica gel, to give 4-(aziridine-1-sulfonylamino)-N-(1-(2-chlorophenyl)-2-((3,3-difluorocyclobutyl)amino)-2-oxoethyl)-N-(3-fluorophenyl)butanamide (50 mg, yield of 21%).

$^1$H-NMR (400 MHz, CDCl$_3$): δ=7.33 (d, J=8.1 Hz, 1H), 7.19-7.06 (m, 3H), 7.05-6.94 (m, 2H), 6.91-6.87 (m, 1H), 6.62 (d, J=6.4 Hz, 1H), 6.44 (s, 1H), 5.74 (t, J=5.8 Hz, 1H), 4.34-4.21 (m, 1H), 3.30-3.19 (m, 2H), 3.08-2.86 (m, 2H), 2.68-2.39 (m, 2H), 2.27 (s, 4H), 2.23-2.19 (m, 2H), 1.97-1.87 (m, 2H).

m/z=559 [M+H]⁺.

Example 14: 3-(aziridin-1-ylsulfonyl)-N-(1-(2-chlorophenyl)-2-((3,3-difluorocyclobutyl)amino)-2-oxoethyl)-N-(3-fluorophenyl)propanamide

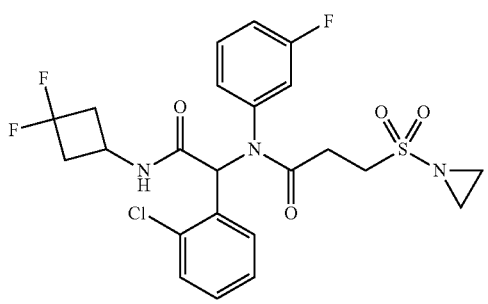 [SMILES: O=C(NC1CC(F)(F)C1)C(c1ccccc1Cl)N(C(=O)CCS(=O)(=O)N1CC1)c1cccc(F)c1]

With reference to step B of Example 1, 3-(aziridine-1-ylsulfonyl)-N-(1-(2-chlorophenyl)-2-((3,3-difluorocyclobutyl)amino)-2-oxoethyl)-N-(3-fluorophenyl) propanamide (46 mg, yield of 26%) was obtained from 3-(aziridin-1-ylsulfonyl)propanoic acid (60 mg, 0.335 mmol) and 1,1-difluoro-3-isocyanocyclobutane (39 mg, 0.335 mmol).

¹H-NMR (400 MHz, CDCl₃): δ=7.34 (d, J=8.0 Hz, 1H), 7.23-7.05 (m, 3H), 7.03-6.87 (m, 4H), 6.52 (s, 1H), 6.40 (d, J=5.2 Hz, 1H), 4.33 (m, 1H), 3.68-3.61 (m, 1H), 3.53-3.41 (m, 1H), 3.05-2.96 (m, 2H), 2.78-2.44 (m, 4H), 2.34 (s, 4H).

m/z=530 [M+H]⁺.

Example 15: 2-(aziridin-1-ylsulfonyl)-N-(1-(2-chlorophenyl)-2-(cyclohexylamino)-2-oxoethyl)-N-(3-fluorophenyl)acetamide

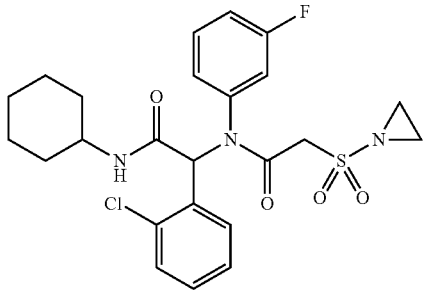 [SMILES: O=C(NC1CCCCC1)C(c1ccccc1Cl)N(C(=O)CS(=O)(=O)N1CC1)c1cccc(F)c1]

Step A: methyl 2-(chlorosulfonyl)acetate

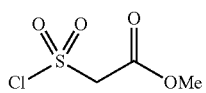

With reference to step A of Example 6, methyl 2-(chlorosulfonyl)acetate (14.7 g, yield of 79%) was obtained from methyl thioglycolate (9.6 mL, 108 mmol).

¹H-NMR (400 MHz, CDCl₃): δ=4.61 (s, 2H), 3.91 (s, 3H).

Step B: methyl 2-(N-(2-chloroethyl)aminosulfonyl)acetate

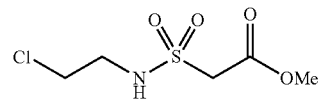 [SMILES: COC(=O)CS(=O)(=O)NCCCl]

With reference to step B of Example 6, methyl 2-(N-(2-chloroethyl)aminosulfonyl)acetate (3.22 g, yield of 18%) was obtained from methyl 2-(chlorosulfonyl)acetate (14.7 g, 85.2 mmol).

¹H-NMR (400 MHz, CDCl₃): δ=5.37 (s, 1H), 4.07 (s, 2H), 3.82 (s, 3H), 3.68 (t, J=5.7 Hz, 2H), 3.55-3.50 (m, 2H).

Step C: 2-(aziridin-1-ylsulfonyl)acetic Acid

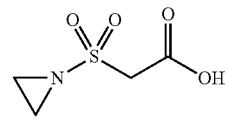

With reference to step C of Example 6, 2-(aziridin-1-ylsulfonyl)acetic acid (268 mg, yield of 70%) was obtained from methyl 2-(N-(2-chloroethyl)aminosulfonyl)acetate (500 mg, 2.32 mmol).

¹H-NMR (400 MHz, CDCl₃): δ=9.11 (s, 1H), 4.24 (s, 2H), 2.51 (s, 4H).

Step D: 2-(aziridin-1-ylsulfonyl)-N-(1-(2-chlorophenyl)-2-(cyclohexylamino)-2-oxoethyl)-N-(3-fluorophenyl)acetamide

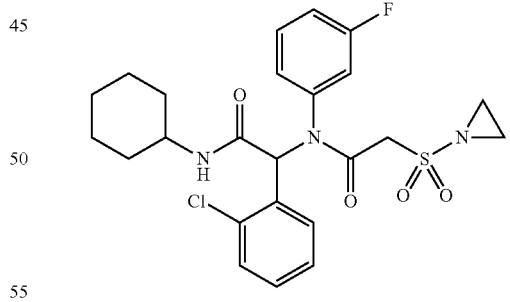

With reference to step B of Example 1, 2-(aziridin-1-ylsulfonyl)-N-(1-(2-chlorophenyl)-2-(cyclohexylamino)-2-oxoethyl)-N-(3-fluorophenyl)acetamide (20 mg, yield of 9%) was obtained from 2-(aziridin-1-ylsulfonyl)acetic acid (70 mg, 0.424 mmol).

¹H-NMR (400 MHz, CDCl₃): δ=7.62 (s, 1H), 7.34 (s, 1H), 7.16 (s, 1H), 7.08-6.80 (m, 4H), 6.67-6.58 (m, 1H), 6.52 (s, 1H), 5.84 (s, 1H), 4.10 (d, J=1.4 Hz, 2H), 3.99-3.78 (m, 1H), 2.49 (d, J=2.5 Hz, 4H), 2.05-1.90 (m, 2H), 1.78-1.63 (m, 4H), 1.50-1.03 (m, 4H).

m/z=508 [M+H]⁺.

Example 16: 2-(aziridine-1-sulfonylamino)-N-(1-(2-chlorophenyl)-2-(cyclohexylamino)-2-oxoethyl)-N-(3,5-difluorophenyl)acetamide

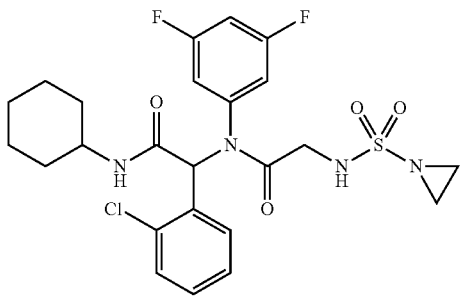 [SMILES: O=C(NC1CCCCC1)C(c1ccccc1Cl)N(C(=O)CNS(=O)(=O)N1CC1)c1cc(F)cc(F)c1]

Step A: 2-((N-(2-chloroethyl)aminosulfonyl)amino)-N-(1-(2-chlorophenyl)-2-(cyclohexylamino)-2-oxoethyl)-N-(3,5-difluorophenyl)acetamide

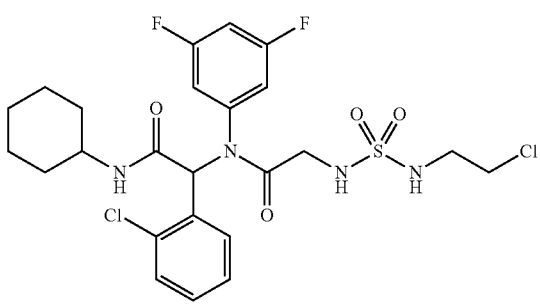 [SMILES: O=C(NC1CCCCC1)C(c1ccccc1Cl)N(C(=O)CNS(=O)(=O)NCCCl)c1cc(F)cc(F)c1]

With reference to step B of Example 1, 2-((N-(2-chloroethyl)aminosulfonyl)amino)-N-(1-(2-chlorophenyl)-2-(cyclohexylamino)-2-oxoethyl)-N-(3,5-difluorophenyl)acetamide (147 mg, yield of 52%) was obtained from 2-(aziridin-1-ylsulfonyl)acetic acid (105 mg, 0.485 mmol) and 3,5-difluoroaniline (63 mg, 0.485 mmol).

m/z=577 [M+H]$^+$.

Step B: 2-(aziridine-1-sulfonylamino)-N-(1-(2-chlorophenyl)-2-(cyclohexylamino)-2-oxoethyl)-N-(3,5-difluorophenyl)acetamide

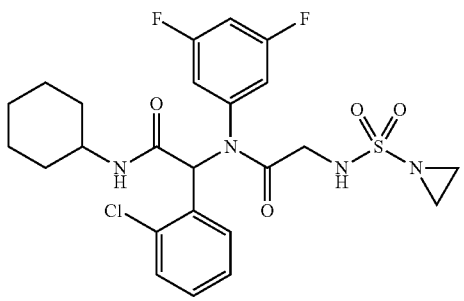 [SMILES: O=C(NC1CCCCC1)C(c1ccccc1Cl)N(C(=O)CNS(=O)(=O)N1CC1)c1cc(F)cc(F)c1]

With reference to step E of Example 1, 2-(aziridine-1-sulfonylamino)-N-(1-(2-chlorophenyl)-2-(cyclohexylamino)-2-oxoethyl)-N-(3,5-difluorophenyl)acetamide (2.95 mg, yield of 2.1%) was obtained from 2-((N-(2-chloroethyl)aminosulfonyl)amino)-N-(1-(2-chlorophenyl)-2-(cyclohexylamino)-2-oxoethyl)-N-(3,5-difluorophenyl)acetamide (147 mg, 0.254 mmol).

$^1$H-NMR (400 MHz, CDCl$_3$): δ=7.58-7.46 (brs, 1H), 7.40-7.36 (m, 1H), 7.26-7.18 (m, 1H), 7.03-7.02 (m, 2H), 6.69-6.60 (m, 1H), 6.40 (s, 1H), 6.38-6.23 (brs, 1H), 5.45-5.40 (m, 2H), 3.90-3.75 (m, 3H), 2.31 (s, 4H), 2.05-1.96 (m, 1H), 1.92-1.84 (m, 1H), 1.78-1.60 (m, 2H), 1.42-1.02 (m, 6H).

m/z=541 [M+H]$^+$.

Example 17: 2-(aziridine-1-sulfonylamino)-N-(1-(2-chlorophenyl)-2-(cyclohexylamino)-2-oxoethyl)-N-(5-fluoropyridin-3-yl)acetamide

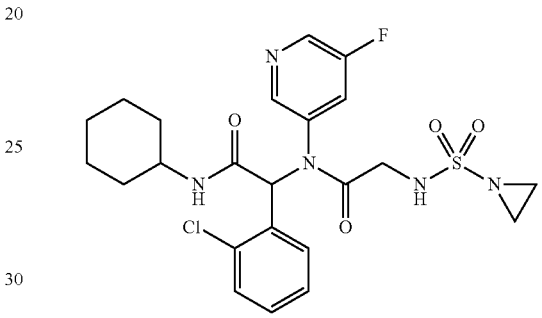

Step A: 2-((N-(2-chloroethyl)aminosulfonyl)amino)-N-(1-(2-chlorophenyl)-2-(cyclohexylamino)-2-oxoethyl)-N-(5-fluoropyridin-3-yl)acetamide

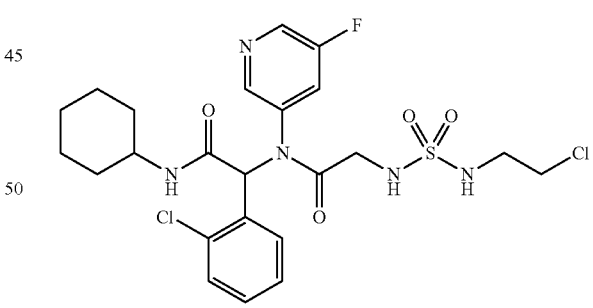

With reference to step B of Example 1, 2-((N-(2-chloroethyl)aminosulfonyl)amino)-N-(1-(2-chlorophenyl)-2-(cyclohexylamino)-2-oxoethyl)-N-(5-fluoropyridin-3-yl)acetamide (71 mg, yield of 26%) was obtained from 2-(aziridin-1-ylsulfonyl)acetic acid (105 mg, 0.485 mmol) and 3-amino-5-fluoropyridine (63 mg, 0.484 mmol).

m/z=560 [M+H]$^+$.

Step B: 2-(aziridine-1-sulfonylamino)-N-(1-(2-chlorophenyl)-2-(cyclohexylamino)-2-oxoethyl)-N-(5-fluoropyridin-3-yl)acetamide

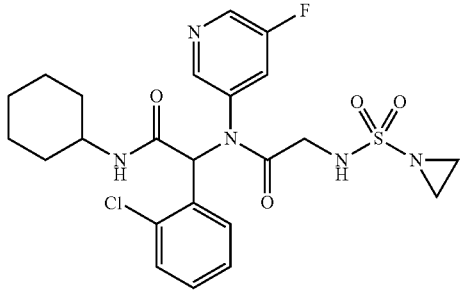 [SMILES: O=C(NC1CCCCC1)C(c1ccccc1Cl)N(C(=O)CNS(=O)(=O)N1CC1)c1cncc(F)c1]

With reference to step E of Example 1, 2-(aziridine-1-sulfonylamino)-N-(1-(2-chlorophenyl)-2-(cyclohexylamino)-2-oxoethyl)-N-(5-fluoropyridin-3-yl)acetamide (15 mg, yield of 22%) was obtained from 2-((N-(2-chloroethyl)aminosulfonyl)amino)-N-(1-(2-chlorophenyl)-2-(cyclohexylamino)-2-oxoethyl)-N-(5-fluoropyridin-3-yl)acetamide (71 mg, 0.127 mmol).

$^1$H-NMR (400 MHz, CDCl$_3$): δ=8.33 (d, J=2.4, 1H), 7.39-7.37 (m, 1H), 7.24-7.17 (m, 2H), 7.03-6.93 (m, 3H), 6.46 (s, 1H), 5.45-5.44 (m, 2H), 3.85-3.68 (m, 3H), 2.31 (s, 4H), 2.02-1.98 (m, 1H), 1.89-1.87 (m, 1H), 1.73-0.96 (m, 8H).

m/z=524 [M+H]$^+$.

Example 18: (S)-1-(aziridin-1-ylsulfonyl)-N—((R)-1-(2-chlorophenyl)-2-(cyclohexylamino)-2-oxoethyl)-N-(3-fluorophenyl)pyrrolidine-2-carboxamide

Example 19: (S)-1-(aziridin-1-ylsulfonyl)-N—((S)-1-(2-chlorophenyl)-2-(cyclohexylamino)-2-oxoethyl)-N-(3-fluorophenyl)pyrrolidine-2-carboxamide (Example 18)

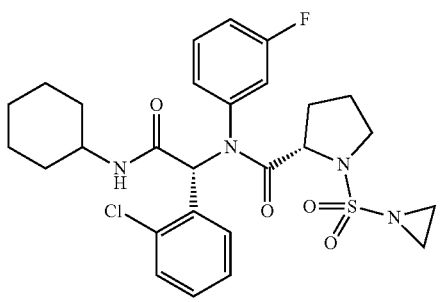

(Example 19)

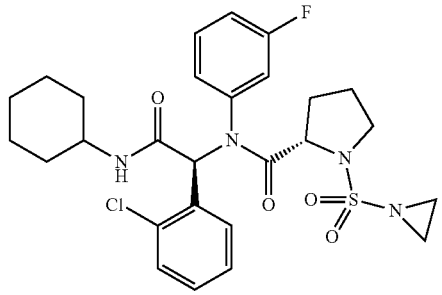

Step A: tert-butyl (S)-1-(N-(2-chloroethyl)aminosulfonyl)pyrrolidine-2-carboxylate

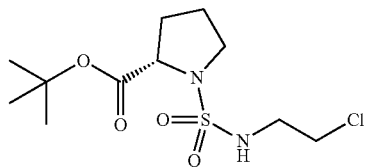 [SMILES: CC(C)(C)OC(=O)[C@@H]1CCCN1S(=O)(=O)NCCCl]

2-(Chloroethyl)aminosulfonyl chloride (471 mg, 2.89 mmol) was added in a solution of L-proline tert-butyl ester hydrochloride (200 mg, 0.96 mmol) and DIEA (622 μL, 4.81 mmol) in dichloromethane at 0° C., and the mixture was warmed up to room temperature and stirred overnight. After completion of the reaction, the reaction mixture was adjusted to a neutral pH by adding with 1N HCl. The organic phase was separated, dried over anhydrous sodium sulfate and concentrated under reduced pressure. A solid product of tert-butyl (S)-1-(N-(2-chloroethyl)aminosulfonyl)pyrrolidine-2-carboxylate (263 mg, yield of 87%) was obtained by separation with column chromatography on silica gel (PE:EA=4:1).

$^1$H-NMR (400 MHz, CDCl$_3$): δ=5.08 (q, J=6.0 Hz, 1H), 4.32-4.26 (m, 1H), 3.73-3.65 (m, 2H), 3.56-3.42 (m, 4H), 2.32-2.22 (m, 1H), 2.03-1.94 (m, 3H), 1.47 (d, J=4.0 Hz, 9H).

Step B: (S)-1-(N-(2-chloroethyl)aminosulfonyl)pyrrolidine-2-carboxylic Acid

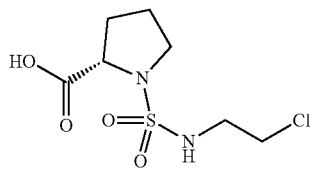 [SMILES: O=C(O)[C@@H]1CCCN1S(=O)(=O)NCCCl]

1 mL of TFA was added in a solution of tert-butyl (S)-1-(N-(2-chloroethyl)aminosulfonyl)pyrrolidine-2-carboxylate (150 mg, 0.48 mmol) in dichloromethane at 0° C., with stirring overnight at room temperature. After completion of the reaction, a solid product of (S)-1-(N-(2-chloroethyl)aminosulfonyl)pyrrolidine-2-carboxylic acid (123 mg, yield of 100%) was obtained by removing TFA and the solvent through spin-evaporation under reduced pressure.

¹H-NMR (400 MHz, DMSO-d₆): δ=12.57 (br s, 1H), 7.53 (t, δ=5.6 Hz, 1H), 4.13-4.10 (m, 1H), 3.67-3.62 (m, 2H), 3.33-3.23 (m, 4H), 2.25-2.14 (m, 1H), 1.90-1.84 (m, 3H).

Step C: (S)-1-(N-(2-chloroethyl)aminosulfonyl)-N—((R)-1-(2-chlorophenyl)-2-cyclohexylamino-2-oxoethyl)-N-(3-fluorophenyl)pyrrolidine-2-carboxamide (C1)

(S)-1-(N-(2-chloroethyl)aminosulfonyl)-N—((S)-1-(2-chlorophenyl)-2-cyclohexylamino-2-oxoethyl)-N-(3-fluorophenyl)pyrrolidine-2-carboxamide (C2)

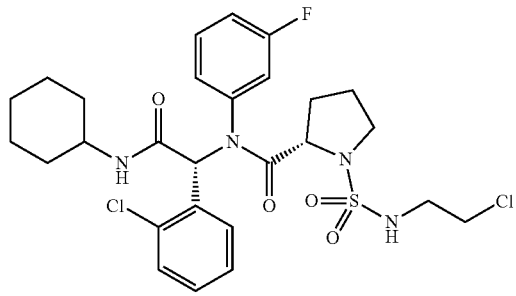

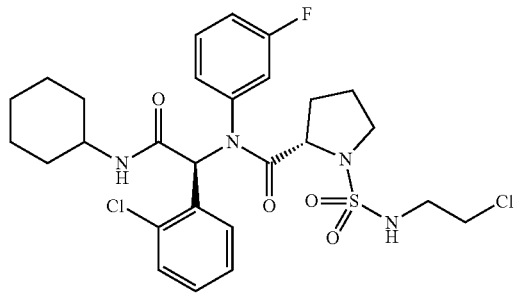

At room temperature, o-chlorobenzaldehyde (66 μL, 0.58 mmol) and m-fluoroaniline (56 μL, 0.58 mmol) were added in 10 mL of methanol; following stirring for 10 min, (S)-1-(N-(2-chloroethyl)aminosulfonyl)pyrrolidine-2-carboxylic acid (149 mg, 0.58 mmol) was added thereto; and cyclohexyl isocyanide (68 mg, 0.58 mmol) was added following stirring for a further 10 min, and the mixture was stirred overnight at room temperature. After completion of the reaction, the solvent was removed under reduced pressure. The solid products of (S)-1-(N-(2-chloroethyl)aminosulfonyl)-N—((R)-1-(2-chlorophenyl)-2-cyclohexylamino-2-oxoethyl)-N-(3-fluorophenyl)pyrrolidine-2-carboxamide (46 mg, yield of 13.2%) and (S)-1-(N-(2-chloroethyl)aminosulfonyl)-N—((S)-1-(2-chlorophenyl)-2-cyclohexylamino-2-oxoethyl)-N-(3-fluorophenyl)pyrrolidine-2-carboxamide (46 mg, yield of 13.2%) were obtained by separation through column chromatography on silica gel (PE:EA=2:1).

C1: ¹H-NMR (400 MHz, CDCl₃): δ=7.34-7.31 (m, 2H), 7.13 (t, J=7.2 Hz, 2H), 6.93-6.90 (m, 3H), 6.61 (m, 1H), 6.36 (d, J=7.6 Hz, 2H), 5.49 (t, J=4.0 Hz, 1H), 4.13 (t, J=6.8 Hz, 1H), 3.95-3.86 (m, 1H), 3.71-3.68 (m, 2H), 3.55-3.46 (m, 4H), 2.07-1.63 (m, 6H), 1.39-1.18 (m, 8H).
m/z=599 [M+H]⁺.

C2: ¹H-NMR (400 MHz, CDCl₃): δ=7.58 (br s, 1H), 7.32 (d, J=8.0 Hz, 1H), 7.13 (t, J=6.4 Hz, 2H), 6.98-6.93 (m, 4H), 6.86 (t, J=8.4 Hz, 1H), 6.51 (s, 1H), 5.37 (d, J=7.6 Hz, 1H), 5.23 (t, J=4.0 Hz, 1H), 4.30-4.27 (m, 1H), 3.87-3.82 (m, 1H), 3.76-3.72 (m, 2H), 3.55-3.46 (m, 4H), 2.10-1.61 (m, 9H), 1.38-1.02 (m, 5H).
m/z=599 [M+H]⁺.

Step D: (S)-1-(aziridin-1-ylsulfonyl)-N—((R)-1-(2-chlorophenyl)-2-(cyclohexylamino)-2-oxoethyl)-N-(3-fluorophenyl)pyrrolidine-2-carboxamide (Example 18)

(S)-1-(aziridin-1-ylsulfonyl)-N—((S)-1-(2-chlorophenyl)-2-(cyclohexylamino)-2-oxoethyl)-N-(3-fluorophenyl)pyrrolidine-2-carboxamide (Example 19)

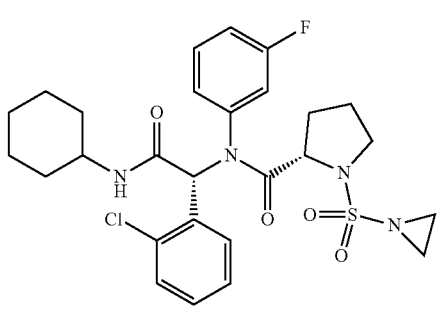
(Example 18)

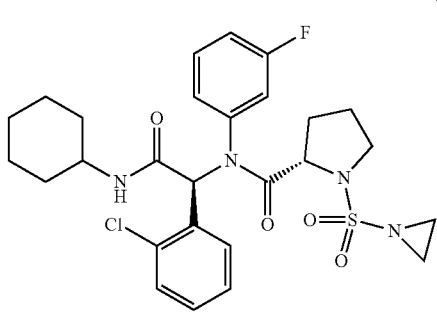
(Example 19)

(S)-1-(N-(2-chloroethyl)aminosulfonyl)-N—((R)-1-(2-chlorophenyl)-2-cyclohexylamino-2-oxoethyl)-N-(3-fluorophenyl)pyrrolidine-2-carboxamide (C1) (62 mg, 0.10 mmol) and potassium carbonate (29 mg, 0.21 mmol) were added in 5 mL of DMF at room temperature, and the mixture was stirred overnight at room temperature. After completion of the reaction, the mixture was added with 20 mL of dichloromethane, and washed with water (30 mL×3). The organic phase was dried over anhydrous sodium sulfate, and separated by column chromatography on silica gel (PE:EA=2:1), to give a solid product of (S)-1-(aziridin-1-ylsulfonyl)-N—((R)-1-(2-chlorophenyl)-2-(cyclohexylamino)-2-oxoethyl)-N-(3-fluorophenyl)pyrrolidine-2-carboxamide (45 mg, yield of 77%).

(S)-1-(aziridin-1-ylsulfonyl)-N—((S)-1-(2-chlorophenyl)-2-(cyclohexylamino)-2-oxoethyl)-N-(3-fluorophenyl)pyrrolidine-2-carboxamide was obtained from C2 by the same method.

Example 18: ¹H-NMR (400 MHz, CDCl₃): δ=7.31 (d, J=8.0 Hz, 2H), 7.12 (t, J=7.6 Hz, 2H), 7.02-6.92 (m, 3H), 6.56 (s, 1H), 6.45 (d, J=7.2 Hz, 2H), 4.23-4.20 (m, 1H), 3.91-3.83 (m, 1H), 3.73-3.67 (m, 1H), 3.56-3.52 (m, 1H), 2.24 (s, 4H), 1.98-1.86 (m, 5H), 1.75-1.62 (m, 3H), 1.41-1.14 (m, 6H).

m/z=563 [M+H]⁺.

Example 19: ¹H-NMR (400 MHz, CDCl₃): δ=7.64 (br s, 1H), 7.31 (br s, 1H), 7.11 (br s, 1H), 7.02-6.92 (m, 3H), 6.86-6.79 (m, 2H), 6.51 (s, 1H), 5.44 (br s, 1H), 4.36-4.31 (m, 1H), 3.88-3.81 (m, 1H), 3.70-3.65 (m, 1H), 3.56-3.52 (m, 1H), 2.27 (s, 4H), 2.19-2.10 (m, 2H), 2.00-1.79 (m, 4H), 1.74-1.68 (m, 2H), 1.40-1.01 (m, 6H).

m/z=563 [M+H]⁺.

Example 20: 5-(aziridin-1-ylsulfonyl)-N-(1-(2-chlorophenyl)-2-(cyclohexylamino)-2-oxoethyl)-N-(3-fluorophenyl)pentanamide

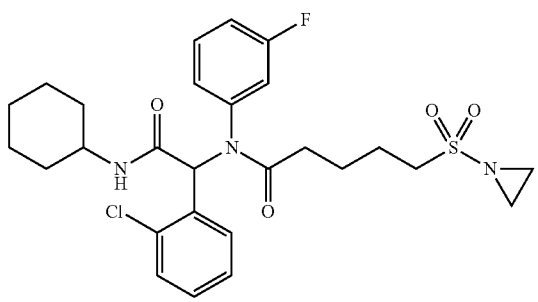 [SMILES: O=C(NC1CCCCC1)C(c1ccccc1Cl)N(C(=O)CCCCS(=O)(=O)N1CC1)c1cccc(F)c1]

Step A: methyl 5-(chlorosulfonyl)pentanoate

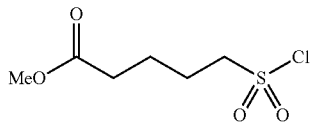 [SMILES: COC(=O)CCCCS(=O)(=O)Cl]

To a saturated solution of sodium thiosulfate pentahydrate (3.3 g, 13.3 mmol) in 50% methanol, methyl 5-chloropentanoate (2 g, 13.3 mmol) was added with vigorously stirring, and the reaction solution was then heated to reflux and reacted for about 3 h, until the reaction mixture became in one phase. A concentrate was obtained by evaporation under reduced pressure, and then added with acetic acid and ice as reaction solvents. With stirring and in an ice bath, chlorine gas was introduced until the reaction solution turned pale green. Chlorine gas was continuously introduced for another 0.5 h, and it was then driven off by introducing nitrogen gas in the reaction system. The reaction solution was extracted with dichloromethane. The combined organic phase was washed with brine, dried over anhydrous sodium sulfate, filtered and concentrated in vacuo, to give methyl 5-(chlorosulfonyl)pentanoate (2.23 g, yield of 78%).

Step B: methyl 5-(N-(2-chloroethyl)aminosulfonyl)pentanoate

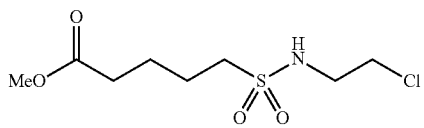 [SMILES: COC(=O)CCCCS(=O)(=O)NCCCl]

With reference to step B of Example 6, methyl 5-(N-(2-chloroethyl)aminosulfonyl)pentanoate (335 mg, yield of 40%) was obtained from methyl 5-(chlorosulfonyl)pentanoate (700 mg, 3.26 mmol).

¹H-NMR (400 MHz, CDCl₃): δ=4.71 (t, J=6.1 Hz, 1H), 3.76-3.62 (m, 5H), 3.57-3.44 (m, 2H), 3.17-3.04 (m, 2H), 2.40 (t, J=7.1 Hz, 2H), 1.95-1.73 (m, 4H).

Step C: 5-(aziridin-1-ylsulfonyl)pentanoic Acid

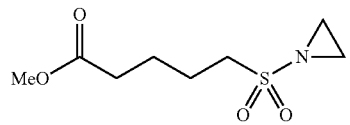 [SMILES: COC(=O)CCCCS(=O)(=O)N1CC1]

With reference to step C of Example 6, 5-(aziridin-1-ylsulfonyl)pentanoic acid (130 mg, yield of 92%) was obtained from methyl 5-(N-(2-chloroethyl)aminosulfonyl)pentanoate (175 mg, 0.68 mmol).

Step D: 5-(aziridin-1-ylsulfonyl)-N-(1-(2-chlorophenyl)-2-(cyclohexylamino)-2-oxoethyl)-N-(3-fluorophenyl)pentanamide

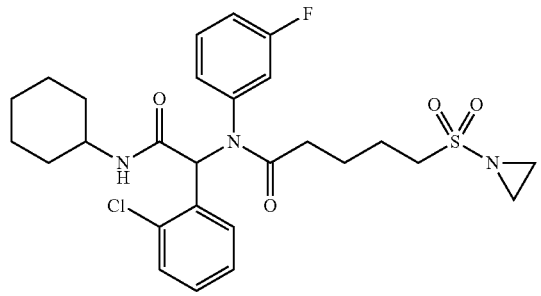 [SMILES: O=C(NC1CCCCC1)C(c1ccccc1Cl)N(C(=O)CCCCS(=O)(=O)N1CC1)c1cccc(F)c1]

(RS)-5-(aziridin-1-ylsulfonyl)-N-(1-(2-chlorophenyl)-2-(cyclohexylamino)-2-oxoethyl)-N-(3-fluorophenyl)pentanamide (43 mg, yield of 14%) was obtained from 5-(aziridin-1-ylsulfonyl)pentanoic acid (120 mg, 0.579 mmol, 1 eq) by the synthesis procedure as described in step B of Example 1.

¹H-NMR (400 MHz, CDCl₃): δ=7.32 (d, J=7.8 Hz, 1H), 7.17-7.04 (m, 3H), 7.05-6.92 (m, 3H), 6.91-6.82 (m, 1H), 6.40 (s, 1H), 5.47 (d, J=8.1 Hz, 1H), 3.83 (m, 1H), 3.08 (t, J=7.6 Hz, 2H), 2.33 (s, 4H), 2.12 (t, J=6.9 Hz, 2H), 1.99 (d, J=9.4 Hz, 1H), 1.93-1.54 (m, 9H), 1.42-0.94 (m, 4H).

m/z=550 [M+H]⁺.

Example 21: 4-(aziridin-1-ylsulfonyl)-N-(1-(2-chlorophenyl)-2-(cyclohexylamino)-2-oxoethyl)-N-(3-fluorophenyl)butanamide

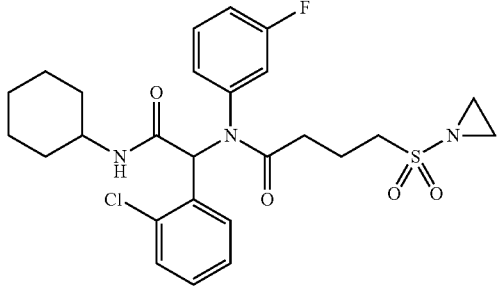 [SMILES: O=C(NC1CCCCC1)C(c1ccccc1Cl)N(C(=O)CCCS(=O)(=O)N1CC1)c1cccc(F)c1]

Step A: a mixture of ethyl 4-(chlorosulfonyl)butanoate and ethyl 4-(bromosulfonyl)butanoate

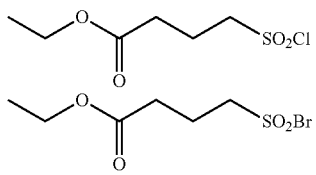

With reference to step A of Example 19, a mixture of ethyl 4-(chlorosulfonyl)butanoate and ethyl 4-(bromosulfonyl)butanoate (6.07 g, yield of 98%) was obtained from ethyl 4-bromobutanoate (5 g, 26 mmol).

Step B: ethyl 4-(N-(2-chloroethyl)aminosulfonyl)butanoate

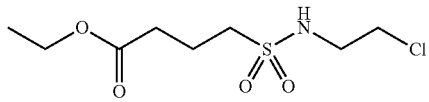

Ethyl 4-(N-(2-chloroethyl)aminosulfonyl)butanoate (387 mg, yield of 36%) was obtained from ethyl 4-(chlorosulfonyl)butanoate and ethyl 4-(bromosulfonyl)butanoate (1 g, 4.22 mmol) by the synthesis procedure as described in step B of Example 6.

$^1$H-NMR (400 MHz, CDCl$_3$): δ=4.75 (t, J=6.0 Hz, 1H), 4.15 (q, J=7.1 Hz, 2H), 3.68 (t, J=5.6 Hz, 2H), 3.50-3.46 (m, 2H), 3.20-3.11 (m, 2H), 2.51 (t, J=7.0 Hz, 2H), 2.21-2.09 (m, 2H), 1.27 (t, J=7.1 Hz, 3H).

Step C: 4-(aziridin-1-ylsulfonyl)butanoic Acid

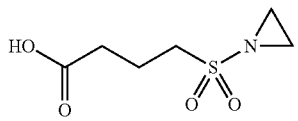 [SMILES: O=C(O)CCCS(=O)(=O)N1CC1]

With reference to step C of Example 6, 4-(aziridin-1-ylsulfonyl)butanoic acid (104 mg, yield of 66%) was obtained from ethyl 4-(N-(2-chloroethyl)aminosulfonyl)butanoate (210 mg, 0.815 mmol).

Step D: 4-(aziridin-1-ylsulfonyl)-N-(1-(2-chlorophenyl)-2-(cyclohexylamino)-2-oxoethyl)-N-(3-fluorophenyl)butanamide

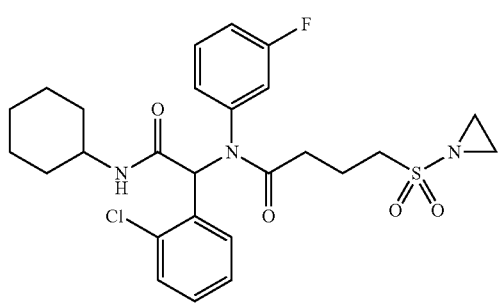 [SMILES: O=C(NC1CCCCC1)C(c1ccccc1Cl)N(C(=O)CCCS(=O)(=O)N1CC1)c1cccc(F)c1]

With reference to step B of Example 1, 4-(aziridin-1-ylsulfonyl)-N-(1-(2-chlorophenyl)-2-(cyclohexylamino)-2-oxoethyl)-N-(3-fluorophenyl)butanamide (26 mg, yield of 9%) was obtained from 4-(aziridin-1-ylsulfonyl)butanoic acid (104 mg, 0.538 mmol).

$^1$H-NMR (400 MHz, CDCl$_3$): δ=7.33 (d, J=7.4 Hz, 1H), 7.17-7.03 (m, 3H), 7.03-6.91 (m, 3H), 6.91-6.82 (m, 1H), 6.44 (s, 1H), 5.51 (d, J=7.9 Hz, 1H), 3.85 (m, 1H), 3.24 (t, J=7.6 Hz, 2H), 2.40-2.28 (m, 4H), 2.27-2.16 (m, 4H), 2.02-1.88 (m, 2H), 1.79-1.55 (m, 4H), 1.44-0.99 (m, 4H). m/z=536 [M+H]$^+$.

Example 22: 3-(aziridine-1-sulfonylamino)-N-(1-(2-chlorophenyl)-2-cyclohexylamino-2-oxoethyl)-N-(3-fluorophenyl)cyclobutyl carboxamide

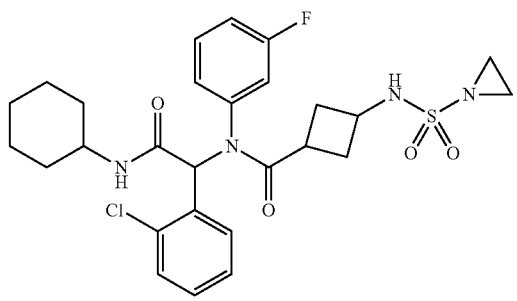 [SMILES: O=C(NC1CCCCC1)C(c1ccccc1Cl)N(C(=O)C1CC(NS(=O)(=O)N2CC2)C1)c1cccc(F)c1]

Step A: benzyl 3-phthalimidocyclobutyl carboxylate

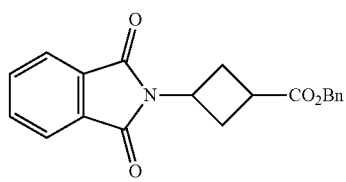 [SMILES: O=C(OCc1ccccc1)C1CC(N2C(=O)c3ccccc3C2=O)C1]

Under protection of nitrogen gas, benzyl 3-hydroxycyclobutyl carboxylate (500 mg, 2.43 mmol), phthalimide (357 mg, 2.43 mmol) and triphenylphosphine (1.91 g, 7.28 mmol) were added in 50 mL of tetrahydrofuran. After cooling down to 0° C., the reaction mixture was added dropwise with DIAD (1.43 mL, 7.28 mmol), and then warmed up to room temperature and stirred overnight. After completion of the reaction, the solvent was removed under reduced pressure, and a solid product of benzyl 3-phthalimidocyclobutyl carboxylate (293 mg, yield of 36%) was obtained by separation through column chromatography on silica gel (PE:EA=2:1).

$^1$H-NMR (400 MHz, CDCl$_3$): δ=7.84-7.82 (m, 2H), 7.72-7.70 (m, 2H), 7.39-7.34 (m, 5H), 5.19 (s, 2H), 5.07-5.04 (m, 1H), 3.40-3.34 (m, 1H), 3.19-3.14 (m, 2H), 2.68-2.62 (m, 2H).

Step B: 3-phthalimidocyclobutyl carboxylic Acid

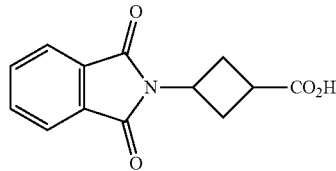 [SMILES: O=C(O)C1CC(N2C(=O)c3ccccc3C2=O)C1]

Benzyl 3-phthalimidocyclobutyl carboxylate (293 mg, 0.87 mmol) and 10% palladium on carbon (93 mg, 0.09 mmol) were added in 10 mL of ethanol at room temperature. Air was drawn off, and hydrogen gas was introduced, with stirring overnight. After completion of the reaction, the palladium on carbon was removed by filtration, and a solid product of 3-phthalimidocyclobutyl carboxylic acid (214 mg, yield of 100%) was obtained by concentration.

$^1$H-NMR (400 MHz, CDCl$_3$): δ=7.85-7.83 (m, 2H), 7.73-7.71 (m, 2H), 5.12-5.06 (m, 2H), 3.37-3.34 (m, 1H), 3.25-3.16 (m, 2H), 2.72-2.66 (m, 2H).

Step C: N-(1-(2-chlorophenyl)-2-cyclohexylamino-2-oxoethyl)-3-(1,3-dioxoisoindol-2-yl)-N-(3-fluorophenyl)cyclobutyl carboxamide

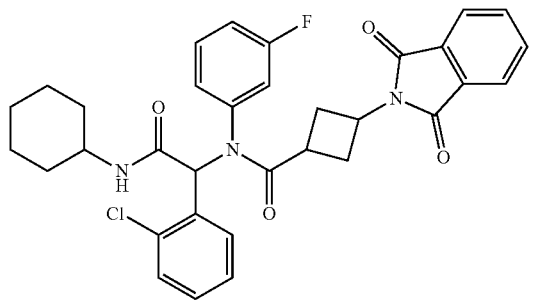 [SMILES: O=C(NC1CCCCC1)C(c1ccccc1Cl)N(C(=O)C1CC(N2C(=O)c3ccccc3C2=O)C1)c1cccc(F)c1]

At room temperature, o-chlorobenzaldehyde (104 µL, 0.92 mmol) and m-fluoroaniline (89 µL, 0.92 mmol) were added in 10 mL of methanol, 3-phthalimidocyclobutyl carboxylic acid (214 mg, 0.87 mmol) was added thereto after stirring for 10 min, and cyclohexyl isocyanide (67 mg, 0.61 mmol) was then added following stirring for another 10 min. The mixture was stirred overnight at room temperature. After completion of the reaction, the solvent was removed under reduced pressure, and a solid product of N-(1-(2-chlorophenyl)-2-cyclohexylamino-2-oxoethyl)-3-(1,3-dioxoisoindol-2-yl)-N-(3-fluorophenyl)cyclobutyl carboxamide (217 mg, yield of 42%) was obtained by separation through column chromatography on silica gel (PE:EA=2:1).

$^1$H-NMR (400 MHz, CDCl$_3$): δ=7.79-7.76 (m, 2H), 7.68-7.65 (m, 2H), 7.32 (d, J=8.0 Hz, 1H), 7.14-7.04 (m, 4H), 6.98-6.94 (m, 2H), 6.87-6.82 (m, 1H), 6.47 (s, 1H), 5.54 (d, J=8.0 Hz, 1H), 5.10-5.06 (m, 1H), 3.90-3.85 (m, 1H), 3.19-3.15 (m, 1H), 2.83-2.68 (m, 4H), 2.06-2.02 (m, 1H), 1.93-1.90 (m, 1H), 1.76-1.63 (m, 2H), 1.43-1.00 (m, 6H).

m/z=588 [M+H]$^+$.

Step D: 3-amino-N-(1-(2-chlorophenyl)-2-cyclohexylamino-2-oxoethyl)-N-(3-fluorophenyl)cyclobutyl carboxamide

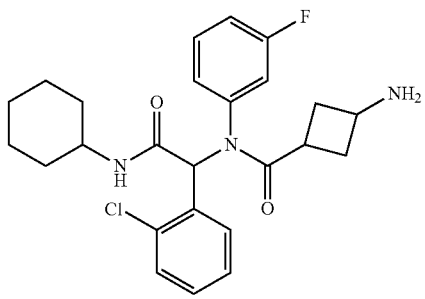 [SMILES: NC1CC(C(=O)N(c2cccc(F)c2)C(C(=O)NC2CCCCC2)c2ccccc2Cl)C1]

Hydrazine hydrate (94 µL, 1.93 mmol) was added in a solution of N-(1-(2-chlorophenyl)-2-cyclohexylamino-2-oxoethyl)-3-(1,3-dioxoisoindol-2-yl)-N-(3-fluorophenyl) cyclobutyl carboxamide (217 mg, 0.37 mmol) in ethanol, followed by stirring at 80° C. for 4 h. After completion of the reaction, the mixture was filtered, and the obtained mother solution was concentrated and separated by column chromatography on silica gel (PE:EA=5:1) to give a solid product of 3-amino-N-(1-(2-chlorophenyl)-2-cyclohexylamino-2-oxoethyl)-N-(3-fluorophenyl)cyclobutyl carboxamide (118 mg, yield of 71%).

$^1$H-NMR (400 MHz, CDCl$_3$): δ=7.31 (d, J=8.0 Hz, 1H), 7.11 (t, J=7.2 Hz, 1H), 7.05-7.03 (m, 2H), 6.97-6.93 (m, 1H), 6.85-6.81 (m, 2H), 6.43 (s, 1H), 5.61 (d, J=8.0 Hz, 1H), 3.88-3.83 (m, 1H), 3.70-3.67 (m, 1H), 2.96-2.92 (m, 1H), 2.66-2.60 (m, 2H), 2.02-1.97 (m, 1H), 1.92-1.87 (m, 4H), 1.77-1.58 (m, 4H), 1.38-1.01 (m, 6H).

m/z=458 [M+H]$^+$.

Step E: 3-((N-(2-chloroethyl)sulfonylamino)amino)-N-(1-(2-chlorophenyl)-2-cyclohexylamino-2-oxoethyl)-N-(3-fluorophenyl)-cyclobutyl carboxamide

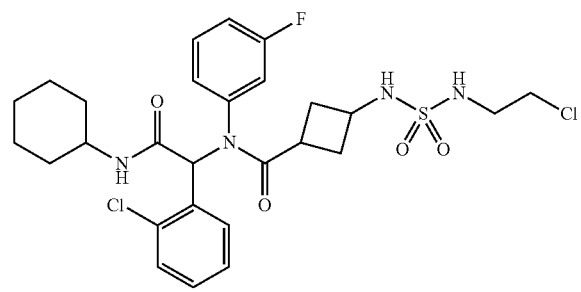 [SMILES: O=C(NC1CCCCC1)C(c1ccccc1Cl)N(C(=O)C1CC(NS(=O)(=O)NCCCl)C1)c1cccc(F)c1]

2-(Chloroethyl)aminosulfonyl chloride (84 mg, 0.52 mmol) was added in a solution of 3-amino-N-(1-(2-chlorophenyl)-2-cyclohexylamino-2-oxoethyl)-N-(3-fluorophenyl)cyclobutyl carboxamide (118 mg, 0.26 mmol) and DIEA (170 µL, 1.03 mmol) in dichloromethane at 0° C. The mixture was warmed up to room temperature and stirred overnight. After completion of the reaction, the reaction solution was adjusted to a neutral pH by adding with 1N HCl. The organic phase was separated, dried over anhydrous sodium sulfate, concentrated under reduced pressure, and separated by column chromatography on silica gel (PE:EA=4:1), to give a solid product (140 mg, yield of 90%).

¹H-NMR (400 MHz, CDCl₃): δ=7.32 (d, J=8.0 Hz, 1H), 7.12 (t, J=6.8 Hz, 1H), 6.99-6.92 (m, 3H), 6.86-6.82 (m, 1H), 6.42 (s, 1H), 5.52 (d, J=8.0 Hz, 1H), 4.77 (t, J=6.4 Hz, 1H), 4.42 (d, J=8.4 Hz, 1H), 4.15-4.09 (m, 1H), 3.86-3.83 (m, 1H), 3.67-3.64 (m, 2H), 3.34-3.31 (m, 2H), 2.94-2.88 (m, 1H), 2.77-2.73 (m, 2H), 2.05-1.88 (m, 4H), 1.77-1.58 (m, 4H), 1.39-1.01 (m, 6H).

m/z=599 [M+H]⁺.

Step F: 3-(aziridine-1-sulfonylamino)-N-(1-(2-chlorophenyl)-2-cyclohexylamino-2-oxoethyl)-N-(3-fluorophenyl)cyclobutyl carboxamide

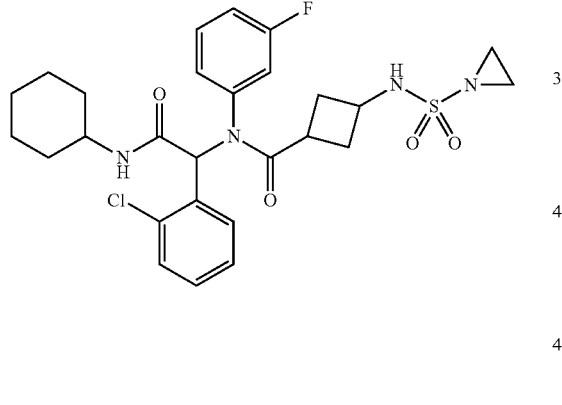

(RS)-3-[N-(2-chloroethyl)sulfamoyl]amino-N-[1-(2-chlorophenyl)-2-cyclohexylamino-2-oxoethyl]-N-(3-fluorophenyl)-cyclobutyl carboxamide (140 mg, 0.23 mmol) and potassium carbonate (65 mg, 0.47 mmol) were added in 5 mL of DMF at room temperature, followed by stirring overnight at room temperature. After completion of the reaction, the mixture was added with 20 mL of dichloromethane, and then washed with water (30 mL×3). The organic phase was dried over anhydrous sodium sulfate, and separated by column chromatography on silica gel (PE:EA=1:1) to give the title product (73 mg, yield of 56%).

¹H-NMR (400 MHz, CDCl₃): δ=7.32 (d, J=6.8 Hz, 1H), 7.12 (t, J=7.2 Hz, 1H), 7.06 (br s, 1H), 7.01-6.93 (m, 2H), 6.85 (t, J=6.8 Hz, 1H), 6.42 (s, 1H), 5.47 (d, J=8.0 Hz, 1H), 4.42 (d, J=8.0 Hz, 1H), 3.87-3.84 (m, 1H), 2.96-2.89 (m, 1H), 2.79-2.75 (m, 2H), 2.26 (s, 4H), 2.05-1.88 (m, 4H), 1.75-1.59 (m, 4H), 1.39-1.01 (m, 6H).

m/z=563 [M+H]⁺.

Example 23: 2-(aziridine-1-sulfonylamino)-N-(1-(2-chlorophenyl)-2-((3,3-difluorocyclobutyl)amino)-2-oxoethyl)-N-(3-trifluoromethylphenyl)acetamide

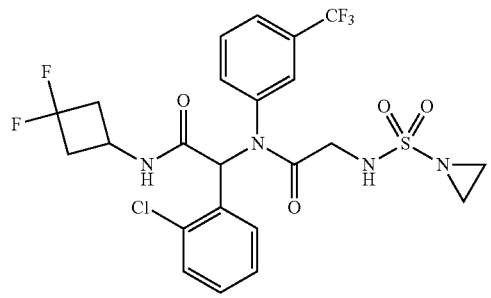

Step A: 2-((N-(2-chloroethyl)sulfonylamino)amino)-N-(1-(2-chlorophenyl)-2-((3,3-difluorocyclobutyl))amino)-2-oxoethyl)-N-(3-trifluoromethylphenyl)acetamide

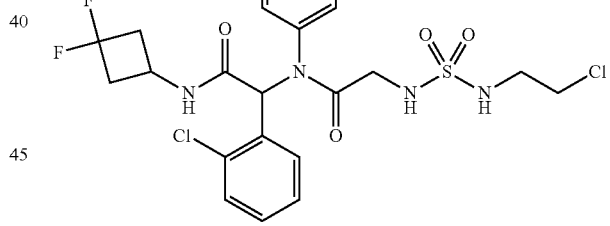

With reference to step C of Example 13, 2-((N-(2-chloroethyl)sulfonylamino)amino)-N-(1-(2-chlorophenyl)-2-((3,3-difluorocyclobutyl))amino)-2-oxoethyl)-N-(3-trifluoromethylphenyl)acetamide (98 mg, yield of 43%) was obtained from 3-(trifluoromethyl)aniline (45.7 µL, 0.37 mmol) and 2-((N-(2-chloroethyl)aminosulfonyl)amino)acetic acid (3 g, 17.9 mmol).

¹H-NMR (400 MHz, CDCl₃): δ=8.17-7.86 (m, 1H), 7.49 (d, J=6.9 Hz, 1H), 7.36-7.34 (m, 1H), 7.19-7.15 (m, 2H), 6.97-6.81 (m, 3H), 6.49 (s, 1H), 6.18 (d, J=6.4 Hz, 1H), 5.59 (t, J=5.1 Hz, 1H), 4.77 (t, J=4.0 Hz, 1H), 4.31 (s, 1H), 3.67 (t, J=5.7 Hz, 2H), 3.57 (s, 2H), 3.45-3.35 (m, 2H), 3.10-2.72 (m, 2H), 2.60-2.55 (m, 1H), 2.49-2.37 (m, 1H).

m/z=617 [M+H]⁺.

Step B: 2-(aziridine-1-sulfonylamino)-N-(1-(2-chlorophenyl)-2-((3,3-difluorocyclobutyl)amino)-2-oxoethyl)-N-(3-trifluoromethylphenyl) acetamide

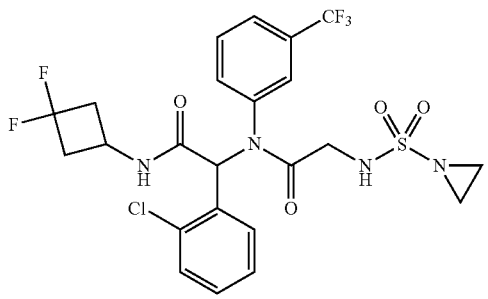

With reference to step E of Example 1, 2-(aziridine-1-sulfonylamino)-N-(1-(2-chlorophenyl)-2-((3,3-difluorocyclobutyl)amino)-2-oxoethyl)-N-(3-trifluoromethylphenyl) acetamide (33 mg, yield of 37%) was obtained from 2-((N-(2-chloroethyl)sulfonylamino)amino)-N-(1-(2-chlorophenyl)-2-((3,3-difluorocyclobutyl)amino)-2-oxoethyl)-N-(3-trifluoromethylphenyl)acetamide (95 mg, 0.154 mmol).

$^1$H-NMR (400 MHz, CDCl$_3$): δ=8.24-7.86 (m, 1H), 7.48 (d, J=7.3 Hz, 1H), 7.37-7.34 (m, 2H), 7.17 (m, 1H), 6.96-6.84 (m, 3H), 6.46 (s, 1H), 6.04 (d, J=6.6 Hz, 1H), 5.61 (s, 1H), 4.31 (s, 1H), 3.72 (s, 2H), 3.11-2.95 (m, 2H), 2.64-2.48 (m, 1H), 2.46-2.41 (m, 1H), 2.31 (s, 4H).

m/z=581 [M+H]$^+$.

Example 24: 1-(aziridin-1-ylsulfonyl)-N-(1-(2-chlorophenyl)-2-cyclohexylamino-2-oxoethyl)-N-(3-fluorophenyl)azetidine-3-carboxamide

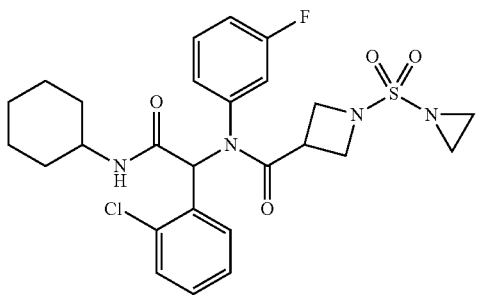 [SMILES: O=C(NC1CCCCC1)C(c1ccccc1Cl)N(C(=O)C1CN(S(=O)(=O)N2CC2)C1)c1cccc(F)c1]

Step A: tert-butyl 3-((1-(2-chlorophenyl))-2-(cyclohexylamino)-2-oxoethyl)(3-fluorophenyl)carbamoyl)azetidine-1-carboxylate

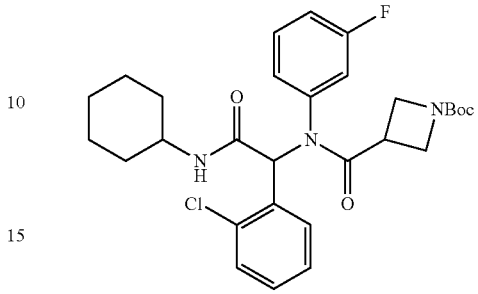

At room temperature, o-chlorobenzaldehyde (113 μL, 1.00 mmol) and m-fluoroaniline (96 μL, 1.00 mmol) were added in 10 mL of methanol, 1-N-Boc-3-azetidine carboxylic acid (201 mg, 1.00 mmol) was added thereto after stirring for 10 min, and cyclohexyl isocyanide (110 mg, 1.00 mmol) was then added following stirring for another 10 min. The mixture was stirred overnight at room temperature. After completion of the reaction, the solvent was removed under reduced pressure, and a solid product of tert-butyl 3-((1-(2-chlorophenyl))-2-(cyclohexylamino)-2-oxoethyl)(3-fluorophenyl)carbamoyl)azetidine-1-carboxylate (330 mg, yield of 61%) was obtained by separation through column chromatography on silica gel (PE:EA=2:1).

$^1$H-NMR (400 MHz, CDCl$_3$): δ=7.33 (d, J=8.4 Hz, 1H), 7.14 (t, J=8.8 Hz, 3H), 7.00-6.94 (m, 3H), 6.88-6.84 (m, 1H), 6.44 (s, 1H), 5.47-5.45 (m, 1H), 4.18-4.14 (m, 2H), 3.87-3.82 (m, 1H), 3.69-3.59 (m, 2H), 3.22-3.18 (m, 1H), 2.05-2.00 (m, 1H), 1.91-1.89 (m, 1H), 1.75-1.59 (m, 3H), 1.40 (s, 9H), 1.36-0.99 (m, 5H).

m/z=544 [M+H]$^+$.

Step B: N-(1-(2-chlorophenyl)-2-cyclohexylamino-2-oxoethyl)-N-(3-fluorophenyl)azetidine-3-carboxamide

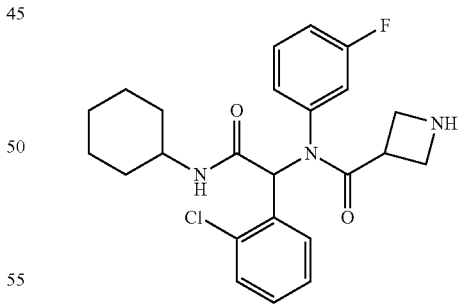

1 mL of TFA was added in a solution of tert-butyl 3-((1-(2-chlorophenyl))-2-(cyclohexylamino)-2-oxoethyl)(3-fluorophenyl)carbamoyl)azetidine-1-carboxylate (330 mg, 0.61 mmol) in dichloromethane at 0° C., following by stirring overnight at room temperature. After completion of the reaction, TFA and the solvent were removed by spin-evaporation under reduced pressure, and a solid product of N-(1-(2-chlorophenyl)-2-cyclohexylamino-2-oxoethyl)-N-(3-fluorophenyl)azetidine-3-carboxamide (200 mg, yield of 74%) was then obtained.

¹H-NMR (400 MHz, CDCl₃): δ=7.32 (d, J=8.0 Hz, 1H), 7.16-7.10 (m, 3H), 6.98-6.97 (m, 3H), 6.94-6.88 (m, 1H), 6.44 (s, 1H), 5.91 (d, J=8.0 Hz, 1H), 4.19 (t, J=9.2 Hz, 2H), 3.82-3.79 (m, 1H), 3.72 (t, J=8.8 Hz, 1H), 3.62 (t, J=8.8 Hz, 1H), 3.53-3.49 (m, 1H), 1.97-1.94 (m, 1H), 1.89-1.85 (m, 1H), 1.73-1.58 (m, 3H), 1.52-1.47 (s, 1H), 1.36-1.02 (m, 5H).

m/z=444 [M+H]⁺.

Step C: 1-(N-(2-chloroethyl)aminosulfonyl)-N-(1-(2-chlorophenyl)-2-cyclohexylamino-2-oxoethyl)-N-(3-fluorophenyl)-azetidine-3-carboxamide

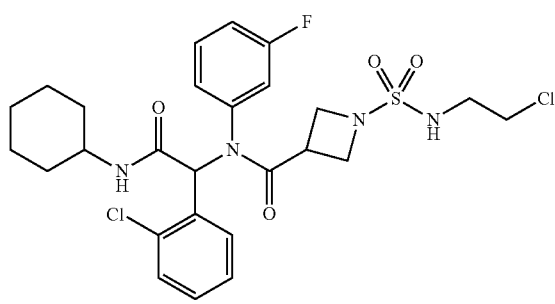 [SMILES: O=C(NC1CCCCC1)C(c1ccccc1Cl)N(C(=O)C1CN(S(=O)(=O)NCCCl)C1)c1cccc(F)c1]

2-(Chloroethyl)aminosulfonyl chloride (147 mg, 0.90 mmol) was added in a solution of N-(1-(2-chlorophenyl)-2-cyclohexylamino-2-oxoethyl)-N-(3-fluorophenyl)azetidine-3-carboxamide (200 mg, 0.45 mmol) and DIEA (320 μL, 1.81 mmol) in dichloromethane at 0° C., and the mixture was warmed up to room temperature and stirred overnight. After completion of the reaction, the mixture was adjusted to a neutral pH by adding with 1N HCl. The organic phase was separated, dried over anhydrous sodium sulfate, concentrated under reduced pressure, and separated by column chromatography on silica gel (PE:EA=2:1), to give a solid product of 1-(N-(2-chloroethyl)aminosulfonyl)-N-(1-(2-chlorophenyl)-2-cyclohexylamino-2-oxoethyl)-N-(3-fluorophenyl)-azetidine-3-carboxamide (100 mg, yield of 38%).

¹H-NMR (400 MHz, CDCl₃): δ=7.34 (d, J=8.0 Hz, 1H), 7.15-7.13 (m, 3H), 6.98-6.97 (m, 3H), 6.89 (t, J=8.0 Hz, 1H), 6.43 (s, 1H), 5.47 (d, J=8.4 Hz, 1H), 4.69 (t, J=6.4 Hz, 1H), 4.17-4.10 (m, 2H), 3.87-3.83 (m, 1H), 3.68-3.63 (m, 3H), 3.59 (t, J=8.8 Hz, 1H), 3.46-3.43 (m, 2H), 3.26 (t, J=8.8 Hz, 1H), 2.02-2.00 (m, 1H), 1.91-1.89 (m, 1H), 1.76-1.64 (m, 2H), 1.40-1.02 (m, 6H).

m/z=585 [M+H]⁺.

Step D: 1-(aziridin-1-ylsulfonyl)-N-(1-(2-chlorophenyl)-2-cyclohexylamino-2-oxoethyl)-N-(3-fluorophenyl)azetidine-3-carboxamide

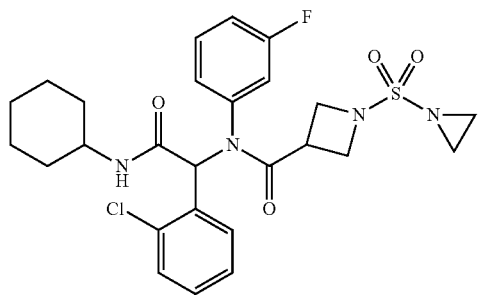 [SMILES: O=C(NC1CCCCC1)C(c1ccccc1Cl)N(C(=O)C1CN(S(=O)(=O)N2CC2)C1)c1cccc(F)c1]

1-(N-(2-chloroethyl)aminosulfonyl)-N-(1-(2-chlorophenyl)-2-cyclohexylamino-2-oxoethyl)-N-(3-fluorophenyl)-azetidine-3-carboxamide (100 mg, 0.17 mmol) and potassium carbonate (48 mg, 0.34 mmol) were added in 5 mL of DMF at room temperature, followed by stirring overnight at room temperature. After completion of the reaction, the mixture was added with 20 mL of dichloromethane, and washed with water (30 mL×3). The organic phase was dried over anhydrous sodium sulfate and separated by column chromatography on silica gel (PE:EA=1:1), to give a solid product of 1-(aziridin-1-ylsulfonyl)-N-(1-(2-chlorophenyl)-2-cyclohexylamino-2-oxoethyl)-N-(3-fluorophenyl)azetidine-3-carboxamide (56 mg, yield of 60%).

¹H-NMR (400 MHz, CDCl₃): δ=7.34 (d, J=7.6 Hz, 1H), 7.16-7.12 (m, 3H), 6.98-6.94 (m, 3H), 6.91-6.88 (m, 1H), 6.44 (s, 1H), 5.48 (d, J=7.6 Hz, 1H), 4.39-4.34 (m, 2H), 3.87-3.82 (m, 1H), 3.72 (t, J=8.0 Hz, 1H), 3.65 (d, J=7.6 Hz, 1H), 3.38-3.30 (m, 1H), 2.33 (s, 4H), 2.02-1.99 (m, 1H), 1.91-1.88 (m, 1H), 1.75-1.59 (m, 3H), 1.42-0.99 (m, 5H).

m/z=549 [M+H]⁺.

Example 25: (S)-2-(aziridine-1-sulfonylamino)-N-(1-(2-chlorophenyl)-2-((3,3-difluorocyclobutyl)amino)-2-oxoethyl)-N-(3-fluorophenyl)acetamide

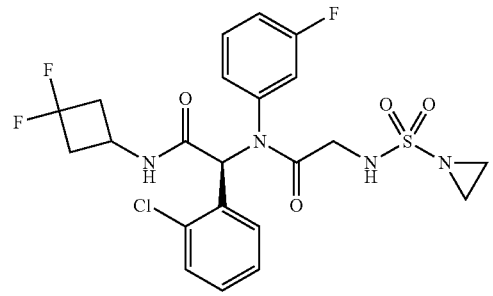

Step A: 2-oxazolidinone-3-sulfonyl chloride

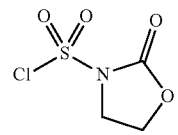

In an ice bath, to a solution of chlorosulfonyl isocyanate (30.0 g, 212.0 mmol) in dry dichloromethane, a solution of 2-bromoethanol (15.0 mL, 212 mmol) in dichloromethane was slowly added dropwise with stirring. The reaction was carried out at 0° C. for 4 h, and then concentrated under reduced pressure to give 2-oxazolidinone-3-sulfonyl chloride (39.4 g, yield of 100%).

¹H-NMR (400 MHz, CDCl₃): δ=4.63 (t, J=5.9 Hz, 2H), 3.59 (t, J=5.9 Hz, 2H).

Step B: benzyl (S)-2-[(1-(4-methoxyphenyl)ethyl)amino]acetate

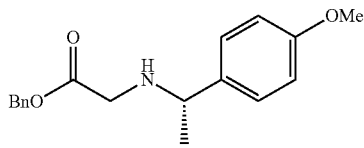 [SMILES: COc1ccc([C@H](C)NCC(=O)OCc2ccccc2)cc1]

Benzyl bromoacetate (1.95 mL, 13.2 mmol) was added in a solution of (S)-1-(4-methoxyphenyl)ethylamine (1.95 mL, 12.0 mmol) and triethylamine (5 mL, 36.1 mmol) in dichloromethane. The reaction solution was stirred overnight at room temperature, quenched by adding with water, and extracted with dichloromethane. The combined organic phase was washed with brine, dried over sodium sulfate, filtered and concentrated in vacuo, and separated by column chromatography on silica gel, to give benzyl (S)-2-[(1-(4-methoxyphenyl)ethyl)amino]acetate (2.2 g, yield of 62%).

$^1$H-NMR (400 MHz, CDCl$_3$): δ=7.40-7.29 (m, 5H), 7.23-7.18 (m, 2H), 6.88-6.82 (m, 2H), 5.13 (d, J=1.0 Hz, 2H), 3.79 (s, 3H), 3.75 (q, J=6.5 Hz, 1H), 3.30 (q, J=17.5 Hz, 2H), 1.35 (d, J=6.6 Hz, 3H).

m/z=300 [M+H]$^+$.

Step C: benzyl (S)-2-(N-(1-(4-methoxyphenyl)ethyl)-2-oxazolidinone-3-sulfonylamino)acetate

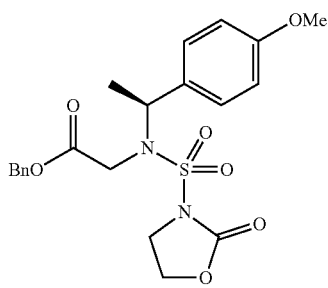 [SMILES: COc1ccc([C@H](C)N(CC(=O)OCc2ccccc2)S(=O)(=O)N2CCOC2=O)cc1]

In an ice bath and with stirring, a solution of benzyl (S)-2-[(1-(4-methoxyphenyl)ethyl)amino]acetate (2.2 g, 7.4 mmol) in dichloromethane was added with triethylamine (2.1 mL, 14.8 mmol), and then slowly added with 2-oxazolidinone-3-sulfonyl chloride (2.1 g, 11.1 mmol). After completion of the dropwise addition, the reaction solution was warmed up to room temperature and stirred overnight. The reaction solution was added with saturated ammonium chloride solution to quench the reaction, and extracted with dichloromethane. The combined organic phase was washed with brine, dried over sodium sulfate, filtered and concentrated in vacuo, and separated by column chromatography on silica gel, to give benzyl (S)-2-(N-(1-(4-methoxyphenyl)ethyl)-2-oxazolidinone-3-sulfonylamino)acetate (2.1 g, yield of 64%).

$^1$H-NMR (400 MHz, CDCl$_3$): δ=7.43-7.23 (m, 6H), 6.90-6.80 (m, 2H), 5.40 (q, J=7.0 Hz, 1H), 5.02 (d, J=12.4 Hz, 2H), 4.33-4.14 (m, 3H), 4.05-3.80 (m, 3H), 3.78 (s, 3H), 1.55 (d, J=7.1 Hz, 3H).

m/z=449 [M+H]$^+$.

Step D: (S)-2-(N-(1-(4-methoxyphenyl)ethyl)-2-oxazolidinone-3-sulfonylamino)acetic Acid

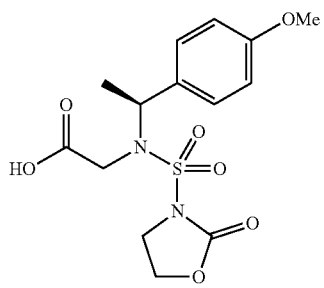 [SMILES: COc1ccc([C@H](C)N(CC(=O)O)S(=O)(=O)N2CCOC2=O)cc1]

At room temperature, palladium on carbon (1.5 g) was added with stirring in a solution of benzyl (S)-2-(N-(1-(4-methoxyphenyl)ethyl)-2-oxazolidinone-3-sulfonylamino)acetate (1.5 g, 3.3 mmol) in methanol. The reaction was purged with hydrogen gas three times, followed by reacting overnight at room temperature. The palladium on carbon was removed by filtration, and (S)-2-(N-(1-(4-methoxyphenyl)ethyl)-2-oxazolidinone-3-sulfonylamino)acetic acid (1.2 g, yield of 100%) was obtained by concentration in vacuo.

$^1$H-NMR (400 MHz, CDCl$_3$): δ=7.31 (d, J=8.6 Hz, 2H), 6.89-6.86 (m, 2H), 5.36-5.26 (m, 1H), 4.39-4.21 (m, 3H), 4.06-3.82 (m, 3H), 3.80 (s, 3H), 1.60 (d, J=7.1 Hz, 3H).

Step E: (S)-2-(2-chlorophenyl)-N-(3,3-difluorocyclobutyl)-2-(N-(3-fluorophenyl)-2-(N-((S)-1-(4-methoxyphenyl)ethyl)-2-oxazolidinone-3-sulfonylamino)acetamido)acetamide

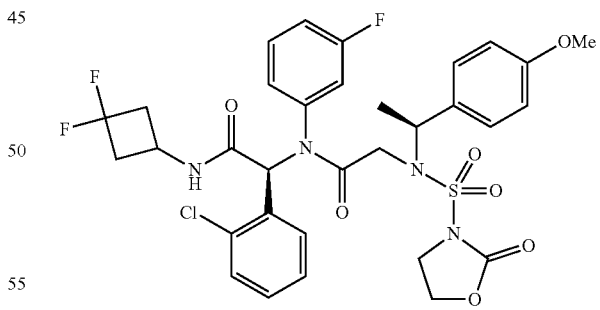

At room temperature and with stirring, a solution of 3-fluoroaniline (105.7 μL, 1.1 mmol) in methanol was added with o-chlorobenzaldehyde (123.8 μL, 1.1 mmol), added with (3)-2-(N-(1-(4-methoxyphenyl)ethyl)-2-oxazolidinone-3-sulfonylamino)acetic acid (394 mg, 1.1 mmol) after reacting 15 min, and then added with 1,1-difluoro-3-cyclobutyl isocyanide (128.8 mg, 1.1 mmol) after further reacting for 30 min. The reaction was performed overnight at room temperature. The reaction solution was evaporated and concentrated under reduced pressure, and then separated by column chromatography on silica gel to give (S)-2-(2-chlorophenyl)-N-(3,3-difluorocyclobutyl)-2-(N-(3-fluorophenyl)-2-(N—((S)-1-(4-methoxyphenyl)ethyl)-2-oxazolidinone-3-sulfonylamino)acetamido)acetamide (70 mg, yield of 9%).

¹H-NMR (400 MHz, CDCl₃): δ=7.59-7.35 (m, 1H), 7.36-7.23 (m, 3H), 7.13 (m, 2H), 7.02-6.79 (m, 6H), 6.36 (s, 1H), 6.13 (s, 1H), 5.37 (q, J=6.9 Hz, 1H), 4.31-4.29 (t, J=8.2 Hz, 3H), 4.00-3.91 (m, 3H), 3.80 (s, 3H), 3.69 (s, 1H), 3.04-2.94 (m, 2H), 2.69-2.39 (m, 2H), 1.54 (d, J=7.0 Hz, 3H).

m/z=709 [M+H]⁺.

Step F: (S)-2-(2-chlorophenyl)-N-(3,3-difluorocyclobutyl)-2-(N-(3-fluorophenyl)-2-((N-(2-hydroxyethyl)aminosulfonyl)((S)-1-(4-methoxyphenyl)ethyl)amino)acetamido)acetamide

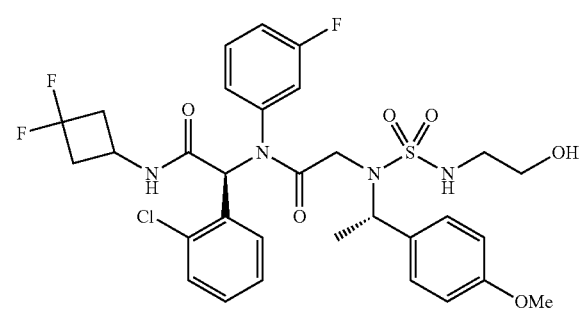

With stirring and in an ice bath, a sodium hydroxide solution (0.24 mL, 1 M, 0.24 mmol) was added dropwise to a solution of (S)-2-(2-chlorophenyl)-N-(3,3-difluorocyclobutyl)-2-(N-(3-fluorophenyl)-2-(N—((S)-1-(4-methoxyphenyl)ethyl)-2-oxazolidinone-3-sulfonylamino)acetamido)acetamide (59 mg, 0.08 mmol) in methanol. After completion of the dropwise addition, the mixture was warmed up to room temperature and stirred for 0.5 h, and then extracted with ethyl acetate. The combined organic phase was washed with brine, dried over sodium sulfate, filtered and concentrated in vacuo, and separated by column chromatography on silica gel, to give (S)-2-(2-chlorophenyl)-N-(3,3-difluorocyclobutyl)-2-(N-(3-fluorophenyl)-2-((N-(2-hydroxyethyl)aminosulfonyl)((S)-1-(4-methoxyphenyl)ethyl)amino)acetamido)acetamide (41 mg, yield of 72%).

¹H-NMR (400 MHz, CDCl₃): δ=7.52 (s, 1H), 7.33-7.26 (m, 2H), 7.17-7.11 (m, 2H), 7.02-6.88 (m, 4H), 6.82 (m, 3H), 6.37 (s, 1H), 6.16-5.96 (m, 2H), 5.12 (q, J=6.8 Hz, 1H), 4.31 (s, 1H), 3.85-3.82 (m, 2H), 3.78 (s, 3H), 3.75-3.65 (m, 1H), 3.46-3.17 (m, 3H), 3.16-2.91 (m, 2H), 2.70-2.36 (m, 3H), 1.53 (d, J=7.1 Hz, 3H).

m/z=683 [M+H]⁺.

Step G: (S)-2-(2-chlorophenyl)-N-(3,3-difluorocyclobutyl)-2-(N-(3-fluorophenyl)-2-((N-(2-hydroxyethyl)aminosulfonyl)amino)acetamido)acetamide

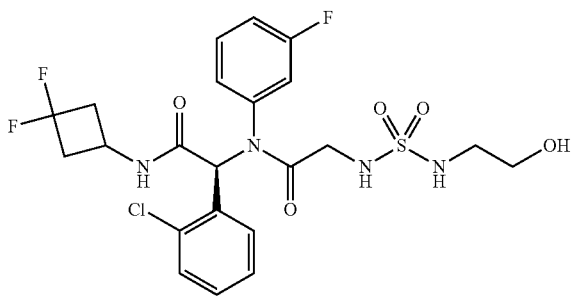 [SMILES: Cc1ccc(S(=O)(=O)OCCNS(=O)(=O)NCC(=O)N(c2cccc(F)c2)[C@H](C(=O)NC2CC(F)(F)C2)c2ccccc2Cl)cc1]

With stirring and in an ice bath, trifluoroacetic acid (0.6 mL) was added dropwise in a solution of (S)-2-(2-chlorophenyl)-N-(3,3-difluorocyclobutyl)-2-(N-(3-fluorophenyl)-2-((N-(2-hydroxyethyl)aminosulfonyl)((S)-1-(4-methoxyphenyl)ethyl)amino)acetamido)acetamide (41 mg, 0.06 mmol) in dichloromethane. After completion of the dropwise addition, the mixture was stirred for 0.5 h. After evaporation under reduced pressure, the resulting mixture was added with dichloromethane, washed with saturated sodium hydrogen carbonate solution, dried over sodium sulfate, filtered and concentrated in vacuo, and separated by column chromatography on silica gel, to give (S)-2-(2-chlorophenyl)-N-(3,3-difluorocyclobutyl)-2-(N-(3-fluorophenyl)-2-((N-(2-hydroxyethyl)aminosulfonyl)amino)acetamido)acetamide (32 mg, yield of 97%).

¹H-NMR (400 MHz, CDCl₃): δ=7.36 (d, J=7.9 Hz, 1H), 7.23-7.10 (m, 3H), 7.06-6.89 (m, 4H), 6.41 (s, 1H), 6.14 (d, J=6.4 Hz, 1H), 5.51 (t, J=5.3 Hz, 1H), 4.88 (t, J=5.8 Hz, 1H), 4.29 (s, 1H), 3.79-3.71 (m, 2H), 3.62 (d, J=5.1 Hz, 2H), 3.26-3.22 (m, 2H), 3.18-2.91 (m, 3H), 2.60-2.43 (m, 2H).

m/z=549 [M+H]⁺.

Step H: (S)-2-((N-(2-((1-(2-chlorophenyl)-2-((3,3-difluorocyclobutyl)amino)-2-oxoethyl)(3-fluorophenyl)amino)-2-oxoethyl)sulfamoyl)amino)ethyl-4-methyl benzenesulfonate

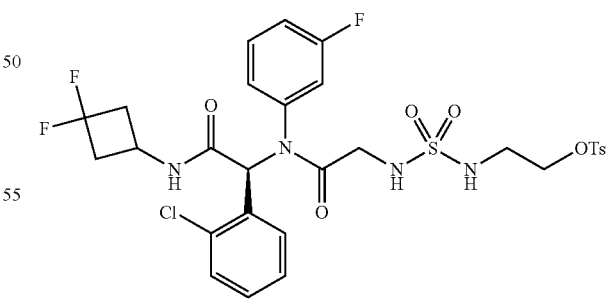

With stirring and in an ice bath, triethylamine (25 μL, 0.18 mmol) was added in a solution of (S)-2-(2-chlorophenyl)-N-(3,3-difluorocyclobutyl)-2-(N-(3-fluorophenyl)-2-((N-(2-hydroxyethyl)aminosulfonyl)amino)acetamido)acetamide (32 mg, 0.06 mmol) in dichloromethane, followed by adding with p-toluenesulfonyl chloride (20 mg, 0.1 mmol). After completion of the dropwise addition, the reaction solution was warmed up to room temperature and stirred overnight. The reaction solution was added with saturated ammonium chloride solution to quench the reaction, and then extracted with dichloromethane. The combined organic phase was washed with brine, dried over sodium sulfate, filtered and concentrated in vacuo, and separated by column chromatography on silica gel, to give (S)-2-((N-(2-((1-(2-chlorophenyl)-2-((3,3-difluorocyclobutyl)amino)-2-oxoethyl)(3-fluorophenyl)amino)-2-oxoethyl)sulfamoyl)amino) ethyl-4-methyl benzenesulfonate (32 mg, yield of 50%). m/z=703 [M+H]+.

Step I: (S)-2-(aziridine-1-sulfonylamino)-N-(1-(2-chlorophenyl)-2-((3,3-difluorocyclobutyl)amino)-2-oxoethyl)-N-(3-fluorophenyl)acetamide

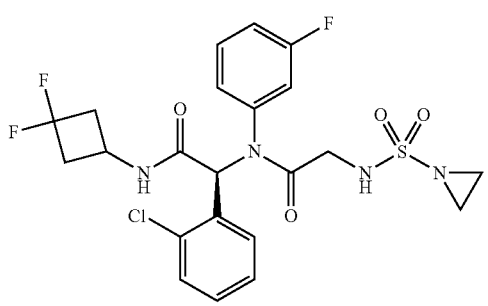 [SMILES: O=C(NC1CC(F)(F)C1)[C@H](c1ccccc1Cl)N(C(=O)CNS(=O)(=O)N1CC1)c1cccc(F)c1]

Potassium carbonate (8 mg, 0.06 mmol) was added in a solution of (S)-2-((N-(2-((1-(2-chlorophenyl)-2-((3,3-difluorocyclobutyl)amino)-2-oxoethyl)(3-fluorophenyl) amino)-2-oxoethyl)sulfamoyl)amino)ethyl-4-methyl benzenesulfonate (21 mg, 0.03 mmol) in DMF. The reaction was stirred overnight at room temperature, quenched by adding with water, and then extracted with ethyl acetate. The combined organic phase was washed with brine three times, dried over sodium sulfate, filtered and concentrated in vacuo, and separated by column chromatography on silica gel, to give (S)-2-(aziridine-1-sulfonylamino)-N-(1-(2-chlorophenyl)-2-((3,3-difluorocyclobutyl)amino)-2-oxoethyl)-N-(3-fluorophenyl)acetamide (14 mg, yield of 88%).
1H-NMR (400 MHz, CDCl3): δ=7.52 (s, 1H), 7.36 (d, J=7.9 Hz, 1H), 7.22-7.08 (m, 2H), 7.04-6.90 (m, 3H), 6.79-6.47 (m, 1H), 6.44 (s, 1H), 6.12 (d, J=6.4 Hz, 1H), 5.71 (s, 1H), 4.29 (s, 1H), 3.75 (d, J=16.7 Hz, 2H), 3.07-2.93 (m, 2H), 2.63-2.37 (m, 2H), 2.30 (s, 4H).
m/z=531 [M+H]+.

Example 26: (R)-2-(aziridine-1-sulfonylamino)-N-(1-(2-chlorophenyl)-2-((3,3-difluorocyclobutyl) amino)-2-oxoethyl)-N-(3-fluorophenyl)acetamide

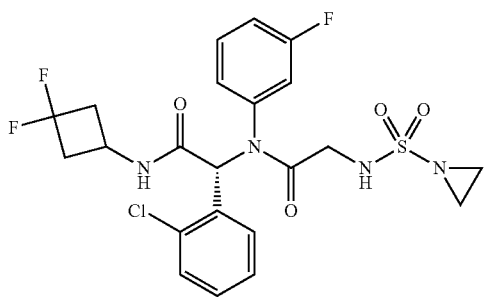 [SMILES: O=C(NC1CC(F)(F)C1)[C@@H](c1ccccc1Cl)N(C(=O)CNS(=O)(=O)N1CC1)c1cccc(F)c1]

Step A: (R)-2-(2-chlorophenyl)-N-(3,3-difluorocyclobutyl)-2-(N-(3-fluorophenyl)-2-(N—((S)-1-(4-methoxyphenyl)ethyl)-2-oxazolidinone-3-sulfonylamino)acetamido)acetamide

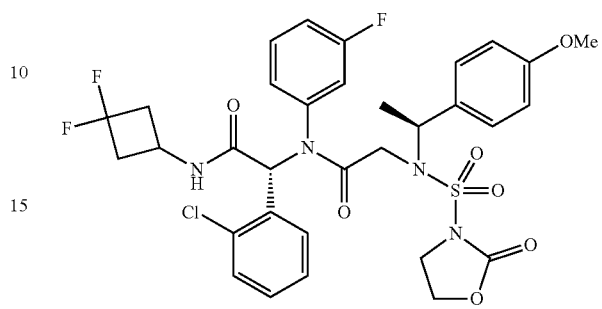

(R)-2-(2-chlorophenyl)-N-(3,3-difluorocyclobutyl)-2-(N-(3-fluorophenyl)-2-(N—((S)-1-(4-methoxyphenyl)ethyl)-2-oxazolidinone-3-sulfonylamino)acetamido)acetamide was obtained by separation in step E of Example 25 (65 mg, yield of 8%).
1H-NMR (400 MHz, CDCl3): δ=7.37 (d, J=8.0 Hz, 1H), 7.25 (m, 2H), 7.17 (m, 2H), 7.00-6.80 (m, 6H), 6.75 (s, 1H), 6.58 (s, 1H), 6.50-6.10 (brs, 1H), 5.37 (q, J=7.0 Hz, 1H), 4.44-4.20 (m, 3H), 4.09 (d, J=18.6 Hz, 1H), 3.98-3.82 (m, 2H), 3.77 (s, 3H), 3.46 (d, J=18.5 Hz, 1H), 3.08-2.89 (m, 2H), 2.79-2.56 (m, 2H), 1.62 (d, J=7.1 Hz, 3H).
m/z=709 [M+H]+.

Step B: (R)-2-(2-chlorophenyl)-N-(3,3-difluorocyclobutyl)-2-(N-(3-fluorophenyl)-2-((N-(2-hydroxyethyl)aminosulfonyl)((S)-1-(4-methoxyphenyl)ethyl) amino)acetamido)acetamide

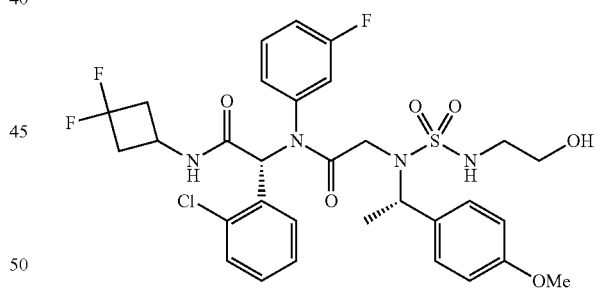

A sodium hydroxide solution (0.18 mL, 1 M, 0.18 mmol) was added dropwise with stirring to a solution of (R)-2-(2-chlorophenyl)-N-(3,3-difluorocyclobutyl)-2-(N-(3-fluorophenyl)-2-(N—((S)-1-(4-methoxyphenyl)ethyl)-2-oxazolidinone-3-sulfonylamino)acetamido)acetamide (44 mg, 0.06 mmol) in methanol in an ice bath. After completion of the dropwise addition, the mixture was warmed up to room temperature and stirred for 0.5 h, and then extracted with ethyl acetate. The combined organic phase was washed with brine, dried over sodium sulfate, filtered and concentrated in vacuo, and separated by column chromatography on silica gel, to give (R)-2-(2-chlorophenyl)-N-(3,3-difluorocyclobutyl)-2-(N-(3-fluorophenyl)-2-((N-(2-hydroxyethyl) aminosulfonyl)((S)-1-(4-methoxyphenyl)ethyl)amino)acetamido)acetamide (32 mg, yield of 76%).

¹H-NMR (400 MHz, CDCl₃): δ=7.35 (d, J=8.0 Hz, 1H), 7.28-7.23 (m, 2H), 7.18-7.13 (m, 2H), 7.02-6.76 (m, 7H), 6.39 (s, 1H), 6.20 (d, J=6.3 Hz, 1H), 5.84 (t, J=6.2 Hz, 1H), 5.12 (q, J=6.8 Hz, 1H), 4.30 (s, 1H), 3.82 (s, 2H), 3.77 (s, 3H), 3.68 (d, J=17.8 Hz, 1H), 3.43-3.36 (m, 2H), 3.27 (d, J=17.7 Hz, 1H), 3.13-2.93 (m, 2H), 2.61-2.49 (m, 3H), 1.58 (d, J=7.0 Hz, 2H).

m/z=684 [M+H]⁺.

Step C: (R)-2-(2-chlorophenyl)-N-(3,3-difluorocyclobutyl)-2-(N-(3-fluorophenyl)-2-((N-(2-hydroxyethyl)aminosulfonyl)amino)acetamido)acetamide

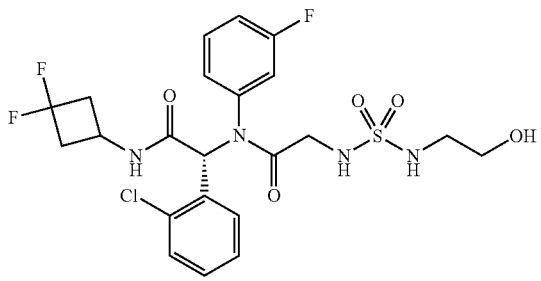 [SMILES: O=C(NC1CC(F)(F)C1)[C@@H](c1ccccc1Cl)N(C(=O)CNS(=O)(=O)NCCO)c1cccc(F)c1]

In an ice bath, trifluoroacetic acid (0.4 mL) was added dropwise with stirring to a solution of (R)-2-(2-chlorophenyl)-N-(3,3-difluorocyclobutyl)-2-(N-(3-fluorophenyl)-2-{[N-(2-hydroxyethyl)aminosulfonyl][(S)-1-(4-methoxyphenyl)ethyl]amino}acetamido)acetamide (32 mg, 0.047 mmol) in dichloromethane. After completion of the dropwise addition, the mixture was warmed up to room temperature and stirred for 0.5 h. After evaporation under reduced pressure, the resulting mixture was added with dichloromethane, washed with saturated sodium hydrogen carbonate solution, dried over sodium sulfate, filtered and concentrated in vacuo, and separated by column chromatography on silica gel, to give (R)-2-(2-chlorophenyl)-N-(3,3-difluorocyclobutyl)-2-(N-(3-fluorophenyl)-2-((N-(2-hydroxyethyl)aminosulfonyl)amino)acetamido)acetamide (25 mg, yield of 97%).

¹H-NMR (400 MHz, CDCl₃): δ=7.36 (d, J=8.1 Hz, 1H), 7.24-7.07 (m, 3H), 7.07-6.90 (m, 4H), 6.42 (s, 1H), 6.14 (d, J=6.5 Hz, 1H), 5.52 (t, J=5.1 Hz, 1H), 4.89 (t, J=5.9 Hz, 1H), 4.29 (s, 1H), 3.79-3.72 (m, 2H), 3.62 (d, J=5.1 Hz, 2H), 3.27-3.23 (m, 2H), 3.07-2.97 (m, 3H), 2.70-2.35 (m, 2H).

m/z=549 [M+H]⁺.

Step D: (R)-2-((N-(2-((1-(2-chlorophenyl)-2-((3,3-difluorocyclobutyl)amino)-2-oxoethyl)(3-fluorophenyl)amino)-2-oxoethyl)aminosulfonyl)amino)ethyl-4-methyl benzenesulfonate

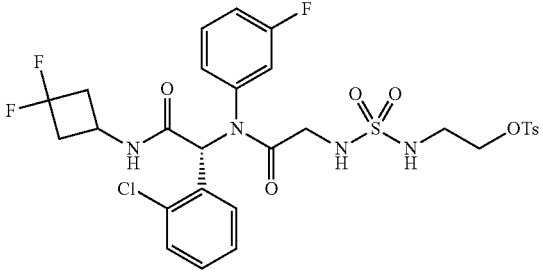 [SMILES: Cc1ccc(S(=O)(=O)OCCNS(=O)(=O)NCC(=O)N(c2cccc(F)c2)[C@@H](C(=O)NC2CC(F)(F)C2)c2ccccc2Cl)cc1]

With stirring and in an ice bath, triethylamine (12.6 μL, 0.091 mmol) was added to a solution of (R)-2-(2-chlorophenyl)-N-(3,3-difluorocyclobutyl)-2-(N-(3-fluorophenyl)-2-{[N-(2-hydroxyethyl)aminosulfonyl]amino}acetamido) acetamide (25 mg, 0.045 mmol) in dichloromethane, followed by adding p-toluenesulfonyl chloride (10 mg, 0.055 mmol). After completion of the dropwise addition, the reaction solution was warmed up to room temperature and stirred overnight. The reaction solution was added with saturated ammonium chloride solution to quench the reaction, and then extracted with dichloromethane. The combined organic phase was washed with brine, dried over sodium sulfate, filtered and concentrated in vacuo, and separated by column chromatography on silica gel, to give (R)-2-((N-(2-((1-(2-chlorophenyl)-2-((3,3-difluorocyclobutyl)amino)-2-oxoethyl)(3-fluorophenyl)amino)-2-oxoethyl)aminosulfonyl)amino)ethyl-4-methyl benzenesulfonate (10 mg, yield of 32%).

¹H-NMR (400 MHz, CDCl₃): δ=7.80 (d, J=8.3 Hz, 2H), 7.41-7.31 (m, 3H), 7.22-7.11 (m, 3H), 7.04-6.91 (m, 4H), 6.47 (s, 1H), 6.36 (d, J=6.5 Hz, 1H), 5.50 (t, J=5.3 Hz, 1H), 5.02 (t, J=6.3 Hz, 1H), 4.30 (s, 1H), 4.14 (t, J=5.3 Hz, 2H), 3.66-3.52 (m, 2H), 3.41-3.26 (m, 2H), 3.09-2.89 (m, 2H), 2.66-2.37 (m, 5H).

m/z=703 [M+H]⁺.

Step E: (R)-2-(aziridine-1-sulfonylamino)-N-(1-(2-chlorophenyl)-2-((3,3-difluorocyclobutyl)amino)-2-oxoethyl)-N-(3-fluorophenyl)acetamide

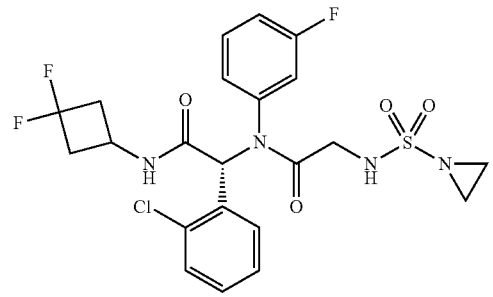 [SMILES: O=C(NC1CC(F)(F)C1)[C@@H](c1ccccc1Cl)N(C(=O)CNS(=O)(=O)N1CC1)c1cccc(F)c1]

Potassium carbonate (4 mg, 0.024 mmol) was added in a solution of (R)-2-[(N-{2-[{1-(2-chlorophenyl)-2-[(3,3-difluorocyclobutyl)amino]-2-oxoethyl}(3-fluorophenyl) amino]-2-oxoethyl}aminosulfonyl)amino]ethyl-4-methyl benzenesulfonate (10 mg, 0.014 mmol) in DMF. The reaction was stirred overnight at room temperature, and quenched by adding water, followed by extraction with ethyl acetate. The combined organic phase was washed with brine three times, dried over sodium sulfate, filtered and concentrated in vacuo purify, and separated by column chromatography on silica gel, to give (R)-2-(aziridine-1-sulfonylamino)-N-(1-(2-chlorophenyl)-2-((3,3-difluorocyclobutyl)amino)-2-oxoethyl)-N-(3-fluorophenyl) acetamide (5 mg, yield of 66%).

¹H-NMR (400 MHz, CDCl₃): δ=7.78-7.44 (m, 1H), 7.36 (d, J=8.0 Hz, 1H), 7.18-7.14 (m, 2H), 7.05-6.91 (m, 3H), 6.77-6.49 (m, 1H), 6.44 (s, 1H), 6.10 (d, J=6.2 Hz, 1H), 5.67 (t, J=4.8 Hz, 1H), 4.30 (s, 1H), 3.82-3.68 (m, 2H), 3.07-2.92 (m, 2H), 2.60-2.44 (m, 2H), 2.30 (s, 4H).

m/z=531 [M+H]⁺.

Example 27: 1-(aziridin-1-ylsulfonyl)-N-(1-(2-chlorophenyl)-2-cyclohexylamino-2-oxoethyl)-N-(3-fluorophenyl)pyrrolidine-3-carboxamide

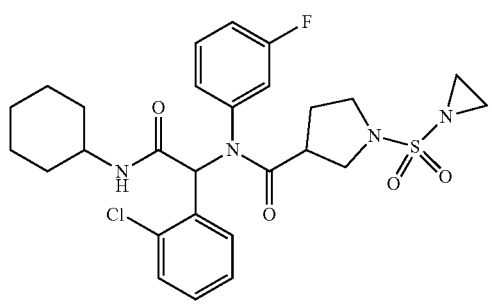 [SMILES: O=C(NC1CCCCC1)C(c1ccccc1Cl)N(C(=O)C1CCN(S(=O)(=O)N2CC2)C1)c1cccc(F)c1]

Step A: tert-butyl 3-((1-(2-chlorophenyl)-2-cyclohexylamino-2-oxoethyl)(3-fluorophenyl)carbamoyl)pyrrolidine-1-carboxylate

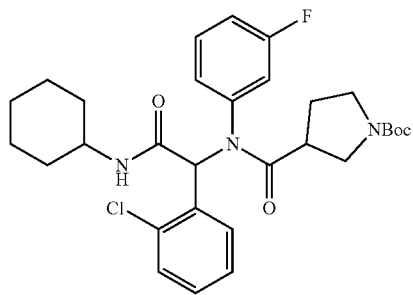 [SMILES: CC(C)(C)OC(=O)N1CCC(C(=O)N(c2cccc(F)c2)C(C(=O)NC2CCCCC2)c2ccccc2Cl)C1]

At room temperature, o-chlorobenzaldehyde (226 μL, 2.00 mmol) and m-fluoroaniline (192 μL, 2.00 mmol) were added to 10 mL of methanol, 1-Boc-pyrrolidine-3-carboxylic acid (430 mg, 2.00 mmol) was added thereto after stirring for 10 min, and cyclohexyl isocyanide (220 mg, 2.00 mmol) was added after further stirring for another 10 min. The reaction was stirred overnight at room temperature. After completion of the reaction, the solvent was removed under reduced pressure and a solid product of tert-butyl 3-((1-(2-chlorophenyl)-2-cyclohexylamino-2-oxoethyl)(3-fluorophenyl)carbamoyl)pyrrolidine-1-carboxylate (678 mg, yield of 61%) was obtained by separation through column chromatography on silica gel (PE:EA=2:1).

¹H-NMR (400 MHz, CDCl₃): δ=7.35-7.31 (m, 1H), 7.16-7.11 (m, 3H), 7.02-6.87 (m, 4H), 6.45-6.42 (m, 1H), 5.58-5.47 (m, 1H), 3.85-3.83 (m, 1H), 3.52-3.45 (m, 3H), 3.14-3.12 (m, 1H), 2.85-2.81 (m, 1H), 2.23-2.16 (m, 1H), 2.01-1.98 (m, 1H), 1.90-1.88 (m, 2H), 1.74-1.56 (m, 2H), 1.42 (s, 9H), 1.38-0.98 (m, 6H).

m/z=558 [M+H]⁺.

Step B: 1-(N-(2-chloroethyl)sulfamoyl)-N-(1-(2-chlorophenyl)-2-cyclohexylamino-2-oxoethyl)-N-(3-fluorophenyl)pyrrolidine-3-carboxamide

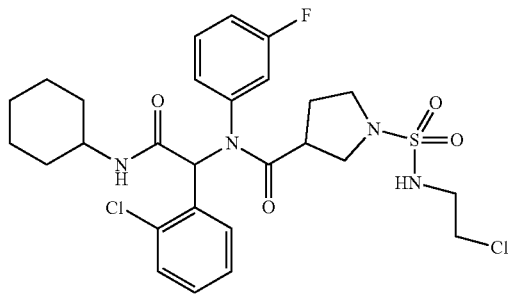 [SMILES: O=C(NC1CCCCC1)C(c1ccccc1Cl)N(C(=O)C1CCN(S(=O)(=O)NCCCl)C1)c1cccc(F)c1]

3 mL of TFA was added in a solution of tert-butyl 3-((1-(2-chlorophenyl)-2-cyclohexylamino-2-oxoethyl)(3-fluorophenyl)carbamoyl)pyrrolidine-1-carboxylate (678 mg, 1.21 mmol) in dichloromethane and stirred at room temperature for 1 h. After completion of the reaction, TFA and the solvent were removed by spin-evaporation under reduced pressure, and a solid product (620 mg) was obtained. 2-(Chloroethyl)aminosulfonyl chloride (441 mg, 2.71 mmol) was added to a solution of the solid compound (620 mg, 1.35 mmol) and DIEA (895 μL, 5.41 mmol) in dichloromethane at 0° C., then warmed up to room temperature and stirred overnight. After completion of the reaction, the reaction mixture was adjusted to a neutral pH by adding 1N HCl. The organic phase was separated, dried over anhydrous sodium sulfate, concentrated under reduced pressure, and separated by column chromatography on silica gel (PE:EA=2:1), to give a further solid product of 1-(N-(2-chloroethyl)sulfamoyl)-N-(1-(2-chlorophenyl)-2-cyclohexylamino-2-oxoethyl)-N-(3-fluorophenyl)pyrrolidine-3-carboxamide (481 mg, yield of 66%).

¹H-NMR (400 MHz, CDCl₃): δ=7.63 (br s, 1H), 7.35-7.32 (m, 1H), 7.16-7.12 (m, 2H), 6.98-6.97 (m, 2H), 6.91-6.87 (m, 1H), 6.42 (d, J=5.6 Hz, 1H), 5.52-5.46 (m, 1H), 5.02-4.98 (m, 1H), 3.87-3.80 (m, 1H), 3.68-3.56 (m, 3H), 3.52-3.22 (m, 5H), 2.99-2.95 (m, 1H), 2.26-2.21 (m, 1H), 1.96-1.89 (m, 3H), 1.74-1.59 (m, 3H), 1.42-1.30 (m, 3H), 1.21-1.01 (m, 3H).

m/z=599 [M+H]⁺.

Step C: 1-(aziridin-1-ylsulfonyl)-N-(1-(2-chlorophenyl)-2-cyclohexylamino-2-oxoethyl)-N-(3-fluorophenyl)pyrrolidine-3-carboxamide

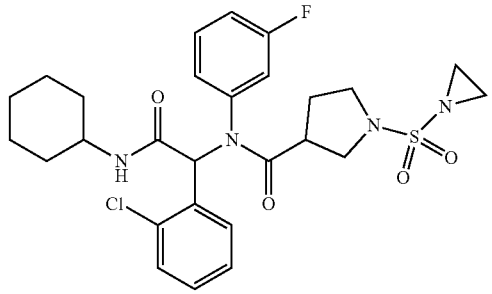 [SMILES: O=C(NC1CCCCC1)C(c1ccccc1Cl)N(C(=O)C1CCN(S(=O)(=O)N2CC2)C1)c1cccc(F)c1]

1-(N-(2-chloroethyl)sulfamoyl)-N-(1-(2-chlorophenyl)-2-cyclohexylamino-2-oxoethyl)-N-(3-fluorophenyl)pyrrolidine-3-carboxamide (481 mg, 0.80 mmol) and potassium carbonate (22 mg, 1.60 mmol) were added to 15 mL of DMF at room temperature, with stirring overnight at room temperature. After completion of the reaction, the mixture was added with 20 mL of dichloromethane, and then washed with water (30 mL×3). The organic phase was dried over anhydrous sodium sulfate, and separated by column chromatography on silica gel (PE:EA=2:1) to give the title compound (397 mg, yield of 88%).

$^1$H-NMR (400 MHz, CDCl$_3$): δ=7.68 (br s, 1H), 7.35-7.32 (m, 1H), 7.15-7.11 (m, 1H), 7.01-6.97 (m, 2H), 6.92-6.87 (m, 1H), 6.44-6.40 (m, 1H), 5.45 (d, J=8.0 Hz, 1H), 3.84-3.82 (m, 1H), 3.67-3.47 (m, 3H), 3.39-3.32 (m, 1H), 2.97-2.93 (m, 1H), 2.31-2.25 (m, 1H), 2.23 (s, 4H), 1.98-1.90 (m, 3H), 1.79-1.58 (m, 3H), 1.38-1.24 (m, 3H), 1.172-1.01 (m, 3H).

m/z=563 [M+H]$^+$.

Example 28: 2-(aziridine-1-sulfonylamino)-N-(1-(2-chlorophenyl)-2-((3,3-difluorocyclobutyl)amino)-2-oxoethyl)-N-(3-aminosulfonylphenyl)acetamide

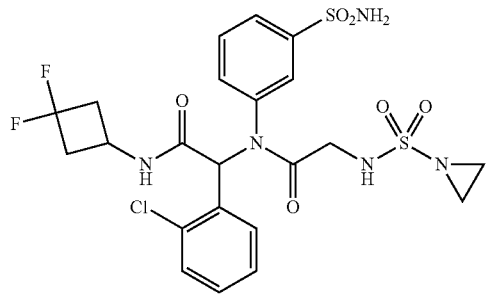 [SMILES: NS(=O)(=O)c1cccc(N(C(=O)CNS(=O)(=O)N2CC2)C(C(=O)NC2CC(F)(F)C2)c2ccccc2Cl)c1]

Step A: 2-((N-(2-chloroethyl)aminosulfonyl)amino)-N-(1-(2-chlorophenyl)-2-((3,3-difluorocyclobutyl)amino)-2-oxoethyl)-N-(3-aminosulfonylphenyl)acetamide

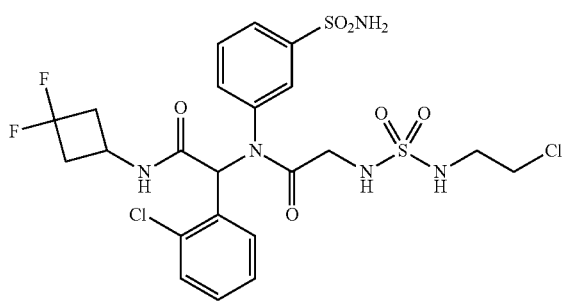 [SMILES: NS(=O)(=O)c1cccc(N(C(=O)CNS(=O)(=O)NCCCl)C(C(=O)NC2CC(F)(F)C2)c2ccccc2Cl)c1]

With reference to step C of Example 13, 2-((N-(2-chloroethyl)aminosulfonyl)amino)-N-(1-(2-chlorophenyl)-2-((3,3-difluorocyclobutyl))amino)-2-oxoethyl)-N-(3-aminosulfonylphenyl)acetamide (80 mg, yield of 34%) was obtained from 3-aminobenzenesulfonamide (45.7 μL, 0.37 mmol) and 2-((N-(2-chloroethyl)aminosulfonyl)amino)acetic acid (3 g, 17.9 mmol).

$^1$H-NMR (400 MHz, CDCl$_3$): δ=8.50-8.36 (m, 1H), 8.11-7.93 (m, 1H), 7.81 (d, J=7.6 Hz, 1H), 7.55-7.45 (m, 1H), 7.38 (d, J=8.0 Hz, 1H), 7.20 (t, J=8.5 Hz, 1H), 7.07-6.92 (m, 2H), 6.53 (s, 2H), 5.85 (t, J=4.4 Hz, 1H), 5.66-5.21 (m, 3H), 4.27 (s, 1H), 3.67 (t, J=5.9 Hz, 2H), 3.51 (s, 2H), 3.44-3.38 (m, 2H), 3.04-2.91 (m, 2H), 2.60-2.39 (m, 2H).

m/z=628 [M+H]$^+$.

Step B: 2-(aziridine-1-sulfonylamino)-N-(1-(2-chlorophenyl)-2-((3,3-difluorocyclobutyl)amino)-2-oxoethyl)-N-(3-aminosulfonylphenyl)acetamide

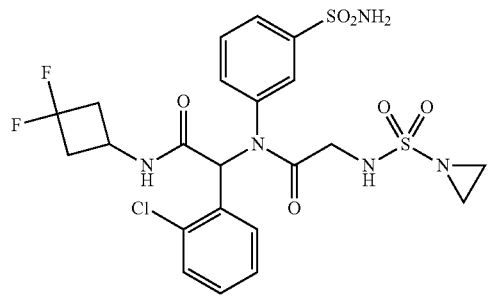 [SMILES: NS(=O)(=O)c1cccc(N(C(=O)CNS(=O)(=O)N2CC2)C(C(=O)NC2CC(F)(F)C2)c2ccccc2Cl)c1]

With reference to step E of Example 1, 2-(aziridine-1-sulfonylamino)-N-(1-(2-chlorophenyl)-2-((3,3-difluorocyclobutyl)amino)-2-oxoethyl)-N-(3-aminosulfonylphenyl)acetamide (20 mg, yield of 27%) was obtained from 2-((N-(2-chloroethyl)aminosulfonyl)amino)-N-(1-(2-chlorophenyl)-2-((3,3-difluorocyclobutyl)amino)-2-oxoethyl)-N-(3-aminosulfonylphenyl)acetamide (80 mg, 0.127 mmol).

$^1$H-NMR (400 MHz, CDCl$_3$): δ=8.50 and 8.00 (brs, 1H), 7.80 (d, J=6.3 Hz, 1H), 7.57 and 7.52 (brs, 1H), 7.36 (d, J=8.0 Hz, 1H), 7.21-7.15 (m, 2H), 7.00 (s, 2H), 6.71-6.65 (m, 1H), 6.50 (s, 1H), 6.24 (s, 1H), 5.68 (s, 1H), 5.34-5.21 (m, 1H), 4.22 (s, 1H), 3.84 (s, 2H), 3.04-2.81 (m, 2H), 2.60-2.26 (m, 6H).

m/z=592 [M+H]$^+$.

Example 29: 2-(aziridine-1-sulfonylamino)-N-(1-(2-chlorophenyl)-2-((3,3-difluorocyclobutyl)amino)-2-oxoethyl)-N-(3,4-difluorophenyl)acetamide

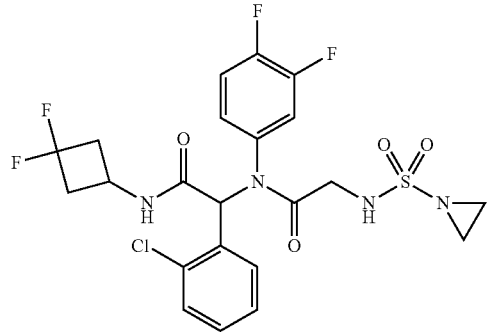 [SMILES: O=C(NC1CC(F)(F)C1)C(c1ccccc1Cl)N(C(=O)CNS(=O)(=O)N1CC1)c1ccc(F)c(F)c1]

Step A: 2-((N-(2-chloroethyl)aminosulfonyl)amino)-N-(1-(2-chlorophenyl)-2-((3,3-difluorocyclobutyl))amino)-2-oxoethyl)-N-(3,4-difluorophenyl)acetamide

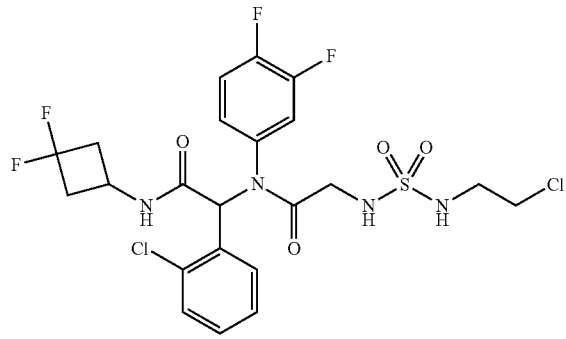 [SMILES: O=C(NC1CC(F)(F)C1)C(c1ccccc1Cl)N(C(=O)CNS(=O)(=O)NCCCl)c1ccc(F)c(F)c1]

With reference to step C of Example 13, 2-((N-(2-chloroethyl)aminosulfonyl)amino)-N-(1-(2-chlorophenyl)-2-((3,3-difluorocyclobutyl)amino)-2-oxoethyl)-N-(3,4-difluorophenyl)acetamide (4.67 g, yield of 90%) was obtained from 3,4-difluoroaniline (63 mg, 0.49 mmol) and 2-((N-(2-chloroethyl)aminosulfonyl)amino)acetic acid (106 mg, 0.49 mmol).

$^1$H-NMR (400 MHz, CDCl$_3$): δ=7.83-7.54 (m, 1H), 7.38 (d, J=7.7 Hz, 1H), 7.21 (t, J=7.4 Hz, 1H), 7.04 (t, J=7.2 Hz, 1H), 6.95 (d, J=7.9 Hz, 1H), 6.90-6.78 (m, 1H), 6.57 (s, 1H), 6.44 (s, 1H), 6.12 (d, J=6.6 Hz, 1H), 5.57 (t, J=5.0 Hz, 1H), 4.77 (t, J=6.4 Hz, 1H), 4.30 (s, 1H), 3.67 (t, J=5.7 Hz, 2H), 3.60-2.56 (m, 2H), 3.44-3.33 (m, 2H), 3.11-2.91 (m, 2H), 2.64-2.39 (m, 2H).

m/z=585 [M+H]$^+$.

Step B: 2-(aziridine-1-sulfonylamino)-N-(1-(2-chlorophenyl)-2-((3,3-difluorocyclobutyl)amino)-2-oxoethyl)-N-(3,4-difluorophenyl)acetamide

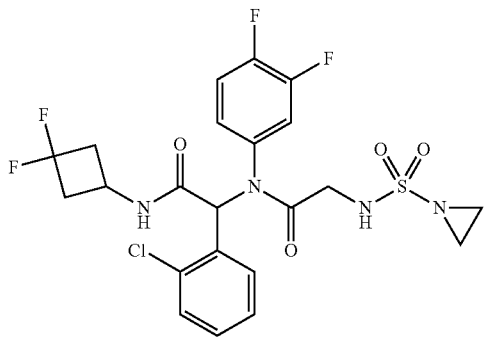 [SMILES: O=C(NC1CC(F)(F)C1)C(c1ccccc1Cl)N(C(=O)CNS(=O)(=O)N1CC1)c1ccc(F)c(F)c1]

With reference to step E of Example 1, 2-(aziridine-1-sulfonylamino)-N-(1-(2-chlorophenyl)-2-((3,3-difluorocyclobutyl)amino)-2-oxoethyl)-N-(3,4-difluorophenyl)acetamide (62 mg, yield of 70%) was obtained from 2-((N-(2-chloroethyl)aminosulfonyl)amino)-N-(1-(2-chlorophenyl)-2-((3,3-difluorocyclobutyl)amino)-2-oxoethyl)-N-(3,4-difluorophenyl)acetamide (95 mg, 0.162 mmol).

$^1$H-NMR (400 MHz, CDCl$_3$): δ=7.81-7.63 (m, 1H), 7.39 (d, J=7.9 Hz, 1H), 7.23 (t, J=7.6 Hz, 1H), 7.05 (t, J=7.2 Hz, 1H), 7.01-6.94 (m, 1H), 6.88 (s, 1H), 6.57 (s, 1H), 6.44 (s, 1H), 6.17 (d, J=6.5 Hz, 1H), 5.79 (t, J=4.8 Hz, 1H), 4.30 (s, 1H), 3.82-3.69 (m, 2H), 3.17-2.90 (m, 2H), 2.61-2.56 (m, 1H), 2.47-2.42 (m, 1H), 2.32 (s, 4H).

m/z=549 [M+H]$^+$.

Example 30: 2-(aziridine-1-sulfonylamino)-N-(1-(2-chlorophenyl)-2-(4,4-difluorocyclohexylamino)-2-oxoethyl)-N-(3-fluorophenyl)acetamide

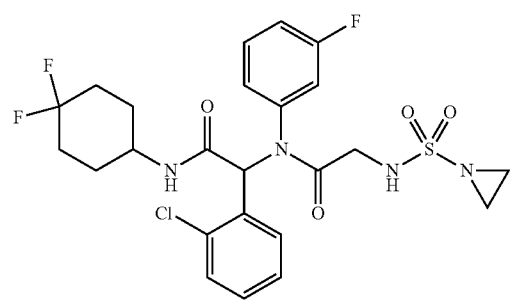 [SMILES: O=C(NC1CCC(F)(F)CC1)C(c1ccccc1Cl)N(C(=O)CNS(=O)(=O)N1CC1)c1cccc(F)c1]

Step A: tert-butyl 4-oxocyclohexylcarbamate

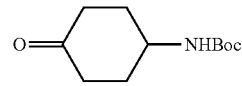

In an ice bath, Dess-Martin oxidant (29.0 g, 68.3 mmol) was added dropwise with stirring to a solution of N-4-Boc-aminocyclohexanol (9.8 g, 45.52 mmol) in dichloromethane (200 mL), and the reaction mixture was warmed up to room temperature and stirred overnight. The reaction was carefully quenched with saturated aqueous sodium thiosulfate solution in an ice bath, followed by extraction with dichloromethane three times. The combined organic phase was washed with brine, dried over sodium sulfate, filtered and concentrated in vacuo, and separated by column chromatography on silica gel, to give tert-butyl 4-oxocyclohexylcarbamate (7.96 g, yield of 82.1%).

Step B: tert-butyl (4,4-difluorocyclohexyl)carbamate

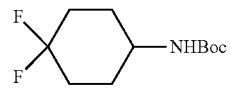

In an ice-salt bath, diethylaminosulfur trifluoride (8.54 g, 52.981 mmol) was added dropwise with stirring to a solution of tert-butyl 4-oxocyclohexylcarbamate (7.96 g, 37.323 mmol) in dichloromethane (200 mL), and the reaction mixture was slowly warmed up to room temperature and stirred overnight. The reaction was carefully quenched with saturated aqueous ammonium chloride solution in an ice bath, followed by extraction with dichloromethane three times. The combined organic phase was washed with brine, dried over sodium sulfate, filtered and concentrated in vacuo, and separated by column chromatography on silica gel, to give tert-butyl (4,4-difluorocyclohexyl)carbamate (approximately 70%) and tert-butyl 4-fluorocyclohexyl-3-alkenylcarboxylate (approximately 30%).

In an ice bath, m-CPBA (6.9 g, 40.0 mmol) was slowly added dropwise with stirring to a solution of the above mixture in dichloromethane, and the system was maintained at a temperature of below 5° C. After completion of the dropwise addition, the mixture was warmed up to room temperature and stirred overnight. The reaction was carefully quenched with saturated aqueous sodium thiosulfate solution in an ice bath, and stirred at room temperature for 0.5 h, followed by extraction with dichloromethane three times. The combined organic phase was washed with brine, dried over sodium sulfate, filtered and concentrated in vacuo. The product obtained was directly used in the next step without further purification.

The above residue concentrated was dissolved in methanol, and sodium borohydride (630 mg, 16.662 mmol) was added portionwise at a small amount thereto in an ice bath. The reaction mixture was warmed up to room temperature and stirred overnight. The solvent methanol was concentrated in vacuo, and the reaction then was quenched by adding water in an ice bath, and further stirred at room temperature for a half hour for completely quenching, followed by extraction with ethyl acetate three times. The combined organic phase was washed with brine, dried over sodium sulfate, filtered and concentrated in vacuo, to give tert-butyl (4,4-difluorocyclohexyl)carbamate (4.8 g, yield of 54.7%).

$^1$H-NMR (400 MHz, CDCl$_3$): δ=4.46 (s, 1H), 3.59 (s, 1H), 2.25-1.69 (m, 6H), 1.61-1.20 (m, 11H).

Step C: 4,4-difluorocyclohexylamine hydrochloride

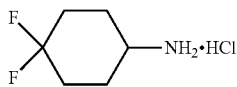

A mixture of tert-butyl (4,4-difluorocyclohexyl)carbamate (1.4 g, 5.950 mmol) and 6N HCl/MeOH (14 mL) was stirred at room temperature for 2 h, and concentrated in vacuo to give 4,4-difluorocyclohexylamine hydrochloride (1.02 g, yield of 100%), which was used directly in the next step without purification.

$^1$H-NMR (400 MHz, CDCl$_3$): δ=4.89 (s, 2H), 3.32-3.26 (m, 1H), 2.14-2.01 (m, 4H), 2.02-1.85 (m, 2H), 1.74-1.65 (m, 2H).

Step D: N-(4,4-difluorocyclohexyl)carboxamide

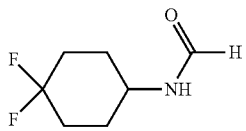

A mixture of 4,4-difluorocyclohexylamine hydrochloride (1.02 g, 5.943 mmol), TEA (1.82 g, 17.830 mmol) and ethyl formate (14 mL) was sealed with stirring overnight at 80° C., then concentrated in vacuo and separated by column chromatography on silica gel, to give N-(4,4-difluorocyclohexyl)carboxamide (854 mg, yield of 88.0%).

$^1$H-NMR (400 MHz, CDCl$_3$): δ=8.14 (s, 1H), 5.98 (s, 1H), 3.96-3.90 (m, 1H), 2.54-2.19 (m, 1H), 2.15-1.39 (m, 7H).

Step E: 1,1-difluoro-4-isocyanocyclohexane

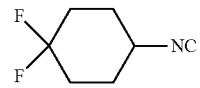

In an ice bath, a solution of triphosgene (129 mg, 0.434 mmol) in dichloromethane was added dropwise with stirring to a mixture of N-(4,4-difluorocyclohexyl)carboxamide (202 mg, 1.24 mmol) and TEA (437 mg, 3.72 mmol) in dichloromethane, and stirred at room temperature for 2 h. Dichloromethane was removed by spin-evaporation in the ice bath, and the obtained residue was added with ethyl ether, further separated by column chromatography on silica gel (ethyl ether as an eluent), and spin-evaporated in the ice bath, to give the title compound (180 mg, yield of 100%), which was used directly in the next step.

Step F: 2-(N-(2-chloroethyl)aminosulfonylamino)-N-(1-(2-chlorophenyl)-2-(4,4-difluorocyclohexylamino)-2-oxoethyl)-N-(3-fluorophenyl)acetamide

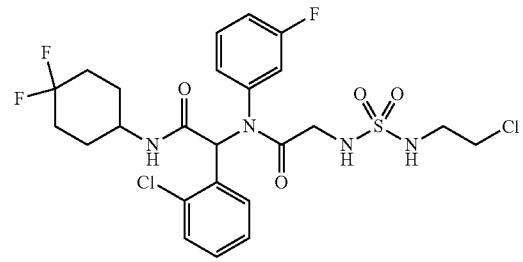 [SMILES: O=C(NC1CCC(F)(F)CC1)C(c1ccccc1Cl)N(C(=O)CNS(=O)(=O)NCCCl)c1cccc(F)c1]

A mixture of 2-chloro-benzaldehyde (64 mg, 0.462 mmol) and 3-fluoroaniline (52 mg, 0.462 mmol) in MeOH (6.0 mL) was stirred at room temperature for 30 min. 2-(N-(2-chloroethyl)aminosulfonylamino)acetic acid (100 mg, 0.462 mmol) was added thereto and the reaction mixture was stirred for 10 min. 1,1-Difluoro-4-isocyanocyclohexane (67 mg, 0.462 mmol) was then added, and the reaction mixture was stirred overnight at room temperature. The solvent was removed in vacuo and 2-(N-(2-chloroethyl)aminosulfonylamino)-N-(1-(2-chlorophenyl)-2-(4,4-difluorocyclohexylamino)-2-oxoethyl)-N-(3-fluorophenyl)acetamide (190 mg, yield of 69.1%) was obtained by separation through column chromatography on silica gel, which was used directly in the next step.

m/z=595 [M+H]$^+$.

Step G: 2-(aziridine-1-sulfonylamino)-N-(1-(2-chlorophenyl)-2-(4,4-difluorocyclohexylamino)-2-oxoethyl)-N-(3-fluorophenyl)acetamide

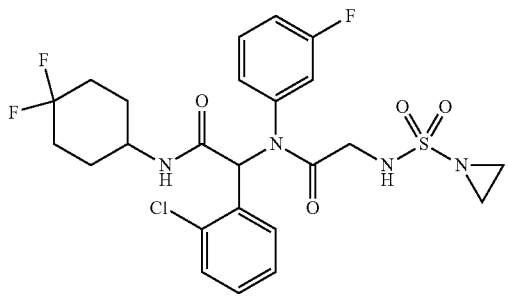 [SMILES: O=C(NC1CCC(F)(F)CC1)C(c1ccccc1Cl)N(C(=O)CNS(=O)(=O)N1CC1)c1cccc(F)c1]

At room temperature, potassium carbonate (132 mg, 0.576 mmol) was added with stirring to a solution of 2-(N-(2-chloroethyl)aminosulfonylamino)-N-(1-(2-chlorophenyl)-2-(4,4-difluorocyclohexylamino)2-oxoethyl)-N-(3-fluorophenyl)acetamide (190 mg, 0.319 mmol) in DMF. The reaction mixture was stirred overnight at room temperature. After completion of the reaction, the mixture was added with water, and extracted with ethyl acetate. The combined organic phase was washed with brine, dried over sodium sulfate, filtered and concentrated in vacuo, and separated by column chromatography on silica gel, to give 2-(aziridine-1-sulfonylamino)-N-(1-(2-chlorophenyl)-2-(4,4-difluorocyclohexylamino)-2-oxoethyl)-N-(3-fluorophenyl)acetamide (140 mg, yield of 78.7%).

$^1$H-NMR (400 MHz, CDCl$_3$): δ=7.37-7.33 (m, 2H), 7.23-7.10 (m, 2H), 7.07-6.87 (m, 4H), 6.41 (s, 1H), 5.53 (dd, J=11.7, 6.5 Hz, 2H), 3.96 (s, 1H), 3.77-3.69 (m, 2H), 2.30-2.23 (m, 4H), 2.14-1.75 (m, 6H), 1.59 (d, J=10.0 Hz, 2H).

m/z=559 [M+H]$^+$.

Example 31: 2-(2-chlorophenyl)-N-cyclohexyl-2-(N-(3-fluorophenyl)-2-(((R)-2-methylaziridine)-1-sulfonylamino)acetamido)acetamide

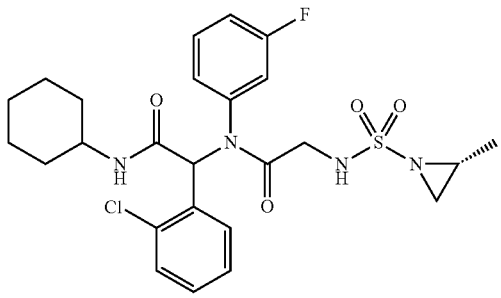 [SMILES: C[C@@H]1CN1S(=O)(=O)NCC(=O)N(c1cccc(F)c1)C(C(=O)NC1CCCCC1)c1ccccc1Cl]

Step A: methyl 2-[(chlorosulfonyl)amino]acetate

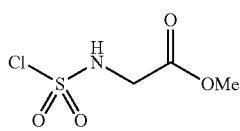

Chlorosulfonic acid (18.7 mL, 230.7 mmol) was added to a solution of glycine methyl ester hydrochloride (5.0 g, 39.8 mmol) in acetonitrile. The reaction solution was then heated to 80° C. and reacted for 18 h, and evaporated under reduced pressure, to give methyl 2-[(chlorosulfonyl)amino]acetate (6.5 g, yield of 87%).

Step B: methyl (R)-2-(2-methylaziridine-1-sulfonylamino)acetate

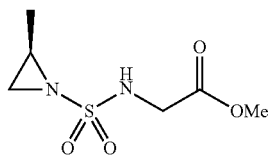

With stirring and in an ice bath, triethylamine (1.8 mL, 13.3 mmol) was added to a solution of D-aminopropanol (500 mg, 6.66 mmol) in dichloromethane, and methyl 2-[(chlorosulfonyl)amino]acetate (1.37 g, 7.30 mmol) was then added dropwise. After completion of the dropwise addition, the reaction solution was warmed up to room temperature and stirred overnight. The reaction solution was added with saturated ammonium chloride solution to quench the reaction, and extracted with dichloromethane. The combined organic phase was washed with brine, dried over sodium sulfate, filtered and concentrated in vacuo, and separated by column chromatography on silica gel, to give methyl (R)-2-(2-methylaziridine-1-sulfonylamino)acetate (99 mg, yield of 7%).

$^1$H-NMR (400 MHz, CDCl$_3$): δ=4.92 (s, 1H), 4.02 (d, J=5.5 Hz, 2H), 3.80 (s, 3H), 2.78-2.66 (m, 1H), 2.52 (d, J=6.9 Hz, 1H), 2.02 (d, J=4.5 Hz, 1H), 1.29 (d, J=5.6 Hz, 3H).

Step C: (R)-2-(2-methylaziridine-1-sulfonylamino)acetic Acid

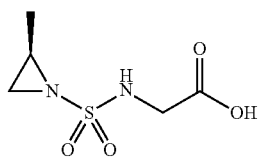

Lithium hydroxide (44 mg, 1.8 mmol) was added to a mixed solution of methyl (R)-2-(2-methylaziridine-1-sulfonylamino)acetate (95 mg, 0.456 mmol) in methanol and water (methanol/water=5/1). The reaction was stirred overnight at room temperature, and evaporated under reduced pressure to remove MeOH. The reaction solution was adjusted to a pH of 4 by using hydrochloric acid solution with pH=1, then extracted with ethyl acetate, dried over sodium sulfate, filtered and concentrated in vacuo, to give (R)-2-(2-methylaziridine-1-sulfonylamino)acetic acid (26 mg, yield of 29%).

$^1$H-NMR (400 MHz, CDCl$_3$): δ=8.88 (s, 1H), 5.48 (s, 1H), 4.05 (s, 2H), 2.73 (d, J=4.9 Hz, 1H), 2.52 (d, J=6.6 Hz, 1H), 2.06 (d, J=4.2 Hz, 1H), 1.30 (d, J=5.3 Hz, 3H).

Step D: 2-(2-chlorophenyl)-N-cyclohexyl-2-(N-(3-fluorophenyl)-2-(((R)-2-methylaziridine)-1-sulfonylamino)acetamido)acetamide

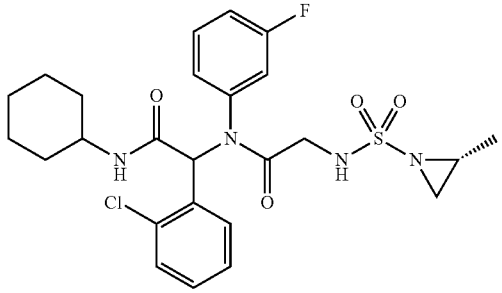 [SMILES: C[C@@H]1CN1S(=O)(=O)NCC(=O)N(c1cccc(F)c1)C(C(=O)NC1CCCCC1)c1ccccc1Cl]

With reference to step B of Example 1, 2-(2-chlorophenyl)-N-cyclohexyl-2-(N-(3-fluorophenyl)-2-(((R)-2-methylaziridine)-1-sulfonylamino)acetamido)acetamide (45 mg, yield of 81%) was obtained from (R)-2-(2-methylaziridine-1-sulfonylamino)acetic acid (20 mg, 0.103 mmol).

$^1$H-NMR (400 MHz, CDCl$_3$): δ=7.80-7.56 (m, 1H), 7.36 (d, J=8.0 Hz, 1H), 7.18-7.17 (m, 2H), 7.01-6.89 (m, 4H), 6.42 (d, J=5.1 Hz, 1H), 5.53-5.30 (m, 2H), 3.88-3.60 (m, 3H), 2.69-2.68 (m, 1H), 2.50-2.48 (m, 1H), 2.02-1.88 (m, 2H), 1.89-1.86 (m, 1H), 1.75-1.58 (m, 4H), 1.43-1.28 (m, 5H), 1.27-0.96 (m, 2H).

m/z=537 [M+H]$^+$.

Example 32: 2-(2-chlorophenyl)-N-cyclohexyl-2-(N-(3-fluorophenyl)-2-(((S)-2-methylaziridine)-1-sulfonylamino)acetamido)acetamide

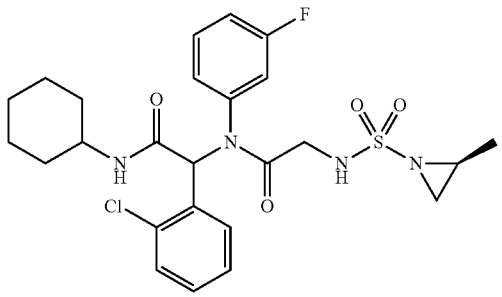 [SMILES: C[C@H]1CN1S(=O)(=O)NCC(=O)N(c1cccc(F)c1)C(C(=O)NC1CCCCC1)c1ccccc1Cl]

Step A: methyl (S)-2-(2-methylaziridine-1-sulfonylamino)acetate

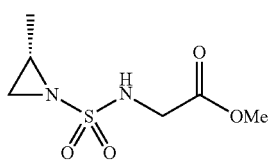

With reference to step B of Example 31, methyl (S)-2-(2-methylaziridine-1-sulfonylamino)acetate (160 mg, yield of 6%) was obtained from L-aminopropanol (1 g, 13.3 mmol).

$^1$H-NMR (400 MHz, CDCl$_3$): δ=4.93 (s, 1H), 4.06-4.00 (m, 2H), 3.86-3.76 (m, 3H), 2.77-2.65 (m, 1H), 2.52 (d, J=6.9 Hz, 1H), 2.02 (d, J=4.5 Hz, 1H), 1.36-1.26 (m, 3H).

Step B: (S)-2-(2-methylaziridine-1-sulfonylamino)acetic Acid

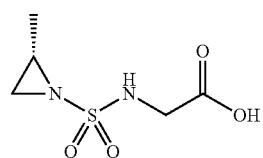

With reference to step B of Example 31, (S)-2-(2-methylaziridine-1-sulfonylamino)acetic acid (80 mg, yield of 90%) was obtained from methyl (S)-2-(2-methylaziridine-1-sulfonylamino)acetate (95 mg, 0.457 mmol).

$^1$H-NMR (400 MHz, CDCl$_3$): δ=12.73 (s, 1H), 7.79 (t, J=5.2 Hz, 1H), 3.72 (d, J=5.4 Hz, 2H), 2.50-2.45 (m, 1H), 2.25 (d, J=7.2 Hz, 1H), 1.99 (d, J=4.4 Hz, 1H), 1.17 (d, J=5.6 Hz, 3H).

Step C: 2-(2-chlorophenyl)-N-cyclohexyl-2-(N-(3-fluorophenyl)-2-(((S)-2-methylaziridine)-1-sulfonylamino)acetamido)acetamide

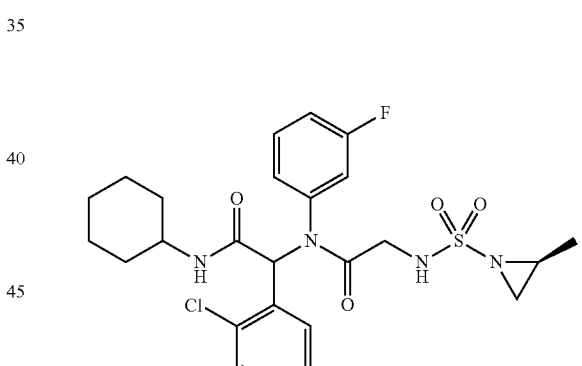

With reference to step B of Example 1, 2-(2-chlorophenyl)-N-cyclohexyl-2-(N-(3-fluorophenyl)-2-(((S)-2-methylaziridine)-1-sulfonylamino)acetamido)acetamide (60 mg, yield of 56%) was obtained from (S)-2-(2-methylaziridine-1-sulfonylamino)acetic acid (39 mg, 0.20 mmol).

$^1$H-NMR (400 MHz, CDCl$_3$): δ=7.70-7.66 (m, 1H), 7.34 (d, J=8.0 Hz, 1H), 7.16-7.14 (m, 2H), 7.24-6.68 (m, 4H), 6.42 (d, J=4.9 Hz, 1H), 5.52-5.47 (m, 2H), 3.89-3.60 (m, 3H), 2.70-2.66 (m, 1H), 2.49-2.45 (m, 1H), 2.20-1.97 (m, 2H), 1.88-1.85 (m, 1H), 1.79-1.51 (m, 4H), 1.51-0.94 (m, 7H).

m/z=537 [M+H]$^+$.

119

Example 33: 2-(2-chlorophenyl)-2-(N-(3-cyano-5-fluorophenyl)-2-(((S)-2-methylaziridine)-1-sulfonylamino)acetamido)-N-(3,3-difluorocyclobutyl)acetamide

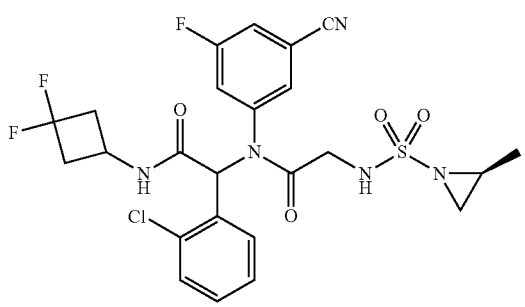 [SMILES: C[C@H]1CN1S(=O)(=O)NCC(=O)N(c1cc(F)cc(C#N)c1)C(C(=O)NC1CC(F)(F)C1)c1ccccc1Cl]

With reference to step C of Example 13, 2-(2-chlorophenyl)-2-(N-(3-cyano-5-fluorophenyl)-2-(((S)-2-methylaziridine)-1-sulfonylamino)acetamido)-N-(3,3-difluorocyclobutyl)acetamide (3.9 mg, yield of 3.4%) was obtained from 3-amino-5-fluorobenzonitrile (27 mg, 0.2 mmol) and (S)-2-(2-methylaziridine-1-sulfonylamino)acetic acid (20 mg, 0.103 mmol).

$^1$H-NMR (400 MHz, CDCl$_3$): δ=8.02-7.97 (m, 1H), 7.41 (d, J=8.0 Hz, 1H), 7.29-7.19 (m, 1H), 7.07-7.03 (m, 2H), 6.97-6.93 (m, 1H), 6.93-6.80 (m, 1H), 6.45 (d, J=7.7 Hz, 1H), 6.25-6.22 (m, 1H), 5.77 (d, J=21.2 Hz, 1H), 4.29 (s, 1H), 3.80-3.67 (m, 3H), 3.17-2.74 (m, 2H), 2.75-2.69 (m, 1H), 2.56-2.43 (m, 2H), 2.03 (t, J=4.8 Hz, 1H), 1.30 (d, J=8.0 Hz, 3H).

m/z=570 [M+H]$^+$.

Example 34: (S)-1-(aziridin-1-ylsulfonyl)-N—((S)-1-(2-chlorophenyl)-2-((3,3-difluorocyclobutyl)amino)-2-oxoethyl)-N-(3-fluorophenyl)pyrrolidine-3-carboxamide Example 35: (S)-1-(aziridin-1-ylsulfonyl)-N—((R)-1-(2-chlorophenyl)-2-((3,3-difluorocyclobutyl)amino)-2-oxoethyl)-N-(3-fluorophenyl)pyrrolidine-3-carboxamide (Example 34)

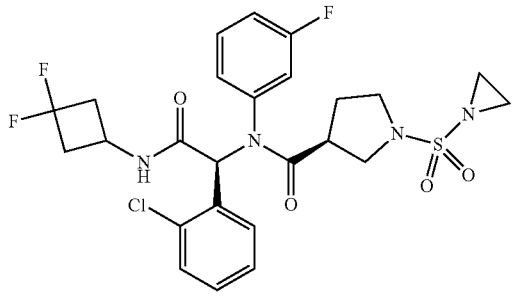

120

-continued (Example 35)

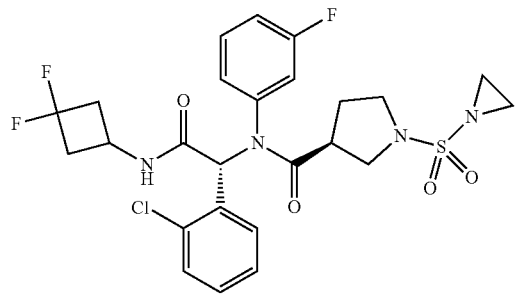

Step A: tert-butyl (S)-3-((1-(2-chlorophenyl)-2-((3,3-difluorocyclobutyl)amino)-2-oxoethyl)(3-fluorophenyl)carbamoyl)pyrrolidine-1-carboxylate

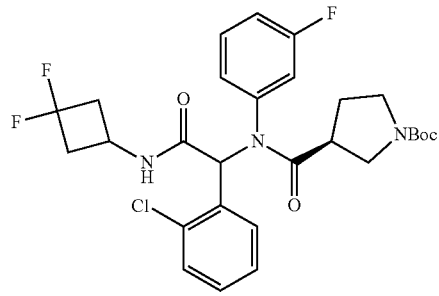 [SMILES: CC(C)(C)OC(=O)N1CC[C@H](C(=O)N(c2cccc(F)c2)C(C(=O)NC2CC(F)(F)C2)c2ccccc2Cl)C1]

At room temperature, o-Chlorobenzaldehyde (210 μL, 1.85 mmol) and m-fluoroaniline (179 μL, 1.85 mmol) were added to 10 mL of methanol, (S)-1-Boc-pyrrolidine-3-carboxylic acid (400 mg, 1.85 mmol) was added thereto after stirring for 10 min, and 1,1-difluoro-3-isocyanocyclobutane (217 mg, 1.85 mmol) was added following further stirring for another 10 min. The mixture was stirred overnight at room temperature. After completion of the reaction, the solvent was removed under reduced pressure, and a solid product of tert-butyl (S)-3-((1-(2-chlorophenyl)-2-((3,3-difluorocyclobutyl)amino)-2-oxoethyl)(3-fluorophenyl)carbamoyl)pyrrolidine-1-carboxylate (346 mg, yield of 32%) was obtained by separation through column chromatography on silica gel (PE:EA=2:1).

$^1$H-NMR (400 MHz, CDCl$_3$): δ=7.53-7.48 (m, 1H), 7.37-7.33 (m, 2H), 7.18-7.16 (m, 2H), 7.00-6.89 (m, 3H), 6.45-6.42 (m, 1H), 6.29-6.22 (m, 1H), 4.32-4.30 (m, 1H), 3.65-3.37 (m, 4H), 3.12-2.98 (m, 2H), 2.85-2.81 (m, 1H), 2.55-2.52 (m, 1H), 2.41-2.36 (m, 1H), 2.23-2.21 (m, 1H), 2.05 (s, 1H), 1.46 (s, 9H).

m/z=566 [M+H]$^+$.

Step B: (3S)-1-(N-(2-chloroethyl)aminosulfonyl)-N-(1-(2-chlorophenyl)-2-((3,3-difluorocyclobutyl)amino)-2-oxoethyl)-N-(3-fluorophenyl)pyrrolidine-3-carboxamide Step C: (S)-1-(aziridin-1-ylsulfonyl)-N—((S)-1-(2-chlorophenyl)-2-((3,3-difluorocyclobutyl)amino)-2-oxoethyl)-N-(3-fluorophenyl)pyrrolidine-3-carboxamide (Example 34)

(S)-1-(aziridin-1-ylsulfonyl)-N—((R)-1-(2-chlorophenyl)-2-((3,3-difluorocyclobutyl)amino)-2-oxoethyl)-N-(3-fluorophenyl)pyrrolidine-3-carboxamide (Example 35)

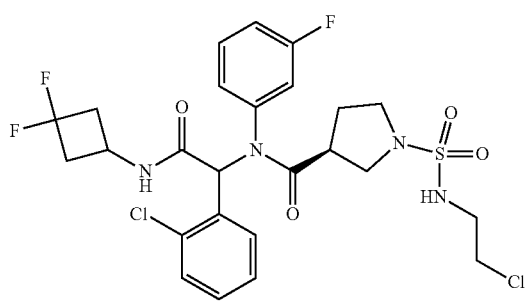 [SMILES: O=C(NC1CC(F)(F)C1)C(c1ccccc1Cl)N(C(=O)[C@H]1CCN(S(=O)(=O)NCCCl)C1)c1cccc(F)c1]

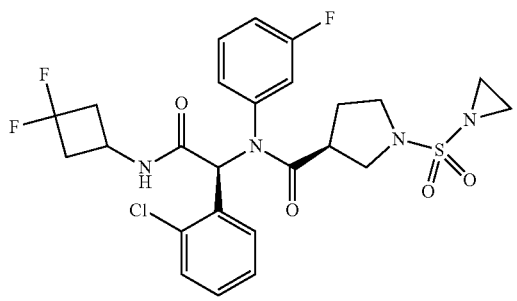

(Example 34)

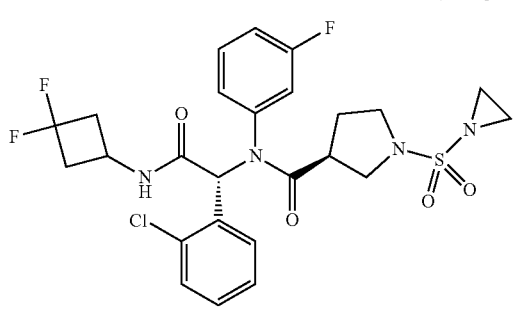

(Example 35)

0.5 mL of TFA was added to a solution of tert-butyl (S)-3-((1-(2-chlorophenyl)-2-((3,3-difluorocyclobutyl)amino)-2-oxoethyl)(3-fluorophenyl)carbamoyl)pyrrolidine-1-carboxylate (173 mg, 0.31 mmol) in dichloromethane, and stirred at room temperature for 1 h. After completion of the reaction, TFA and the solvent therein were removed by evaporation under reduced pressure to give a solid product (140 mg). 2-(Chloroethyl)aminosulfonyl chloride (98 mg, 0.60 mmol) was added to a solution of the above solid compound (140 mg, 0.30 mmol) and DIEA (198 µL, 1.20 mmol) in dichloromethane at 0° C., warmed up to room temperature and stirred overnight. After completion of the reaction, the mixture was adjusted to a neutral pH by adding 1N HCl. The organic phase was separated, dried over anhydrous sodium sulfate, concentrated under reduced pressure, and separated by column chromatography on silica gel (PE:EA=2:1), to give a further solid product of (3S)-1-(N-(2-chloroethyl)aminosulfonyl)-N-(1-(2-chlorophenyl)-2-((3,3-difluorocyclobutyl)amino)-2-oxoethyl)-N-(3-fluorophenyl)pyrrolidine-3-carboxamide (60 mg, yield of 32%).

$^1$H-NMR (400 MHz, CDCl$_3$): δ=7.53 (br s, 1H), 7.36-7.34 (m, 1H), 7.20-7.17 (m, 1H), 7.10 (brs, 1H), 7.00-6.91 (m, 3H), 6.60 (brs, 1H), 6.44-6.42 (m, 1H), 6.14-6.06 (m, 1H), 4.94-4.87 (m, 1H), 4.32-4.30 (m, 1H), 3.69-3.65 (m, 2H), 3.57-3.50 (m, 1H), 3.46-3.25 (m, 5H), 3.06-2.95 (m, 3H), 2.59-2.36 (m, 2H), 2.27-2.18 (m, 1H), 1.94-1.90 (m, 1H).

m/z=607 [M+H]$^+$.

(3S)-1-(N-(2-chloroethyl)aminosulfonyl)-N-(1-(2-chlorophenyl)-2-(3,3-difluorocyclobutyl)amino)-2-oxoethyl)-N-(3-fluorophenyl)pyrrolidine-3-carboxamide (30 mg, 0.049 mmol) and potassium carbonate (14 mg, 0.098 mmol) were added in 1 mL of DMF at room temperature, and stirred overnight at room temperature. After completion of the reaction, the mixture was added with 20 mL of dichloromethane, and washed with water (30 mL×3). The organic phase was dried over anhydrous sodium sulfate, and then separated by column chromatography on silica gel (PE:EA=1:1), to give a solid product of (S)-1-(aziridin-1-ylsulfonyl)-N—((S)-1-(2-chlorophenyl)-2-((3,3-difluorocyclobutyl)amino)-2-oxoethyl)-N-(3-fluorophenyl)pyrrolidine-3-carboxamide (6 mg, yield of 21%) and (S)-1-(aziridin-1-ylsulfonyl)-N—((R)-1-(2-chlorophenyl)-2-((3,3-difluorocyclobutyl)amino)-2-oxoethyl)-N-(3-fluorophenyl)pyrrolidine-3-carboxamide (6 mg, yield of 21%).

Example 34: $^1$H-NMR (400 MHz, CDCl$_3$): δ=7.57 (br s, 1H), 7.36-7.34 (m, 1H), 7.19-7.16 (m, 2H), 7.02-6.97 (m, 2H), 6.94-6.90 (m, 2H), 6.44 (s, 1H), 6.33 (d, J=6.4 Hz, 1H), 4.29-4.27 (m, 1H), 3.56-3.44 (m, 3H), 3.37-3.31 (m, 1H), 3.04-2.93 (m, 3H), 2.56-2.51 (m, 1H), 2.41-2.36 (m, 1H), 2.27-2.22 (m, 1H), 2.04 (s, 4H), 2.00-1.95 (m, 1H).

m/z=571 [M+H]$^+$.

Example 35: $^1$H-NMR (400 MHz, CDCl$_3$): δ=7.61 (br s, 1H), 7.36-7.34 (m, 1H), 7.17-7.15 (m, 2H), 7.01-6.91 (m, 4H), 6.48 (s, 1H), 6.31 (d, J=6.4 Hz, 1H), 4.33-4.30 (m, 1H), 3.59-3.47 (m, 3H), 3.35-3.29 (m, 1H), 3.06-2.90 (m, 3H), 2.57-2.50 (m, 1H), 2.41-2.35 (m, 1H), 2.29-2.21 (m, 1H), 2.19 (s, 4H), 2.02-1.93 (m, 1H).

m/z=571 [M+H]$^+$.

Example 36: (R)-1-(aziridin-1-ylsulfonyl)-N—((S)-1-(2-chlorophenyl)-2-((3,3-difluorocyclobutyl)amino)-2-oxoethyl)-N-(3-fluorophenyl)pyrrolidine-3-carboxamide Example 37: (R)-1-(aziridin-1-ylsulfonyl)-N—((R)-1-(2-chlorophenyl)-2-((3,3-difluorocyclobutyl)amino)-2-oxoethyl)-N-(3-fluorophenyl)pyrrolidine-3-carboxamide (Example 36)

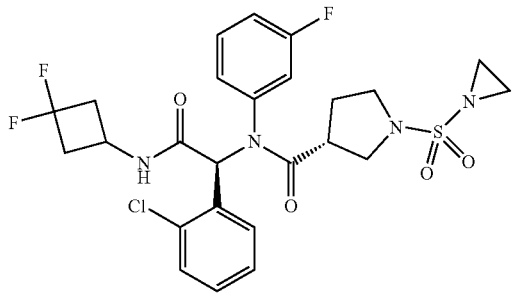

(Example 37)

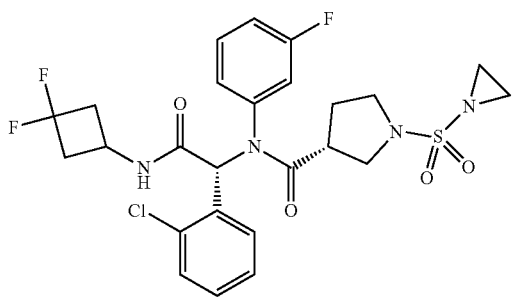

With reference to preparation of Examples 34 and 35, the products of Examples 36 and 37 were prepared by replacing (S)-1-Boc-pyrrolidine-3-carboxylic acid with (R)-1-Boc-pyrrolidine-3-carboxylic acid.

Example 36: $^1$H-NMR (400 MHz, CDCl$_3$): δ=7.61 (br s, 1H), 7.36-7.34 (m, 1H), 7.17-7.15 (m, 2H), 7.01-6.91 (m, 4H), 6.48 (s, 1H), 6.31 (d, J=6.4 Hz, 1H), 4.33-4.30 (m, 1H), 3.59-3.47 (m, 3H), 3.35-3.29 (m, 1H), 3.05-2.90 (m, 3H), 2.58-2.51 (m, 1H), 2.41-2.35 (m, 1H), 2.29-2.21 (m, 1H), 2.19 (s, 4H), 2.02-1.92 (m, 1H).

m/z=571 [M+H]$^+$.

Example 37: $^1$H-NMR (400 MHz, CDCl$_3$): δ=7.57 (br s, 1H), 7.36-7.34 (m, 1H), 7.19-7.16 (m, 2H), 7.02-6.96 (m, 2H), 6.94-6.91 (m, 2H), 6.44 (s, 1H), 6.33 (d, J=6.4 Hz, 1H), 4.29-4.27 (m, 1H), 3.55-3.44 (m, 3H), 3.37-3.31 (m, 1H), 3.04-2.94 (m, 3H), 2.56-2.51 (m, 1H), 2.41-2.36 (m, 1H), 2.27-2.21 (m, 1H), 2.04 (s, 4H), 2.00-1.95 (m, 1H).

m/z=571 [M+H]$^+$.

Bioactivity Experiments

Enzyme Assay:

Resazurin is a traditional redox dye, and after a redox reaction, it can be reduced from a blue resazurin without fluorescence to a pink fluorescent substance, resorufin, which can be measured and quantified with relative fluorescence unit (RFU) of fluorophotometer (E$_x$=530-570 nm, Em=590-620 nm). At present, resazurin is widely used for determining the viability of bacteria, cells, etc. and the enzyme activity detection of oxidoreductase. We detected the decrease of cofactor NADPH to determine the inhibitory activity of a compound against IDHm and detected the generation of cofactor NADPH to determine the inhibitory activity of a compound against IDH WT.

The compound was pre-incubated with IDHm and NADPH, and then the reaction was initiated by adding α-KG and performed for certain time under a linear condition.

Then, Diaphorase (lipoamide dehydrogenase) and the corresponding substrate Resazurin were added thereto for detection. Lipoamide dehydrogenase terminated the IDH2m reaction by decreasing the available cofactor NADPH, which oxidized NADPH to NADP, and reduced resazurin to high fluorescent resorufin. The amount of the remaining cofactor NADPH after a specific reaction time was quantified via an easily detectable fluorophore.

The compound was pre-incubated with IDH-WT and NADP, and then the reaction was initiated by adding isocitric acid, Diaphorase (lipoamide dehydrogenase) and the corresponding substrate Resazurin, and performed for certain time under a linear condition, and followed by detecting the amount of fluorescent substance. NADP was reduced to NADPH in this experiment, and the latter reduced resazurin to high fluorescent resorufin under the action of lipoamide dehydrogenase. The amount of the generated cofactor NADPH after a specific reaction time was quantified via a detectable fluorophore, so as to calculate the inhibitory effect of the compound on IDH-WT.

The specific operation was as follows: 2.5 μl of the compound diluted in a 3-fold gradient was added to a 384-well plate, followed by adding 5 μL of the reaction buffer (20 mM Tris-HCl, pH 7.5; 150 mM NaCl; 10 mM MgCl$_2$; 0.4 mg/mL BSA (Bovine Serum Albumin) and 2 mM DTT (dithiothreitol)) containing 40 nM IDH1 (R132H/R132C) and 20 μM NADPH. Then, the above test mixture was incubated at 23° C. for 16 hours, and then 2.5 μL of the reaction buffer containing 4 mM α-KG was added to initiate the reaction. After they were incubated for 60 minutes at room temperature, 5 μL of the termination mixture (0.4 U/ml Diaphorase and 20 μM Resazurin) formulated with the reaction buffer was added to convert resazurin to resorufin, so as to measure the amount of the remaining NADPH. After incubating at 23° C. for 10 minutes, fluorescence values were determined through Flexstation 3 at Ex535/Em595. The enzyme activity of each compound was respectively determined at 12 concentrations, and the data were calculated using the software GraFit6.0 (Erithacus Software) to obtain the IC$_{50}$ value of each compound.

Binding Mode Determination for the Compounds:

The compounds were incubated with IDH1 (R132H), and then divided into N parts. The reaction was terminated by adding acetonitrile at different time points, and the organic phase was separated by centrifugation. The resulting samples were stored at −80° C. until analysis, and the concentration of the compounds in free from were analyzed by LC-MS/MS, mobile phase A: water (0.1% of formic acid), B: acetonitrile (0.1% of formic acid), strong needle wash solution: acetonitrile:water=9:1, weak needle wash solution: acetonitrile:water=1:9.

The selected compounds prepared as described above were analyzed according to the biological methods herein, and the results are as follows:

1. The inhibitory activities ($IC_{50}$) of the compounds against IDH1 mutants (R132H/R132C) were shown in Table 1.

TABLE 1

| Example No. | IDH1 (R132H) $IC_{50}$ (nM) | IDH1 (R132C) $IC_{50}$ (nM) |
|---|---|---|
| 1 | <20 | — |
| 2 | <500 | — |
| 3 | <10000 | — |
| 4 | <100 | — |
| 5 | <20 | — |
| 6 | <20 | — |
| 7 | <10000 | — |
| 8 | <20 | — |
| 9 | <100 | — |
| 10 | <20 | — |
| 11 | <100 | — |
| 12 | <20 | — |
| 13 | <20 | — |
| 14 | <20 | — |
| 15 | <20 | — |
| 16 | <20 | — |
| 17 | <20 | — |
| 18 | <10000 | — |
| 19 | <100 | — |
| 20 | <20 | — |
| 21 | <20 | — |
| 22 | <20 | — |
| 23 | <100 | — |
| 24 | <20 | — |
| 25 | <20 | <20 |
| 26 | <100 | — |
| 27 | <20 | — |
| 28 | <100 | — |
| 29 | <20 | — |
| 30 | <20 | — |
| 31 | <20 | — |
| 32 | <20 | — |
| 33 | <100 | — |
| 34 | <20 | — |
| 35 | <20 | — |
| 36 | <20 | — |
| 37 | <1000 | — |

2. Test of binding mode of the compound to IDH1 (R132H)

As can be seen from FIG. 1, the compound of Example 10 binding to the enzyme increased over time.

Pharmacokinetic Test

Male SD rats were from Beijing Vital River Laboratory Animal Technology Co., Ltd., and divided into groups (3 rats per group). The rats were intragastically administered with the test sample suspension (5 mg/kg) via a single peroral administration, respectively. The animals were fasted overnight before this study. The fasting time period was from 10 hours before administration to 4 hours after administration. Blood samples were taken at 0.25, 0.5, 1, 2, 4, 6, 8 and 24 hours after administration. After the rats were anesthetized with isoflurane using an anesthesia machine for small animal, and then 0.3 mL whole blood samples were taken from the fundus venous plexus. The blood samples were placed in heparin anticoagulant tubes, and centrifuged for 5 min at 4° C. and 4000 rpm. The plasma was transferred to centrifuge tubes, and stored at −80° C. until analysis. The samples in plasma were extracted through protein precipitation. The liquid extract was analyzed by LC-MS/MS, mobile phase A: water (0.1% of formic acid), B: acetonitrile (0.1% of formic acid), strong needle wash solution: acetonitrile:water=9:1, weak needle wash solution: acetonitrile:water=1:9.

TABLE 2

| Example 10 | |
|---|---|
| Gender of rats | male |
| Oral dose (mg/kg) | 5 |
| $T_{1/2}$(hr) | 1.5 |
| Tmax(hr) | 0.25 |
| Cmax(ng/mL) | 508 |
| $AUC_{INF\_obs}$(hr*ng/mL) | 794 |
| Formulation of dosage forms | 0.5% MC, 0.2% Tween80 |

Figure 2:
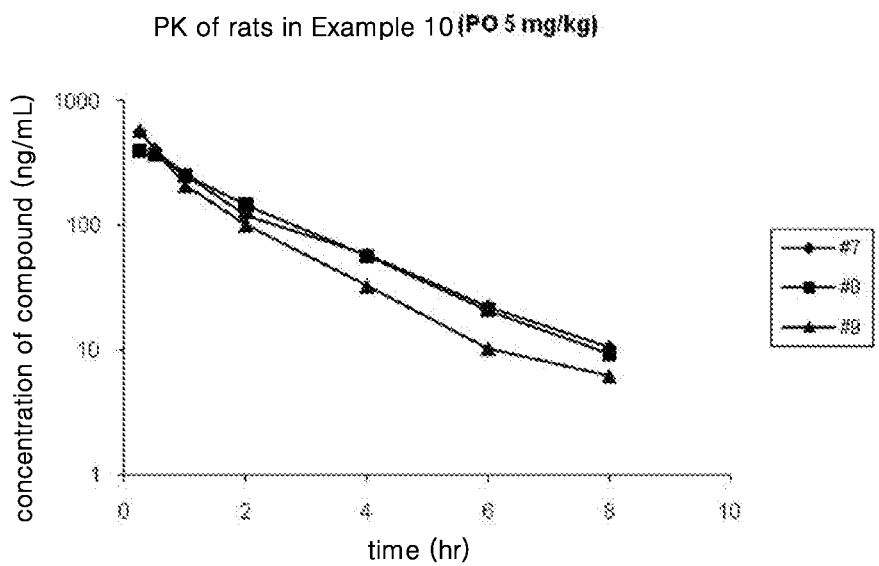
FIG. 2 is a PK plot of the compound of Example 10.
Figure 3:
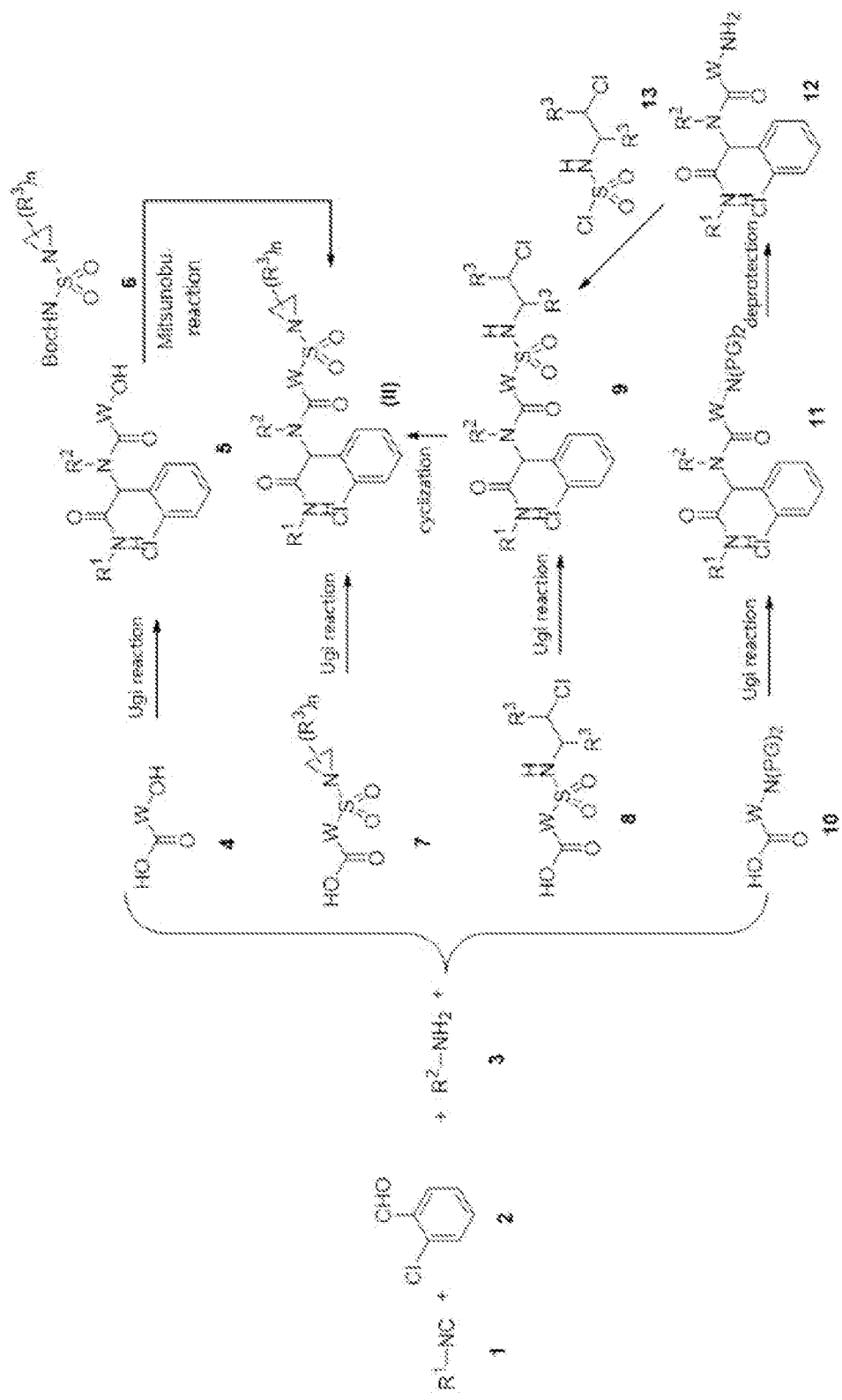
FIG. 3 is a standard method in the art in which the compound of Formula II may be prepared.

As the PK curve shown in FIG. 2 (#7, #8, #9 in FIG. 2 were the number of rats for test) and the data shown in Table 2, the compound of Example 10 has unique pharmacokinetic property, which has decreased drug concentration in vivo over time. This trend is in good agreement with the slow binding mode of the drug to IDH1m, indicating that the drug gradually binds to IDH1 m over time, so that the drug concentration in plasma was gradually decreased.

What is claimed is:

1. A compound of Formula I, or a pharmaceutically acceptable salt, solvate or hydrate thereof,

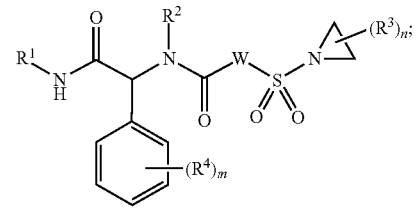

(I)

wherein,

W is $-(X^1)_p-(X^2)_q-(X^3)_r-$;

$X^1$ is selected from $C_{1-6}$ alkylene, which is optionally substituted with one or more groups independently selected from $R^5$;

$X^2$ is selected from pyrrolidinyl, cyclobutyl or azetidinyl;

$X^3$ is selected from $-NR^7-$;

p is 0 or 1;

q is 0 or 1;

r is 0 or 1;

and p, q, r are not 0 simultaneously;

$R^1$ is selected from $C_{3-6}$ cycloalkyl or $C_{3-6}$ heterocycloalkyl, which is optionally substituted with one or more groups independently selected from $R^8$;

$R^2$ is selected from phenyl or pyridyl, which is optionally substituted with one or more groups independently selected from $R^9$;

each of $R^3$ and $R^4$ is independently selected from halogen, amino, hydroxyl, halogenated $C_{1-3}$ alkyl or $C_{1-6}$ alkyl;

$R^5$ and $R^8$ are each independently selected from halogen, amino, hydroxyl, cyano, halogenated $C_{1-3}$ alkyl, $C_{1-6}$ alkyl or $C_{3-6}$ cycloalkyl;

$R^7$ is selected from hydrogen, $C_{1-3}$ alkyl or amino protecting group;

$R^9$ is selected from halogen, amino, hydroxyl, cyano, halogenated $C_{1-3}$ alkyl or aminosulfonyl;

m is 0 or 1;

n is 0 or 1.

2. The compound or the pharmaceutically acceptable salt, solvate or hydrate thereof according to claim 1, wherein the compound has Formula II,

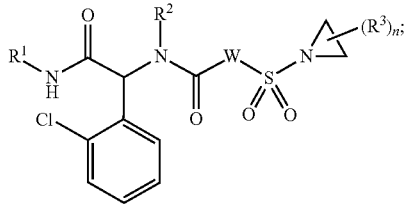
(II)

wherein,
W is —(X$^1$)$_p$—(X$^2$)$_q$—(X$^3$)$_r$—;
X$^1$ is selected from C$_{1-6}$ alkylene, which is optionally substituted with one or more groups independently selected from R$^5$;
X$^2$ is selected from pyrrolidinyl, cyclobutyl or azetidinyl;
X$^3$ is selected from —NR$^7$—;
p is 0 or 1;
q is 0 or 1;
r is 0 or 1;
and p, q, r are not 0 simultaneously;
R$^1$ is selected from C$_{3-6}$ cycloalkyl or C$_{3-6}$ heterocycloalkyl, which is optionally substituted with one or more groups independently selected from R$^8$;
R$^2$ is selected from phenyl or pyridyl, which is optionally substituted with one or more groups independently selected from R$^9$;
each R$^3$ is independently selected from halogen, amino, hydroxyl, halogenated C$_{1-3}$ alkyl or C$_{1-6}$ alkyl;
R$^5$ and R$^8$ are each independently selected from halogen, amino, hydroxyl, cyano, halogenated C$_{1-3}$ alkyl, C$_{1-6}$ alkyl or C$_{3-6}$ cycloalkyl;
R$^7$ is selected from hydrogen, C$_{1-3}$ alkyl or amino protecting group;
R$^9$ is selected from halogen, amino, hydroxyl, cyano, halogenated C$_{1-3}$ alkyl or aminosulfonyl;
n is 0 or 1.

3. The compound or the pharmaceutically acceptable salt, solvate or hydrate thereof according to claim 1, wherein X$^1$ is selected from C$_{1-6}$ alkylene.

4. The compound or the pharmaceutically acceptable salt, solvate or hydrate thereof according to claim 1, wherein X$^3$ is selected from —NH—, —N(CH$_3$)— or —N(Boc)-.

5. The compound or the pharmaceutically acceptable salt, solvate or hydrate thereof according to claim 1, wherein R$^7$ is selected from hydrogen, methyl, ethyl, tert-butoxycarbonyl, benzyloxycarbonyl, p-toluenesulfonyl, triphenylmethyl, formyl, 2-biphenyl-2-propoxycarbonyl or trifluoroacetyl.

6. The compound or the pharmaceutically acceptable salt, solvate or hydrate thereof according to claim 1, wherein W is —CH$_2$NR$^7$—, —CH(CH$_3$)NR$^7$—, —CH$_2$CH$_2$NR$^7$—, —CH$_2$CH$_2$CH$_2$NR$^7$—, —CH$_2$—, —CH$_2$CH$_2$—, —CH$_2$CH$_2$CH$_2$—, —CH$_2$CH$_2$CH$_2$CH$_2$—,

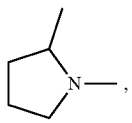 , 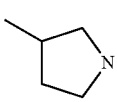 , 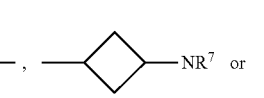 or

 ;

7. The compound or the pharmaceutically acceptable salt, solvate or hydrate thereof according to claim 1, wherein R$^1$ is selected from cyclopropyl, cyclobutyl, cyclopentyl, cyclohexyl, pyrrolidinyl or piperidinyl, which is optionally substituted with one or more groups independently selected from R$^8$.

8. The compound or the pharmaceutically acceptable salt, solvate or hydrate thereof according to claim 1, wherein R$^8$ is selected from halogen.

9. The compound or the pharmaceutically acceptable salt, solvate or hydrate thereof according to claim 1, wherein R$^9$ is selected from halogen, cyano, monofluoromethyl, difluoromethyl, trifluoromethyl, monofluoroethyl, difluoroethyl, trifluoroethyl, tetrafluoroethyl, pentafluoroethyl, monochloromethyl, dichloromethyl, trichloromethyl or aminosulfonyl.

10. The compound or the pharmaceutically acceptable salt, solvate or hydrate thereof according to claim 1, wherein each R$^3$ is independently selected from methyl, ethyl, propyl, isopropyl or t-butyl.

11. The compound or the pharmaceutically acceptable salt, solvate or hydrate thereof according to claim 1, wherein the compound is the following compounds and the pharmaceutically acceptable salts, solvates or hydrates thereof:

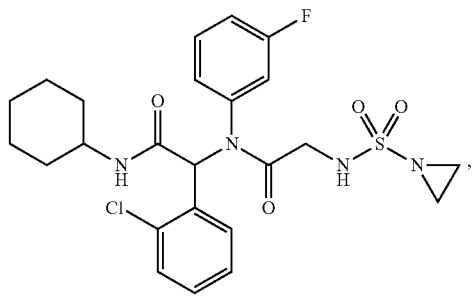,

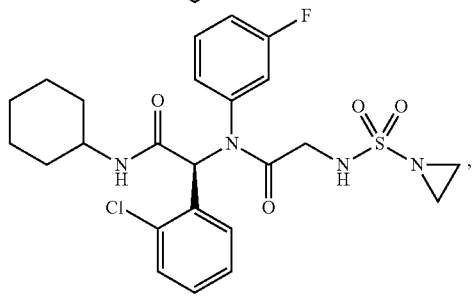,

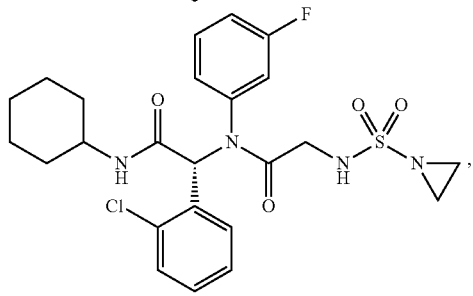,

-continued
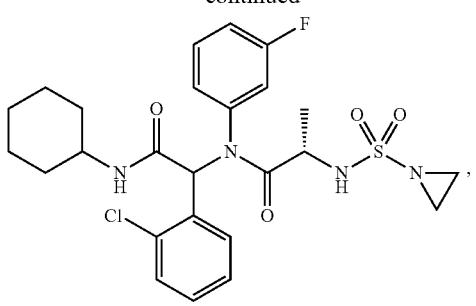
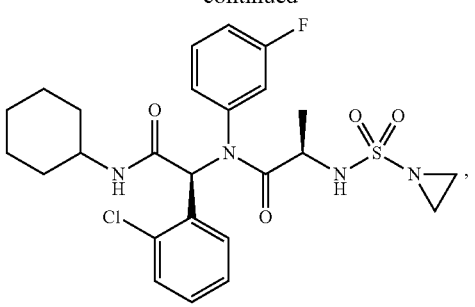
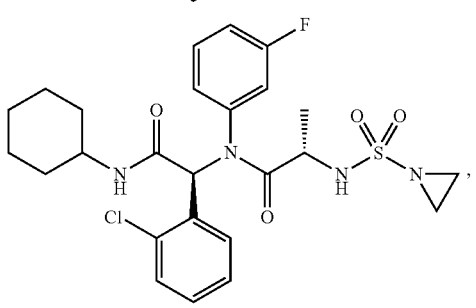
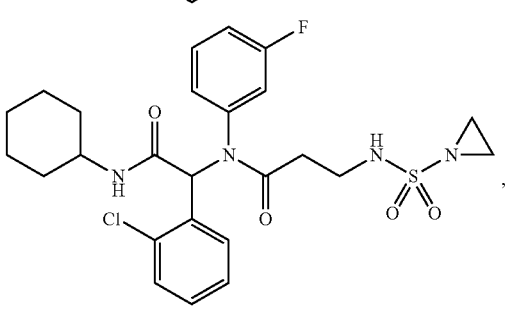
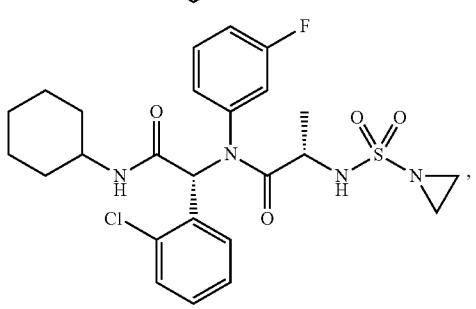
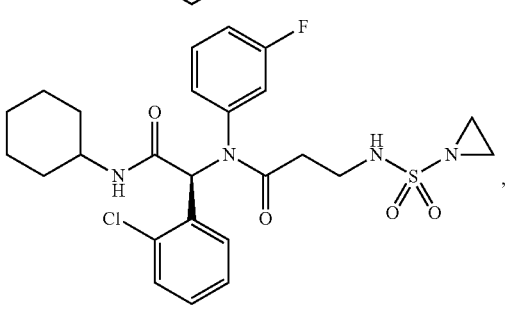
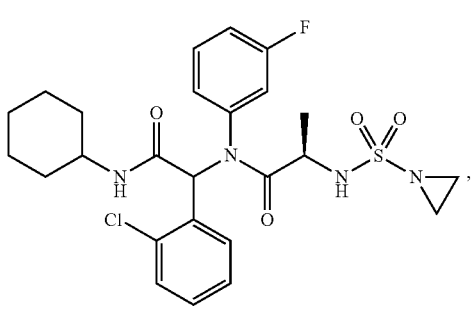
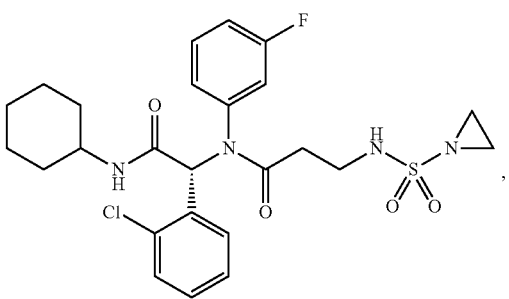
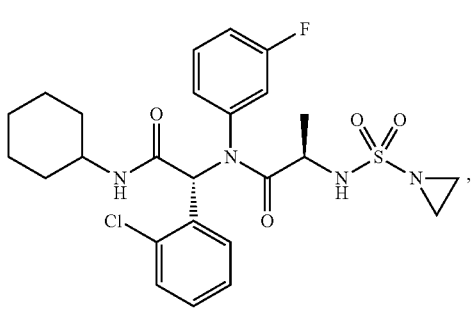
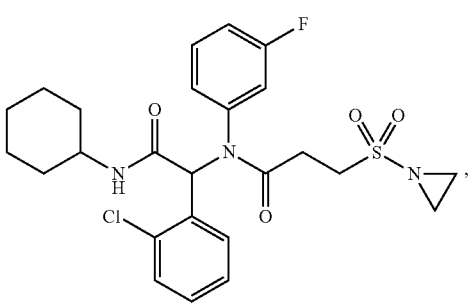

131
-continued
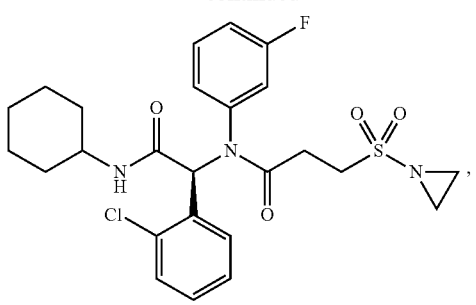
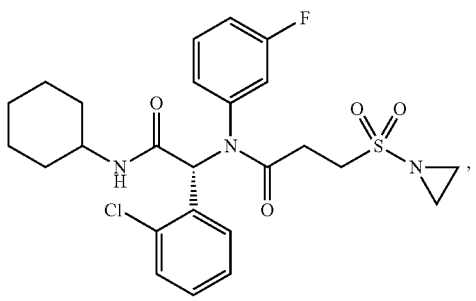
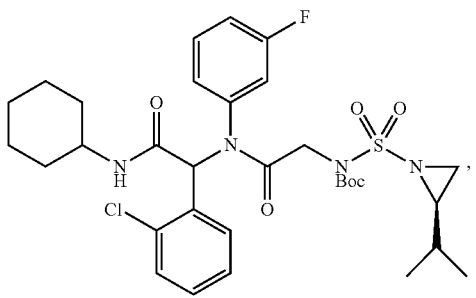
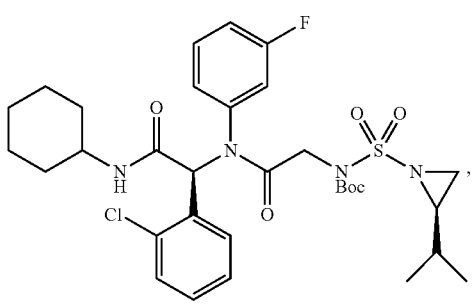
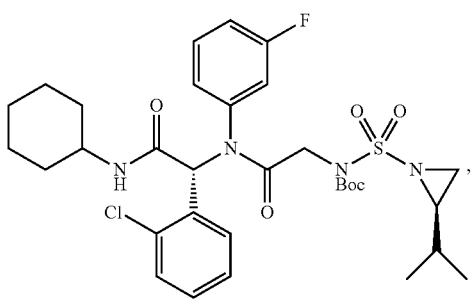
132
-continued
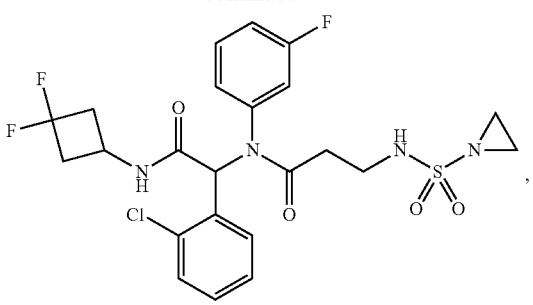
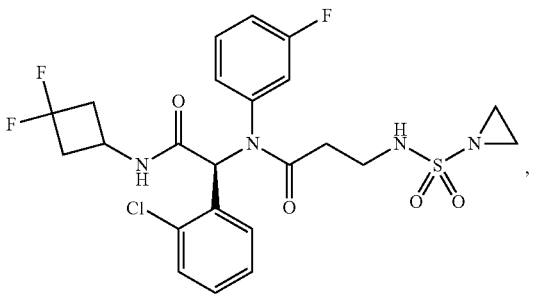
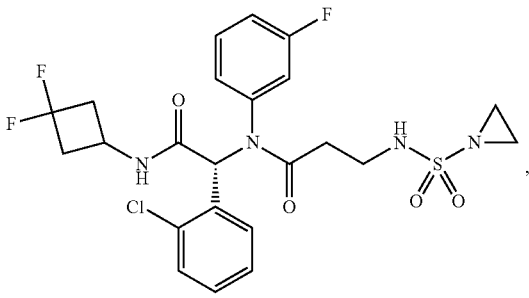
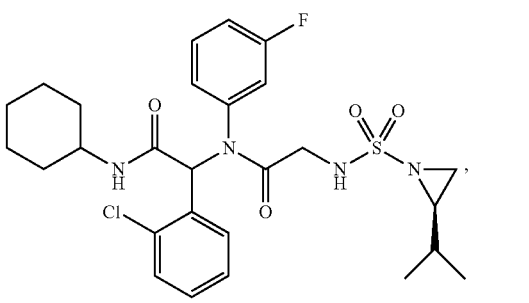
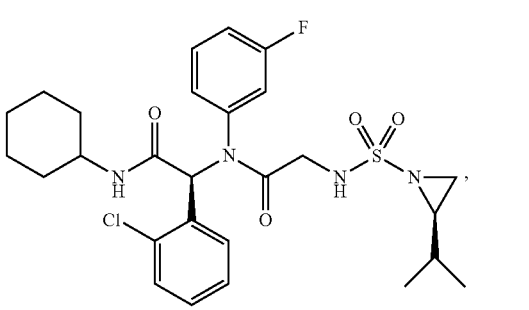

133
-continued
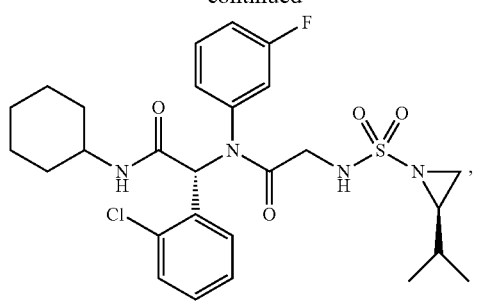
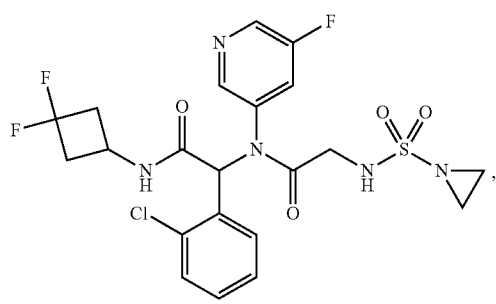
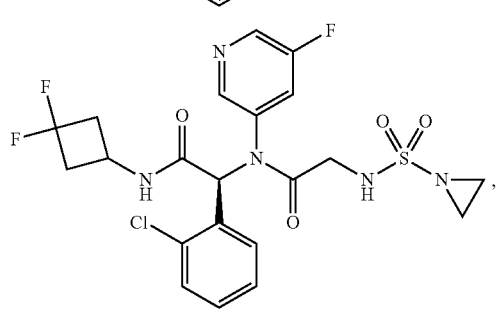
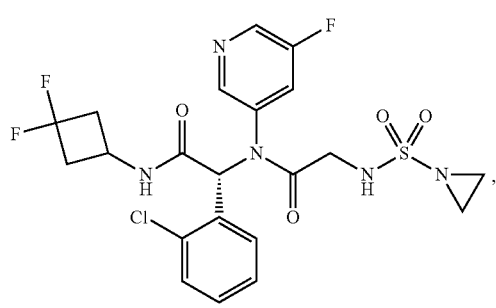
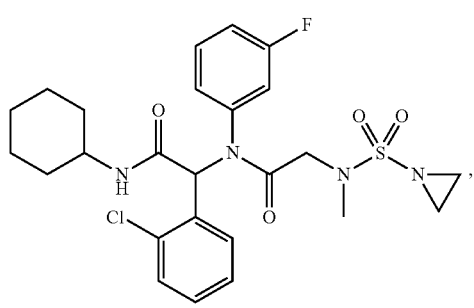
134
-continued
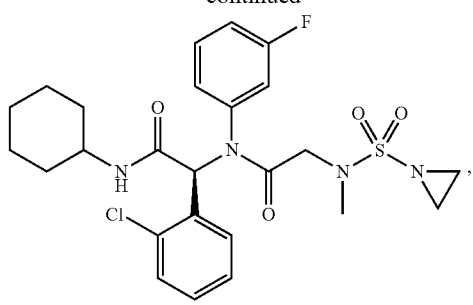
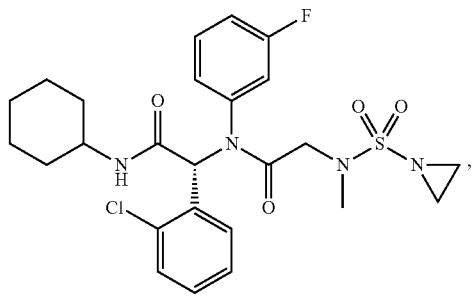
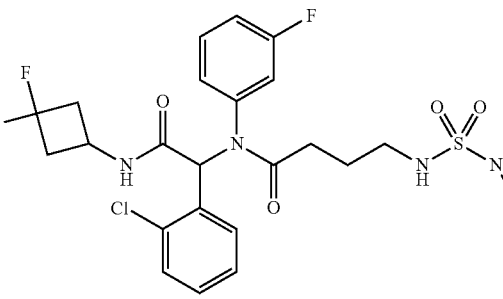
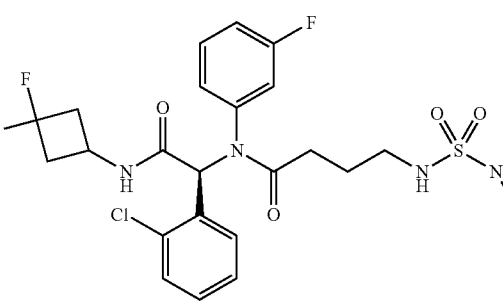
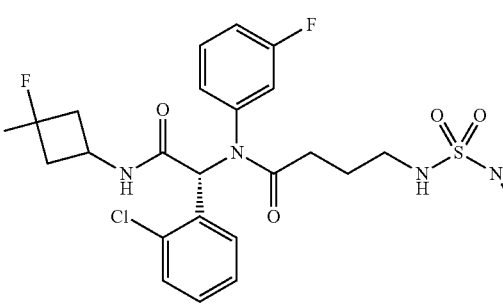

135
-continued
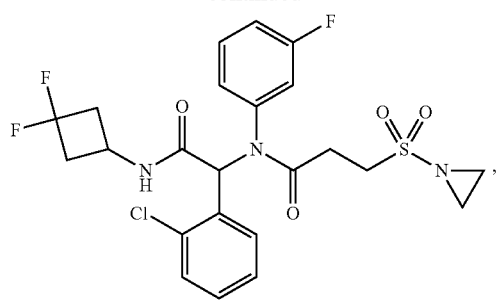
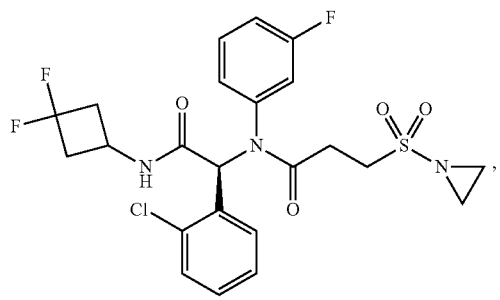
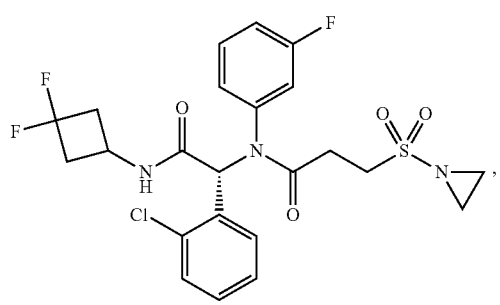
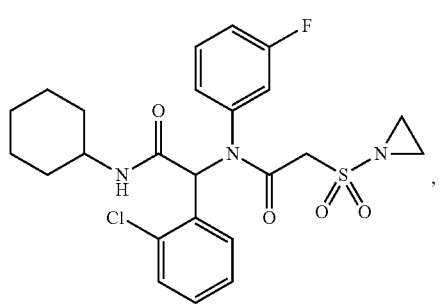
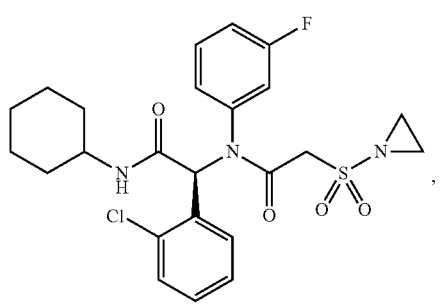
136
-continued
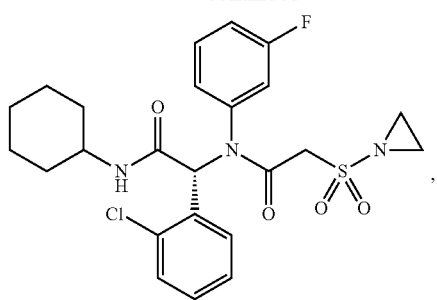
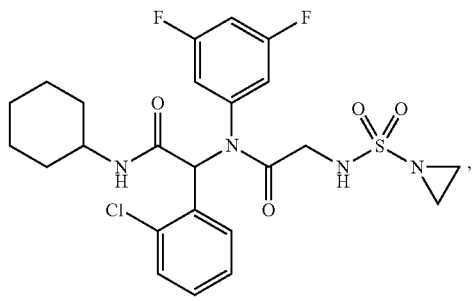
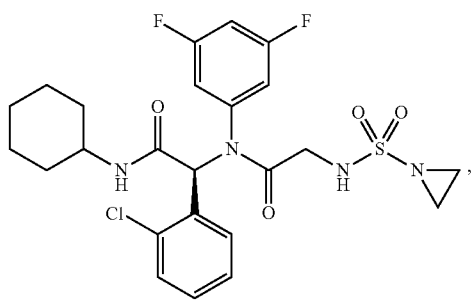
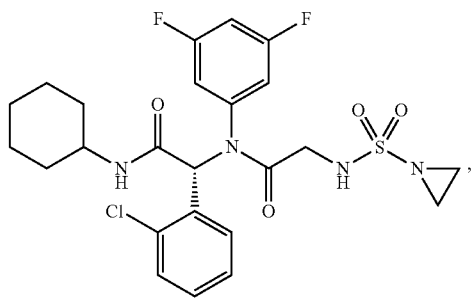
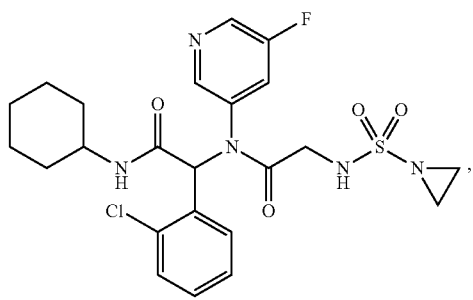

137
-continued
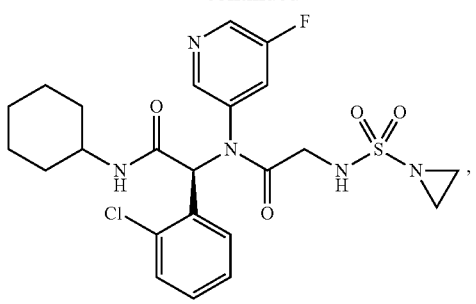
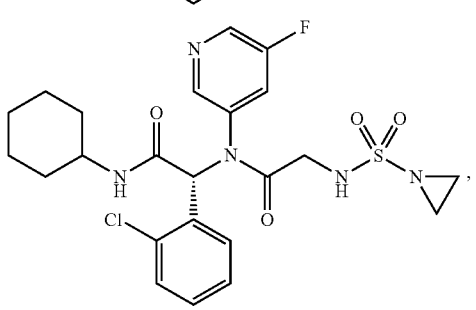
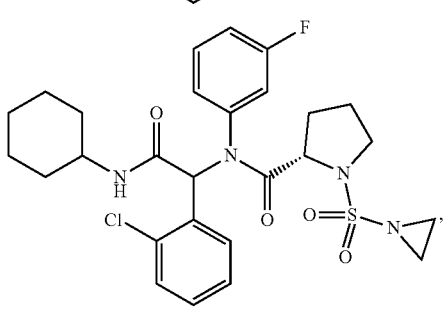
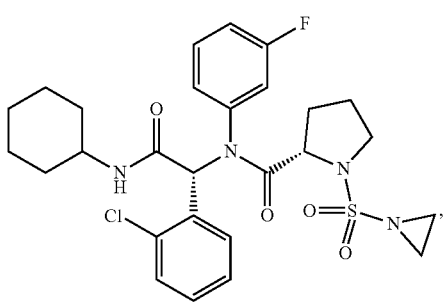
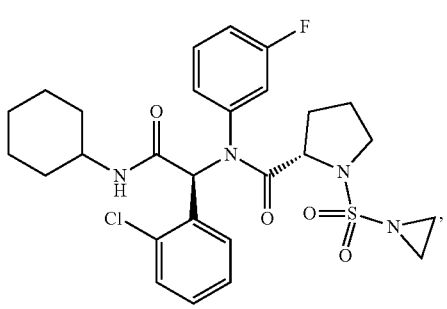
138
-continued
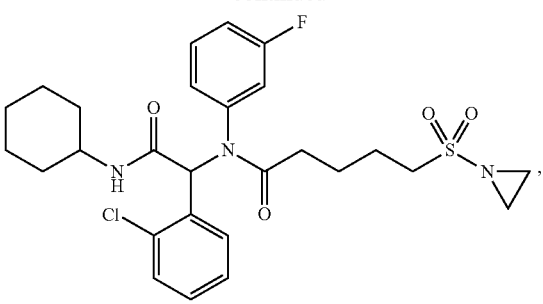
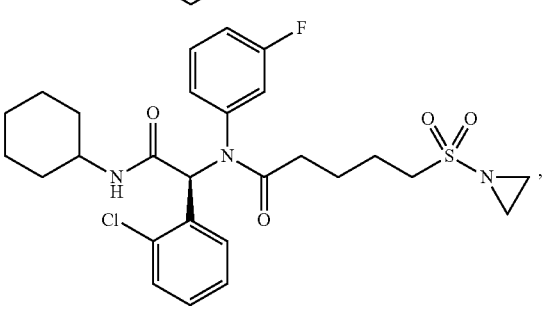
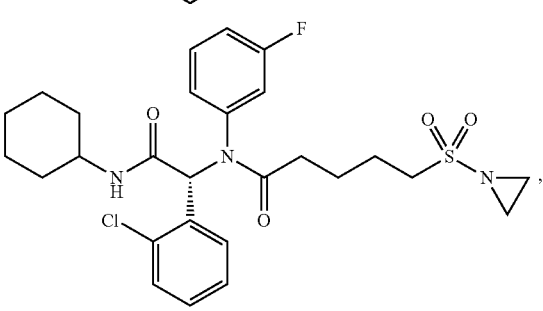
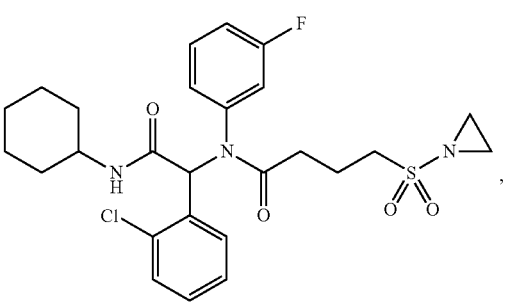
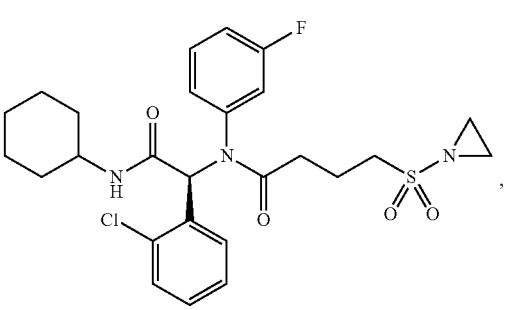

139
-continued
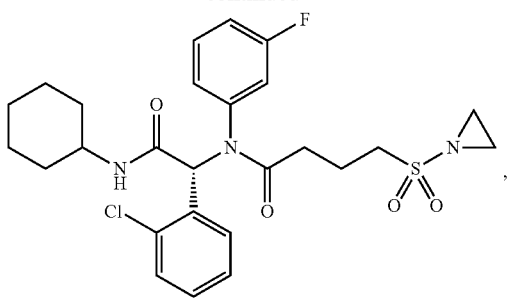
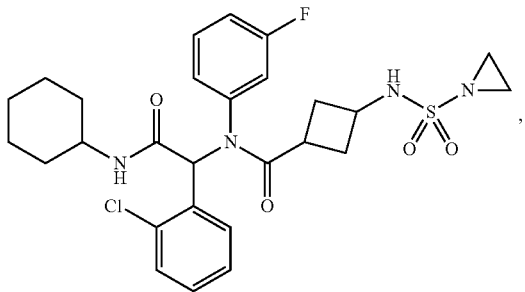
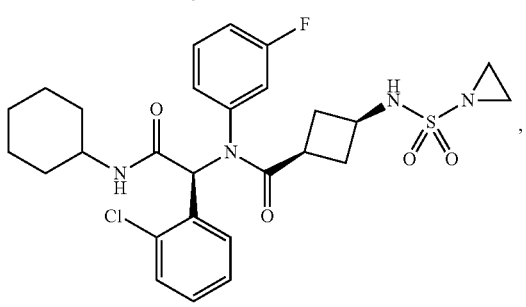
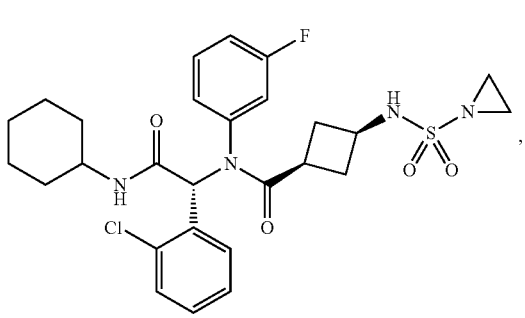
140
-continued
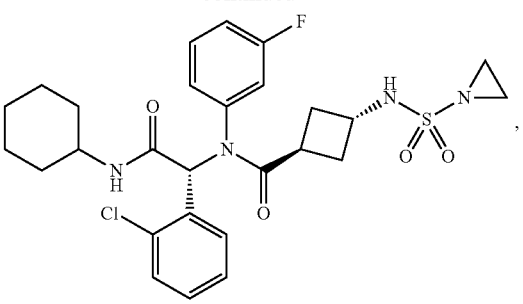
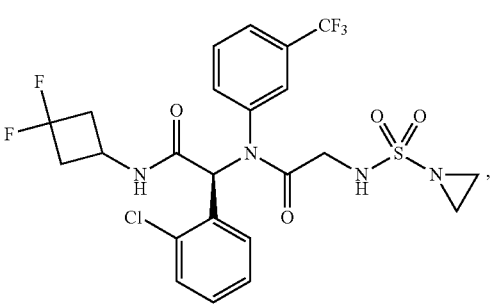
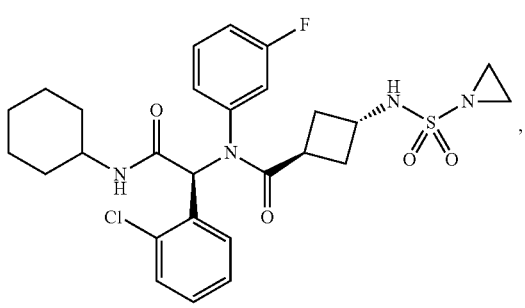
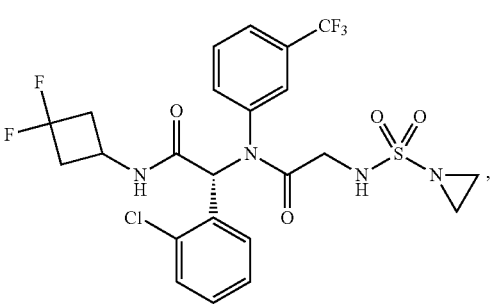
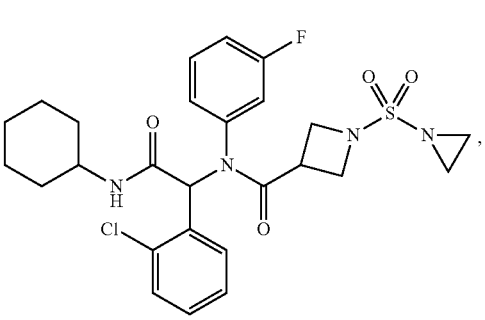

141
-continued
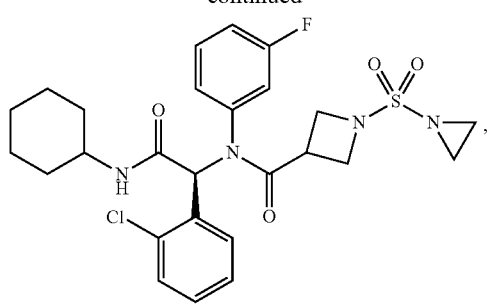
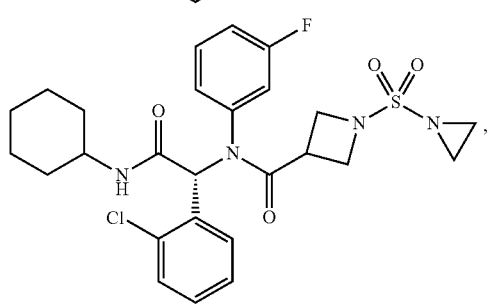
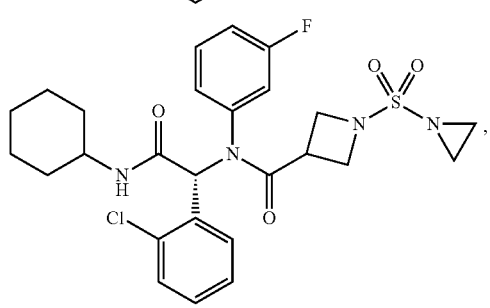
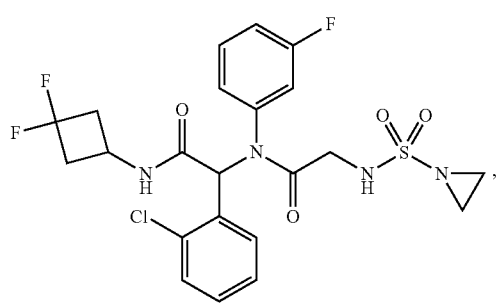
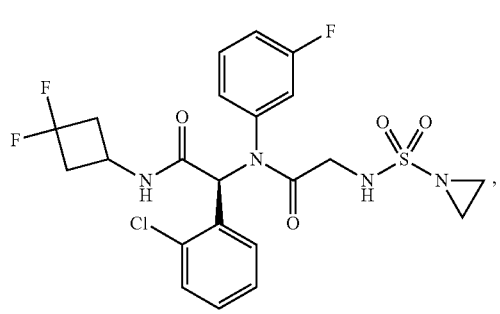
142
-continued
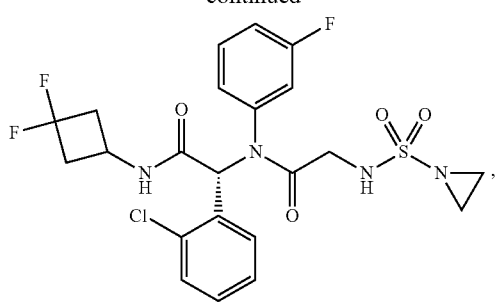
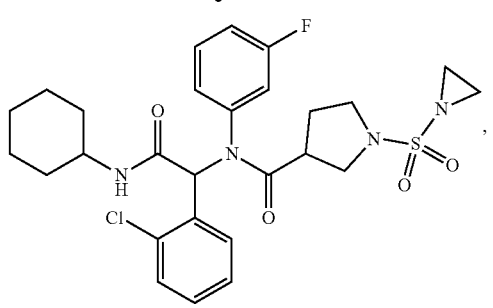
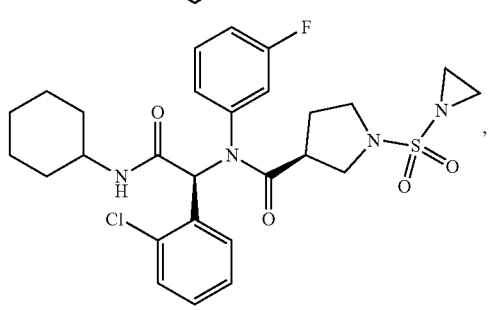
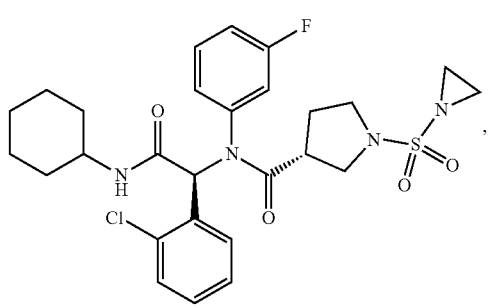
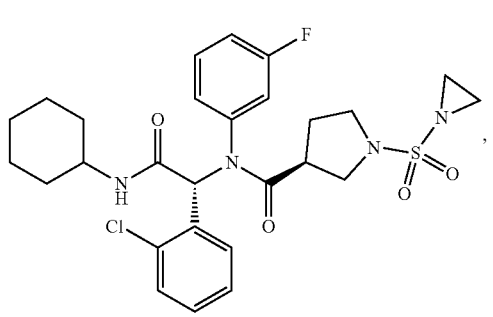

143 -continued
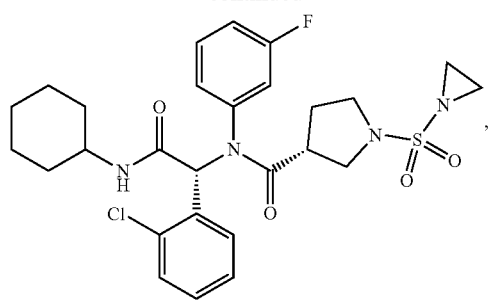
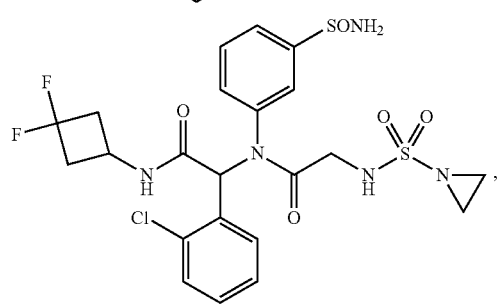
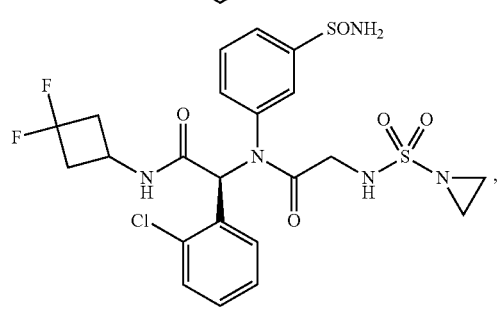
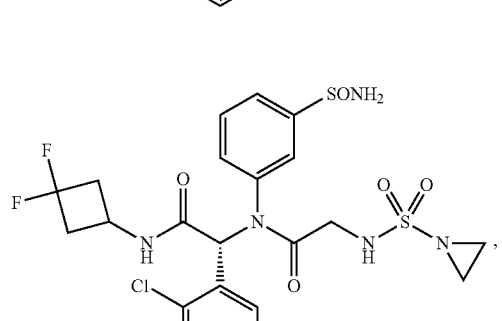
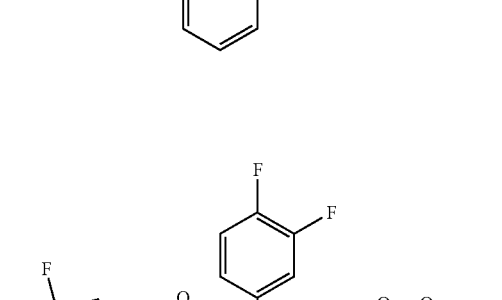
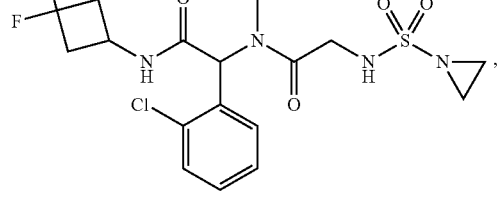
144 -continued
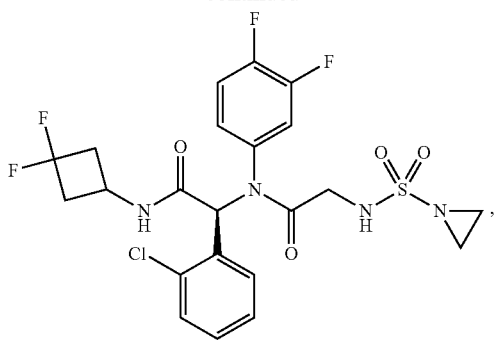
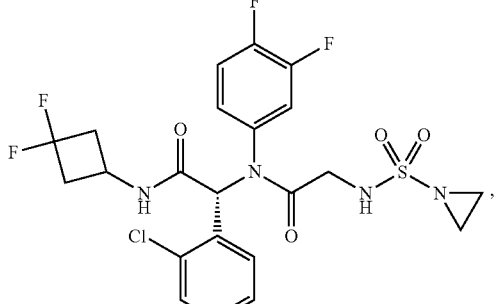
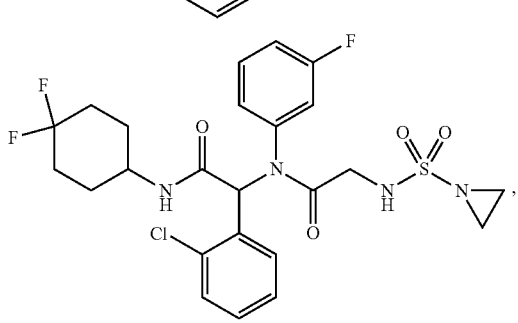
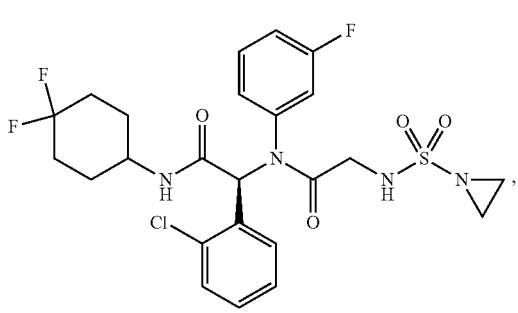
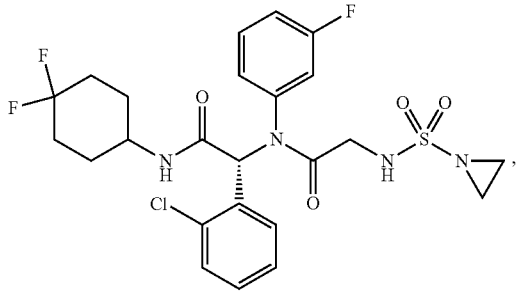

145
-continued
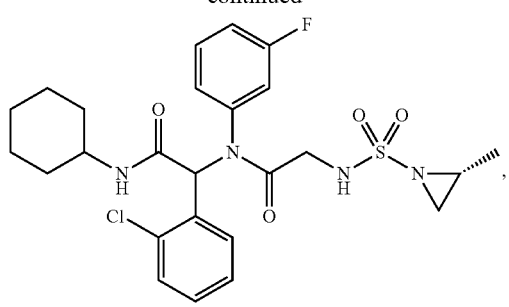
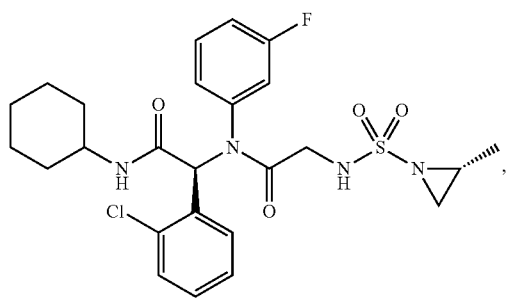
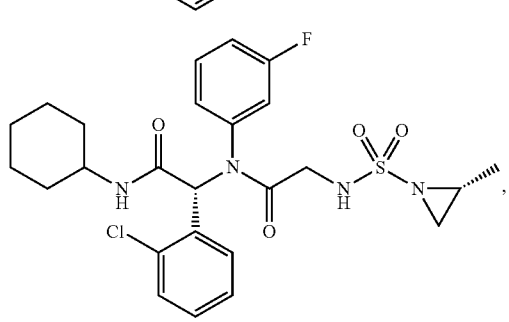
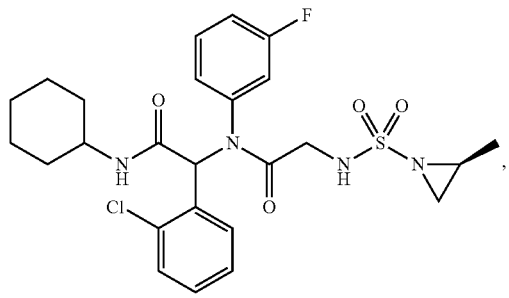
146
-continued
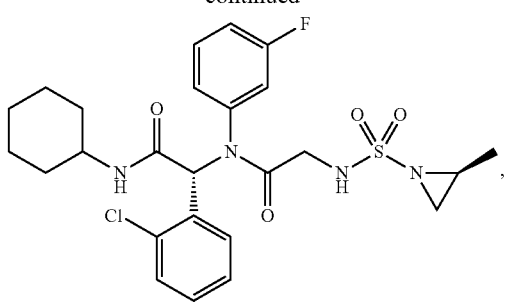
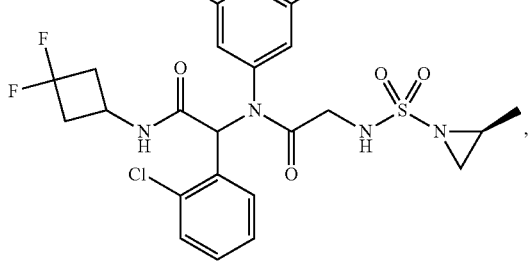
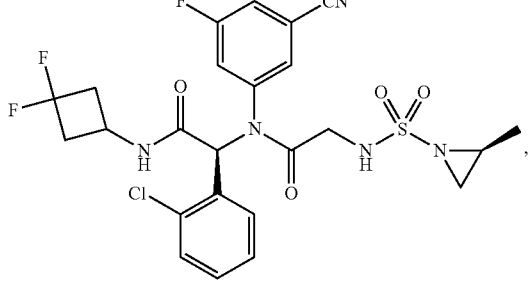
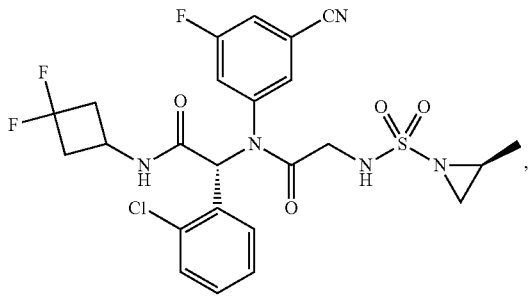
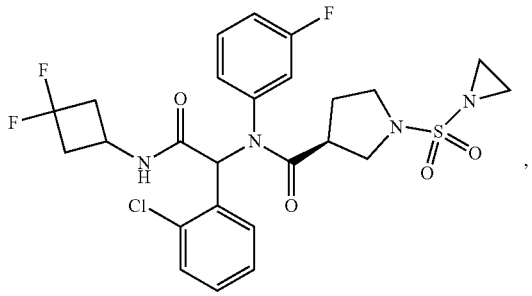

-continued
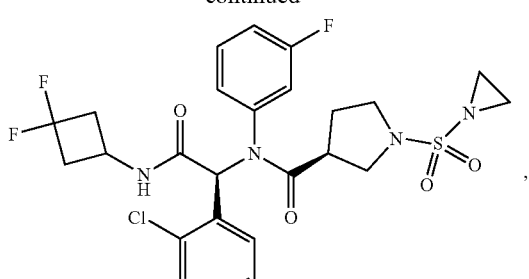
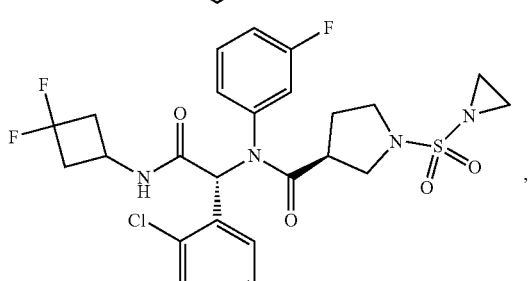
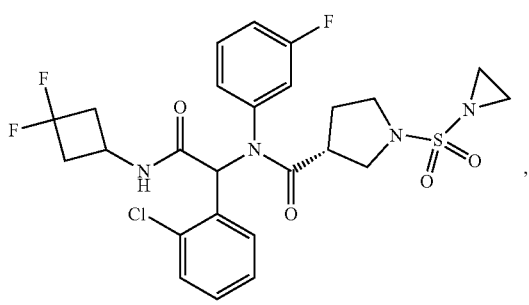
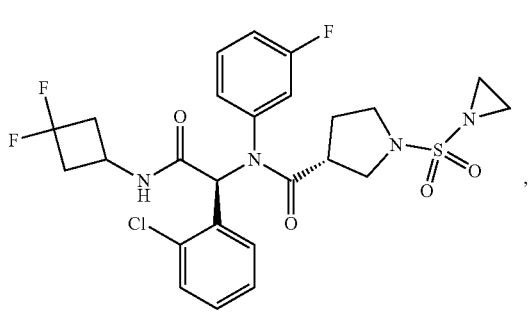
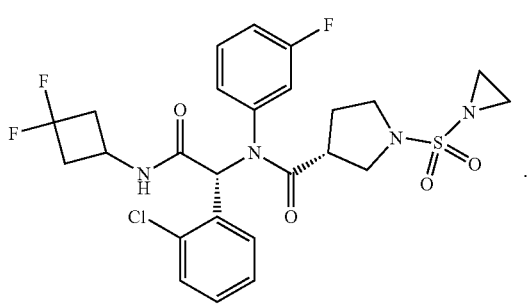 [SMILES: O=C(NC1CC(F)(F)C1)[C@@H](c1ccccc1Cl)N(C(=O)[C@@H]1CCN(S(=O)(=O)N2CC2)C1)c1cccc(F)c1]
12. The compound or the pharmaceutically acceptable salt, solvate or hydrate thereof according to claim 1, wherein the compound is the following compounds and the pharmaceutically acceptable salts, solvates or hydrates thereof:
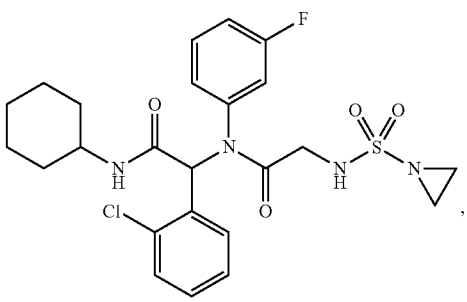
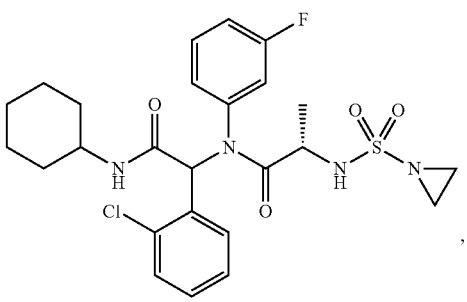
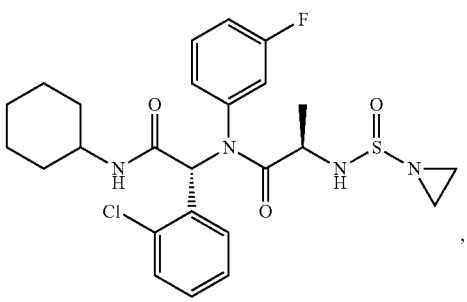
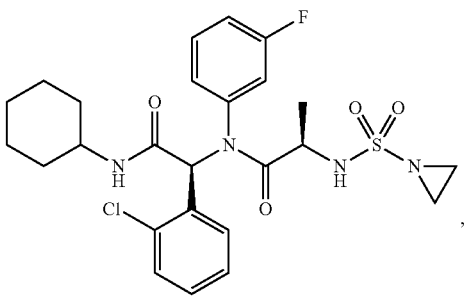
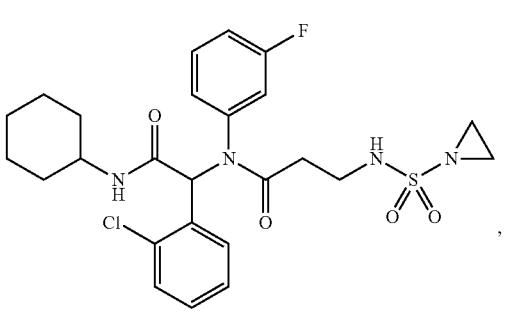

149
-continued
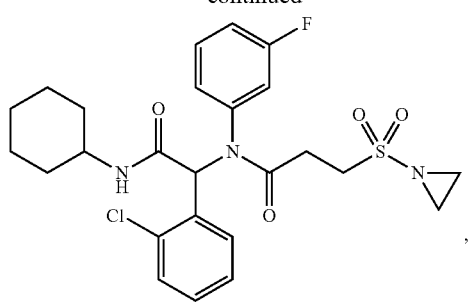
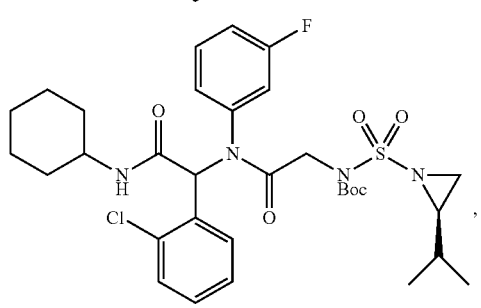
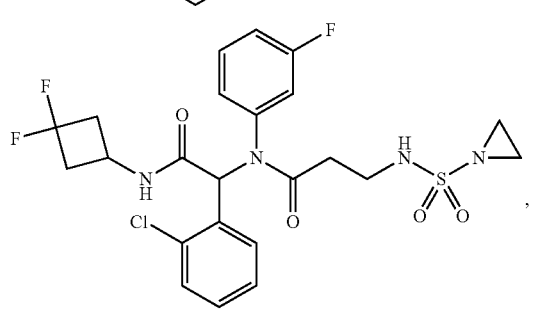
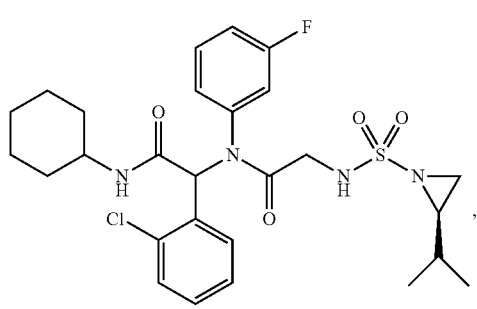
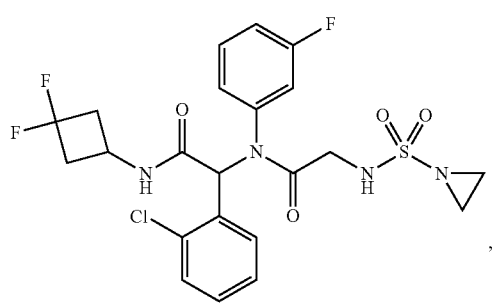
150
-continued
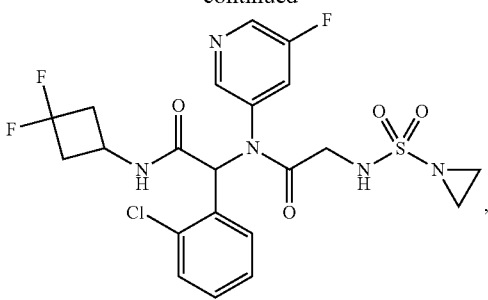
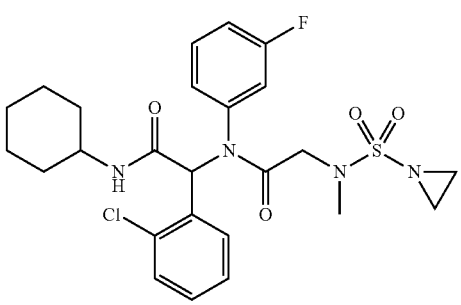
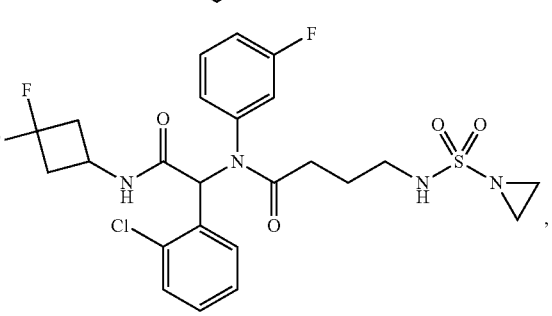
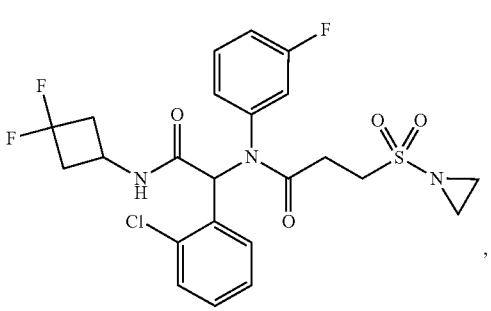
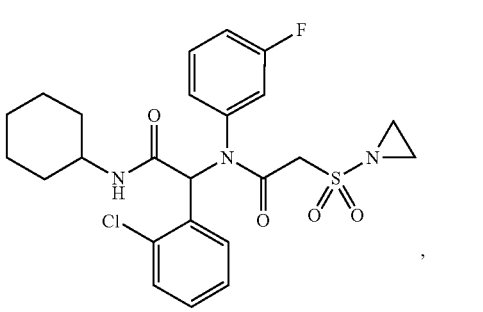

151
-continued
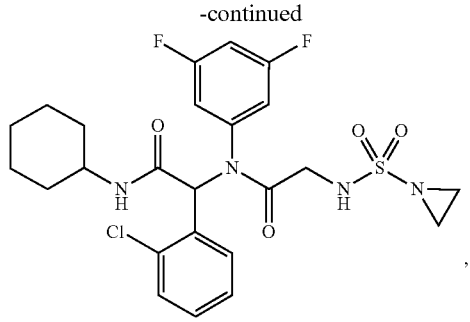
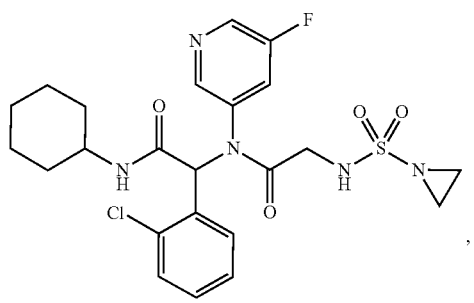
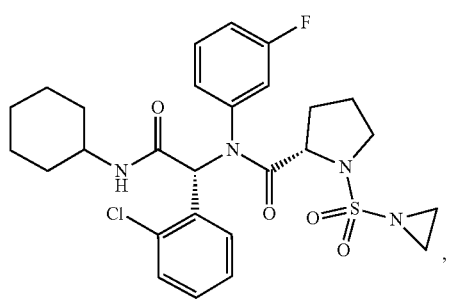
152
-continued
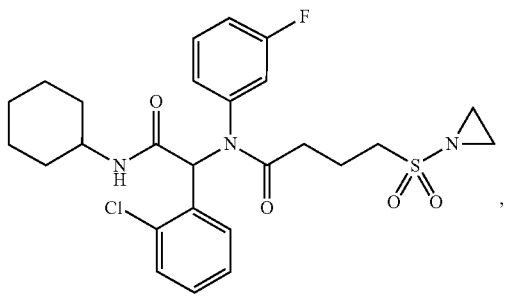
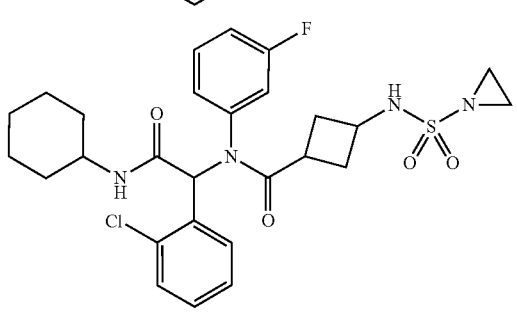
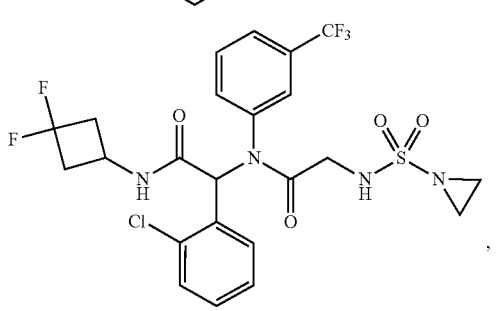
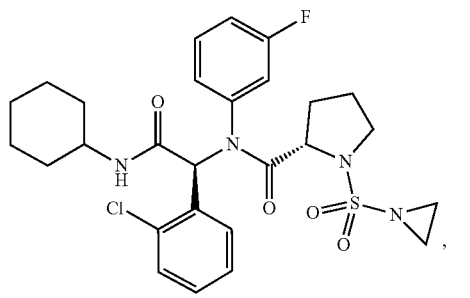
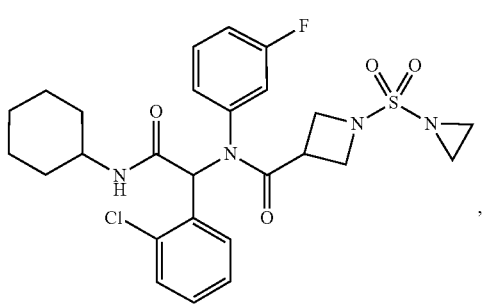
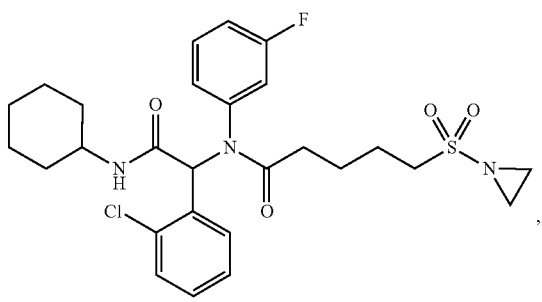
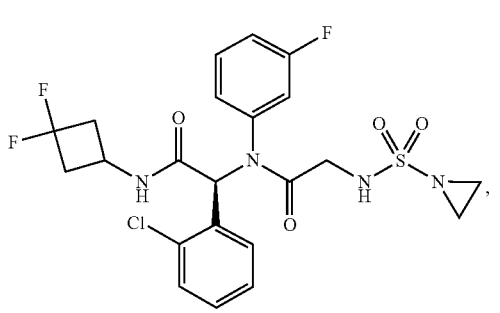

153
-continued
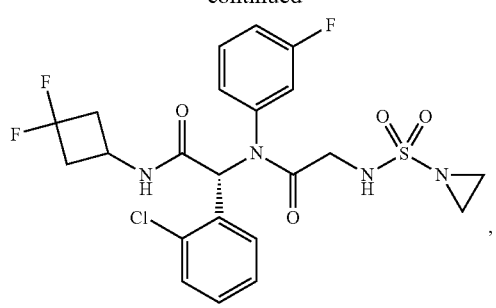
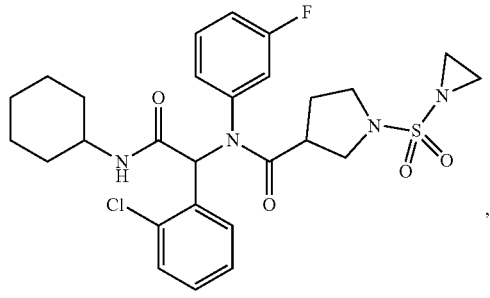
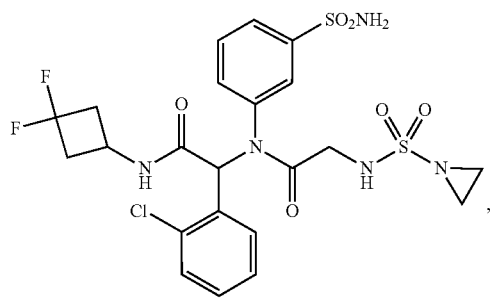
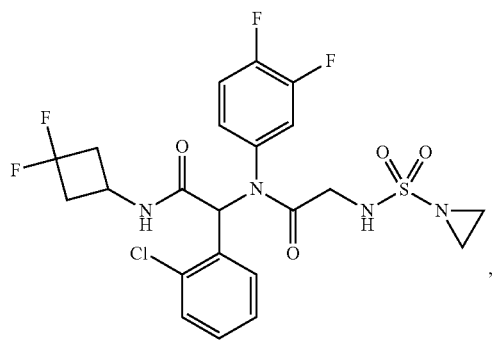
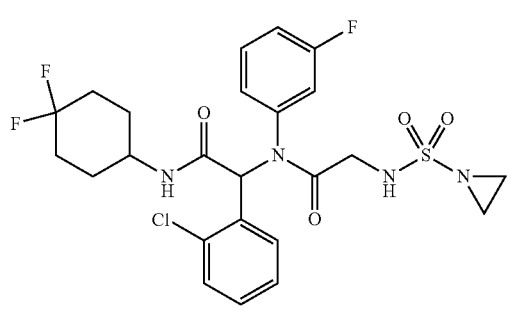
154
-continued
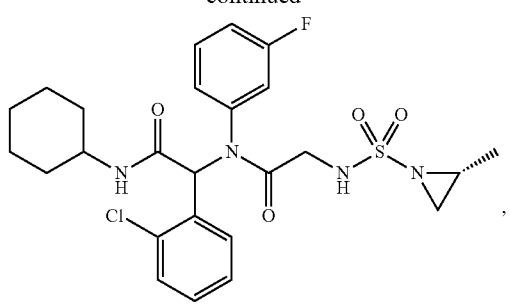
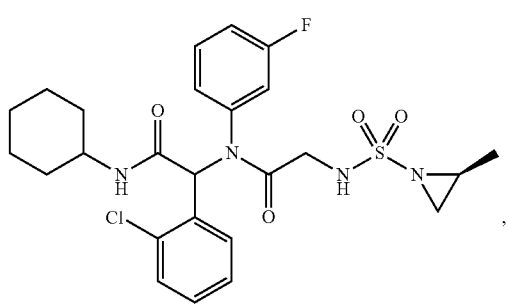
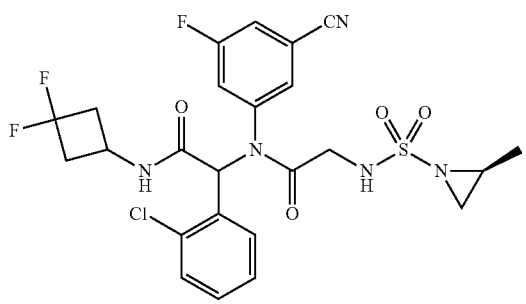
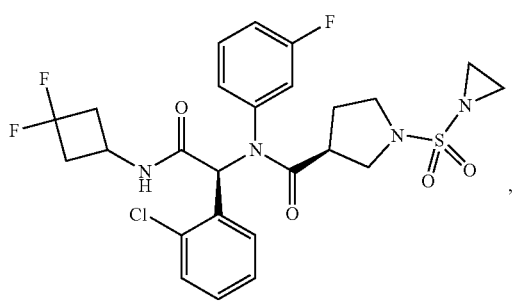

-continued

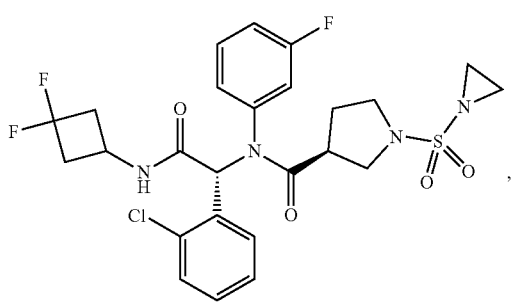

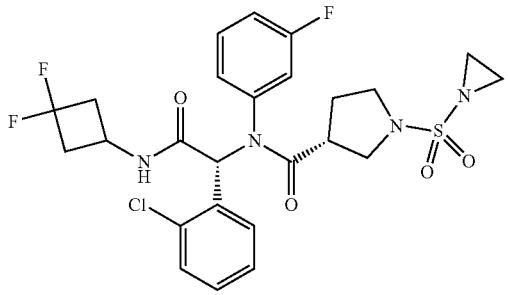

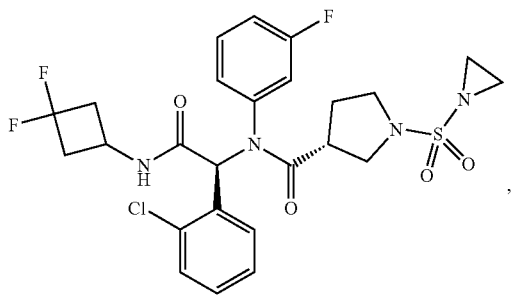

13. A pharmaceutical composition, comprising a therapeutically effective amount of the compound of Formula I or II, or the pharmaceutically acceptable salt, solvate or hydrate thereof of claim 1, and one or more pharmaceutically acceptable carriers or excipients.

14. A method for treating IDH1 mutation-induced cancer, comprising administering a therapeutically effective amount of the compound, or the pharmaceutically acceptable salt, solvate or hydrate thereof of claim 1.

15. The method according to claim 14, wherein the IDH1 mutation has R132X mutation.

16. The method according to claim 14, wherein the IDH1 mutation-induced cancers are selected from glioblastoma, myelodysplastic syndrome, myeloproliferative neoplasm, acute myelogenous leukemia, sarcoma, melanoma, non-small cell lung cancer, chondrosarcoma, bile duct cancer or angioimmunoblastic non-Hodgkin's lymphoma.

* * * * *

UNITED STATES PATENT AND TRADEMARK OFFICE
CERTIFICATE OF CORRECTION

Page 1 of 2

PATENT NO. : 11,203,586 B2
APPLICATION NO. : 16/087396
DATED : December 21, 2021
INVENTOR(S) : Li Zhu et al.

It is certified that error appears in the above-identified patent and that said Letters Patent is hereby corrected as shown below:

In the Claims

At Column 128, Line 5 (Claim 6, approximately Line 16), please delete ";" and insert --.-- therefor.

At Column 141, Lines 25-35 (Claim 11, approximately Lines 838-848), please delete

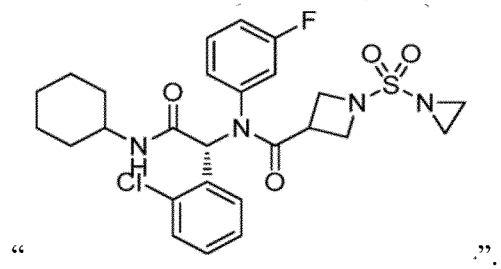

" ".

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,203,586 B2

At Column 143, Lines 15-50 (Claim 11, approximately Lines 957-992), please delete

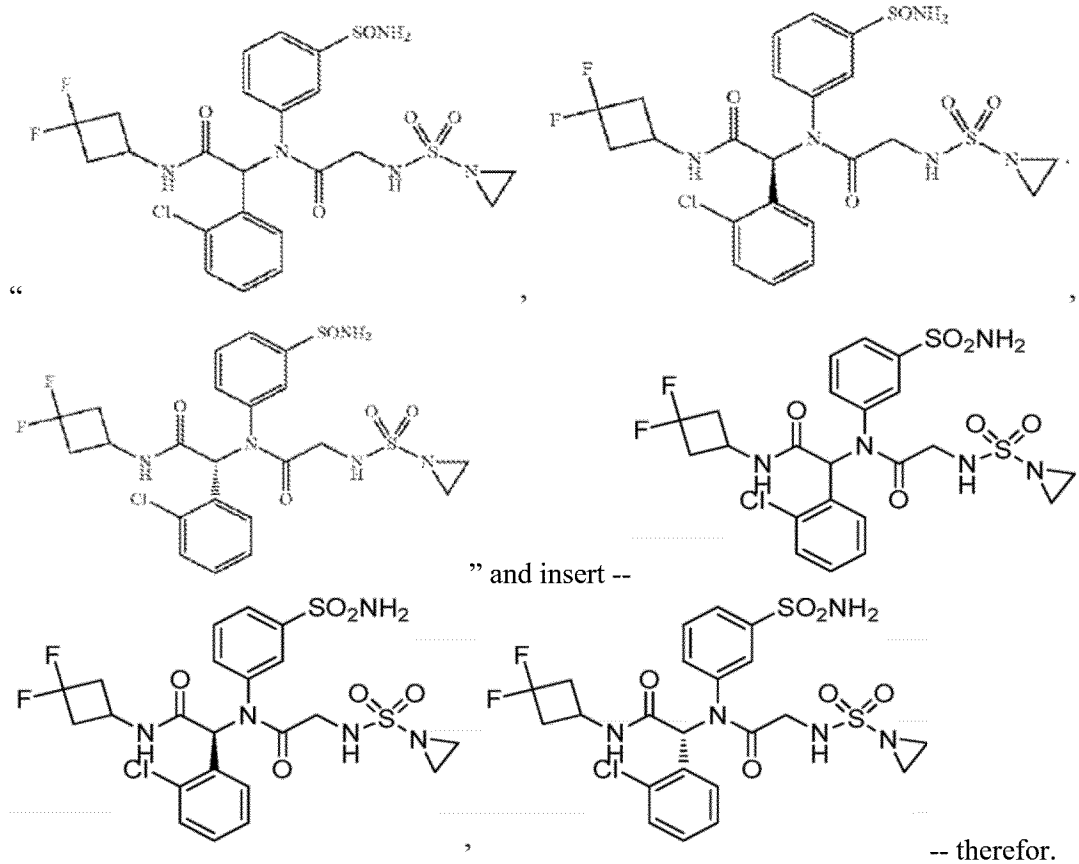

" and insert --

-- therefor.

At Column 148, Lines 30-40 (Claim 12, approximately Lines 30-40), please delete

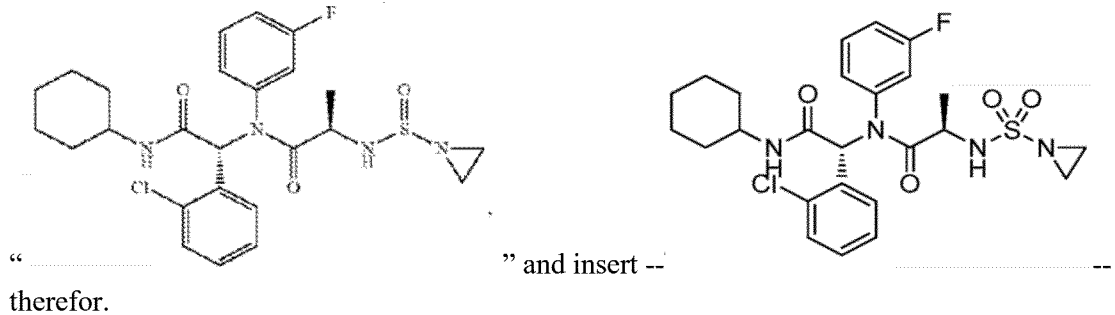

" and insert -- -- therefor.